United States Patent
Wilson

(10) Patent No.: US 11,141,456 B2
(45) Date of Patent: *Oct. 12, 2021

(54) THERAPEUTIC COMPOSITIONS INCLUDING FRATAXIN, LACTOFERRIN, AND MITOCHONDRIAL ENERGY GENERATING ENZYMES, AND USES THEREOF

(71) Applicant: Stealth BioTherapeutics Corp, Monaco (MC)

(72) Inventor: D. Travis Wilson, Newton, MA (US)

(73) Assignee: STEALTH BIOTHERAPEUTICS CORP, Monaco (MC)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,745

(22) Filed: Jan. 17, 2020

(65) Prior Publication Data

US 2020/0323947 A1 Oct. 15, 2020

Related U.S. Application Data

(62) Division of application No. 15/313,767, filed as application No. PCT/US2015/032728 on May 27, 2015, now Pat. No. 10,576,124.

(Continued)

(51) Int. Cl.
| | |
|---|---|
| *A61K 38/10* | (2006.01) |
| *A61K 38/06* | (2006.01) |
| *A61K 38/08* | (2019.01) |
| *A61K 38/07* | (2006.01) |
| *C07K 5/078* | (2006.01) |
| *C07K 5/09* | (2006.01) |
| *C07K 5/087* | (2006.01) |
| *C07K 5/107* | (2006.01) |
| *C07K 5/065* | (2006.01) |
| *C07K 5/113* | (2006.01) |
| *C07K 5/072* | (2006.01) |
| *C07K 5/097* | (2006.01) |
| *A61K 47/64* | (2017.01) |
| *A61K 38/05* | (2006.01) |
| *A61K 38/13* | (2006.01) |
| *A61K 38/17* | (2006.01) |
| *A61K 38/40* | (2006.01) |
| *A61K 38/44* | (2006.01) |

(Continued)

(52) U.S. Cl.
CPC .............. *A61K 38/10* (2013.01); *A61K 38/05* (2013.01); *A61K 38/06* (2013.01); *A61K 38/07* (2013.01); *A61K 38/08* (2013.01); *A61K 38/13* (2013.01); *A61K 38/1709* (2013.01); *A61K 38/40* (2013.01); *A61K 38/44* (2013.01); *A61K 38/443* (2013.01); *A61K 38/45* (2013.01); *A61K 38/46* (2013.01); *A61K 38/51* (2013.01); *A61K 38/53* (2013.01); *A61K 47/645* (2017.08); *C07K 5/06078* (2013.01); *C07K 5/06095* (2013.01); *C07K 5/06156* (2013.01); *C07K 5/0812* (2013.01); *C07K 5/0815* (2013.01); *C07K 5/0817* (2013.01); *C07K 5/0821* (2013.01); *C07K 5/1016* (2013.01); *C07K 5/1021* (2013.01); *C12Y 101/01037* (2013.01); *C12Y 101/01042* (2013.01); *C12Y 102/04002* (2013.01); *C12Y 103/05001* (2013.01); *C12Y 106/05003* (2013.01); *C12Y 109/03001* (2013.01); *C12Y 110/02002* (2013.01); *C12Y 203/03001* (2013.01); *C12Y 306/03014* (2013.01); *C12Y 402/01002* (2013.01); *C12Y 402/01003* (2013.01); *C12Y 602/01004* (2013.01); *C12Y 604/01001* (2013.01)

(58) Field of Classification Search
None
See application file for complete search history.

(56) References Cited

U.S. PATENT DOCUMENTS

| | | |
|---|---|---|
| 4,489,710 A | 12/1984 | Spitler |
| 4,522,811 A | 6/1985 | Eppstein et al. |

(Continued)

FOREIGN PATENT DOCUMENTS

| | | |
|---|---|---|
| EP | 0 308 067 A2 | 3/1989 |
| EP | 0 382 403 B1 | 8/1990 |

(Continued)

OTHER PUBLICATIONS

Adinolfi et al. (Apr. 2009). "Bacterial frataxin CyaY is the gatekeeper of iron-sulfur cluster formation catalyzed by IscS". Nature Structural & Molecular Biology. 16 (4): 390-6. https://www.nature.com/articles/nsmb.1579.*

(Continued)

*Primary Examiner* — Maury A Audet
(74) *Attorney, Agent, or Firm* — Foley & Lardner LLP

(57) ABSTRACT

Disclosed herein are methods and compositions for the treatment and/or prevention of diseases or conditions comprising administration of a therapeutic biological molecule, and/or naturally or artificially occurring derivatives, analogues, or pharmaceutically acceptable salts thereof, alone or in combination with one or more active agents (e.g., an aromatic-cationic peptide). The present technology provides compositions related to aromatic-cationic peptides linked to a therapeutic biological molecule and uses of the same. In some embodiments, the aromatic-cationic peptide comprises 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

12 Claims, 6 Drawing Sheets
Specification includes a Sequence Listing.

Related U.S. Application Data

(60) Provisional application No. 62/003,844, filed on May 28, 2014.

(51) Int. Cl.
*A61K 38/45* (2006.01)
*A61K 38/46* (2006.01)
*A61K 38/51* (2006.01)
*A61K 38/53* (2006.01)

(56) References Cited

U.S. PATENT DOCUMENTS

| | | | |
|---|---|---|---|
| 4,569,789 A | 2/1986 | Blattler et al. | |
| 4,625,014 A | 11/1986 | Senter et al. | |
| 4,638,045 A | 1/1987 | Kohn et al. | |
| 4,671,958 A | 6/1987 | Rodwell et al. | |
| 4,708,934 A | 11/1987 | Gilligan et al. | |
| 5,057,313 A | 10/1991 | Shih et al. | |
| 5,156,840 A | 10/1992 | Goers et al. | |
| 5,580,990 A | 12/1996 | Van Den Berg et al. | |
| 5,674,534 A | 10/1997 | Zale et al. | |
| 5,716,644 A | 2/1998 | Zale et al. | |
| 5,985,566 A | 11/1999 | Houthoff et al. | |
| 6,133,038 A | 10/2000 | Houthoff et al. | |
| 7,989,434 B2 | 8/2011 | Feng | |
| 8,039,273 B2 | 10/2011 | Jeffrey | |
| 8,697,657 B2 * | 4/2014 | Wilson | A61K 38/08 514/21.9 |
| 10,576,124 B2 * | 3/2020 | Wilson | C12Y 101/01042 |
| 2010/0245146 A1 | 9/2010 | Kuo et al. | |
| 2011/0245146 A1 * | 10/2011 | Payne | A61K 47/64 514/1.2 |
| 2013/0059784 A1 * | 3/2013 | Wilson | A61K 38/07 514/15.1 |
| 2013/0303436 A1 * | 11/2013 | Wilson | A61P 27/04 514/1.9 |
| 2016/0166633 A1 * | 6/2016 | Wilson | A61K 38/07 514/17.7 |
| 2018/0207225 A1 * | 7/2018 | Wilson | A61K 31/4412 |

FOREIGN PATENT DOCUMENTS

| | | |
|---|---|---|
| WO | WO-96/40073 A2 | 12/1996 |
| WO | WO-99/15154 A1 | 4/1999 |
| WO | WO-00/38651 A1 | 7/2000 |
| WO | WO-2005/001023 | 1/2005 |
| WO | WO-2014/134562 | 9/2014 |

OTHER PUBLICATIONS

Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss: AREDS Report No. 8," Arch. Ophthalmol. (Oct. 2001), vol. 119, No. 10, pp. 1417-1436.
Allikmets, Rando et al., "Mutation of the Stargardt Disease Gene (ABCR) in Age-Related Macular Degeneration," Science, (Sep. 19, 1997), vol. 277, pp. 1805-1807.
Allikmets, Rando, "Simple and Complex ABCR: Genetic Predisposition to Retinal Disease," Am. J Hum. Genet., (2000), vol. 67, pp. 793-799.
Anderson, Ethan J. et al., "Mitochondrial H2O2 emission and cellular redox state link excess fat intake to insulin resistance in both rodents and humans," J. Clin. Invest., (Mar. 2009), vol. 119, No. 3, pp. 573-581.
Anderson, Ethan J. et al., "Type II skeletal myofibers possess unique properties that potentiate mitochondrial H2O2 generation," Am J Physiol Cell Physiol, (Mar. 2006), vol. 290, pp. C844-C851.
Beauchamp, Martin H. et al., "Role of thromboxane in retinal microvascular degeneration in oxygen-induced retinopathy," J. Appl. Physiol., (2001), vol. 90, pp. 2279-2288.
Belanger, Mireille et al., "Acute Liver Failure: A Critical Appraisal of Available Animal Models," Metabolic Brain Disease, (Dec. 2005), vol. 20, Issue 4, pp. 409-423.
Chonn et al. "Recent Advances in Liposomal Drug-Delivery Systems," Curr. Opin. Biotechnol., (1995), vol. 6, Issue 6, pp. 698-708.
Duan, S.-B. et al., "Nephrotoxicity of high- and low-osmolar contrast media: The protective role of amlodipine in a rat model," Acta Radiol, (Sep. 2000), 41, pp. 503-507.
Fadok et al., "Exposure of Phosphatidylserine on the Surface of Apoptotic Lymphocytes Triggers Specific Recognition and Removal by Macrophages," Journal of Immunology, (1992), vol. 148, pp. 2207-2216.
Foreign Search Report on EP 18210159.2 dated Jun. 19, 2019.
Gan, Quan et al., "Chitosan nanoparticle as protein delivery carrier—Systematic examination of fabrication conditions for efficient loading and release," Colloids and Surfaces B: Biointerfaces, (2007), vol. 59, Issue 1, pp. 24-34.
Gregoriadis. "Engineering Liposomes for Drug Delivery: Progress and Problems," Trends in Biotechnology, (Dec. 1995), vol. 13, No. 12, pp. 527-537.
Han, Xianlin et al., "Shotgun lipidomics of cardiolipin molecular species in lipid extracts of biological samples," J Lipd Res, (2006), 47(4), pp. 864-879.
Heckenlively, John R. et al., "Clinical Findings and Common Symptoms in Retinitis Pigmentosa," Am. J. Ophthalmol., (May 1988), vol. 105, pp. 504-511.
Homburg, Christa H.E. et al., "Human neutrophils lose their surface FcγRiii and acquire Annexin V binding sites during apoptosis in vitro," Blood, (Jan. 1995), vol. 85, No. 2, pp. 532-540.
Ignarro, Louis J. et al., "Endothelium-derived relaxing factor produced and released from artery vein is nitric oxide," Proc. Natl. Acad. Sci. USA, (Dec. 1987), vol. 84, pp. 9265-9269.
International Search Report and Written Opinion issued on PCT/US2015/032728, dated Nov. 13, 2015.
Karan, G. et al., "Lipofuscin accumulation, abnormal electrophysiology, and photoreceptor degeneration in mutant ELOVL4 transgenic mice: A model for macular degeneration," Pro. Natl. Acad. Sci., (Mar. 15, 2005), vol. 102, No. 11, pp. 4164-4169.
Klevering, B. Jeroen et al. "Three Families Displaying the Combination of Stargardt's Disease with Cone-Rod Dystrophy or Retinitis Pigmentosa," Ophthalmology, (Mar. 2004), vol. 111, No. 3, pp. 546-553.
Koopman, G. et al., "Annexin V for Flow Cytometric Detection of Phosphatidylserine Expression on B Cells Undergoing Apoptosis," Blood, (Sep. 1994), vol. 84, No. 5, pp. 1415-1420.
Korshunov, Sergey S. et al., "High protonic potential actuates a mechanism of production of reactive oxygen species in mitochondria," FEBS Letters, (Oct. 1997), vol. 416, Issue 1, pp. 15-18.
Lewis, Richard Alan et al., "Genotype/Phenotype Analysis of a Photoreceptor-Specific ATP-Binding Cassette Transporter Gene, ABCR, in Stargardt Disease," Am. J. Hum. Genet., (1999); vol. 64, pp. 422-434.
Li, Bin et al., "Culture and Characterization of Human Retinal Capillary Endothelial Cell," Chin Ophthal Res, (2005), vol. 23, No. 1, pp. 20-22.
Li, Yunbo et al., "Detection of mitochondria-derived reactive oxygen species production by the chemilumigenic probes lucigenin and luminol," Biochim. Bioiphys. Acta., (Jun. 28, 1999), vol. 1428, Issue 1, pp. 1-12.
Lichtenberg et al. "Liposomes: Preparation, Characterization, and Preservation," Methods Biochem. Anal., (1998), vol. 33, pp. 337-462.
Lim, Kelvin H.H. et al., "The effects of ischaemic preconditioning, diazoxide and 5-hydroxydecanoate on rat heart mitochondrial volume and respiration," J Physiol, (2002), vol. 545, Issue 3, pp. 961-974.
Liu, Yuanbin et al., "Generation of reactive oxygen species by the mitochondrial electron transport chain," J. Neurochem., (2002), vol. 80, Issue 5, pp. 780-787.
McCombs, Peter R. et al., "Acute renal failure following resection of abdominal aortic aneurysm," Surg. Gynecol. Obstet., (1979), vol. 148, pp. 175-178.

(56) References Cited

OTHER PUBLICATIONS

McGwin Jr., Gerald et al., "The association between statin use and age related maculopathy," Br J Ophthalmol, (2003), 87, pp. 1121-1125.
Mizuguchi et al. "Intratumor administration of fusogenic liposomes containing fragment A of diphtheria toxin suppresses tumor growth." Cancer Lett., (1996), vol. 100, Issue 1, pp. 63-69.
Moosmann, Bernd et al., "Secretory Peptide Hormones are Biochemical Antioxidants: Structure-Activity Relationship," Mol Pharmacol., (2002), vol. 61, No. 2, pp. 260-268.
Nishimura, Rick A. et al., "Evaluation of Diastolic Filling of Left Ventricle in Health and Disease:Doppler Echocardiography Is the Clinician's Rosetta Stone," JAAC, (1997), vol. 30, No. 1, pp. 8-18.
Padfield, Katie E. et al., "Burn Injury Causes Mitochondrial Dysfunction in Skeletal Muscle," PNAS, (Apr. 12, 2005), vol. 102, No. 15, pp. 5368-5373.
Palmer, R.M.J. et al., "Nitric oxide release accounts for the biological activity of endothelium-derived relaxing factor," Letters to Nature, (Jun. 1987), vol. 327, pp. 524-526.
Parvez, Zaheer et al., "Contrast Media-induced Lipid Peroxidation in the Rat Kidney," Invest. Radiol., (Sep. 1989), vol. 24, No. 9, pp. 697-702.
Petri, Susanne et al., "Cell-permeable peptide antioxidants as a novel therapeutic approach in a mouse model of amyotrophic lateral sclerosis", Journal of Neurochemistry, (2006), vol. 98, pp. 1141-1148.
Premanand, Chinnaraj et al., "Effect of Curcumin on Proliferation of Human Retinal Endothelial Cells under In Vitro Conditions," Invest. Ophthalmol. Vis. Sci., (May 2006), vol. 47, No. 5, pp. 2179-2184.
Rakowski, Harry et al., "Canadian consensus recommendations for the measurement and reporting of diastolic dysfunction by echocardiography," J Am Soc Echocardiography, (1996), vol. 9, Issue 5, pp. 736-760.
Ray, Martha V.L. et al., "Production of Recombinant Salmon Calcitonin by In Vitro Amidation of an *Escherichia coli* Produced Precursor Peptide," Nature Biotechnology, (1993), vol. 11, Issue 1, pp. 64-70.
Reddy. "Controlled-Release, Pegylation, Liposomal Formulations: New Mechanisms in the Delivery of Injectable Drugs," Ann Pharmacother., (Jul./Aug. 2000), vol. 34, pp. 915-923.
Sabbah, Hani N. et al., "A canine model of chronic heart failure produced by multiple sequential coronary microembolizations," Am J Physiol.—Heart and Circulatory Physiology, (1991), vol. 260, Issue 4, pp. H1379-1384.
Saks, et al., "Permeabilized cell and skinned fiber techniques in studies of mitochondrial function in vivo," Mol Cell Biochem., (Jul. 1998), vol. 184(1-2), pp. 81-100.
Schafer, Freya Q. et al., "Redox environment of the cell as viewed through the redox state of the glutathione disulfide/glutathione couple", Free Radical Biology and Medicine, (2001), vol. 30, Issue 11, pp. 1191-1212.
Search Report issued on EP Application 15799189.4, dated Feb. 5, 2018.
Search Report issued on EP Application 15799189.4, dated May 9, 2018.
Shaban, Hamdy et al, "Phosphatidylglycerol Potently Protects Human Retinal Pigment Epithelial Cells Against Apoptosis Induced by A2E, a Compound Suspected to Cause Age-related Macular Degeneration," Experimental Eye Research, (Jul. 2002), vol. 75, Issue 1, pp. 99-108.
Shaban, Hamdy et al., "A2E and Blue Light in the Retina: The Paradigm of Age-Related Macular Degeneration," Biol. Chem., (Mar./Apr. 2002), vol. 383, pp. 537-545.
Sparrow, Janet R. et al., "A2E-epoxides Damage DNA in Retinal Pigment Epithelial Cells: Vitamin E and Other Antioxidants Inhibit A2E-Epoxide Formation," J. Biol. Chem., (May 2003), vol. 278, No. 20, pp. 18207-18213.
Srinivasan, K. et al., "Combination of high-fat diet-fed and low-dose streptozotocin-treated rat: A model for type 2 diabetes and pharmacological screening," Pharmacological Research, (2005), vol. 52, pp. 313-320.
Stone, Edwin M. et al., "Allelic variation in ABCR associated with Stargardt disease but not age-related macular degeneration," Nature Genetics, (Dec. 1998), vol. 20, pp. 328-329.
St-Pierre, Julie et al., "Topology of Superoxide Production from Different Sites in the Mitochondrial Electron Transport Chain," J. Biol. Chem., (Nov. 2002), vol. 277, No. 47, pp. 44784-44790.
Szeto et al., "Novel Therapies Targeting inner Mitochondrial Membrane-From Discovery to Clinical Development" Pharm Res, vol. 28, 2001, pp. 2669-2679.
Thomas, Merlin C. et al., "Interactions between Renin Angiotension System and Advanced Glycation in the Kidney," J Am Soc Nephrol, (2005), vol. 16, pp. 2976-2984.
Tonkonogi, et al., "Reduced oxidative power but unchanged antioxidative capacity in skeletal muscle from aged humans," Pflügers Arch, (2003), vol. 446, pp. 261-269.
Turrens, Julio F. et al., "Generation of superoxide anion by the NADH dehydrogenase of bovine heart mitochondria," Biochem J., (Oct. 15, 1980), vol. 191, Part 2, pp. 421-427.
Vermes, Istvan et al., "A novel assay for apoptosis Flow cytometric detection of phosphatidylserine expression on early apoptotic cells unsing fluorescein labelled Annexin V," J. Immunol. Meth., (Jul. 17, 1995), vol. 184, Issue 1, pp. 39-51.
Walsh, et al., "The role of phosphorylcreatine and creatine in the regulation of mitochondrial respiration in human skeletal muscle," Journal of Physiology, (2001), vol. 537, No. 3, pp. 971-978.
Weiner, Alan L., "Liposomes for Protein Delivery: Selecting Manufacture and Development Processes," Immunomethods, (1994), 4(3), pp. 201-209.
Whittaker, Mark et al., "Design and Therapeutic Application of Matrix Metalloproteinase Inhibitors," Chemical Reviews, (1999), vol. 99(9), pp. 2735-2776.
Zhao, Kesheng et al., "Transcellular Transport of a Highly Polar 3+ Net Charge Opioid Tetrapeptide," Journal of Pharmacology and Experimental Therapeutics, (2003), vol. 304, No. 1, pp. 425-432.
Zhao, Kesheng et. al., "Cell-permeable Peptide Antioxidants Targeted to Inner Mitochondrial Membrane inhibit Mitochondrial Swelling, Oxidative Cell Death, and Reperfusion Injury," J Biol Chem., (Aug. 2004), vol. 279, No. 33, pp. 34682-34690.

\* cited by examiner

FORMULA P

FORMULA Q

FORMULA R

THERAPEUTIC COMPOSITIONS INCLUDING FRATAXIN, LACTOFERRIN, AND MITOCHONDRIAL ENERGY GENERATING ENZYMES, AND USES THEREOF

CROSS-REFERENCE TO RELATED APPLICATIONS

This application is a Divisional of U.S. patent application Ser. No. 15/313,767, filed Nov. 23, 2016, which is the U.S. National Stage of International Patent Application No. PCT/US2015/032728, filed May 27, 2015, which claims the benefit of and priority to U.S. Provisional Application No. 62/003,844, filed May 28, 2014, the contents of which are incorporated herein by reference in their entireties.

SEQUENCE LISTING

The instant application contains a Sequence Listing which has been submitted electronically in ASCII format and is hereby incorporated by reference in its entirety.

TECHNICAL FIELD

Disclosed herein are methods and compositions related to the treatment and/or amelioration of diseases and conditions comprising administration of a therapeutic biological molecule and/or naturally or artificially occurring derivatives, analogues, or pharmaceutically acceptable salts thereof, alone or in combination with one or more active agents (e.g., an aromatic-cationic peptide). The present technology relates generally to aromatic-cationic peptide compositions where the aromatic-cationic peptide is conjugated to a therapeutic biological molecule and their use in the prevention and treatment of medical diseases and conditions.

BACKGROUND

The following description is provided to assist the understanding of the reader. None of the information provided or references cited is admitted to be prior art.

Biological cells are generally highly selective as to the molecules that are allowed to pass through the cell membrane. As such, the delivery of compounds, such as small molecules and biological molecules into a cell is usually limited by the physical properties of the compound. The small molecules and biological molecules may, for example, be pharmaceutically active compounds.

SUMMARY

The present technology provides compositions and methods useful in the prevention, treatment and/or amelioration of diseases and conditions.

A therapeutic biological molecule (TBM) includes those molecules found in nature as well as synthesized biological molecules. TBMs include, but are not limited to polynucleotides, peptide nucleic acids, and polyamino acids. In some embodiments, the polyamino acid sequence is a peptide, polypeptide, partial or full length protein, chimeric peptide sequence, chimeric polypeptide sequence or a chimeric protein sequence. In some embodiments, the polynucleotide sequence is double-stranded DNA, single-stranded DNA, antisense RNA, mRNA, siRNA, miRNA, a ribozyme, an RNA decoy, or an external guide sequence for ribozymes. TBMs useful in compositions of the present technology include, but are not limited to, e.g., frataxin, lactoferrin, or mitochondrial enzymes, such as, but not limited to NADH-coenzyme Q oxidoreductase, succinate-Q oxidoreductase, electron transfer flavoprotein-Q oxidoreductase, Q-cytochrome c oxidoreductase, cytochrome c oxidase, ATP synthase, pyruvate dehydrogenase, citrate synthase, aconitase, isocitrate dehydrogenase, α-ketoglutarate dehydrogenase, succinyl-CoA synthetase, succinic dehydrogenase, fumarase, malate dehydrogenase, and pyruvate carboxylase.

In one aspect, the present disclosure provides a composition comprising a therapeutic biological molecule (TBM), derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In some embodiments, the composition further comprises one or more additional active agents such as cyclosporine, a cardiac drug, an anti-inflammatory, an anti-hypertensive drug, an antibody, an ophthalmic drug, an antioxidant, a metal complexer, and an antihistamine.

In one aspect, the present disclosure provides a method for treating or preventing mitochondrial permeability transition in a subject, comprising administering to the subject a therapeutically effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In one aspect, the present disclosure provides a method of treating a disease or condition characterized by mitochondrial permeability transition, comprising administering a therapeutically effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In some embodiments, the disease or condition comprises a neurological or neurodegenerative disease or condition, ischemia, reperfusion, hypoxia, atherosclerosis, ureteral obstruction, diabetes, complications of diabetes, arthritis, liver damage, insulin resistance, diabetic nephropathy, acute renal injury, chronic renal injury, acute or chronic renal injury due to exposure to nephrotoxic agents and/or radiocontrast dyes, hypertension, metabolic syndrome, an ophthalmic disease or condition such as dry eye, diabetic retinopathy, cataracts, retinitis pigmentosa, glaucoma, macular degeneration, choroidal neovascularization, retinal degeneration, oxygen-induced retinopathy, cardiomyopathy, ischemic heart disease, heart failure, hypertensive cardiomyopathy, vessel occlusion, vessel occlusion injury, myocardial infarction, coronary artery disease, or oxidative damage.

In some embodiments, the neurological or neurodegenerative disease or condition comprises Alzheimer's disease, Amyotrophic Lateral Sclerosis (ALS), Parkinson's disease, Huntington's disease or Multiple Sclerosis.

In some embodiments, the subject is suffering from ischemia or has an anatomic zone of no-reflow in one or more of cardiovascular tissue, skeletal muscle tissue, cerebral tissue and renal tissue.

In one aspect, the present disclosure provides a method for reducing CD36 expression in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In one aspect, the present disclosure provides a method for treating or preventing a disease or condition characterized by CD36 elevation in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In some embodiments, the subject is diagnosed as having, suspected of having, or at risk of having atherosclerosis, inflammation, abnormal angiogenesis, abnormal lipid metabolism, abnormal removal of apoptotic cells, ischemia such as cerebral ischemia and myocardial ischemia, ischemia-reperfusion, ureteral obstruction, stroke, Alzheimer's Disease, diabetes, diabetic nephropathy, or obesity.

In one aspect, the present disclosure provides a method for reducing oxidative damage in a removed organ or tissue, comprising administering to the removed organ or tissue an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In some embodiments, the removed organ comprises a heart, lung, pancreas, kidney, liver, or skin.

In one aspect, the present disclosure provides a method for preventing the loss of dopamine-producing neurons in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In some embodiments, the subject is diagnosed as having, suspected of having, or at risk of having Parkinson's disease or ALS.

In one aspect, the present disclosure provides a method of reducing oxidative damage associated with a neurodegenerative disease in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In some embodiments, the neurodegenerative disease comprises Alzheimer's disease, Parkinson's disease, or ALS.

In one aspect, the present disclosure provides a method for preventing or treating a burn injury in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In one aspect, the present disclosure provides a method for treating or preventing mechanical ventilation-induced diaphragm dysfunction in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In one aspect, the present disclosure provides a method for treating or preventing no reflow following ischemia-reperfusion injury in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In one aspect, the present disclosure provides a method for preventing norepinephrine uptake in a subject in need of analgesia, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In one aspect, the present disclosure provides a method for treating or preventing drug-induced peripheral neuropathy or hyperalgesia in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In one aspect, the present disclosure provides a method for inhibiting or suppressing pain in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In one aspect, the present disclosure provides a method for treating atherosclerotic renal vascular disease (ARVD) in a subject in need thereof, comprising administering to the subject an effective amount of a composition comprising TBMs, or derivatives, analogues, or pharmaceutically acceptable salts thereof, alone or in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In some embodiments, the composition comprises a TBM, derivative, analogue, or pharmaceutically acceptable salts thereof.

In some embodiments, the composition further comprises one or more of at least one pharmaceutically acceptable pH-lowering agent; and at least one absorption enhancer effective to promote bioavailability of the active agent, and one or more lamination layers.

In some embodiments, the pH-lowering agent is selected from the group consisting of citric acid, tartaric acid and an acid salt of an amino acid.

The present technology provides compositions comprising an aromatic-cationic peptide of the present technology conjugated to a TBM as well as methods for their use. Such molecules are referred to hereinafter as "peptide conjugates." At least one TBM and at least one aromatic-cationic peptide associate to form a peptide conjugate. The TBM and aromatic-cationic peptide can associate by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking. In some embodiments, the peptide conjugates have the general structure shown below:

aromatic-cationic peptide-TBM

In some embodiments, the peptide conjugates have the general structure shown below:

aromatic-cationic peptide-linker-TBM

The type of association between the TBM and aromatic-cationic peptides typically depends on, for example, functional groups available on the TBM and functional groups available on the aromatic-cationic peptide. The peptide conjugate linker may be nonlabile or labile. The peptide conjugate linker may be enzymatically cleavable.

In one aspect, the present technology provides a peptide conjugate comprising a TBM conjugated to an aromatic-cationic peptide, wherein the aromatic-cationic peptide is selected from the group consisting of: 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$, or any peptide described in Section II; and wherein the TBM is a compound described in Section I.

In some embodiments, the TBM is conjugated to the aromatic-cationic peptide by a linker. In some embodiments, the TBM and aromatic-cationic peptide are chemically bonded. In some embodiments, the TBM and aromatic-cationic peptide are physically bonded.

In some embodiments, the aromatic-cationic peptide and the TBM are linked using a labile linkage that is hydrolyzed in vivo to uncouple the aromatic-cationic peptide and the TBM. In some embodiments, the labile linkage comprises an ester linkage.

In another aspect, the present technology provides methods for delivering an aromatic-cationic peptide and/or TBM to a cell, the method comprising contacting the cell with a peptide conjugate, wherein the peptide conjugate comprises the TBM conjugated to an aromatic-cationic peptide, wherein the aromatic-cationic peptide is selected from the group consisting of: 2',6'-dimethyl-Tyr-D-Arg-Phe-Lys-NH$_2$, Phe-D-Arg-Phe-Lys-NH$_2$, or D-Arg-2',6'-Dmt-Phe-NH$_2$, or any peptide described in Section II; and wherein the TBM is a compound described in Section I.

In some embodiments, the TBM is conjugated to the aromatic-cationic peptide by a linker. In some embodiments, the TBM and aromatic-cationic peptide are chemically bonded. In some embodiments, the TBM and aromatic-cationic peptide are physically bonded. In some embodiments, the aromatic-cationic peptide and the TBM are linked using a labile linkage that is hydrolyzed in vivo to uncouple the aromatic-cationic peptide and the TBM. In some embodiments, the labile linkage comprises an ester linkage.

In another aspect, the present technology provides methods for treating, ameliorating or preventing a medical disease or condition in a subject in need thereof, comprising administering a therapeutically effective amount of a composition comprising an aromatic-cationic peptide of the present technology conjugated to a TBM to the subject thereby treating, amelioration or preventing the medical disease or condition.

In some embodiments, the medical disease or condition is characterized by mitochondrial permeability transition.

In some embodiments, the medical disease or condition comprises a neurological or neurodegenerative disease or condition, ischemia, reperfusion, hypoxia, atherosclerosis, ureteral obstruction, diabetes, complications of diabetes, arthritis, liver damage, insulin resistance, diabetic nephropathy, acute renal injury, chronic renal injury, acute or chronic renal injury due to exposure to nephrotoxic agents and/or radiocontrast dyes, hypertension, Metabolic Syndrome, an ophthalmic disease or condition such as dry eye, diabetic retinopathy, cataracts, retinitis pigmentosa, glaucoma, macular degeneration, choroidal neovascularization, retinal degeneration, oxygen-induced retinopathy, cardiomyopathy, ischemic heart disease, heart failure, hypertensive cardiomyopathy, vessel occlusion, vessel occlusion injury, myocardial infarction, coronary artery disease, oxidative damage. In some embodiments, the neurological or neurodegenerative disease or condition comprises Alzheimer's disease, Amyotrophic Lateral Sclerosis (ALS), Parkinson's disease, Huntington's disease or Multiple Sclerosis.

In some embodiments, the subject is suffering from ischemia or has an anatomic zone of no-reflow in one or more of cardiovascular tissue, skeletal muscle tissue, cerebral tissue and renal tissue.

In another aspect, the present technology provides methods for reducing CD36 expression in a subject in need thereof, comprising administering to the subject an effective amount of a composition comprising an aromatic-cationic peptide of the present technology conjugated to a TBM.

In another aspect, the present technology provides methods for treating, ameliorating or preventing a medical disease or condition characterized by CD36 elevation in a subject in need thereof, comprising administering to the subject a therapeutically effective amount of a composition comprising an aromatic-cationic peptide of the present technology conjugated to a TBM.

In some embodiments, the subject is diagnosed as having, is suspected of having, or at risk of having atherosclerosis, inflammation, abnormal angiogenesis, abnormal lipid metabolism, abnormal removal of apoptotic cells, ischemia such as cerebral ischemia and myocardial ischemia, ischemia-reperfusion, ureteral obstruction, stroke, Alzheimer's disease, diabetes, diabetic nephropathy, or obesity.

In another aspect, the present technology provides methods for reducing oxidative damage in a removed organ or tissue, comprising administering to the removed organ or tissue a therapeutically effective amount of a composition comprising an aromatic-cationic peptide of the present technology conjugated to a TBM. In some embodiments, the removed organ comprises a heart, lung, pancreas, kidney, liver, or skin.

In another aspect, the present technology provides methods for preventing the loss of dopamine-producing neurons in a subject in need thereof, comprising administering to the subject a therapeutically effective amount of a composition comprising an aromatic-cationic peptide of the present technology conjugated to a TBM. In some embodiments, the subject is diagnosed as having, suspected of having, or at risk of having Parkinson's disease or ALS.

In another aspect, the present technology provides methods for reducing oxidative damage associated with a neurodegenerative disease in a subject in need thereof, comprising administering to the subject a therapeutically effective amount of a composition comprising an aromatic-cationic peptide of the present technology conjugated to a TBM. In some embodiments, the neurodegenerative diseases comprise Alzheimer's disease, Parkinson's disease, or ALS.

In another aspect, the present technology provides methods for preventing or treating a burn injury in a subject in need thereof, comprising administering to the subject a therapeutically effective amount of a composition comprising an aromatic-cationic peptide of the present technology conjugated to a TBM.

In another aspect, the present technology provides methods for treating or preventing mechanical ventilation-induced diaphragm dysfunction in a subject in need thereof, comprising administering to the subject a therapeutically effective amount of a composition comprising an aromatic-cationic peptide of the present technology conjugated to a TBM.

In another aspect, the present technology provides methods for treating or preventing no reflow following ischemia-reperfusion injury in a subject in need thereof, comprising administering to the subject a therapeutically effective amount of a composition comprising an aromatic-cationic peptide of the present technology conjugated to a TBM.

In another aspect, the present technology provides methods for preventing norepinephrine uptake in a subject in need of analgesia, comprising administering to the subject a therapeutically effective amount of a composition comprising an aromatic-cationic peptide of the present technology conjugated to a TBM.

In another aspect, the present technology provides methods for treating, ameliorating or preventing drug-induced peripheral neuropathy or hyperalgesia in a subject in need thereof, comprising administering to the subject a therapeutically effective amount of a composition comprising an aromatic-cationic peptide of the present technology conjugated to a TBM.

In another aspect, the present technology provides methods for inhibiting or suppressing pain in a subject in need thereof, comprising administering to the subject a therapeutically effective amount of a composition comprising an aromatic-cationic peptide of the present technology conjugated to a TBM.

In another aspect, the present technology provides methods for treating atherosclerotic renal vascular disease (ARVD) in a subject in need thereof, comprising administering to the subject a therapeutically effective amount of a composition comprising an aromatic-cationic peptide of the present technology conjugated to a TBM.

In some embodiments, the aromatic-cationic peptide is defined by Formula A.

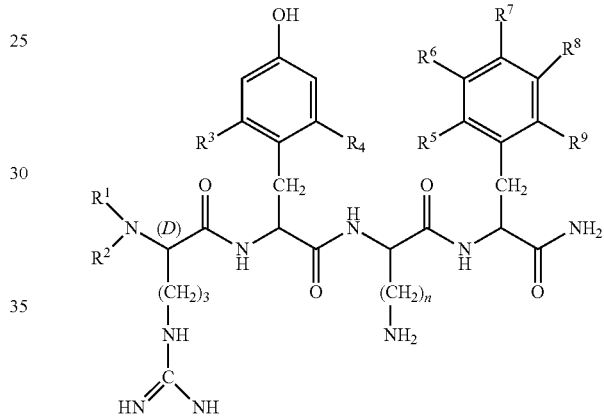

wherein $R^1$ and $R^2$ are each independently selected from
(i) hydrogen;
(ii) linear or branched $C_1$-$C_6$ alkyl;

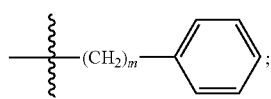

where m = 1-3

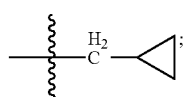

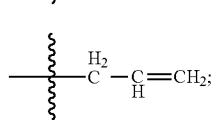

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;

(vi) $C_1$-$C_4$ dialkylamino;
(vii) nitro;
(viii) hydroxyl;
(ix) halogen, where "halogen" encompasses chloro, fluoro, bromo, and iodo;

$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In some embodiments, the peptide is defined by Formula B:

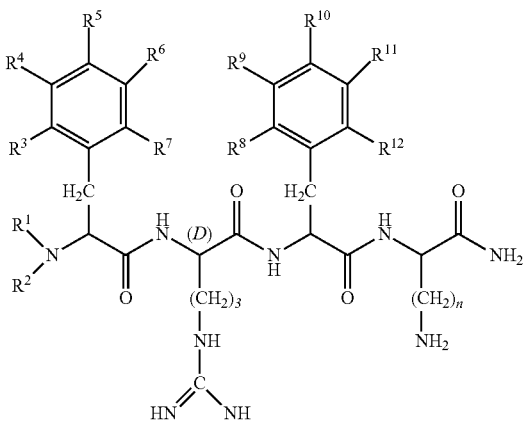

wherein $R^1$ and $R^2$ are each independently selected from
(i) hydrogen;
(ii) linear or branched $C_1$-$C_6$ alkyl;

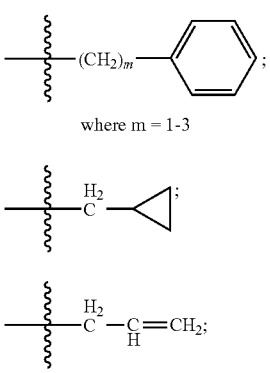

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In some embodiments, the aromatic-cationic peptides of the present technology have a core structural motif of alternating aromatic and cationic amino acids. For example, the peptide may be a tetrapeptide defined by any of Formulas C to F set forth below:

| | |
|---|---|
| Aromatic-Cationic-Aromatic-Cationic | (Formula C) |
| Cationic-Aromatic-Cationic-Aromatic | (Formula D) |
| Aromatic-Aromatic-Cationic-Cationic | (Formula E) |
| Cationic-Cationic-Aromatic-Aromatic | (Formula F) | wherein, Aromatic is a residue selected from the group consisting of: Phe (F), Tyr (Y), and Trp (W). In some embodiments, the Aromatic residue may be substituted with cyclohexylalanine (Cha). In some embodiments, the Cationic residue is a residue selected from the group consisting of: Arg (R), Lys (K), and His (H). In some embodiments, the Cationic residue may be substituted with norleucine (Nle) or 2-amino-heptanoic acid (Ahe).

BRIEF DESCRIPTION OF THE DRAWINGS

In FIG. 5A, R is a TBM containing a pendant COOH group and R' is a linker bearing the formula: -(linker)-OH where linker consists of at least one or more carbon atoms. In FIG. 5B, R is a linker bearing the formula: -(linker)-COOH where linker consists of at least one or more carbon atoms; and R' is a TBM containing a pendant OH group.

DETAILED DESCRIPTION

Figure 1:
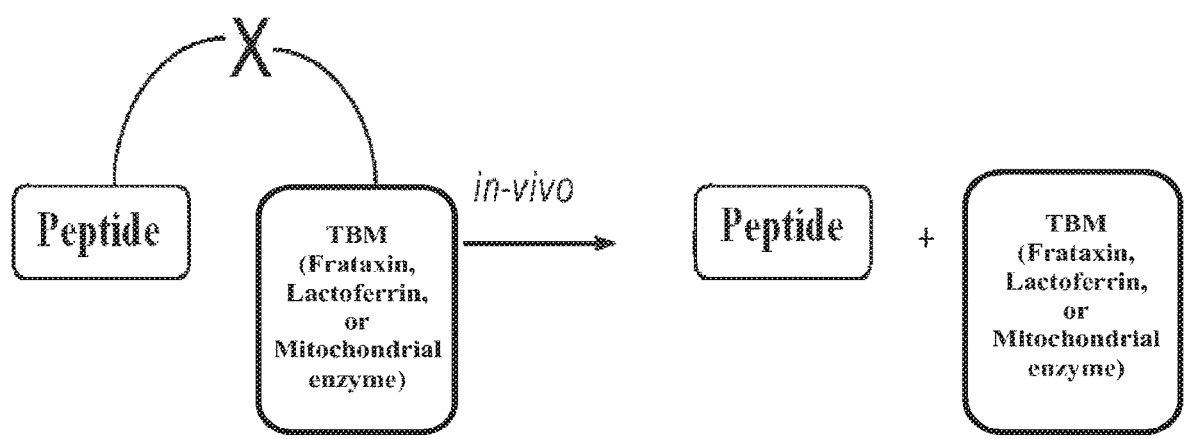
FIG. 1 shows an illustrative example of an aromatic-cationic peptide of the present disclosure linked by a labile bond to a TBM.

It is to be appreciated that certain aspects, modes, embodiments, variations and features of the present technology are described below in various levels of detail in order to provide a substantial understanding of the present technology.

The present technology provides compositions comprising an aromatic-cationic peptide of the present technology conjugated to a TBM. Such molecules are referred to hereinafter as peptide conjugates.

At least one TBM as described in Section I and at least one aromatic-cationic peptide as described in Section II associate to form a peptide conjugate. The TBM and aromatic-cationic peptide can associate by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

In some embodiments, the peptide conjugates have the general structure shown below:

aromatic-cationic peptide-TBM

In some embodiments, the peptide conjugates have the general structure shown below:

aromatic-cationic peptide-linker-TBM

The type of association between the TBM and aromatic-cationic peptides typically depends on, for example, functional groups available on the TBM and functional groups available on the aromatic-cationic peptide. The peptide conjugate linker may be nonlabile or labile. The peptide conjugate linker may be enzymatically cleavable.

While the peptide conjugates described herein can occur and can be used as the neutral (non-salt) peptide conjugate, the description is intended to embrace all salts of the peptide conjugates described herein, as well as methods of using such salts of the peptide conjugates. In one embodiment, the salts of the peptide conjugates comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic peptide conjugate may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic peptide conjugates with amino acids, such as aspartate salts and glutamate salts, can also be prepared. The desired salt of an acidic peptide conjugate can be prepared by methods known to those of skill in the art by treating the compound with a base. Examples of inorganic salts of acid conjugates include, but are not limited to, alkali metal and alkaline earth salts, such as sodium salts, potassium salts, magnesium salts, and calcium salts; ammonium salts; and aluminum salts. Examples of organic salts of acid peptide conjugates include, but are not limited to, procaine, dibenzylamine, N-ethylpiperidine, N,N'-dibenzylethylenediamine, and triethylamine salts. Salts of acidic peptide conjugates with amino acids, such as lysine salts, can also be prepared. The present technology also includes all stereoisomers and geometric isomers of the peptide conjugates, including diastereomers, enantiomers, and cis/trans (E/Z) isomers. The present technology also includes mixtures of stereoisomers and/or geometric isomers in any ratio, including, but not limited to, racemic mixtures.

The definitions of certain terms as used in this specification are provided below. Unless defined otherwise, all technical and scientific terms used herein generally have the same meaning as commonly understood by one of ordinary skill in the art to which this present technology belongs.

As used in this specification and the appended claims, the singular forms "a", "an" and "the" include plural referents unless the content clearly dictates otherwise. For example, reference to "a cell" includes a combination of two or more cells, and the like.

As used herein, the term "about" encompasses the range of experimental error that may occur in a measurement and will be clear to the skilled artisan.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "alkenyl" refers to unsaturated aliphatic groups including straight-chain (linear), branched-chain, cyclic groups, and combinations thereof, having the number of carbon atoms specified, or if no number is specified, having up to 12 carbon atoms, which contain at least one double bond (—C=C—). All double bonds may be independently either (E) or (Z) geometry, as well as arbitrary mixtures thereof. Examples of alkenyl groups include, but are not limited to, —CH$_2$—CH=CH—CH$_3$; and —CH$_2$—CH$_2$— cyclohexenyl, where the ethyl group can be attached to the cyclohexenyl moiety at any available carbon valence.

As used herein, the term "alkoxy" refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, propyloxy (propoxy) (either n-propoxy or i-propoxy), and butoxy (either n-butoxy, i-butoxy, sec-butoxy, or tert-butoxy). The groups listed in the preceding sentence are alkoxy groups; an exemplary alkoxy substituent is methoxy.

As used herein, the term "alkyl" refers to saturated aliphatic groups including straight-chain, branched-chain, cyclic groups, and combinations thereof, having the number of carbon atoms specified, or if no number is specified, having up to 12 carbon atoms. "Straight-chain alkyl" or "linear alkyl" groups refer to alkyl groups that are neither cyclic nor branched, commonly designated as "n-alkyl" groups. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Cycloalkyl groups can consist of one ring, including, but not limited to, groups such as cycloheptyl, or multiple fused rings, including, but not limited to, groups such as adamantyl or norbornyl. In some embodiments, the subset of alkyl groups is $C_1$-$C_5$ alkyl, which is intended to embrace methyl (Me), ethyl (Et), propyl (Pr), n-propyl (nPr), isopropyl (iPr), butyl (Bu), n-butyl (nBu), isobutyl (iBu), sec-butyl (sBu), t-butyl (tBu), cyclopropyl (cyclPr), cyclobutyl (cyclBu), cyclopropyl-methyl (cyclPr-Me), methyl-cyclopropane (Me-cyclPr), pentyl, n-pentyl, isopentyl, neopentyl, sec-pentyl, t-pentyl, 1,2-dimethylpropyl, cyclopentyl, and any other alkyl group containing between one and five carbon atoms, where the $C_1$-$C_5$ alkyl groups can be attached via any valence on the $C_1$-$C_5$ alkyl groups.

Note that "$C_0$ alkyl," when it appears, is intended to mean either a non-existent group, or a hydrogen, which will be understood by the context in which it appears. When a $C_0$ alkyl group appears as the terminal group on a chain, as for example in —(C=O)—$C_0$ alkyl, it is intended as a hydrogen atom; thus, —(C=O)—$C_0$ alkyl is intended to represent (C=O)—H (an aldehyde). When a $C_0$ alkyl group appears between two other groups, as, for example, in —(C=O)—$C_0$ alkyl-$C_0$-$C_{10}$ aryl, it is intended to be a nonentity, thus —(C=O)—$C_0$ alkyl-$C_0$-$C_{10}$ aryl represents —(C=O)—$C_6$-$C_{10}$ aryl. "$C_1$-$C_6$ alkyl" is intended to embrace a saturated linear, branched, cyclic, or a combination thereof, hydrocarbon of 1 to 6 carbon atoms. Examples of "$C_1$-$C_6$ alkyl" are methyl, ethyl, n-propyl, isopropyl, cyclopropyl, n-butyl, isobutyl, sec-butyl, t-butyl, cyclobutyl, cyclopropyl-methyl, methyl-cyclopropyl, pentyl where the point of attachment of the pentyl group to the remainder of the molecule can be at any location on the pentyl moiety, cyclopentyl, hexyl where the point of attachment of the hexyl group to the remainder of the molecule can be at any location on the hexyl moiety, and cyclohexyl.

As used herein, the term "alkynyl" refers to unsaturated aliphatic groups including straight-chain (linear), branched-chain, cyclic groups, and combinations thereof, having the number of carbon atoms specified, or if no number is specified, having up to 12 carbon atoms, which contain at least one triple bond (—C≡C—). "Hydrocarbon chain" or "hydrocarbyl" refers to any combination of straight-chain, branched chain, or cyclic alkyl, alkenyl, or alkynyl groups, and any combination thereof. "Substituted alkenyl" "substituted alkynyl," and "substituted hydrocarbon chain" or "substituted hydrocarbyl" refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the present technology, with a protecting group.

As used herein, the term "amino acid" includes naturally-occurring amino acids and synthetic amino acids, as well as amino acid analogues and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogues refer to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogues have modified R groups (e.g., norleucine) or modified peptide backbones, but retain the same basic chemical structure as a naturally-occurring amino acid. Amino acid mimetics refer to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the terms "Aryl" or "Ar" refers to an aromatic cyclic hydrocarbon group having a single ring (including, but not limited to, groups such as phenyl) or two or more condensed rings (including, but not limited to, groups such as naphthyl or anthryl), and includes both unsubstituted and substituted aryl groups. Aryls, unless otherwise specified, contain from 6 to 12 carbon atoms in the ring portion. A range for aryls is from 6 to 10 carbon atoms in the ring portion. "Substituted aryls" refers to aryls substituted with one or more substituents, including but not limited to, groups such as alkyl, alkenyl, alkynyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the present technology, with a protecting group. "Aralkyl" designates an alkyl-substituted aryl group, where any aryl can attach to the alkyl; the alkyl portion is a straight or branched chain of 1 to 6 carbon atoms. In some embodiments, the alkyl chain contains 1 to 3 carbon atoms. When an aralkyl group is indicated as a substituent, the aralkyl group can be connected to the remainder of the molecule at any available valence on either its alkyl moiety or aryl moiety; e.g., the tolyl aralkyl group can be connected to the remainder of the molecule by replacing any of the five hydrogens on the aromatic ring moiety with the remainder of the molecule, or by replacing one of the alpha-hydrogens on the methyl moiety with the remainder of the molecule. In some embodiments, the aralkyl group is connected to the remainder of the molecule via the alkyl moiety.

In some embodiments, the aryl group is phenyl, which can be substituted or unsubstituted. Examples of substituents for substituted phenyl groups include, but are not limited to, alkyl, halogen (chlorine (—Cl), bromine (—Br), iodine (—I), or fluorine (—F)), hydroxy (—OH), or alkoxy (such as methoxy, ethoxy, n-propoxy or i-propoxy, n-butoxy, i-butoxy, sec-butoxy, or tert-butoxy). In some embodiments, substituted phenyl groups have one or two substituents. In some embodiments, substituted phenyl groups have one substituent.

As used herein, the term "effective amount" refers to a quantity sufficient to achieve a desired therapeutic and/or prophylactic effect, e.g., an amount which results in the prevention of, or a decrease in a disease or disorder or one or more signs or symptoms associated with a disease or disorder. In the context of therapeutic or prophylactic applications, the amount of a composition administered to the subject will depend on the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

As used herein, the terms "halo" and "halogen" as used herein refer to the Group VIIa elements (Group 17 elements in the 1990 IUPAC Periodic Table, IUPAC Nomenclature of Inorganic Chemistry, Recommendations 1990) and include Cl, Br, F and I substituents. In some embodiments, halogen substituents are Cl and F.

As used herein, the term "haloalkenyl" embraces any $C_1$-$C_5$ alkenyl substituent having at least one halogen substituent; the halogen can be attached via any available valence on the $C_1$-$C_5$ alkenyl group. One further subset of $C_1$-$C_5$ haloalkenyl is the subset with exactly one halogen substituent. Another further subset of $C_1$-$C_5$ haloalkenyl is the subset with exactly one chloro substituent. Another further subset of $C_1$-$C_5$ haloalkenyl is the subset with exactly one fluoro substituent. Another further subset of $C_1$-$C_5$ haloalkenyl is the subset of $C_1$-$C_5$ perhaloalkenyl; that is, $C_1$-$C_5$ alkenyl with all available valences replaced by halogens. Another further subset of $C_1$-$C_5$ haloalkenyl is the subset of $C_1$-$C_5$ perfluoroalkenyl; that is, $C_1$-$C_5$ alkenyl with all available valences replaced by fluorines. Another further subset of $C_1$-$C_5$ haloalkenyl is the subset of $C_1$-$C_5$ perchloroalkenyl; that is, $C_1$-$C_5$ alkenyl with all available valences replaced by chlorines.

As used herein, the term "haloalkyl" embraces any alkyl substituent having at least one halogen substituent. "$C_1$-$C_6$ haloalkyl" is intended to embrace any $C_1$-$C_6$ alkyl substituent having at least one halogen substituent; the halogen can be attached via any valence on the $C_1$-$C_6$ alkyl group. Some examples of $C_1$-$C_6$ haloalkyl is —$CF_3$, —$CCl_3$, $CHF_2$, —$CHCl_2$, —$CHBr_2$, —$CH_2F$, —$CH_2Cl$.

As used herein, the term "haloalkynyl" embraces any $C_1$-$C_5$ alkynyl substituent having at least one halogen substituent; the halogen can be attached via any available valence on the $C_1$-$C_5$ alkynyl group. One further subset of $C_1$-$C_5$ haloalkynyl is the subset with exactly one halogen substituent. Another further subset of $C_1$-$C_5$ haloalkynyl is the subset with exactly one chloro substituent. Another further subset of $C_1$-$C_5$ haloalkynyl is the subset with exactly one fluoro substituent. Another further subset of $C_1$-$C_5$ haloalkynyl is the subset of $C_1$-$C_5$ perhaloalkynyl; that is, $C_1$-$C_5$ alkynyl with all available valences replaced by halogens. Another further subset of $C_1$-$C_5$ haloalkynyl is the subset of $C_1$-$C_5$ perfluoroalkynyl; that is, $C_1$-$C_5$ alkynyl with all available valences replaced by fluorines. Another further subset of $C_1$-$C_5$ haloalkynyl is the subset of $C_1$-$C_5$ perchloroalkynyl; that is, $C_1$-$C_5$ alkynyl with all available valences replaced by chlorines.

As used herein, the terms "heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P. In some embodiments, the heteroatoms are N or O. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—$CH_3$, $CH_2$—O—$CH_3$, —$CH_2$—$CH_2$—O—$CH_3$, —S—$CH_2$—$CH_2$—$CH_3$, —$CH_2$—$CH$ ($CH_3$)—S—$CH_3$, —$CH_2$—$CH_2$—NH—$CH_2$—$CH_2$—, 1-ethyl-6-propylpiperidino, and morpholino. Examples of heteroalkenyl groups include, but are not limited to, groups such as $CH$=$CH$—NH—$CH(CH_3)$—$CH_2$—. "Heteroaryl" or "HetAr" refers to an aromatic group having a single ring (including, but not limited to, examples such as pyridyl, imidazolyl, thiophene, or furyl) or two or more condensed rings (including, but not limited to, examples such as indolizinyl or benzothienyl) and having at least one hetero atom, including, but not limited to, heteroatoms such as N, O, P, or S, within the ring. Examples of heteroaryl include pyridine, pyrazine, imidazoline, thiazole, isothiazole, pyrazine, triazine, pyrimidine, pyridazine, pyrazole, thiophene, pyrrole, pyran, furan, indole, quinoline, quinazoline, benz-imidazole, benzothiophene, benzofuran, benzoxazole, benzothiazole, benzotriazole, imidazo-pyridines, pyrazolo-pyridines, pyrazolo-pyrazine, acridine, carbazole, and the like. Unless otherwise specified, heteroalkyl, heteroalkenyl, heteroalkynyl, and heteroaryl groups have between one and five heteroatoms and between one and twelve carbon atoms. "Substituted heteroalkyl," "substituted heteroalkenyl," "substituted heteroalkynyl," and "substituted heteroaryl" groups refer to heteroalkyl, heteroalkenyl, heteroalkynyl, and heteroaryl groups substituted with one or more substituents, including, but not limited to, groups such as alkyl, alkenyl, alkynyl, benzyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the present technology, with a protecting group. Examples of such substituted heteroalkyl groups include, but are not limited to, piperazine, substituted at a nitrogen or carbon by a phenyl or benzyl group, and attached to the remainder of the molecule by any available valence on a carbon or nitrogen, —NH—$SO_2$-phenyl, NH—(C=O)O-alkyl, —NH—(C=O)O-alkylaryl, and —NH—(C=O)-alkyl. If chemically possible, the heteroatom(s) and/or the carbon atoms of the group can be substituted. The heteroatom(s) can also be in oxidized form, if chemically possible.

When moieties, such as alkyl moieties, heteroaryl moieties, etc., are indicated as substituents, the substituent moiety can be attached to the remainder of the molecule at any point on the moiety where chemically possible (i.e., by using any available valence at a given point of the moiety, such as a valence made available by removing one or more hydrogen atoms from the moiety) unless otherwise specified. For example, in the moiety —(C=O)—$C_0$-$C_8$ alkyl-$C_6$-$C_{10}$ aryl-$C_0$-$C_8$ alkyl, if the leftmost $C_0$-$C_8$ alkyl group is a $C_3$ alkyl group, it can be attached to the sp$^2$ carbon of the carbonyl group at any of the three carbon atoms in the chain, unless otherwise specified. Likewise, the $C_6$-$C_{10}$ aryl group can be attached to the alkyl groups at any carbons in the aryl group, unless otherwise specified.

The terms "heterocycle", "heterocyclic", "heterocyclo", and "heterocyclyl" is intended to encompass a monovalent, saturated, or partially unsaturated, carbocyclic radical having one or more rings incorporating one, two, three or four heteroatoms within the ring (e.g. nitrogen, oxygen, sulfur). Examples of heterocycles include morpholine, piperidine, piperazine, thiazolidine, pyrazolidine, pyrazoline, imidazolidine, pyrrolidine, tetrahydropyran, tetrahydrofuran, quinuclidine, and the like.

As used herein, an "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the term "non-naturally-occurring" refers to a composition which is not found in this form in nature. A non-naturally-occurring composition can be derived from a naturally-occurring composition, e.g., as non-limiting examples, via purification, isolation, concentration, chemical modification (e.g., addition or removal of a chemical group), and/or, in the case of mixtures, addition or removal of ingredients or compounds. Alternatively, a non-naturallyoccurring composition can comprise or be derived from a non-naturally-occurring combination of naturally-occurring compositions. Thus, a non-naturally-occurring composition can comprise a mixture of purified, isolated, modified and/or concentrated naturally-occurring compositions, and/or can comprise a mixture of naturally-occurring compositions in forms, concentrations, ratios and/or levels of purity not found in nature.

As used herein, the term "net charge" refers to the balance of the number of positive charges and the number of negative charges carried by the amino acids present in the aromatic-cationic peptides of the present technology. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, "prevention" or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample.

As used herein, the term "protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 3rd Ed. (John Wiley & Sons, Inc., New York). Amino protecting groups include, but are not limited to, mesitylenesulfonyl (Mts), benzyloxycarbonyl (CBz or Z), t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α-,α-dimethyldimethoxybenzyloxycarbonyl (DDZ), 5-bromo-7-nitroindolinyl, and the like. Hydroxyl protecting groups include, but are not limited to, Fmoc, TBS, photolabile protecting groups (such as nitroveratryl oxymethyl ether (Nvom)), Mom (methoxy methyl ether), and Mem (methoxyethoxy methyl ether), NPEOC (4-nitrophenethyloxycarbonyl) and NPEOM (4-nitrophenethyloxymethyloxycarbonyl).

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "subject," "individual," or "patient" can be an individual organism, a vertebrate, a mammal, or a human.

As used herein, a "synergistic therapeutic effect" refers to a greater-than-additive therapeutic effect which is produced by a combination of at least two agents, and which exceeds that which would otherwise result from the individual administration of agents. For example, lower doses of one or more agents may be used in treating a disease or disorder, resulting in increased therapeutic efficacy and decreased side-effects.

As used herein, a "therapeutic biological molecule" (abbreviated as "TBM") refers to those molecules found in nature as well as synthesized biological molecules. TBMs include, but are not limited to polynucleotides, peptide nucleic acids, and polyamino acids. In some embodiments, the polyamino acid sequence is a peptide, polypeptide, partial or full length protein, chimeric peptide sequence, chimeric polypeptide sequence or a chimeric protein sequence. In some embodiments, the polynucleotide sequence is double-stranded DNA, single-stranded DNA, antisense RNA, mRNA, siRNA, miRNA, a ribozyme, an RNA decoy, or an external guide sequence for ribozymes. TBMs useful in compositions of the present technology include, but are not limited to, e.g., frataxin, lactoferrin, or mitochondrial enzymes, such as, but not limited to NADH-coenzyme Q oxidoreductase, succinate-Q oxidoreductase, electron transfer flavoprotein-Q oxidoreductase, Q-cytochrome c oxidoreductase, cytochrome c oxidase, ATP synthase, pyruvate dehydrogenase, citrate synthase, aconitase, isocitrate dehydrogenase, α-ketoglutarate dehydrogenase, succinyl-CoA synthetase, succinic dehydrogenase, fumarase, malate dehydrogenase, and pyruvate carboxylase.

As used herein, a "therapeutically effective amount" of a compound refers to compound levels in which the physiological effects of a disease or disorder are, at a minimum, ameliorated. A therapeutically effective amount can be given in one or more administrations. The amount of a compound which constitutes a therapeutically effective amount will vary depending on the compound, the disorder and its severity, and the general health, age, sex, body weight and tolerance to drugs of the subject to be treated, but can be determined routinely by one of ordinary skill in the art.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

I. Therapeutic Biological Molecules (TBMS)

TBMs described below are useful in compositions of the present technology and include, but are not limited to, frataxin, lactoferrin, or mitochondrial enzymes, such as, but not limited to, NADH-coenzyme Q oxidoreductase, succinate-Q oxidoreductase, electron transfer flavoprotein-Q oxidoreductase, Q-cytochrome c oxidoreductase, cytochrome c oxidase, ATP synthase, pyruvate dehydrogenase, citrate synthase, aconitase, isocitrate dehydrogenase, α-ketoglutarate dehydrogenase, succinyl-CoA synthetase, succinic dehydrogenase, fumarase, malate dehydrogenase, and pyruvate carboxylase.

Frataxin

Frataxin is a highly conserved iron binding protein. Human frataxin is synthesized as a 210 amino acid precursor that is imported to the mitochondria via the mitochondrial targeting signal contained in the N-terminus. The frataxin precursor is subsequently cleaved to a mature 14 kDa protein (residues 81-210).

Frataxin binds both Fe' and Fe' ions in an electrostatic manner and functions as an iron chaperone during Fe—S cluster assembly. Frataxin directly binds to the central Fe—S cluster assembly complex, which is composed of Nfs1 enzyme and Isu scaffold protein. Nfs1 is a cysteine desulfurase used in the synthesis of sulfur bioorganic derivatives and Isu is the transient scaffold protein on which the Fe—S cluster assembles. Frataxin increases the efficiency of Fe—S cluster formation, which is required to activate aconitase. Frataxin also plays a role in mitochondrial iron storage and heme biosynthesis by incorporating mitochondrial iron into protoporphyrin (PIX).

Lactoferrin

Lactoferrin, also known as lactotransferrin, is a major iron-binding and multifunctional protein of the transferrin family found in exocrine fluids such as breast milk, saliva, tears, and mucosal secretions. Lactoferrin is also present in secondary granules of neutrophils (PMNs). Lactoferrin can be purified from milk or recombinantly manufactured. Human lactoferrin is synthesized as a 710 amino acid precursor. Lactoferrins comprise two domains, each containing an iron-binding site and an N-linked glycosylation site. Each domain can reversibly bind one ferric ion with high affinity. Lactoferrin also comprises an N-terminal bacteriocidal domain. Lactoferrins of the present technology also comprise lactoferrin derivatives, including allelic variants. The primary role of lactoferrin is to sequester free iron, thereby removing an essential substrate required for bacterial growth.

Electron Transport Chain Enzymes

Enzymes of the electron transport system use energy released from the oxidation of the reduced coenzyme NADH to pump protons across the inner membrane of the mitochondrion. This causes protons to build up in the intermembrane space, and generates an electrochemical gradient across the membrane. The energy stored in this potential is then used by ATP synthase to produce ATP.

NADH-coenzyme Q oxidoreductase, also known as NADH dehydrogenase or complex I, consists of 46 subunits and has a molecular mass of about 1,000 kDa. The genes that encode the individual proteins are contained in both the cell nucleus and the mitochondrial genome. The reaction that is catalyzed by this enzyme is the two electron oxidation of NADH by coenzyme Q10 or ubiquinone in the mitochondrion membrane. The electrons enter complex I via flavin mononucleotide (FMN), a prosthetic group attached to the complex. The addition of electrons to FMN converts it to its reduced form, $FMNH_2$. The electrons are then transferred through a series of iron-sulfur clusters. As the electrons pass through this complex, four protons are pumped from the matrix into the intermembrane space. Finally, the electrons are transferred from the chain of iron-sulfur clusters to a ubiquinone molecule in the membrane. Reduction of coenzyme Q10 also contributes to the generation of a proton gradient, as two protons are taken up from the matrix as it is reduced to ubiquinol ($QH_2$).

Defects in oxidative phosphorylation can be caused by mutations in genes encoding subunits of the electron transport chain. For example, the function of complex I subunits is altered by mutations in mitochondrial genes including MTND1, MTND2, MTND4, and MIND6.

Succinate-Q oxidoreductase, also known as complex II or succinate dehydrogenase, is a second entry point to the electron transport chain. Complex II consists of four protein subunits and contains a bound flavin adenine dinucleotide (FAD) cofactor, iron-sulfur clusters, and a heme group. Complex II oxidizes succinate to fumarate and reduces ubiquinone. As this reaction releases less energy than the oxidation of NADH, complex II does not transport protons across the membrane and does not contribute to the proton gradient. Complex II is the only enzyme that participates in both the citric acid cycle and the electron transport chain.

Electron transfer flavoprotein-ubiquinone oxidoreductase (ETF-Q oxidoreductase), also known as electron transferring-flavoprotein dehydrogenase, is a third entry point to the electron transport chain. It is an enzyme that accepts electrons from electron-transferring flavoprotein in the mitochondrial matrix, and uses these electrons to reduce ubiquinone. This enzyme contains a flavin and an iron-sulfur cluster that is attached to the surface of the membrane and does not cross the lipid bilayer.

Q-cytochrome c oxidoreductase is also known as cytochrome c reductase, cytochrome bc1 complex, or complex III. In mammals, this enzyme is a dimer, with each subunit complex containing 11 protein subunits, an iron-sulfur cluster and three cytochromes: one cytochrome c1 and two b cytochromes. The iron atoms inside complex III's heme groups alternate between a reduced ferrous (+2) and oxidized ferric (+3) state as the electrons are transferred through the protein.

The reaction catalyzed by complex III is the oxidation of one molecule of ubiquinol and the reduction of two molecules of cytochrome c, which carries only one electron. As only one of the electrons can be transferred from the $QH_2$ donor to a cytochrome c acceptor at a time, the reaction mechanism of complex III occurs in two steps called the Q cycle. In the first step, the enzyme binds three substrates, first, $QH_2$, which is then oxidized, with one electron being passed to the second substrate, cytochrome c. The two protons released from $QH_2$ pass into the intermembrane space. The third substrate is Q, which accepts the second electron from the $QH_2$ and is reduced to $Q^-$, which is the ubisemiquinone free radical. The first two substrates are released, but the ubisemiquinone intermediate remains bound. In the second step, a second molecule of $QH_2$ is bound and again passes its first electron to a cytochrome c acceptor. The second electron is passed to the bound ubisemiquinone, reducing it to $QH_2$ as it gains two protons from the mitochondrial matrix. This $QH_2$ is then released from the enzyme. As coenzyme Q is reduced to ubiquinol on the inner side of the membrane and oxidized to ubiquinone on the other, a net transfer of protons across the membrane occurs, adding to the proton gradient.

Cytochrome c oxidase, also known as complex IV, is the final protein complex in the electron transport chain. The mammalian enzyme contains 13 subunits, two heme groups, as well as multiple metal ion cofactors—in all, three atoms of copper, one of magnesium and one of zinc. This enzyme mediates the final reaction in the electron transport chain and transfers electrons to oxygen, while pumping protons across the membrane. The reaction catalyzed is the oxidation of cytochrome c and the reduction of oxygen. The final electron acceptor oxygen is reduced to water in this step. Both the direct pumping of protons and the consumption of matrix protons in the reduction of oxygen contribute to the proton gradient.

Defects in oxidative phosphorylation can be caused by mutations in genes encoding complex IV subunits as well as by mutations in genes involved in complex IV assembly and in processes that affect complex IV biogenesis. Mutations in mitochondrial genes MTCO1, MTCO2, and MTCO3, and in nuclear genes COX10, COX6B1, SCO1, and SCO2, are implicated in complex IV deficiency. Mutations in nuclear genes SURF1 and COX15 are linked to alterations in complex IV biogenesis.

ATP synthase, also called complex V, is the final enzyme in the oxidative phosphorylation pathway. The enzyme uses the energy stored in a proton gradient across a membrane to drive the synthesis of ATP from ADP and phosphate (Pi). Estimates of the number of protons required to synthesize one ATP have ranged from three to four. This phosphorylation reaction is an equilibrium, which can be shifted by altering the proton-motive force. In the absence of a proton-motive force, the ATP synthase reaction will run from right to left, hydrolyzing ATP and pumping protons out of the matrix across the membrane. However, when the proton-motive force is high, the reaction is forced to run in the opposite direction, allowing protons to flow down their concentration gradient and turning ADP into ATP.

ATP synthase is a massive protein complex with a mushroom-like shape. The mammalian enzyme complex contains 16 subunits and has a mass of approximately 600 kDa. The portion embedded within the membrane is called $F_0$ and contains a ring of c subunits and the proton channel. The stalk and the ball-shaped headpiece are collectively called Fi and is the site of ATP synthesis. The ball-shaped complex at the end of the Fi portion contains six proteins of two different kinds (three α subunits and three β subunits), whereas the stalk consists of one protein: the γ subunit, with the tip of the stalk extending into the ball of α and β subunits. Both the α and β subunits bind nucleotides, but only the β subunits catalyze the ATP synthesis reaction. As protons cross the membrane through the channel in the base of ATP synthase, the $F_0$ proton-driven motor rotates. This rotating ring of c subunits in turn drives the rotation of the central axle (the γ subunit stalk) within the α and β subunits. This movement of the tip of the γ subunit within the ball of α and β subunits provides the energy for the active sites in the β subunits to undergo a cycle of movements that produces and then releases ATP.

This ATP synthesis reaction is called the binding change mechanism and involves the active site of a β subunit cycling between three states. In the "open" state, ADP and phosphate enter the active site. The protein then closes up around the molecules and binds them loosely—the "loose" state. The enzyme then changes shape again and forces these molecules together, with the active site in the resulting "tight" state binding the newly produced ATP molecule with very high affinity. Finally, the active site cycles back to the open state, releasing ATP and binding more ADP and phosphate during the next cycle.

Defects in oxidative phosphorylation can be caused by mutations in genes encoding complex V subunits. Mutations in the mitochondrial gene MTATP6 are linked to altered complex V subunits.

Citric Acid Cycle Enzymes

The citric acid cycle is a key component of the metabolic pathway by which all aerobic organisms generate energy. Through catabolism of sugars, fats, and proteins, a two-carbon organic product acetate in the form of acetyl-CoA is produced. Acetyl-CoA along with two equivalents of water is consumed by the citric acid cycle producing two equivalents of carbon dioxide ($CO_2$) and one equivalent of Coenzyme A. In addition, one complete turn of the cycle converts three equivalents of nicotinamide adenine dinucleotide ($NAD^+$) into three equivalents of reduced NADH, one equivalent of ubiquinone (Q) into one equivalent of reduced ubiquinone ($QH_2$), and one equivalent each of guanosine diphosphate (GDP) and inorganic phosphate ($P_i$) into one equivalent of guanosine triphosphate (GTP). The NADH and $QH_2$ generated by the citric acid cycle are in turn used by the oxidative phosphorylation pathway to generate energy-rich adenosine triphosphate (ATP).

Citrate synthase exists in nearly all living cells and stands as a pace-making enzyme in the first step of the Citric Acid Cycle. Citrate synthase is encoded by nuclear DNA, synthesized using cytoplasmic ribosomes, then transported into the mitochondrial matrix. Citrate synthase catalyzes the condensation reaction of the two-carbon acetate residue from acetyl coenzyme A and a molecule of four-carbon oxaloacetate to form the six-carbon citrate. Oxaloacetate will be regenerated after the completion of one round of the Krebs Cycle. Oxaloacetate is the first substrate to bind to the enzyme. This induces the enzyme to change its conformation, and creates a binding site for the acetyl-CoA. Only when this citroyl-CoA has formed will another conformational change cause thioester hydrolysis and release coenzyme A. This ensures that the energy released from the thioester bond cleavage will drive the condensation.

Aconitase is an enzyme that catalyzes the stereo-specific isomerization of citrate to isocitrate via cis-aconitate in the citric acid cycle. The iron-sulfur cluster of aconitase reacts directly with an enzyme substrate. Aconitase has an active $[Fe4S4]^{2+}$ cluster, which may convert to an inactive $[Fe3S4]^+$ form. Three cysteine (Cys) residues have been shown to be ligands of the [Fe4S4] center. In the inactive form, its structure is divided into four domains. Counting from the N-terminus, only the first three of these domains are involved in close interactions with the [3Fe-4S] cluster, but the active site consists of residues from all four domains, including the larger C-terminal domain. The Fe—S cluster and a $SO_4^{2-}$ anion also reside in the active site. When the enzyme is activated, it gains an additional iron atom, creating a [4Fe-4S] cluster.

Isocitrate dehydrogenase (IDH) is an enzyme that catalyzes the oxidative decarboxylation of isocitrate, producing alpha-ketoglutarate (α-ketoglutarate) and $CO_2$. This is a two-step process, which involves oxidation of isocitrate to oxalosuccinate, followed by the decarboxylation of the carboxyl group beta to the ketone, forming alpha-ketoglutarate. In humans, IDH exists in three isoforms: IDH3 catalyzes the third step of the citric acid cycle while converting NAD+ to NADH in the mitochondria.

The oxoglutarate dehydrogenase complex (OGDC) or α-ketoglutarate dehydrogenase complex is an enzyme complex that catalyzes the following reaction:

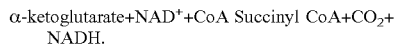
α-ketoglutarate+NAD⁺+CoA Succinyl CoA+CO₂+ NADH.

This reaction proceeds in three steps: (1) decarboxylation of α-ketoglutarate, (2) reduction of NAD+ to NADH, and (3) subsequent transfer to CoA, which forms the end product, succinyl CoA. The energy needed for this oxidation is conserved in the formation of a thioester bond of succinyl CoA.

Succinyl coenzyme A synthetase is a mitochondrial enzyme that catalyzes the reversible reaction of succinyl-CoA to succinate. The enzyme facilitates the coupling of this reaction to the formation of a nucleoside triphosphate molecule (either GTP or ATP) from an inorganic phosphate molecule and a nucleoside diphosphate molecule (either GDP or ADP). The reaction takes place by a three-step mechanism. The first step involves displacement of CoA from succinyl CoA by a nucleophilic inorganic phosphate molecule to form succinyl phosphate. The enzyme then utilizes a histidine residue to remove the phosphate group from succinyl phosphate and generate succinate. Finally, the phosphorylated histidine transfers the phosphate group to a nucleoside diphosphate, which generates the high-energy carrying nucleoside triphosphate.

Succinate dehydrogenase or succinate-coenzyme Q reductase (SQR) or respiratory Complex II is an enzyme complex bound to the inner mitochondrial membrane. It is the only enzyme that participates in both the citric acid cycle and the electron transport chain. SQR catalyzes the oxidation of succinate to fumarate with the reduction of ubiquinone to ubiquinol. This occurs in the inner mitochondria membrane by coupling the two reactions together.

Mitochondrial SQRs are composed of four subunits: two hydrophilic and two hydrophobic. The first two subunits, a flavoprotein (SdhA) and an iron-sulfur protein (SdhB), are hydrophilic. SdhA contains a covalently attached flavin adenine dinucleotide (FAD) cofactor and the succinate binding site and SdhB contains three iron-sulfur clusters: [2Fe-2S], [4Fe-4S], and [3Fe-4S]. The second two subunits are hydrophobic membrane anchor subunits, SdhC and SdhD. The subunits form a membrane-bound cytochrome b complex with six transmembrane helices containing one heme b group and a ubiquinone-binding site. Two phospholipid molecules, one cardiolipin and one phosphatidylethanolamine, are also found in the SdhC and SdhD subunits and serve to occupy the hydrophobic space below the heme b.

Fumarase (or fumarate hydratase) is an enzyme that catalyzes the reversible hydration/dehydration of fumarate to malate. Fumarase comes in two forms: mitochondrial and cytosolic. The mitochondrial isoenzyme is involved in the Citric Acid Cycle, and the cytosolic isoenzyme is involved in the metabolism of amino acids and fumarate. The function of fumarase in the citric acid cycle is to facilitate a transition step in the production of energy in the form of NADH. The primary binding site on fumarase is known as catalytic site A. Studies have revealed that catalytic site A is composed of amino acid residues from three of the four subunits within the tetrameric enzyme. Two potential acid-base catalytic residues in the reaction include His 188 and Lys 324.

Malate dehydrogenase (MDH) is an enzyme that reversibly catalyzes the oxidation of malate to oxaloacetate using the reduction of NAD+ to NADH. This reaction is part of many metabolic pathways, including the citric acid cycle. Pyruvate in the mitochondria is acted upon by pyruvate carboxylase to form oxaloacetate, a citric acid cycle intermediate. In order to facilitate the transfer of oxaloacetate out of the mitochondrion, malate dehydrogenase reduces oxaloacetate to malate, and it then traverses the inner mitochondrial membrane. Once in the cytosol, the malate is oxidized back to oxaloacetate by cytosolic malate dehydrogenase. The active site of malate dehydrogenase is a hydrophobic cavity within the protein complex that has specific binding sites for the substrate and its coenzyme, NAD+. In its active state, MDH undergoes a conformational change that encloses the substrate to minimize solvent exposure and to position key residues in closer proximity to the substrate. The three residues in particular that comprise a catalytic triad are histidine (His-195), aspartate (Asp-168), both of which work together as a proton transfer system, and arginines (Arg-102, Arg-109, Arg-171), which secure the substrate. Kinetic studies show that MDH enzymatic activity is ordered. NAD+/NADH is bound before the substrate.

Pyruvate dehydrogenase complex (PDC) is a complex of three enzymes that transform pyruvate into acetyl-CoA by a process called pyruvate decarboxylation. Acetyl-CoA may then be used in the citric acid cycle to carry out cellular respiration, and this complex links the glycolysis metabolic pathway to the citric acid cycle, ultimately releasing energy via NADH. Pyruvate decarboxylation is also known as the "pyruvate dehydrogenase reaction" because it also involves the oxidation of pyruvate. Pyruvate dehydrogenase complex is located in the mitochondrial matrix of eukaryotes. It is organized in dodecahedral symmetry, and consists of a total of 96 subunits, organized into three functional proteins: pyruvate dehydrogenase, dihydrolipoyl transacetylase, and dihydrolipoyl dehydrogenase.

Pyruvate carboxylase (PC) is an enzyme of the ligase class that catalyzes the carboxylation of pyruvate to form oxaloacetate. The enzyme is a mitochondrial protein containing a biotin prosthetic group, requiring magnesium or manganese and acetyl CoA. Most well characterized forms of active PC consist of four identical subunits arranged in a tetrahedron-like structure. Each subunit contains a single biotin moiety acting as a swinging arm to transport carbon dioxide to the catalytic site that is formed at the interface between adjacent monomers. Each subunit of the functional tetramer contains four domains: the biotin carboxylation (BC) domain, the transcarboxylation (CT) domain, the biotin carboxyl carrier (BCCP) domain and the PC tetramerization (PT) domain. Pyruvate carboxylase uses a covalently attached biotin cofactor which is used to catalyze the ATP-dependent carboxylation of pyruvate to oxaloacetate in two steps. Biotin is initially carboxylated at the BC active site by ATP and bicarbonate. The carboxyl group is subsequently transferred by carboxybiotin to a second active site in the CT domain, where pyruvate is carboxylated to generate oxaloacetate. The BCCP domain transfers the tethered cofactor between the two remote active sites.

II. Aromatic-Cationic Peptides as Active Agents

The aromatic-cationic peptides of the present technology are water-soluble, highly polar, and can readily penetrate cell membranes.

The aromatic-cationic peptides of the present technology include a minimum of three amino acids, covalently joined by peptide bonds.

The maximum number of amino acids present in the aromatic-cationic peptides of the present technology is about twenty amino acids covalently joined by peptide bonds. In some embodiments, the maximum number of amino acids is about twelve. In some embodiments, the maximum number of amino acids is about nine. In some embodiments, the maximum number of amino acids is about six. In some embodiments, the maximum number of amino acids is four.

In some aspects, the present technology provides an aromatic-cationic peptide or a pharmaceutically acceptable salt thereof such as acetate salt or trifluoroacetate salt. In some embodiments, the peptide comprises at least one net positive charge; a minimum of three amino acids; a maximum of about twenty amino acids;

a relationship between the minimum number of net positive charges ($p_m$) and the total number of amino acid residues (r) wherein 3 $p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1.

In some embodiments, the peptide comprises the amino acid sequence 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$. In some embodiments, the peptide comprises one or more of the peptides of Table A:

TABLE A

Tyr-D-Arg-Phe-Lys-NH$_2$
D-Arg-Dmt-Lys-Phe-NH$_2$
D-Arg-Dmt-Phe-Lys-NH$_2$
D-Arg-Phe-Lys-Dmt-NH$_2$
D-Arg-Phe-Dmt-Lys-NH$_2$
D-Arg-Lys-Dmt-Phe-NH$_2$
D-Arg-Lys-Phe-Dmt-NH$_2$
D-Arg-Dmt-Lys-Phe-Cys-NH$_2$
D-Arg-Dmt-Lys-Phe-Glu-Cys-Gly-NH$_2$
D-Arg-Dmt-Lys-Phe-Ser-Cys-NH$_2$
D-Arg-Dmt-Lys-Phe-Gly-Cys-NH$_2$
Phe-Lys-Dmt-D-Arg-NH$_2$
Phe-Lys-D-Arg-Dmt-NH$_2$
Phe-D-Arg-Phe-Lys-NH$_2$
Phe-D-Arg-Phe-Lys-Cys-NH$_2$
Phe-D-Arg-Phe-Lys-Glu-Cys-Gly-NH$_2$
Phe-D-Arg-Phe-Lys-Ser-Cys-NH$_2$
Phe-D-Arg-Phe-Lys-Gly-Cys-NH$_2$
Phe-D-Arg-Dmt-Lys-NH$_2$
Phe-D-Arg-Dmt-Lys-Cys-NH$_2$
Phe-D-Arg-Dmt-Lys-Glu-Cys-Gly-NH$_2$
Phe-D-Arg-Dmt-Lys-Ser-Cys-NH$_2$
Phe-D-Arg-Dmt-Lys-Gly-Cys-NH$_2$
Phe-D-Arg-Lys-Dmt-NH$_2$
Phe-Dmt-D-Arg-Lys-NH$_2$
Phe-Dmt-Lys-D-Arg-NH$_2$
Lys-Phe-D-Arg-Dmt-NH$_2$
Lys-Phe-Dmt-D-Arg-NH$_2$
Lys-Dmt-D-Arg-Phe-NH$_2$
Lys-Dmt-Phe-D-Arg-NH$_2$
Lys-D-Arg-Phe-Dmt-NH$_2$
Lys-D-Arg-Dmt-Phe-NH$_2$
D-Arg-Dmt-D-Arg-Phe-NH$_2$
D-Arg-Dmt-D-Arg-Dmt-NH$_2$
D-Arg-Dmt-D-Arg-Tyr-NH$_2$
D-Arg-Dmt-D-Arg-Trp-NH$_2$
Trg-D-Arg-Tyr-Lys-NH$_2$
Trp-D-Arg-Trp-Lys-NH$_2$
Trp-D-Arg-Dmt-Lys-NH$_2$
D-Arg-Trp-Lys-Phe-NH$_2$
D-Arg-Trp-Phe-Lys-NH$_2$
D-Arg-Trp-Lys-Dmt-NH$_2$
D-Arg-Trp-Dmt-Lys-NH$_2$
D-Arg-Lys-Trp-Phe-NH$_2$
D-Arg-Lys-Trp-Dmt-NH$_2$
Cha-D-Arg-Phe-Lys-NH$_2$
Ala-D-Arg-Phe-Lys-NH$_2$

TABLE A-continued

2',6'-Dmp-D-Arg-2',6'-Dmt-Lys-NH$_2$
2',6'-Dmp-D-Arg-Phe-Lys-NH$_2$
2',6'-Dmt-D-Arg-Phe-Orn-NH$_2$
2',6'-Dmt-D-Arg-Phe-Ahp(2-aminoheptanoicacid)-NH$_2$
2',6'-Dmt-D-Arg-Phe-Lys-NH$_2$
2',6'-Dmt-D-Cit-PheLys-NH$_2$
Ala-D-Phe-D-Arg-Tyr-Lys-D-Trp-His-D-Tyr-Gly-Phe
Arg-D-Leu-D-Tyr-Phe-Lys-Glu-D-Lys-Arg-D-Trp-Lys-D-Phe-Tyr-D-Arg-Gly
Asp-Arg-D-Phe-Cys-Phe-D-Arg-D-Lys-Tyr-Arg-D-Tyr-Trp-D-His-Tyr-D-Phe-Lys-Phe
Asp-D-Trp-Lys-Tyr-D-His-Phe-Arg-D-Gly-Lys-NH$_2$
D-Arg-2',6'-Dmt-Lys-Phe-NH$_2$
D-Glu-Asp-Lys-D-Arg-D-His-Phe-Phe-D-Val-Tyr-Arg-Tyr-D-Tyr-Arg-His-Phe-NH$_2$
D-His-Glu-Lys-Tyr-D-Phe-Arg
D-His-Lys-Tyr-D-Phe-Glu-D-Asp-D-Asp-D-His-D-Lys-Arg-Trp-NH$_2$
D-Tyr-Trp-Lys-NH$_2$
Glu-Arg-D-Lys-Tyr-D-Val-Phe-D-His-Trp-Arg-D-Gly-Tyr-Arg-D-Met-NH$_2$
Gly-Ala-Lys-Phe-D-Lys-Glu-Arg-Tyr-His-D-Arg-D-Arg-Asp-Tyr-Trp-D-His-Trp-His-D-Lys-Asp.
Gly-D-Phe-Lys-His-D-Arg-Tyr-NH$_2$
His-Tyr-D-Arg-Trp-Lys-Phe-D-Asp-Ala-Arg-Cys-D-Tyr-His-Phe-D-Lys-Tyr-His-Ser-NH$_2$
Lys-D-Arg-Tyr-NH$_2$
Lys-D-Gln-Tyr-Arg-D-Phe-Trp-NH$_2$
Lys-Trp-D-Tyr-Arg-Asn-Phe-Tyr-D-His-NH$_2$
Met-Tyr-D-Arg-Phe-Arg-NH$_2$
Met-Tyr-D-Lys-Phe-Arg
Phe-Arg-D-His-Asp
Phe-D-Arg-2',6'-Dmt-Lys-NH$_2$
Phe-D-Arg-His
Phe-D-Arg-Lys-Trp-Tyr-D-Arg-His
Phe-Phe-D-Tyr-Arg-Glu-Asp-D-Lys-Arg-D-Arg-His-Phe-NH$_2$
Phe-Tyr-Lys-D-Arg-Trp-His-D-Lys-D-Lys-Glu-Arg-D-Tyr-Thr
Thr-Gly-Tyr-Arg-D-His-Phe-Trp-D-His-Lys
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$
Trp-D-Lys-Tyr-Arg-NH$_2$
Trp-Lys-Phe-D-Asp-Arg-Tyr-D-His-Lys
Tyr-Asp-D-Lys-Tyr-Phe-D-Lys-D-Arg-Phe-Pro-D-Tyr-His-Lys
Tyr-D-Arg-Phe-Lys-Glu-NH$_2$
Tyr-D-His-Phe-D-Arg-Asp-Lys-D-Arg-His-Trp-D-His-Phe
Tyr-His-D-Gly-Met
Val-D-Lys-His-Tyr-D-Phe-Ser-Tyr-Arg-NH$_2$
Gly-D-Phe-Lys-Tyr-His-D-Arg-Tyr-NH$_2$
Asp-D-Trp-Lys-Tyr-D-His-Phe-Arg-D-Gly-Lys-NH$_2$
D-His-Lys-Tyr-D-Phe-Glu-D-Asp-D-His-D-Lys-Arg-Trp-NH$_2$
Tyr-D-His-Phe-D-Arg-Asp-Lys-D-Arg-His-Trp-D-His-Phe
Phe-Try-Lys-D-Arg-Trp-His-D-Lys-D-Lys-Glu-Arg-D-Tyr-Thr
Tyr-Asp-D-Lys-Tyr-Phe-D-Lys-D-Arg-Phe-Pro-D-Tyr-His-Lys
Glu-Arg-D-Lys-Tyr-D-Val-Phe-D-His-Trp-Arg-D-Gly-Tyr-Arg-D-Met-NH$_2$
Arg-D-Leu-D-Tyr-Phe-Lys-Glu-D-Lys-Arg-D-Trp-Lys-D-Phe-Tyr-D-Arg-Gly
Gly-Ala-Lys-Phe-D-Lys-Glu-Arg-Tyr-His-D-Arg-D-Arg-Asp-Tyr-Trp-D-His-Trp-His-D-Lys-Asp
D-Arg-Tyr-Lys-Phe-NH$_2$
D-Arg-D-Dmt-Lys-Phe-NH$_2$
D-Arg-Dmt-D-Lys-Phe-NH$_2$
D-Arg-Dmt-Lys-D-Phe-NH$_2$
D-Arg-D-Dmt-D-Lys-D-Phe-NH$_2$
Phe-D-Arg-D-Phe-Lys-NH$_2$
Phe-D-Arg-Phe-D-Lys-NH$_2$
D-Phe-D-Arg-D-Phe-D-Lys-NH$_2$
Lys-D-Phe-Arg-Dmt-NH$_2$
D-Arg-Arg-Dmt-Phe-NH$_2$
Dmt-D-Phe-Arg-Lys-NH$_2$
Phe-D-Dmt-Arg-Lys-NH$_2$
D-Arg-Dmt-Lys-NH$_2$
Arg-D-Dmt-Lys-NH$_2$
D-Arg-Dmt-Phe-NH$_2$
Arg-D-Dmt-Arg-NH$_2$
Dmt-D-Arg-NH$_2$
D-Arg-Dmt-NH$_2$
D-Dmt-Arg-NH$_2$
Arg-D-Dmt-NH$_2$
D-Arg-D-Dmt-NH$_2$ TABLE A-continued

- D-Arg-D-Tyr-Lys-Phe-NH$_2$
- D-Arg-Tyr-D-Lys-Phe-NH$_2$
- D-Arg-Tyr-Lys-D-Phe-NH$_2$
- D-Arg-D-Tyr-D-Lys-D-Phe-NH$_2$
- Lys-D-Phe-Arg-Tyr-NH$_2$
- D-Arg-Arg-Tyr-Phe-NH$_2$
- Tyr-D-Phe-Arg-Lys-NH$_2$
- Phe-D-Tyr-Arg-Lys-NH$_2$
- D-Arg-Tyr-Lys-NH$_2$
- Arg-D-Tyr-Lys-NH$_2$
- D-Arg-Tyr-Phe-NH$_2$
- Arg-D-Tyr-Arg-NH$_2$
- Tyr-D-Arg-NH$_2$
- D-Arg-Tyr-NH$_2$
- D-Tyr-Arg-NH$_2$
- Arg-D-Tyr-NH$_2$
- D-Arg-D-Tyr-NH$_2$
- Dmt-Lys-Phe-NH$_2$
- Lys-Dmt-D-Arg-NH$_2$
- Phe-Lys-Dmt-NH$_2$
- D-Arg-Phe-Lys-NH$_2$
- D-Arg-Cha-Lys-NH$_2$
- D-Arg-Trp-Lys-NH$_2$
- Dmt-Lys-D-Phe-NH$_2$
- Dmt-Lys-NH$_2$
- Lys-Phe-NH$_2$
- D-Arg-Cha-Lys-Cha-NH$_2$
- D-Nle-Dmt-Ahe-Phe-NH$_2$
- D-Nle-Cha-Ahe-Cha-NH$_2$
- D-Arg-Dmt-D-Lys-NH$_2$
- D-Arg-Dmt-D-Lys-Phe-NH$_2$
- Lys-Trp-D-Arg-NH$_2$
- H-Lys-D-Phe-Arg-Dmt-NH$_2$
- H-D-Arg-Lys-Dmt-Phe-NH$_2$
- H-D-Arg-Lys-Phe-Dmt-NH$_2$
- H-D-Arg-Arg-Dmt-Phe-NH$_2$
- H-D-Arg-Dmt-Phe-Lys-NH$_2$
- H-D-Arg-Phe-Dmt-Lys-NH$_2$
- H-Dmt-D-Phe-Arg-Lys-NH$_2$
- H-Phe-D-Dmt-Arg-Lys-NH$_2$
- H-D-Arg-Dmt-Lys-NH$_2$
- H-D-Arg-Dmt-D-Lys-D-Phe-NH$_2$
- H-D-Arg-Dmt-Lys-OH
- H-D-Arg-D-Dmt-Lys-Phe-NH$_2$
- H-D-Arg-Dmt-OH
- H-D-Arg-Dmt-Phe-NH$_2$
- H-Dmt-D-Arg-NH$_2$
- H-Phe-D-Arg-D-Phe-Lys-NH$_2$
- H-Phe-D-Arg-Phe-D-Lys-NH$_2$
- H-D-Phe-D-Arg-D-Phe-D-Lys-NH$_2$
- H-D-Arg-D-Dmt-D-Lys-D-Phe-NH$_2$
- H-D-Arg-Cha-Lys-NH$_2$
- H-D-Arg-Cha-Lys-Cha-NH$_2$
- H-Arg-D-Dmt-Lys-NH$_2$
- H-Arg-D-Dmt-Arg-NH$_2$
- H-D-Dmt-Arg-NH$_2$
- H-Arg-D-Dmt-NH$_2$
- H-D-Arg-D-Dmt-NH$_2$
- 6-Butyric acid CoQ0-Phe-D-Arg-Phe-Lys-NH$_2$
- 6-Decanoic acid CoQ0-Phe-D-Arg-Phe-Lys-NH$_2$
- Arg-Arg-Dmt-Phe
- Arg-Cha-Lys
- Arg-Dmt
- Arg-Dmt-Arg
- Arg-Dmt-Lys
- Arg-Dmt-Lys-Phe
- Arg-Dmt-Lys-Phe-Cys
- Arg-Dmt-Phe
- Arg-Dmt-Phe-Lys
- Arg-Lys-Dmt-Phe
- Arg-Lys-Phe-Dmt
- Arg-Phe-Dmt-Lys
- Arg-Phe-Lys
- Arg-Trp-Lys
- Arg-Tyr-Lys
- Arg-Tyr-Lys-Phe
- D-Arg-D-Dmt-D-Lys-L-Phe-NH$_2$
- D-Arg-D-Dmt-L-Lys-D-Phe-NH$_2$
- D-Arg-D-Dmt-L-Lys-L-Phe-NH$_2$
- D-Arg-Dmt-D-Lys-NH$_2$
- D-Arg-Dmt-Lys-NH$_2$
- D-Arg-Dmt-Lys-Phe-Cys
- D-Arg-L-Dmt-D-Lys-D-Phe-NH$_2$
- D-Arg-L-Dmt-D-Lys-L-Phe-NH$_2$
- D-Arg-L-Dmt-L-Lys-D-Phe-NH$_2$
- Dmt-Arg
- Dmt-Lys
- Dmt-Lys-Phe
- Dmt-Phe-Arg-Lys
- H-Arg-D-Dmt-Lys-Phe-NH$_2$
- H-Arg-Dmt-Lys-Phe-NH$_2$
- H-D-Arg-2,6-dichloro-L-tyrosine-L-Lys-L-Phe-NH$_2$
- H-D-Arg-2,6-dichlorotyrosine-Lys-Phe-NH$_2$
- H-D-Arg-2,6-difluoro-L-tyrosine-L-Lys-L-Phe-NH$_2$
- H-D-Arg-2,6-difluorotyrosine-Lys-Phe-NH$_2$
- H-D-Arg-2,6-dimethyl-L-phenylalanine-L-Lys-L-Phe-NH$_2$
- H-D-Arg-2,6-dimethylphenylalanine-Lys-Phe-NH$_2$
- H-D-Arg-4-methoxy-2,6-dimethyl-L-tyrosine-L-Lys-L-Phe-NH$_2$
- H-D-Arg-4-methoxy-2,6-dimethyltyrosine-Lys-Phe-NH$_2$
- H-D-Arg-Dmt-Lys-2,6-dimethylphenylalanine-NH$_2$
- H-D-Arg-Dmt-Lys-3-hydroxyphenylalanine-NH$_2$
- H-D-Arg-Dmt-Lys-Phe-OH
- H-D-Arg-Dmt-N6-acetyllysine-Phe-NH$_2$
- H-D-Arg-D-Phe-L-Lys-L-Phe-NH$_2$
- H-D-Arg-D-Trp-L-Lys-L-Phe-NH$_2$
- H-D-Arg-D-Tyr-L-Lys-L-Phe-NH$_2$
- H-D-Arg-L-Dmt-L-Lys-2,6-dimethyl-L-phenylalanine-NH$_2$
- H-D-Arg-L-Dmt-L-Lys-3-hydroxy-L-phenylalanine-NH$_2$
- H-D-Arg-L-Dmt-L-Lys-D-Dmt-NH$_2$
- H-D-Arg-L-Dmt-L-Lys-D-Trp-NH$_2$
- H-D-Arg-L-Dmt-L-Lys-D-Tyr-NH$_2$
- H-D-Arg-L-Dmt-L-Lys-L-Dmt-NH$_2$
- H-D-Arg-L-Dmt-L-Lys-L-Trp-NH$_2$
- H-D-Arg-L-Dmt-L-Lys-L-Tyr-NH$_2$
- H-D-Arg-L-Dmt-L-Phe-L-Lys-NH$_2$
- H-D-Arg-L-Dmt-N6-acetyl-L-lysine-L-Phe-NH$_2$
- H-D-Arg-L-Lys-L-Dmt-L-Phe-NH$_2$
- H-D-Arg-L-Lys-L-Phe-L-Dmt-NH$_2$
- H-D-Arg-L-Phe-L-Dmt-L-Lys-NH$_2$
- H-D-Arg-L-Phe-L-Lys-L-Dmt-NH$_2$
- H-D-Arg-L-Phe-L-Lys-L-Phe-NH$_2$
- H-D-Arg-L-Trp-L-Lys-L-Phe-NH$_2$
- H-D-Arg-L-Tyr-L-Lys-L-Phe-NH$_2$
- H-D-Arg-Phe-Lys-Dmt-NH$_2$
- H-D-Arg-Tyr-Lys-Phe-NH$_2$
- H-D-His-L-Dmt-L-Lys-L-Phe-NH$_2$
- H-D-Lys-L-Dmt-L-Lys-L-Phe-NH$_2$
- H-Dmt-D-Arg-Lys-Phe-NH$_2$
- H-Dmt-D-Arg-Phe-Lys-NH$_2$
- H-Dmt-Lys-D-Arg-Phe-NH$_2$
- H-Dmt-Lys-Phe-D-Arg-NH$_2$
- H-Dmt-Phe-D-Arg-Lys-NH$_2$
- H-Dmt-Phe-Lys-D-Arg-NH$_2$
- H-D-N2-acetylarginine-Dmt-Lys-Phe-NH$_2$
- H-D-N8-acetylarginine-Dmt-Lys-Phe-NH$_2$
- H-L-Dmt-D-Arg-L-Lys-L-Phe-NH$_2$
- H-L-Dmt-D-Arg-L-Phe-L-Lys-NH$_2$
- H-L-Dmt-L-Lys-D-Arg-L-Phe-NH$_2$
- H-L-Dmt-L-Lys-L-Phe-D-Arg-NH$_2$
- H-L-Dmt-L-Phe-D-Arg-L-Lys-NH$_2$
- H-L-Dmt-L-Phe-L-Arg-L-Lys-NH$_2$
- H-L-Dmt-L-Phe-L-Lys-D-Arg-NH$_2$
- H-L-His-L-Dmt-L-Lys-L-Phe-NH$_2$
- H-L-Lys-D-Arg-L-Dmt-L-Phe-NH$_2$
- H-L-Lys-D-Arg-L-Phe-L-Dmt-NH$_2$
- H-L-Lys-L-Dmt-D-Arg-L-Phe-NH$_2$
- H-L-Lys-L-Dmt-L-Lys-L-Phe-NH$_2$
- H-L-Lys-L-Dmt-L-Phe-D-Arg-NH$_2$
- H-L-Lys-L-Phe-D-Arg-L-Dmt-NH$_2$
- H-L-Lys-L-Phe-L-Dmt-D-Arg-NH$_2$
- H-L-Phe-D-Arg-L-Dmt-L-Lys-NH$_2$
- H-L-Phe-L-Arg-L-Dmt-L-Lys-NH$_2$
- H-L-Phe-L-Dmt-D-Arg-L-Lys-NH$_2$
- H-L-Phe-L-Dmt-L-Lys-D-Arg-NH$_2$
- H-L-Phe-L-Lys-D-Arg-L-Dmt-NH$_2$
- H-L-Phe-L-Lys-L-Dmt-D-Arg-NH$_2$
- H-Lys-D-Arg-Dmt-Phe-NH$_2$
- H-Lys-D-Arg-Phe-Dmt-NH$_2$
- H-Lys-Dmt-D-Arg-Phe-NH$_2$
- H-Lys-Dmt-Phe-D-Arg-NH$_2$
- H-Lys-Phe-D-Arg-Dmt-NH$_2$ TABLE A-continued H-Lys-Phe-Dmt-D-Arg-NH₂
H-N2-acetyl-D-arginine-L-Dmt-L-Lys-L-Phe-NH₂
H-N7-acetyl-D-arginine-Dmt-Lys-Phe-NH₂
H-Phe(d5)-D-Arg-Phe(d5)-Lys-NH₂
H-Phe-Arg-Phe-Lys-NH₂
H-Phe-D-Arg-Dmt-Lys-NH₂
H-Phe-D-Arg-Lys-Dmt-NH₂
H-Phe-D-Arg-Phe-Lys-Glu-Cys-Gly-NH₂
H-Phe-Dmt-D-Arg-Lys-NH₂
H-Phe-Dmt-Lys-D-Arg-NH₂
H-Phe-Lys-D-Arg-Dmt-NH₂
H-Phe-Lys-Dmt-D-Arg-NH₂
L-Arg-D-Dmt-D-Lys-D-Phe-NH₂
L-Arg-D-Dmt-D-Lys-L-Phe-NH₂
L-Arg-D-Dmt-L-Lys-D-Phe-NH₂
L-Arg-D-Dmt-L-Lys-L-Phe-NH₂
L-Arg-L-Dmt-D-Lys-D-Phe-NH₂
L-Arg-L-Dmt-D-Lys-L-Phe-NH₂
L-Arg-L-Dmt-L-Lys-D-Phe-NH₂
L-Arg-L-Dmt-L-Lys-L-Phe-NH₂
Lys-Dmt-Arf
Lys-Phe
Lys-Phe-Arg-Dmt
Lys-Trp-Arg
Phe-Arg-Dmt-Lys
Phe-Arg-Phe-Lys
Phe-Arg-Phe-Lys-Glu-Cys-Gly
Phe-Dmt-Arg-Lys
Phe-Lys-Dmt
Succinic monoester CoQ0-Phe-D-Arg-Phe-Lys-NH₂
Arg-Dmt-Lys-Phe-NH₂
Phe-Dmt-Arg-Lys-NH₂
Phe-Lys-Dmt-Arg-NH₂
Dmt-Arg-Lys-Phe-NH₂
Lys-Dmt-Arg-Phe-NH₂
Phe-Dmt-Lys-Arg-NH₂
Arg-Lys-Dmt-Phe-NH₂
Arg-Dmt-Phe-Lys-NH₂
D-Arg-Dmt-Lys-Phe-NH₂
Dmt-D-Arg-Phe-Lys-NH₂
H-Phe-D-Arg Phe-Lys-Cys-NH₂
D-Arg-Dmt-Lys-Trp-NH₂
D-Arg-Trp-Lys-Trp-NH₂
D-Arg-Dmt-Lys-Phe-Met-NH₂
H-D-Arg-Dmt-Lys(NαMe)-Phe-NH₂
H-D-Arg-Dmt-Lys-Phe(NMe)—NH₂
H-D-Arg-Dmt-Lys(NαMe)-Phe(NMe)—NH₂
H-D-Arg(NαMe)-Dmt(NMe)-Lys(NαMe)-Phe(NMe)—NH₂
D-Arg-Dmt-LyS-Phe-LyS-Trp-NH₂
D-Arg-Dmt-Lys-Dmt-Lys-Trp-NH₂
D-Arg-Dmt-Lys-Phe-Met-NH₂
D-Arg-Dmt-Lys-Dmt-Lys-Met-NH₂
H-D-Arg-Dmt-Lys-Phe-Sar-Gly-Cys-NH₂
H-D-Arg-Ψ[CH₂—NH]Dmt-Lys-Phe-NH₂
H-D-Arg-Dmt-Ψ[CH₂—NH]Lys-Phe-NH₂
H-D-Arg-Dmt-LysΨ[CH₂—NH]Phe-NH₂
H-D-Arg-Dmt-Ψ[CH₂—NH]Lys-Ψ[CH₂—NH]Phe-NH₂
D-Arg-2'6'Dmt-Lys-Phe-NH2
H-Phe-D-Arg-Phe-Lys-Cys-NH2
Gly-Ala-Lys-Phe-D-Lys-Glu-Arg-Tyr-His-D-Arg-D-Arg-Asp-Tyr-Trp-D-His-Trp-His-D-Lys-Asp
Dmt-D-Arg-Phe-(atn)Dap-NH₂
Dmt-D-Arg-Phe-(dns)Dap-NH₂
Dmt-D-Arg-Ald-Lys-NH₂
Dmt-D-Arg-Phe-Lys-Ald-NH₂

2',6'-dimethyltyrosine (2'6'-Dmt);
dimethyltyrosine (Dmt)

In one embodiment, the aromatic-cationic peptide is defined by Formula A:

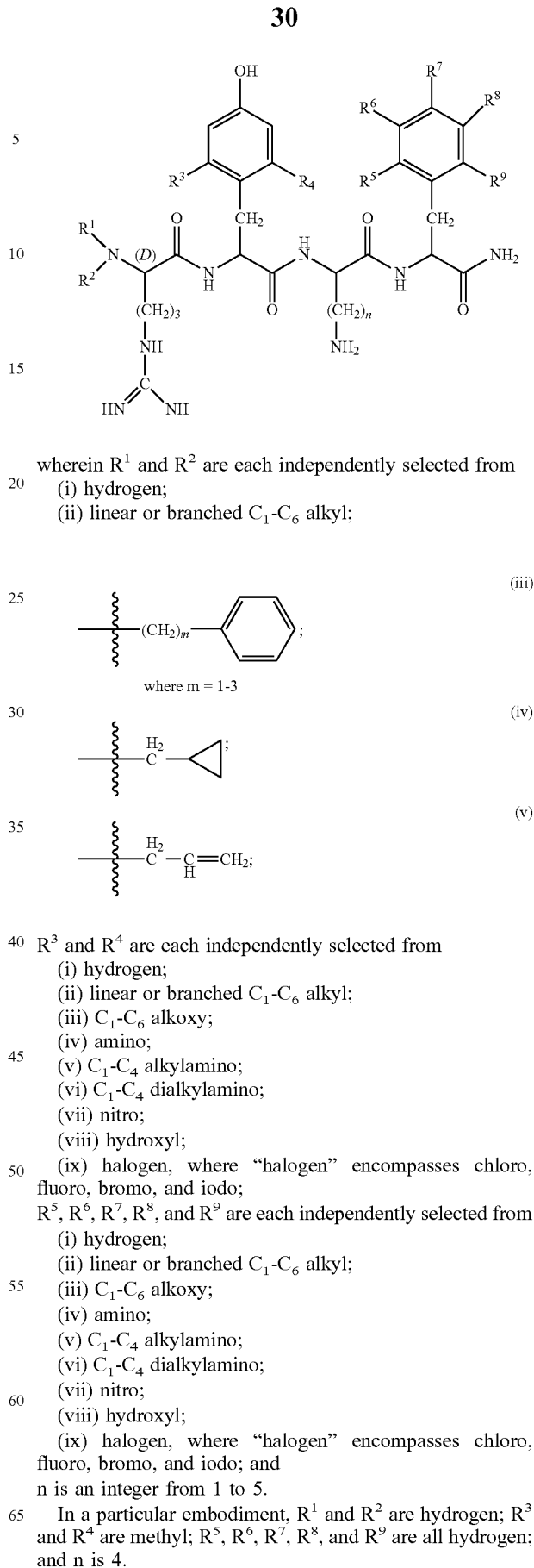

wherein $R^1$ and $R^2$ are each independently selected from
(i) hydrogen;
(ii) linear or branched $C_1$-$C_6$ alkyl;

(iii)

where m = 1-3

(iv)

(v)

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;
$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by Formula B:

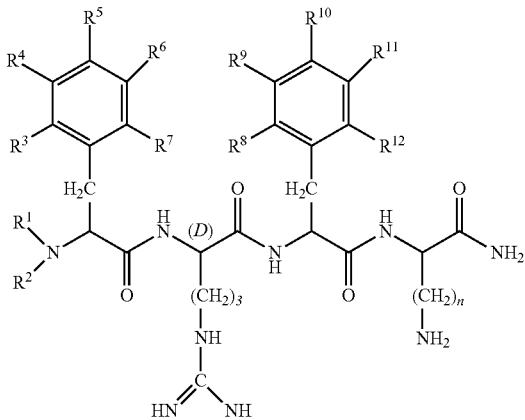

wherein $R^1$ and $R^2$ are each independently selected from
(i) hydrogen;
(ii) linear or branched $C_1$-$C_6$ alkyl;

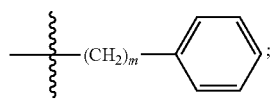  (iii)

where m = 1-3

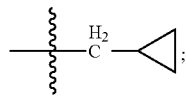  (iv)

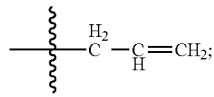  (v)

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the aromatic-cationic peptides of the present technology have a core structural motif of alternating aromatic and cationic amino acids. For example, the peptide may be a tetrapeptide defined by any of Formulas C to F set forth below:

Aromatic-Cationic-Aromatic-Cationic (Formula C)

Cationic-Aromatic-Cationic-Aromatic (Formula D)

Aromatic-Aromatic-Cationic-Cationic (Formula E)

Cationic-Cationic-Aromatic-Aromatic (Formula F)

wherein, Aromatic is a residue selected from the group consisting of: Phe (F), Tyr (Y), and Trp (W). In some embodiments, the Aromatic residue may be substituted with cyclohexylalanine (Cha). In some embodiments, the Cationic residue is a residue selected from the group consisting of: Arg (R), Lys (K), and His (H). In some embodiments, the Cationic residue may be substituted with norleucine (Nle) or 2-amino-heptanoic acid (Ahe).

The amino acids of the aromatic-cationic peptides of the present technology can be any amino acid. As used herein, the term "amino acid" is used to refer to any organic molecule that contains at least one amino group and at least one carboxyl group. In some embodiments, at least one amino group is at the α position relative to the carboxyl group.

The amino acids may be naturally occurring. Naturally occurring amino acids include, for example, the twenty most common levorotatory (L,) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val).

Other naturally occurring amino acids include, for example, amino acids that are synthesized in metabolic processes not associated with protein synthesis. For example, the amino acids ornithine and citrulline are synthesized in mammalian metabolism during the production of urea.

The peptides useful in the present technology can contain one or more non-naturally occurring amino acids. The non-naturally occurring amino acids may be (L-), dextrorotatory (D-), or mixtures thereof. In some embodiments, the peptide has no amino acids that are naturally occurring.

Non-naturally occurring amino acids are those amino acids that typically are not synthesized in normal metabolic processes in living organisms, and do not naturally occur in proteins. In certain embodiments, the non-naturally occurring amino acids useful in the present technology are also not recognized by common proteases.

The non-naturally occurring amino acid can be present at any position in the peptide. For example, the non-naturally occurring amino acid can be at the N terminus, the C-terminus, or at any position between the N-terminus and the C-terminus.

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta-, and para-aminobenzoic acid. Some examples of alkylaryl amino acids include ortho-, meta-, and para-aminophenyl acetic acid, and γ-phenyl-β-aminobutyric acid.

Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid in a peptide useful in the present methods is the derivatization of a carboxyl group of an aspartic acid or a glutamic acid residue of the peptide. One example of derivatization is amidation with ammonia or with a primary or secondary amine, e.g., methylamine, ethylamine, dimethylamine or diethylamine. Another example of derivatization includes esterification with, for example, methyl or ethyl alcohol.

Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

In some embodiments, the non-naturally occurring amino acids are resistant, and in some embodiments insensitive, to common proteases. Examples of non-naturally occurring amino acids that are resistant or insensitive to proteases include the dextrorotatory (D-) form of any of the above-mentioned naturally occurring L-amino acids, as well as L- and/or D non-naturally occurring amino acids. The D-amino acids do not normally occur in proteins, although they are found in certain peptide antibiotics that are synthesized by means other than the normal ribosomal protein synthetic machinery of the cell, as used herein, the D-amino acids are considered to be non-naturally occurring amino acids.

In order to minimize protease sensitivity, the peptides useful in the methods of the present technology should have less than five, less than four, less than three, or less than two contiguous L-amino acids recognized by common proteases, irrespective of whether the amino acids are naturally or non-naturally occurring. In some embodiments, the peptide has only D-amino acids, and no L-amino acids.

If the peptide contains protease sensitive sequences of amino acids, at least one of the amino acids is a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

It is important that the aromatic-cationic peptides have a minimum number of net positive charges at physiological pH in comparison to the total number of amino acid residues in the peptide. The minimum number of net positive charges at physiological pH is referred to below as ($p_m$). The total number of amino acid residues in the peptide is referred to below as (r).

The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein 3 $p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein 2 $p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, or a minimum of two net positive charges, or a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally-occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t+1$, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges (3a ≤ $p_t$ + 1 or a = $p_t$ = 1)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges (2a ≤ $p_t$ + 1 or a = $p_t$ = 1)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

In some embodiments, carboxyl groups, especially the terminal carboxyl group of a C-terminal amino acid, are amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethyl amido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present technology may also be amidated wherever they occur within the peptide. The amidation at these internal positions may be with ammonia or any of the primary or secondary amines described herein.

In one embodiment, the aromatic-cationic peptide useful in the methods of the present technology is a tripeptide having two net positive charges and at least one aromatic amino acid. In a particular embodiment, the aromatic-cationic peptide useful in the methods of the present technology is a tripeptide having two net positive charges and two aromatic amino acids.

Aromatic-cationic peptides useful in the methods of the present technology include, but are not limited to, the following peptide examples:

TABLE 5

EXEMPLARY PEPTIDES

2'6'-Dmp-D-Arg-2'6'-Dmt-Lys-NH$_2$
2'6'-Dmp-D-Arg-Phe-Lys-NH$_2$
2'6'-Dmt-D-Arg-Phe Orn-NH$_2$
2'6'-Dmt-D-Arg-Phe-Ahp(2-aminoheptanoic acid)-NH$_2$
2'6'-Dmt-D-Arg-Phe-Lys-NH$_2$
2'6'-Dmt-D-Cit-Phe Lys-NH$_2$
Ala-D-Phe-D-Arg-Tyr-Lys-D-Trp-His-D-Tyr-Gly-Phe
Arg-D-Leu-D-Tyr-Phe-Lys-Glu-D-Lys-Arg-D-Trp-Lys-D-Phe-Tyr-D-Arg-Gly
Asp-Arg-D-Phe-Cys-Phe-D-Arg-D-Lys-Tyr-Arg-D-Tyr-Trp-D-His-Tyr- TABLE 5-continued

EXEMPLARY PEPTIDES

D-Phe-Lys-Phe
Asp-D-Trp-Lys-Tyr-D-His-Phe-Arg-D-Gly-Lys-NH$_2$
D-Arg-2'6'-Dmt-Lys-Phe-NH$_2$

TABLE 5-continued

EXEMPLARY PEPTIDES

D-Glu-Asp-Lys-D-Arg-D-His-Phe-Phe-D-Val-Tyr-Arg-Tyr-D-Tyr-Arg-His-Phe-NH$_2$
D-His-Glu-Lys-Tyr-D-Phe-Arg
D-His-Lys-Tyr-D-Phe-Glu-D-Asp-D-Asp-D-His-D-Lys-Arg-Trp-NH$_2$
D-Tyr-Trp-Lys-NH$_2$
Glu-Arg-D-Lys-Tyr-D-Val-Phe-D-His-Trp-Arg-D-Gly-Tyr-Arg-D-Met-NH$_2$
Gly-Ala-Lys-Phe-D-Lys-Glu-Arg-Tyr-His-D-Arg-D-Arg-Asp-Tyr-Trp-D-His-Trp-His-D-Lys-Asp
Gly-D-Phe-Lys-His-D-Arg-Tyr-NH$_2$
His-Tyr-D-Arg-Trp-Lys-Phe-D-Asp-Ala-Arg-Cys-D-Tyr-His-Phe-D-Lys-Tyr-His-Ser-NH$_2$
Lys-D-Arg-Tyr-NH$_2$
Lys-D-Gln-Tyr-Arg-D-Phe-Trp-NH$_2$
Lys-Trp-D-Tyr-Arg-Asn-Phe-Tyr-D-His-NH$_2$
Met-Tyr-D-Arg-Phe-Arg-NH$_2$
Met-Tyr-D-Lys-Phe-Arg
Phe-Arg-D-His-Asp
Phe-D-Arg-2'6'-Dmt-Lys-NH$_2$
Phe-D-Arg-His
Phe-D-Arg-Lys-Trp-Tyr-D-Arg-His
Phe-D-Arg-Phe-Lys-NH$_2$
Phe-Phe-D-Tyr-Arg-Glu-Asp-D-Lys-Arg-D-Arg-His-Phe-NH$_2$
Phe-Tyr-Lys-D-Arg-Trp-His-D-Lys-D-Lys-Glu-Arg-D-Tyr-Thr
Thr-Gly-Tyr-Arg-D-His-Phe-Trp-D-His-Lys
Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$
Trp-D-Lys-Tyr-Arg-NH$_2$
Trp-Lys-Phe-D-Asp-Arg-Tyr-D-His-Lys
Tyr-Asp-D-Lys-Tyr-Phe-D-Lys-D-Arg-Phe-Pro-D-Tyr-His-Lys
Tyr-D-Arg-Phe-Lys-Glu-NH$_2$
Tyr-D-Arg-Phe-Lys-NH$_2$
Tyr-D-His-Phe-D-Arg-Asp-Lys-D-Arg-His-Trp-D-His-Phe

TABLE 5-continued

EXEMPLARY PEPTIDES

Tyr-His-D-Gly-Met
Val-D-Lys-His-Tyr-D-Phe-Ser-Tyr-Arg-NH$_2$
D-Arg-Dmt-Lys-Trp-NH$_2$
D-Arg-Trp-Lys-Trp-NH$_2$
D-Arg-Dmt-Lys-Phe-Met-NH$_2$
H-D-Arg-Dmt-Lys(NαMe)-Phe-NH$_2$
H-D-Arg-Dmt-Lys-Phe(NMe)—NH$_2$
H-D-Arg-Dmt-Lys(NαMe)-Phe(NMe)—NH$_2$
H-D-Arg(NαMe)-Dmt(NMe)-Lys(NαMe)-Phe(NMe)—NH$_2$
D-Arg-Dmt-Lys-Phe-Lys-Trp-NH$_2$
D-Arg-Dmt-Lys-Dmt-Lys-Trp-NH$_2$
D-Arg-Dmt-Lys-Phe-Lys-Met-NH$_2$
D-Arg-Dmt-Lys-Dmt-Lys-Met-NH$_2$
H-D-Arg-Dmt-Lys-Phe-Sar-Gly-Cys-NH$_2$
H-D-Arg-Ψ[CH2—NH]Dmt-Lys-Phe-NH$_2$
H-D-Arg-Dmt-Ψ[CH2—NH]Lys-Phe-NH$_2$
H-D-Arg-Dmt-LysΨ[CH2—NH]Phe-NH$_2$
H-D-Arg-Dmt-Ψ[CH2—NH]Lys-Ψ[CH2—NH]Phe-NH$_2$
D-Arg-Tyr-Lys-Phe-NH$_2$
D-Arg-Dmt-D-Lys-Phe-NH$_2$
D-Arg-Dmt-Lys-D-Phe-NH$_2$
Phe-D-Arg-D-Phe-Lys-NH$_2$
Phe-D-Arg-Phe-D-Lys-NH$_2$
D-Phe-D-Arg-D-Phe-D-Lys-NH$_2$
Lys-D-Phe-Arg-Dmt-NH$_2$
D-Arg-Arg-Dmt-Phe-NH$_2$
Dmt-D-Phe-Arg-Lys-NH$_2$
Phe-D-Dmt-Arg-Lys-NH$_2$
D-Arg-Dmt-Lys-NH$_2$
Arg-D-Dmt-Lys-NH$_2$
D-Arg-Dmt-Phe-NH$_2$
Arg-D-Dmt-Arg-NH$_2$
Dmt-D-Arg-NH$_2$
D-Arg-Dmt-NH$_2$
D-Dmt-Arg-NH$_2$
Arg-D-Dmt-NH$_2$
D-Arg-D-Dmt-NH$_2$
D-Arg-D-Tyr-Lys-Phe-NH$_2$
D-Arg-Tyr-D-Lys-Phe-NH$_2$
D-Arg-Tyr-Lys-D-Phe-NH$_2$
D-Arg-D-Tyr-D-Lys-D-Phe-NH$_2$
Lys-D-Phe-Arg-Tyr-NH$_2$
D-Arg-Arg-Tyr-Phe-NH$_2$
Tyr-D-Phe-Arg-Lys-NH$_2$
Phe-D-Tyr-Arg-Lys-NH$_2$
D-Arg-Tyr-Lys-NH$_2$
Arg-D-Tyr-Lys-NH$_2$
D-Arg-Tyr-Phe-NH$_2$
Arg-D-Tyr-Arg-NH$_2$
Tyr-D-Arg-NH$_2$
D-Arg-Tyr-NH$_2$
D-Tyr-Arg-NH$_2$
Arg-D-Tyr-NH$_2$
D-Arg-D-Tyr-NH$_2$
Dmt-Lys-Phe-NH$_2$
Lys-Dmt-D-Arg-NH$_2$
Phe-Lys-Dmt-NH$_2$
D-Arg-Phe-Lys-NH$_2$
D-Arg-Cha-Lys-NH$_2$
D-Arg-Trp-Lys-NH$_2$
Dmt-Lys-D-Phe-NH$_2$
Dmt-Lys-NH$_2$
Lys-Phe-NH$_2$
D-Arg-Cha-Lys-Cha-NH$_2$
D-Nle-Dmt-Ahe-Phe-NH$_2$
D-Nle-Cha-Ahe-Cha-NH$_2$

Cha = cyclohexyl alanine
Dmt = dimethyltyrosine
Dmp = dimethylphenylalanine

In some embodiments, the aromatic-cationic peptide is a peptide having:
- at least one net positive charge;
- a minimum of four amino acids;
- a maximum of about twenty amino acids;
- a relationship between the minimum number of net positive charges ($p_m$) and the total number of amino acid residues (r) wherein 3 $p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1.

In one embodiment, 2 $p_m$ is the largest number that is less than or equal to r+1, and a may be equal to $p_t$. The aromatic-cationic peptide may be a water-soluble peptide having a minimum of two or a minimum of three positive charges.

In one embodiment, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In one embodiment, the peptides have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyltyrosine (Hmt).

In one embodiment, a peptide has the formula Tyr-D-Arg-Phe-Lys-NH$_2$. Tyr-D-Arg-Phe-Lys-NH$_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-NH$_2$ can be a modified derivative of tyrosine such as in 2',6'-dimethyltyrosine to produce the compound having the formula 2',6'-Dmt-D-Arg-Phe-Lys-NH$_2$. 2',6'-Dmt-D-Arg-Phe-Lys-NH$_2$ has a molecular weight of 640 and carries a net three positive charge at physiological pH. 2',6'-Dmt-D-Arg-Phe-Lys-NH$_2$ readily penetrates the plasma membrane of several mammalian cell types in an energy-independent manner (Zhao et al., *J. Pharmacol Exp Ther.*, 304:425-432, 2003).

Alternatively, in some embodiments, the aromatic-cationic peptide does not have a tyrosine residue or a derivative of tyrosine at the N-terminus (i.e., amino acid position 1). The amino acid at the N-terminus can be any naturally-occurring or non-naturally-occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have a tyrosine residue or a derivative of tyrosine at the N-terminus is a peptide with the formula Phe-D-Arg-Phe-Lys-NH$_2$. Alternatively, the N-terminal phenylalanine can be a derivative of phenylalanine such as 2',6'-dimethylphenylalanine (2'6'-Dmp). In one embodiment, the amino acid sequence of 2',6'-Dmt-D-Arg-Phe-Lys-NH$_2$ is rearranged such that Dmt is not at the N-terminus. An example of such an aromatic-cationic peptide is a peptide having the formula of D-Arg-2'6'-Dmt-Lys-Phe-NH$_2$.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);

(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group are referred to as a conservative substitution and may preserve the physicochemical characteristics of the original peptide. In contrast, substitutions of an amino acid in a peptide by another amino acid in a different group are generally more likely to alter the characteristics of the original peptide.

Examples of peptides that have a tyrosine residue or a tyrosine derivative at the N-terminus include, but are not limited to, the aromatic-cationic peptides shown in Table 6.

TABLE 6

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |
| 2'6'Dmt | D-Arg | Phe | Lys-NH(CH$_2$)$_2$—NH-dns | NH$_2$ |
| 2'6'Dmt | D-Arg | Phe | Lys-NH(CH$_2$)$_2$—NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D-Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |

TABLE 6-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |
| Tmt | D-Lys | Phe | Orn | NH$_2$ |
| Tmt | D-Lys | Phe | Dab | NH$_2$ |
| Tmt | D-Lys | Phe | Dap | NH$_2$ |
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |

TABLE 6-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not have a tyrosine residue or a tyrosine derivative at the N-terminus include, but are not limited to, the aromatic-cationic peptides shown in Table 7.

TABLE 7

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| Phe | Lys | Dmt | D-Arg | NH$_2$ |
| Phe | Lys | D-Arg | Dmt | NH$_2$ |
| Phe | D-Arg | Phe | Lys | NH$_2$ |
| Phe | D-Arg | Dmt | Lys | NH$_2$ |
| Phe | D-Arg | Lys | Dmt | NH$_2$ |
| Phe | Dmt | D-Arg | Lys | NH$_2$ |
| Phe | Dmt | Lys | D-Arg | NH$_2$ |
| Lys | Phe | D-Arg | Dmt | NH$_2$ |
| Lys | Phe | Dmt | D-Arg | NH$_2$ |
| Lys | Dmt | D-Arg | Phe | NH$_2$ |
| Lys | Dmt | Phe | D-Arg | NH$_2$ |
| Lys | D-Arg | Phe | Dmt | NH$_2$ |
| Lys | D-Arg | Dmt | Phe | NH$_2$ |
| D-Arg | Dmt | D-Arg | Phe | NH$_2$ |
| D-Arg | Dmt | D-Arg | Dmt | NH$_2$ |
| D-Arg | Dmt | D-Arg | Tyr | NH$_2$ |
| D-Arg | Dmt | D-Arg | Trp | NH$_2$ |
| Trp | D-Arg | Phe | Lys | NH$_2$ |
| Trp | D-Arg | Tyr | Lys | NH$_2$ |
| Trp | D-Arg | Trp | Lys | NH$_2$ |
| Trp | D-Arg | Dmt | Lys | NH$_2$ |
| D-Arg | Trp | Lys | Phe | NH$_2$ |
| D-Arg | Trp | Phe | Lys | NH$_2$ |
| D-Arg | Trp | Lys | Dmt | NH$_2$ |
| D-Arg | Trp | Dmt | Lys | NH$_2$ |
| D-Arg | Lys | Trp | Phe | NH$_2$ |
| D-Arg | Lys | Trp | Dmt | NH$_2$ |
| Cha | D-Arg | Phe | Lys | NH$_2$ |
| Ala | D-Arg | Phe | Lys | NH$_2$ |

Cha = cyclohexyl alanine

The amino acids of the peptides shown in Table 6 and 7 may be in either the L- or the D-configuration.

III. Uses Of Compositions of the Present Technology

In some aspects, the methods disclosed herein provide therapies for the treatment of medical disease or conditions and/or side effects associated with existing therapeutics against medical diseases or conditions comprising administering an effective amount of TBM alone or in combination with one or more aromatic-cationic peptides or pharmaceutically acceptable salts thereof, such as acetate, tartrate or trifluoroacetate.

In another aspect, the present technology provides methods for treating, ameliorating or preventing a medical disease or condition in a subject in need thereof, comprising administering a therapeutically effective amount of a composition comprising an aromatic-cationic peptide of the present technology conjugated to a TBM to the subject thereby treating, amelioration or preventing the medical disease or condition. Thus, for example, one or more peptide conjugate(s) may be: (1) co-formulated and administered or delivered alone or simultaneously in a combined formulation with other TBMs or aromatic-cationic peptides; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Administering combinations of aromatic peptides and TBMs can result in synergistic biological effect when administered in a therapeutically effective amount to a subject suffering from a medical disease or condition and in need of treatment. An advantage of such an approach is that lower doses of aromatic-cationic peptide and/or TBM may be needed to prevent, ameliorate or treat a medical disease or condition in a subject. Further, potential side-effects of treatment may be avoided by use of lower dosages of aromatic-cationic peptide and/or TBM. In some embodiments, the combination therapy comprises administering to a subject in need thereof an aromatic-cationic peptide composition combined with one or more TBMs. In some embodiments, the TBM and the aromatic-cationic peptide are chemically linked. In some embodiments, the TBM and the aromatic-cationic peptide are physically linked. In some embodiments, the TBM and the aromatic-cationic peptide are not linked.

Ischemia in a tissue or organ of a mammal is a multifaceted pathological condition which is caused by oxygen deprivation (hypoxia) and/or glucose (e.g., substrate) deprivation. Oxygen and/or glucose deprivation in cells of a tissue or organ leads to a reduction or total loss of energy generating capacity and consequent loss of function of active ion transport across the cell membranes. Oxygen and/or glucose deprivation also leads to pathological changes in other cell membranes, including permeability transition in the mitochondrial membranes. In addition other molecules, such as apoptotic proteins normally compartmentalized within the mitochondria, may leak out into the cytoplasm and cause apoptotic cell death. Profound ischemia can lead to necrotic cell death.

Ischemia or hypoxia in a particular tissue or organ may be caused by a loss or severe reduction in blood supply to the tissue or organ. The loss or severe reduction in blood supply may, for example, be due to thromboembolic stroke, coronary atherosclerosis, or peripheral vascular disease. The tissue affected by ischemia or hypoxia is typically muscle, such as cardiac, skeletal, or smooth muscle.

The organ affected by ischemia or hypoxia may be any organ that is subject to ischemia or hypoxia. Examples of organs affected by ischemia or hypoxia include brain, heart, kidney, and prostate. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

Ischemia or hypoxia in skeletal muscle or smooth muscle may arise from similar causes. For example, ischemia or hypoxia in intestinal smooth muscle or skeletal muscle of the limbs may also be caused by atherosclerotic or thrombotic blockages.

Reperfusion is the restoration of blood flow to any organ or tissue in which the flow of blood is decreased or blocked. For example, blood flow can be restored to any organ or tissue affected by ischemia or hypoxia. The restoration of blood flow (reperfusion) can occur by any method known to those in the art. For instance, reperfusion of ischemic cardiac tissues may arise from angioplasty, coronary artery bypass graft, or the use of thrombolytic drugs.

In some embodiments, TBMs (or derivatives, analogues, or pharmaceutically acceptable salts thereof) are useful in reducing oxLDL-induced CD36 mRNA and protein levels, and foam cell formation in mouse peritoneal macrophages. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in reducing oxLDL-induced CD36 mRNA and protein levels, and foam cell formation in mouse peritoneal macrophages.

In some embodiments, TBMs (or derivatives, analogues, or pharmaceutically acceptable salts thereof) are useful in reducing infarct volume and hemispheric swelling in a subject suffering from acute cerebral ischemia. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing infarct volume and hemispheric swelling in a subject suffering from acute cerebral ischemia.

In some embodiments, TBMs (or derivatives, analogues, or pharmaceutically acceptable salts thereof) are useful in reducing the decrease in reduced glutathione (GSH) in post-ischemic brain in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing the decrease in reduced glutathione (GSH) in post-ischemic brain in a subject in need thereof.

In some embodiments, TBMs (or derivatives, analogues, or pharmaceutically acceptable salts thereof) are useful in reducing CD36 expression in post-ischemic brain in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing CD36 expression in post-ischemic brain in a subject in need thereof.

In some embodiments, TBMs (or derivatives, analogues, or pharmaceutically acceptable salts thereof) are useful in reducing CD36 expression in renal tubular cells after unilateral ureteral obstruction (UUO) in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing CD36 expression in renal tubular cells after unilateral ureteral obstruction (UUO) in a subject in need thereof.

In some embodiments, TBMs (or derivatives, analogues, or pharmaceutically acceptable salts thereof) are useful in reducing lipid peroxidation in a kidney after UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing lipid peroxidation in a kidney after UUO.

In some embodiments, TBMs (or derivatives, analogues, or pharmaceutically acceptable salts thereof) are useful in reducing tubular cell apoptosis in an obstructed kidney after UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg- 2',6'-Dmt-Lys-Phe-NH$_2$) are useful in reducing tubular cell apoptosis in an obstructed kidney after UUO.

In some embodiments, TBMs (or derivatives, analogues, or pharmaceutically acceptable salts thereof) are useful in reducing macrophage infiltration in an obstructed kidney induced by UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing macrophage infiltration in an obstructed kidney induced by UUO.

In some embodiments, TBMs (or derivatives, analogues, or pharmaceutically acceptable salts thereof) are useful in reducing interstitial fibrosis in an obstructed kidney after UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing interstitial fibrosis in an obstructed kidney after UUO.

In some embodiments, TBMs (or derivatives, analogues, or pharmaceutically acceptable salts thereof) are useful in reducing up-regulation of CD36 expression in cold storage of isolated hearts. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing up-regulation of CD36 expression in cold storage of isolated hearts.

In some embodiments, TBMs (or derivatives, analogues, or pharmaceutically acceptable salts thereof) are useful in reducing lipid peroxidation in cardiac tissue (e.g., heart) subjected to warm reperfusion after prolonged cold ischemia. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing lipid peroxidation in cardiac tissue (e.g., heart) subjected to warm reperfusion after prolonged cold ischemia.

In some embodiments, TBMs (or derivatives, analogues, or pharmaceutically acceptable salts thereof) are useful in abolishing endothelial apoptosis in cardiac tissue (e.g., heart) subjected to warm reperfusion after prolonged cold ischemia. In other embodiments, TBMs (or derivatives, analogues, or pharmaceutically acceptable salts thereof) in combination with one or more active agents (e.g., aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in abolishing endothelial apoptosis in cardiac tissue (e.g., heart) subjected to warm reperfusion after prolonged cold ischemia.

In some embodiments, TBMs (or derivatives, analogues, or pharmaceutically acceptable salts thereof) are useful in preserving coronary flow in cardiac tissue (e.g., heart) subjected to warm reperfusion after prolonged cold ischemia. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in preserving coronary flow in cardiac tissue (e.g., heart) subjected to warm reperfusion after prolonged cold ischemia.

In some embodiments, TBMs (or derivatives, analogues, or pharmaceutically acceptable salts thereof) are useful in preventing damage to renal proximal tubules in diabetic subjects. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in preventing damage to renal proximal tubules in diabetic subjects.

In some embodiments, TBMs (or derivatives, analogues, or pharmaceutically acceptable salts thereof) are useful in preventing renal tubular epithelial cell apoptosis in diabetic subjects. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in preventing renal tubular epithelial cell apoptosis in diabetic subjects.

In some embodiments, TBMs (or derivatives, analogues, or pharmaceutically acceptable salts thereof) or peptide conjugates of the present technology are useful in methods for reducing elevated CD36 expression associated with various diseases and conditions. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Examples of diseases and conditions characterized by increased CD36 expression include, but are not limited to atherosclerosis, inflammation, abnormal angiogenesis, abnormal lipid metabolism, abnormal removal of apoptotic cells, ischemia such as cerebral ischemia and myocardial ischemia, ischemia-reperfusion, ureteral obstruction, stroke, Alzheimer's Disease, diabetes, diabetic nephropathy and obesity.

In some embodiments, TBMs (or derivatives, analogues, or pharmaceutically acceptable salts thereof) or peptide conjugates of the present technology are useful in methods for reducing CD36 expression in subjects suffering from complications of diabetes. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Complications of diabetes include, but are not limited to, nephropathy, neuropathy, retinopathy, coronary artery disease, and peripheral vascular disease.

In some embodiments, TBMs (or derivatives, analogues, or pharmaceutically acceptable salts thereof) or peptide conjugates of the present technology are useful in methods for reducing CD36 expression in removed organs and tissues. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. The method comprises contacting the removed organ or tissue with an effective amount of a composition described herein. An organ or tissue may, for example, be removed from a donor for autologous or heterologous transplantation. Examples of organs and tissues amenable to methods of the present technology include, but are not limited to, heart, lungs, pancreas, kidney, liver, skin, etc.

In some embodiments, TBMs (or derivatives, analogues, or pharmaceutically acceptable salts thereof) will translocate to and accumulate within mitochondria. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology will translocate to and accumulate within mitochondria.

In some embodiments, TBMs (or derivatives, analogues, or pharmaceutically acceptable salts thereof) are useful in protecting against mitochondrial permeability transition (MPT) induced by Ca$^{2+}$ overload and 3-nitropropionic acid (3NP). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in protecting against mitochondrial permeability transition (MPT) induced by Ca$^{2+}$ overload and 3-nitropropionic acid (3NP).

In some embodiments, TBMs (or derivatives, analogues, or pharmaceutically acceptable salts thereof) are useful in inhibiting mitochondrial swelling and cytochrome c release. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in inhibiting mitochondrial swelling and cytochrome c release.

In some embodiments, TBMs (or derivatives, analogues, or pharmaceutically acceptable salts thereof) are useful in protecting myocardial contractile force during ischemia-reperfusion in cardiac tissue. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in protecting myocardial contractile force during ischemia-reperfusion in cardiac tissue.

In some embodiments, TBMs (or derivatives, analogues, or pharmaceutically acceptable salts thereof) that are administered with a cardioplegic solution are useful in enhancing contractile function after prolonged ischemia in isolated perfused cardiac tissue (e.g., heart). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) that are administered with a cardioplegic solution are useful in enhancing contractile function after prolonged ischemia in isolated perfused cardiac tissue (e.g., heart).

In some embodiments, TBMs (or derivatives, analogues, or pharmaceutically acceptable salts thereof) or peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in treating any disease or condition that is associated with, for example, MPT. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Such diseases and conditions include, but are not limited to, e.g., ischemia and/or reperfusion of a tissue or organ, hypoxia, diseases and conditions of the eye, myocardial infarction and any of a number of neurodegenerative diseases. Mammals in need of treatment or prevention of MPT are those mammals suffering from these diseases or conditions.

The methods and compositions of the present disclosure can also be used in the treatment or prophylaxis of neurodegenerative diseases associated with MPT. Neurodegenerative diseases associated with MPT include, for instance, Parkinson's disease, Alzheimer's disease, Huntington's disease and Amyotrophic Lateral Sclerosis (ALS, also known as Lou Gehrig's disease). The methods and compositions disclosed herein can be used to delay the onset or slow the progression of these and other neurodegenerative diseases associated with MPT. The methods and compositions of the present technology are useful in the treatment of humans suffering from the early stages of neurodegenerative diseases associated with MPT and in humans predisposed to these diseases.

In some embodiments, TBMs (or derivatives, analogues, or pharmaceutically acceptable salts thereof) are useful in preserving an organ of a mammal prior to transplantation. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in preserving an organ of a mammal prior to transplantation. For example, a removed organ can be susceptible to MPT due to lack of blood flow. Therefore, the compositions of the present disclosure can be administered to a subject prior to organ removal, for example, and used to prevent MPT in the removed organ.

The removed organ may be placed in a standard buffered solution, such as those commonly used in the art. For example, a removed heart may be placed in a cardioplegic solution containing the compositions described herein. The concentration of compositions in the standard buffered solution can be easily determined by those skilled in the art. Such concentrations may be, for example, between about 0.1 nM to about 10 µM.

In some embodiments, TBMs (or derivatives, analogues, or pharmaceutically acceptable salts thereof) or peptide conjugates of the present technology may also be administered to a mammal taking a drug to treat a condition or disease. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

If a side effect of the drug includes MPT, mammals taking such drugs would greatly benefit from administration of the compositions disclosed herein. An example of a drug which induces cell toxicity by effecting MPT is the chemotherapy drug Adriamycin. In some embodiments, TBMs (or derivatives, analogues, or pharmaceutically acceptable salts thereof) are useful in ameliorating, diminishing or preventing the side effects of drugs such as adriamycin. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In certain embodiments, peptide conjugates of the present technology are useful in ameliorating, diminishing or preventing the side effects of drugs such as adriamycin.

In some embodiments, TBMs (or derivatives, analogues, or pharmaceutically acceptable salts thereof) are useful in dose-dependently scavenging H$_2$O$_2$. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in dose-dependently scavenging H$_2$O$_2$.

In some embodiments, TBMs (or derivatives, analogues, or pharmaceutically acceptable salts thereof) are useful in dose-dependently inhibiting linoleic acid peroxidation induced by ABAP and reducing the rate of linoleic acid peroxidation induced by ABAP. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in dose-dependently inhibiting linoleic acid peroxidation induced by ABAP and reducing the rate of linoleic acid peroxidation induced by ABAP.

In some embodiments, TBMs (or derivatives, analogues, or pharmaceutically acceptable salts thereof) are useful in inhibiting mitochondrial production of hydrogen peroxide, e.g., as measured by luminol chemiluminescence under basal conditions and/or upon stimulation by antimycin. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in inhibiting mitochondrial production of hydrogen peroxide, e.g., as measured by luminol chemiluminescence under basal conditions and/or upon stimulation by antimycin.

In some embodiments, TBMs (or derivatives, analogues, or pharmaceutically acceptable salts thereof) are useful in reducing spontaneous generation of hydrogen peroxide by mitochondria in certain stress or disease states. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in reducing spontaneous generation of hydrogen peroxide by mitochondria in certain stress or disease states.

In some embodiments, TBMs (or derivatives, analogues, or pharmaceutically acceptable salts thereof) are useful in inhibiting spontaneous production of hydrogen peroxide in mitochondria and hydrogen peroxide production, e.g., as stimulated by antimycin. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) are useful in inhibiting spontaneous production of hydrogen peroxide in mitochondria and hydrogen peroxide production, e.g., as stimulated by antimycin.

In some embodiments, TBMs (or derivatives, analogues, or pharmaceutically acceptable salts thereof) are useful in decreasing intracellular ROS (reactive oxygen species) and increasing survival in cells of a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in decreasing intracellular ROS (reactive oxygen species) and increasing survival in cells of a subject in need thereof.

In some embodiments, TBMs (or derivatives, analogues, or pharmaceutically acceptable salts thereof) are useful in preventing loss of cell viability in subjects suffering from a disease or condition characterized by mitochondrial permeability transition. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in preventing loss of cell viability in subjects suffering from a disease or condition characterized by mitochondrial permeability transition.

In some embodiments, TBMs (or derivatives, analogues, or pharmaceutically acceptable salts thereof) are useful in decreasing the percent of cells showing increased caspase activity in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in decreasing the percent of cells showing increased caspase activity in a subject in need thereof.

In some embodiments, TBMs (or derivatives, analogues, or pharmaceutically acceptable salts thereof) are useful in decreasing the rate of ROS accumulation in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in decreasing the rate of ROS accumulation in a subject in need thereof.

In some embodiments, TBMs (or derivatives, analogues, or pharmaceutically acceptable salts thereof) are useful in inhibiting lipid peroxidation in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in inhibiting lipid peroxidation in a subject in need thereof.

In some embodiments, TBMs (or derivatives, analogues, or pharmaceutically acceptable salts thereof) are useful in preventing mitochondrial depolarization and ROS accumulation in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in preventing mitochondrial depolarization and ROS accumulation in a subject in need thereof.

In some embodiments, TBMs (or derivatives, analogues, or pharmaceutically acceptable salts thereof) are useful in preventing apoptosis in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in preventing apoptosis in a subject in need thereof.

In some embodiments, TBMs (or derivatives, analogues, or pharmaceutically acceptable salts thereof) are useful in improving coronary flow in cardiac tissue (e.g., heart) subjected to warm reperfusion after prolonged (e.g., 18 hours) cold ischemia. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in improving coronary flow in cardiac tissue (e.g., heart) subjected to warm reperfusion after prolonged (e.g., 18 hours) cold ischemia.

In some embodiments, TBMs (or derivatives, analogues, or pharmaceutically acceptable salts thereof) are useful in preventing apoptosis in endothelial cells and myocytes in cardiac tissue (e.g., heart) subjected to warm reperfusion after prolonged (e.g., 18 hours) cold ischemia. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in preventing apoptosis in endothelial cells and myocytes in cardiac tissue (e.g., heart) subjected to warm reperfusion after prolonged (e.g., 18 hours) cold ischemia.

In some embodiments, TBMs (or derivatives, analogues, or pharmaceutically acceptable salts thereof) are useful in improving survival of pancreatic cells in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in improving survival of pancreatic cells in a subject in need thereof.

In some embodiments, TBMs (or derivatives, analogues, or pharmaceutically acceptable salts thereof) are useful in reducing apoptosis and increasing viability in islet cells of pancreas in subjects in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in reducing apoptosis and increasing viability in islet cells of pancreas in subjects in need thereof.

In some embodiments, TBMs (or derivatives, analogues, or pharmaceutically acceptable salts thereof) are useful in reducing oxidative damage in pancreatic islet cells in subjects in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in reducing oxidative damage in pancreatic islet cells in subjects in need thereof.

In some embodiments, TBMs (or derivatives, analogues, or pharmaceutically acceptable salts thereof) are useful in protecting dopaminergic cells against MPP+ toxicity in subjects in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in protecting dopaminergic cells against MPP+ toxicity in subjects in need thereof.

In some embodiments, TBMs (or derivatives, analogues, or pharmaceutically acceptable salts thereof) are useful in preventing loss of dopaminergic neurons in subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in preventing loss of dopaminergic neurons in subject in need thereof.

In some embodiments, TBMs (or derivatives, analogues, or pharmaceutically acceptable salts thereof) are useful in increasing striatal dopamine, DOPAC (3,4-dihydroxyphenylacetic acid) and HVA (homovanillic acid) levels in subjects in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2', 6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in increasing striatal dopamine, DOPAC and HVA levels in subjects in need thereof.

In some embodiments, TBMs (or derivatives, analogues, or pharmaceutically acceptable salts thereof) or peptide conjugates of the present technology (e.g., those including D-Arg-2'6'-Dmt-Lys-Phe-NH$_2$) are useful to reduce oxidative damage in a mammal in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. By way of example, but not by way of limitation, mammals in need of reducing oxidative damage are those mammals suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical (HO), superoxide anion radical ($O_2.^-$), nitric oxide (NO.), hydrogen peroxide ($H_2O_2$), hypochlorous acid (HOCl), and peroxynitrite anion ($ONOO^-$).

In some embodiments, a mammal in need thereof may be a mammal undergoing a treatment associated with oxidative damage. For example, the mammal may be undergoing reperfusion. "Reperfusion" refers to the restoration of blood flow to any organ or tissue in which the flow of blood is decreased or blocked. The restoration of blood flow during reperfusion leads to respiratory burst and formation of free radicals.

In some embodiments, a mammal in need thereof is a mammal suffering from a disease or condition associated with oxidative damage. The oxidative damage can occur in any cell, tissue or organ of the mammal. Examples of cells, tissues or organs affected by oxidative damage include, but are not limited to, endothelial cells, epithelial cells, nervous system cells, skin, heart, lung, kidney, eye and liver. For example, lipid peroxidation and an inflammatory process are associated with oxidative damage for a disease or condition.

"Lipid peroxidation" refers to oxidative modification of lipids. The lipids can be present in the membrane of a cell. This modification of membrane lipids typically results in change and/or damage to the membrane function of a cell. In addition, lipid peroxidation can also occur in lipids or lipoproteins exogenous to a cell. For example, low-density lipoproteins are susceptible to lipid peroxidation. An example of a condition associated with lipid peroxidation is atherosclerosis. Reducing oxidative damage associated with atherosclerosis is important because atherosclerosis is implicated in, for example, heart attacks and coronary artery disease.

"Inflammatory process" refers to the activation of the immune system. Typically, the immune system is activated by an antigenic substance. The antigenic substance can be any substance recognized by the immune system, and include self-derived and foreign-derived substances. Non-limiting examples of diseases or conditions resulting from an inflammatory response to self-derived substances include arthritis and multiple sclerosis. Non-limiting examples of foreign substances include viruses and bacteria.

The virus can be any virus which activates an inflammatory process, and associated with oxidative damage. Examples of viruses include, hepatitis A, B or C virus, human immunodeficiency virus, influenza virus, and bovine diarrhea virus. For example, hepatitis virus can elicit an inflammatory process and formation of free radicals, thereby damaging the liver.

The bacteria can be any bacteria, and include gram-negative and gram-positive bacteria. Gram-negative bacteria contain lipopolysaccharide in the bacteria wall. Examples of gram-negative bacteria include *Escherichia coli, Klebsiella pneumoniae, Proteus species, Pseudomonas aeruginosa, Serratia*, and *Bacteroides*. Examples of gram-positive bacteria include pneumococci and streptococci.

In some embodiments, TBMs (or derivatives, analogues, or pharmaceutically acceptable salts thereof) or the peptide conjugates of the present technology (e.g., those including D-Arg-2'6'-Dmt-Lys-Phe-NH$_2$) are useful in reducing oxidative damage associated with a neurodegenerative disease or condition. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. The neurodegenerative disease can affect any cell, tissue or organ of the central and peripheral nervous system. Non-limiting examples of such cells, tissues and organs include, the brain, spinal cord, neurons, ganglia, Schwann cells, astrocytes, oligodendrocytes and microglia.

The neurodegenerative condition can be an acute condition, such as a stroke or a traumatic brain or spinal cord injury. In some embodiments, the neurodegenerative disease or condition is a chronic neurodegenerative condition. In a chronic neurodegenerative condition, the free radicals can, for example, cause damage to a protein. An example of such a protein is amyloid precursor protein. Non-limiting examples of chronic neurodegenerative diseases associated with damage by free radicals include Parkinson's disease, Alzheimer's disease, Huntington's disease and Amyotrophic Lateral Sclerosis (ALS).

In some embodiments, TBMs (or derivatives, analogues, or pharmaceutically acceptable salts thereof) are useful in treating preeclampsia, diabetes, and symptoms of and conditions associated with aging, such as macular degeneration, and wrinkles. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in treating preeclampsia, diabetes, and symptoms of and conditions associated with aging, such as macular degeneration, and wrinkles.

In some embodiments, TBMs (or derivatives, analogues, or pharmaceutically acceptable salts thereof) or peptide conjugates of the present technology are useful in reducing oxidative damage in an organ of a mammal prior to transplantation. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. For example, a removed organ, when subjected to reperfusion after transplantation can be susceptible to oxidative damage. Therefore, the compositions of the present technology can be used to reduce oxidative damage from reperfusion of the transplanted organ.

The organ can be any organ suitable for transplantation. In some embodiments, the organ is a removed organ. Examples of such organs include, the heart, liver, kidney, lung, and pancreatic islets. In some embodiments, the removed organ is placed in a suitable medium, such as in a standard buffered solution commonly used in the art. The concentration of disclosed compositions in the standard buffered solution can be easily determined by those skilled in the art. Such concentrations may be, for example, between about 0.01 nM to about 10 μM, about 0.1 nM to about 10 μM, about 1 μM to about 5 μM, or about 1 nM to about 100 nM.

In some embodiments, TBMs (or derivatives, analogues, or pharmaceutically acceptable salts thereof) or peptide conjugates of the present technology are useful in reducing oxidative damage in a cell in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Cells in need of reducing oxidative damage are generally those cells in which the cell membrane or DNA has been damaged by free radicals, for example, ROS and/or RNS. Examples of cells capable of sustaining oxidative damage include, but are not limited to, pancreatic islet cells, myocytes, endothelial cells, neuronal cells, stem cells, and other cell types discussed herein.

The cells can be tissue culture cells. Alternatively, the cells may be obtained from a mammal. In one instance, the cells can be damaged by oxidative damage as a result of a cellular insult. Cellular insults include, for example, a disease or condition (e.g., diabetes, etc.) or ultraviolet radiation (e.g., sun, etc.). For example, pancreatic islet cells damaged by oxidative damage as a result of diabetes can be obtained from a mammal.

Due to reduction of oxidative damage, the treated cells may be capable of regenerating. Such regenerated cells may be re-introduced into the mammal from which they were derived as a therapeutic treatment for a disease or condition. As mentioned above, one such condition is diabetes.

Oxidative damage is considered to be "reduced" if the amount of oxidative damage in a mammal, a removed organ, or a cell is decreased after administration of an effective amount of the compositions described herein. Typically, oxidative damage is considered to be reduced if the oxidative damage is decreased by at least about 1%, 5%, 10%, at least about 25%, at least about 50%, at least about 75%, or at least about 90%.

In some embodiments, TBMs (or derivatives, analogues, or pharmaceutically acceptable salts thereof) are useful in regulating oxidation state of muscle tissue. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in regulating oxidation state of muscle tissue.

In some embodiments, TBMs (or derivatives, analogues, or pharmaceutically acceptable salts thereof) are useful in regulating oxidation state of muscle tissue in lean and obese human subjects. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2', 6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in regulating oxidation state of muscle tissue in lean and obese human subjects.

In some embodiments, TBMs (or derivatives, analogues, or pharmaceutically acceptable salts thereof) are useful in regulating insulin resistance in muscle tissue. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peptide conjugates of the present technology (e.g., those including D-Arg-2'6'-Dmt-Lys-Phe-NH$_2$) are useful in regulating insulin resistance in muscle tissue.

In some embodiments, insulin resistance induced by obesity or a high-fat diet affects mitochondrial bioenergetics. Without wishing to be bound by theory, it is thought that the oversupply of metabolic substrates causes a reduction on the function of the mitochondrial respiratory system, and an increase in ROS production and shift in the overall redox environment to a more oxidized state. If persistent, this leads to development of insulin resistance. Linking mitochondrial bioenergetics to the etiology of insulin resistance has a number of clinical implications. For example, it is known that insulin resistance (NIDDM) in humans often results in weight gain and, in selected individuals, increased variability of blood sugar with resulting metabolic and clinical consequences. The examples shown herein demonstrate that treatment of mitochondrial defects with the compositions disclosed herein provides a new and surprising approach to treating or preventing insulin resistance without the metabolic side-effects of increased insulin.

In some embodiments, TBMs (or derivatives, analogues, or pharmaceutically acceptable salts thereof) are useful in reducing insulin resistance. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in reducing insulin resistance.

In some embodiments, TBMs (or derivatives, analogues, or pharmaceutically acceptable salts thereof) or peptide conjugates of the present technology are useful for prophylactic and therapeutic methods of treating a subject at risk of (or susceptible to) a disorder, or a subject having a disorder associated with insulin resistance. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Insulin resistance is generally associated with type II diabetes, coronary artery disease, renal dysfunction, atherosclerosis, obesity, hyperlipidemia, and essential hypertension. Insulin resistance is also associated with fatty liver, which can progress to chronic inflammation (NASH; "nonalcoholic steatohepatitis"), fibrosis, and cirrhosis. Cumulatively, insulin resistance syndromes, including, but not limited to diabetes, underlie many of the major causes of morbidity and death of people over age 40.

In some embodiments, TBMs (or derivatives, analogues, or pharmaceutically acceptable salts thereof) are useful in methods for the prevention and/or treatment of insulin resistance and associated syndromes in a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in methods for the prevention and/or treatment of insulin resistance and associated syndromes in a subject in need thereof.

In some embodiments, TBMs (or derivatives, analogues, or pharmaceutically acceptable salts thereof) are useful in improving the sensitivity of mammalian skeletal muscle tissues to insulin. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in improving the sensitivity of mammalian skeletal muscle tissues to insulin.

In some embodiments, TBMs (or derivatives, analogues, or pharmaceutically acceptable salts thereof) are useful in preventing drug-induced obesity, insulin resistance, and/or diabetes, wherein the compound is administered with a drug that shows the side-effect of causing one or more of these conditions (e.g., olanzapine, Zyprexa®). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in preventing drug-induced obesity, insulin resistance, and/or diabetes, wherein the compound is administered with a drug that shows the side-effect of causing one or more of these conditions (e.g., olanzapine, ZYPREXA®).

Increased or decreased insulin resistance or sensitivity can be readily detected by quantifying body weight, fasting glucose/insulin/free fatty acid, oral glucose tolerance (OGTT), in vitro muscle insulin sensitivity, markers of insulin signaling (e.g., Akt-P, IRS-P), mitochondrial function (e.g., respiration or H$_2$O$_2$ production), markers of intracellular oxidative stress (e.g., lipid peroxidation, GSH/GSSG ratio or aconitase activity), or mitochondrial enzyme activity.

In some embodiments, TBMs (or derivatives, analogues, or pharmaceutically acceptable salts thereof) are useful in methods for preventing, in a subject, a disease or condition associated with insulin resistance in skeletal muscle tissues via modulating one or more signs or markers of insulin resistance, e.g., body weight, fasting glucose/insulin/free fatty acid, oral glucose tolerance (OGTT), in vitro muscle insulin sensitivity, markers of insulin signaling (e.g., Akt-P, IRS-P), mitochondrial function (e.g., respiration or H$_2$O$_2$ production), markers of intracellular oxidative stress (e.g., lipid peroxidation, GSH/GSSG ratio or aconitase activity), or mitochondrial enzyme activity. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in methods for preventing, in a subject, a disease or condition associated with insulin resistance in skeletal muscle tissues via modulating one or more signs or markers of insulin resistance, e.g., body weight, fasting glucose/insulin/free fatty acid, oral glucose tolerance (OGTT), in vitro muscle insulin sensitivity, markers of insulin signaling (e.g., Akt-P, IRS-P), mitochondrial function (e.g., respiration or $H_2O_2$ production), markers of intracellular oxidative stress (e.g., lipid peroxidation, GSH/GSSG ratio or aconitase activity), or mitochondrial enzyme activity.

In some embodiments, TBMs (or derivatives, analogues, or pharmaceutically acceptable salts thereof) are useful in treating subjects at risk for a disease that is caused or contributed to by aberrant mitochondrial function or insulin resistance. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, peptide conjugates of the present technology are useful in treating subjects at risk for a disease that is caused or contributed to by aberrant mitochondrial function or insulin resistance.

In prophylactic applications, the compositions of the present technology are administered to a subject susceptible to, or otherwise at risk of a disease or condition in an amount sufficient to eliminate or reduce the risk, or delay the onset of the disease, including biochemical, histological and/or behavioral symptoms of the disease, its complications and intermediate pathological phenotypes presenting during development of the disease. Administration of prophylactic TBMs (or derivatives, analogues, or pharmaceutically acceptable salts thereof), alone or in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$), or peptide conjugates of the present technology can occur prior to the manifestation of symptoms characteristic of the aberrancy, such that a disease or disorder is prevented or, alternatively, delayed in its progression. Depending upon the type of aberrancy, the compositions of the present technology will act to enhance or improve mitochondrial function, and can be used for treating the subject.

In some embodiments, TBMs (or derivatives, analogues, or pharmaceutically acceptable salts thereof) are useful in methods of modulating insulin resistance or sensitivity in a subject for therapeutic purposes. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, peptide conjugates of the present technology are useful in methods of modulating insulin resistance or sensitivity in a subject for therapeutic purposes.

In some embodiments, TBMs (or derivatives, analogues, or pharmaceutically acceptable salts thereof) are useful in curing or partially arresting the symptoms of the disease (biochemical, histological and/or behavioral), including its complications and intermediate pathological phenotypes in development of the disease. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, peptide conjugates of the present technology are useful in curing or partially arresting the symptoms of the disease (biochemical, histological and/or behavioral), including its complications and intermediate pathological phenotypes in development of the disease. As such, the present technology provides methods of treating an individual afflicted with an insulin resistance-associated disease or disorder.

In some embodiments, TBMs (or derivatives, analogues, or pharmaceutically acceptable salts thereof) are useful in improving the histopathological score resulting from ischemia and reperfusion. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, peptide conjugates of the present technology are useful in improving the histopathological score resulting from ischemia and reperfusion.

In some embodiments, TBMs (or derivatives, analogues, or pharmaceutically acceptable salts thereof) are useful in increasing the rate of ATP production after reperfusion in renal tissue following ischemia. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, peptide conjugates of the present technology are useful in increasing the rate of ATP production after reperfusion in renal tissue following ischemia.

In some embodiments, TBMs (or derivatives, analogues, or pharmaceutically acceptable salts thereof) are useful in improving renal mitochondrial respiration following ischemia. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, peptide conjugates of the present technology are useful in improving renal mitochondrial respiration following ischemia.

In some embodiments, TBMs (or derivatives, analogues, or pharmaceutically acceptable salts thereof) are useful in decreasing medullary fibrosis in UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, peptide conjugates of the present technology are useful in decreasing medullary fibrosis in UUO.

In some embodiments, TBMs (or derivatives, analogues, or pharmaceutically acceptable salts thereof) are useful in decreasing interstitial fibrosis in UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, peptide conjugates of the present technology are useful in decreasing interstitial fibrosis in UUO.

In some embodiments, TBMs (or derivatives, analogues, or pharmaceutically acceptable salts thereof) are useful in decreasing tubular apoptosis in UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in decreasing tubular apoptosis in UUO.

In some embodiments, TBMs (or derivatives, analogues, or pharmaceutically acceptable salts thereof) are useful in decreasing macrophage infiltration in UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in decreasing macrophage infiltration in UUO.

In some embodiments, TBMs (or derivatives, analogues, or pharmaceutically acceptable salts thereof) are useful in increasing tubular proliferation in UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in increasing tubular proliferation in UUO.

In some embodiments, TBMs (or derivatives, analogues, or pharmaceutically acceptable salts thereof) are useful in decreasing oxidative damage in UUO. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in decreasing oxidative damage in UUO.

In some embodiments, TBMs (or derivatives, analogues, or pharmaceutically acceptable salts thereof) are useful in reducing renal dysfunction caused by a radiocontrast dye. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in reducing renal dysfunction caused by a radiocontrast dye.

In some embodiments, TBMs (or derivatives, analogues, or pharmaceutically acceptable salts thereof) are useful in protecting renal tubules from radiocontrast dye injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in protecting renal tubules from radiocontrast dye injury.

In some embodiments, TBMs (or derivatives, analogues, or pharmaceutically acceptable salts thereof) are useful in preventing renal tubular apoptosis induced by radiocontrast dye injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, peptide conjugates of the present technology are useful in preventing renal tubular apoptosis induced by radiocontrast dye injury.

In some embodiments, TBMs (or derivatives, analogues, or pharmaceutically acceptable salts thereof) or peptide conjugates of the present technology are useful in protecting a subject's kidney from renal injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Acute renal injury (ARI) refers to a reduction of renal function and filtration of waste products from a patient's blood. ARI is typically characterized as including a decline of glomerular filtration rate (GFR) to a level so low that little or no urine is formed. Therefore, substances usually eliminated by the kidney remain in the body.

The causes of ARI may be caused by various factors, falling into three categories: (1) pre-renal ARI, in which the kidneys fail to receive adequate blood supply, e.g., due to reduced systemic blood pressure as in shock/cardiac arrest, or subsequent to hemorrhage; (2) intrinsic ARI, in which the failure occurs within the kidney, e.g., due to drug-induced toxicity; and (3) post-renal ARI, caused by impairment of urine flow out of the kidney, as in ureteral obstruction due to kidney stones or bladder/prostate cancer. ARI may be associated with any one or a combination of these categories.

An example of a condition in which kidneys fail to receive adequate blood supply to the kidney is ischemia. Ischemia is a major cause of ARI. Ischemia of one or both kidneys is a common problem experienced during aortic surgery, renal transplantation, or during cardiovascular anesthesia. Surgical procedures involving clamping of the aorta and/or renal arteries, e.g., surgery for supra- and juxta-renal abdominal aortic aneurysms and renal transplantation, are also particularly liable to produce renal ischemia, leading to significant postoperative complications and early allograft rejection. In high-risk patients undergoing these surgeries, the incidence of renal dysfunction has been reported to be as high as 50%. The skilled artisan will understand that the above described causes of ischemia are not limited to the kidney, but may occur in other organs during surgical procedures.

Renal ischemia may be caused by loss of blood, loss of fluid from the body as a result of severe diarrhea or burns, shock, and ischemia associated with storage of the donor kidney prior to transplantation. In these situations, the blood flow to the kidney may be reduced to a dangerously low level for a time period great enough to cause ischemic injury to the tubular epithelial cells, sloughing off of the epithelial cells into the tubular lumen, obstruction of tubular flow that leads to loss of glomerular filtration and ARI.

Subjects may also become vulnerable to ARI after receiving anesthesia, surgery, or α-adrenergic agonists because of related systemic or renal vasoconstriction. Additionally, systemic vasodilation caused by anaphylaxis, and antihypertensive drugs, sepsis or drug overdose may also cause ARI because the body's natural defense is to shut down, i.e., vasoconstriction of non-essential organs such as the kidneys.

Accordingly, in some embodiments, a subject at risk for ARI may be a subject undergoing an interruption or reduction of blood supply or blood pressure to the kidney. In some embodiments, these subjects may be administered TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology prior to or simultaneously with such interruption or reduction of blood supply. Likewise, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology may be administered after the therapeutic agent to treat ischemia.

Another cause of ARI includes drug-induced toxicity. For example, nephrotoxins can cause direct toxicity on tubular epithelial cells. Nephrotoxins include, but are not limited to, therapeutic drugs, e.g., cisplatin, gentamicin, cephaloridine, cyclosporin, amphotericin, radiocontrast dye (described in further detail below), pesticides (e.g., paraquat), and environmental contaminants (e.g., trichloroethylene and dichloroacetylene). Other examples include puromycin aminonucleoside (PAN); aminoglycosides, such as gentamicin; cephalosporins, such as cephaloridine; calcineurin inhibitors, such as tacrolimus or sirolimus. Drug-induced nephrotoxicity may also be caused by non-steroidal anti-inflammatories, antiretrovirals, anticytokines, immunosuppressants, oncological drugs, or angiotensin-converting-enzyme (ACE) inhibitors. The drug-induced nephrotoxicity may further be caused by analgesic abuse, ciprofloxacin, clopidogrel, cocaine, cox-2 inhibitors, diuretics, foscarnet, gold, ifosfamide, immunoglobulin, Chinese herbs, interferon, lithium, mannitol, mesalamine, mitomycin, nitrosoureas, penicillamine, penicillins, pentamidine, quinine, rifampin, streptozocin, sulfonamides, ticlopidine, triamterene, valproic acid, doxorubicin, glycerol, cidofovir, tobramycin, neomycin sulfate, colistimethate, vancomycin, amikacin, cefotaxime, cisplatin, acyclovir, lithium, interleukin-2, cyclosporin, or indinavir.

In addition to direct toxicity on tubular epithelial cells, some nephrotoxins also reduce renal perfusion, causing injury to zones known to have limited oxygen availability (inner medullary region). Such nephrotoxins include amphotericin and radiocontrast dyes. Renal failure can result even from clinically relevant doses of these drugs when combined with ischemia, volume depletion, obstruction, or infection. An example is the use of radiocontrast dye in patients with impaired renal function. The incidence of contrast dye-induced nephropathy (CIN) is 3-8% in the normal patient, but increases to 25% for patients with diabetes mellitus. Most cases of ARI occur in patients with predisposing co-morbidities (McCombs, P. R. & Roberts, B., *Surg Gynecol. Obstet.*, 148:175-178 (1979)).

Accordingly, in one embodiment, a subject at risk for ARI is receiving one or more therapeutic drugs that have a nephrotoxic effect. The subject is administered TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology prior to or simultaneously with such therapeutic agents. Likewise, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology may be administered after the therapeutic agent to treat nephrotoxicity.

In one embodiment, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject at risk for CIN, in order to prevent the condition. CIN is an important cause of acute renal failure. CIN is defined as acute renal failure occurring within 48 hours of exposure to intravascular radiographic contrast material, and remains a common complication of radiographic procedures.

CIN arises when a subject is exposed to radiocontrast dye, such as during coronary, cardiac, or neuro-angiography procedures. Contrast dye is essential for many diagnostic and interventional procedures because it enables doctors to visualize blocked body tissues. A creatinine test can be used to monitor the onset of CIN, treatment of the condition, and efficacy of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology in treating or preventing CIN.

In some embodiments, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject prior to or simultaneously with the administration of a contrast agent in order to provide protection against CIN. For example, the subject may receive the compositions from about 1 to 2 hours, about 1 to 6 hours, about 1 to 12 hours, about 1 to 24 hours, or about 1 to 48 hours prior to receiving the contrast agent. Likewise, the subject may be administered the compositions at about the same time as the contrast agent. Moreover, administration of the compositions to the subject may continue following administration of the contrast agent. In some embodiments, the subject continues to receive the compositions at intervals of about 1, 2, 3, 4, 5, 6, 7, 8, 12, 24, and 48 hours following administration of the contrast agent, in order to provide a protective or prophylactic effect against CIN.

In some embodiments, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject after administration of a contrast agent in order to treat CIN. For example, the subject receives the compositions from about 1 to 2 hours, about 1 to 6 hours, about 1 to 12 hours, about 1 to 24 hours, about 1 to 48 hours, or about 1 to 72 hours after receiving the contrast agent. For instance, the subject may exhibit one or more signs or symptoms of CIN prior to receiving the compositions of the present technology, such as increased serum creatinine levels and/or decreased urine volume. Administration of the compositions of the present technology improves one or more of these indicators of kidney function in the subject compared to a control subject not administered the compositions.

In one embodiment of the method, a subject in need thereof may be a subject having impairment of urine flow. Obstruction of the flow of urine can occur anywhere in the urinary tract and has many possible causes, including but not limited to, kidney stones or bladder/prostate cancer. UUO is a common clinical disorder associated with obstructed urine flow. It is also associated with tubular cell apoptosis, macrophage infiltration, and interstitial fibrosis. Interstitial fibrosis leads to a hypoxic environment and contributes to progressive decline in renal function despite surgical correction. Thus, a subject having or at risk for UUO may be administered TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to prevent or treat ARI.

In yet another aspect of the present technology, a method for protecting a kidney from renal fibrosis in a mammal in need thereof is provided. The method comprises administering to the mammal an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology as described herein. The compositions described herein can be administered to a mammal in need thereof, as described herein, by any method known to those skilled in the art.

In some embodiments, TBMs (or derivatives, analogues, or pharmaceutically acceptable salts thereof) or peptide conjugates of the present technology are useful in methods for treating ARI in a mammal in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. The method comprises administering to the mammal an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology as described herein. The compositions described herein can be administered to a mammal in need thereof, as described herein, by any method known to those skilled in the art. The methods of the present technology may be particularly useful in patients with renal insufficiency, renal failure, or end-stage renal disease attributable at least in part to a nephrotoxicity of a drug or chemical. Other indications may include creatinine clearance levels of lower than 97 (men) and 88 (women) mL/min, or a blood urea level of 20-25 mg/dl or higher. Furthermore, the treatment may be useful in patients with microalbuminuria, macroalbuminuria, and/or proteinuria levels of over 1, 2, 3, 4, 5, 6, 7, 8, 9, or 10 g or more per a 24 hour period, and/or serum creatinine levels of about 1.0, 1.5, 2.0, 2.5, 3, 3.5, 4.0, 4.5, 5, 5.5, 6, 7, 8, 9, 10 mg/dl or higher.

The methods of the present technology can be used to slow or reverse the progression of renal disease in patients whose renal function is below normal, relative to control subjects. In some embodiments, the methods of the present technology slow the loss of renal function. By way of example, but not by way of limitation, in some embodiments, loss of renal function is slowed by at least 1%, 5%, 10%, 20%, 30%, 40%, 50%, 60%, 70%, 80%, 90%, 100% or more, relative to control subjects. In other embodiments, the methods of the present technology improve the patient's serum creatinine levels, proteinuria, and/or urinary albumin excretion. By way of example, but not by way of limitation, in some embodiments, the patient's serum creatinine levels, proteinuria, and/or urinary albumin excretion is improved by at least 1%, 10%, 20%, 30%, 40%, 50%, 60%, 70%, or more, relative to control subjects. Non-limiting illustrative methods for assessing renal function are described herein and, for example, in WO 01/66140.

In some embodiments, TBMs (or derivatives, analogues, or pharmaceutically acceptable salts thereof) or peptide conjugates of the present technology are useful in protecting a subject's kidney from ARI prior to transplantation. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. For example, a removed kidney can be placed in a solution containing the compositions described herein. The concentration of compositions in the standard buffered solution can be easily determined by those skilled in the art. Such concentrations may be, for example, between about 0.01 nM to about 10 µM, about 0.1 nM to about 10 µM, about 1 µM to about 5 µM, or about 1 nM to about 100 nM.

In some embodiments, TBMs (or derivatives, analogues, or pharmaceutically acceptable salts thereof) or peptide conjugates of the present technology are useful in preventing or treating ARI and are also applicable to tissue injury and organ failure in other systems besides the kidney. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, TBMs (or derivatives, analogues, or pharmaceutically acceptable salts thereof) or peptide conjugates of the present technology are useful in minimizing cell death, inflammation, and fibrosis. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in methods of treating a subject having a tissue injury, e.g., noninfectious pathological conditions such as pancreatitis, ischemia, multiple trauma, hemorrhagic shock, and immune-mediated organ injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. The tissue injury can be associated with, for example, aortic aneurysm repair, multiple trauma, peripheral vascular disease, renal vascular disease, myocardial infarction, stroke, sepsis, and multi-organ failure. In one aspect, the present technology relates to a method of treating a subject having a tissue such as from heart, brain, vasculature, gut, liver, kidney and eye that is subject to an injury and/or ischemic event. The method includes administering to the subject a therapeutically effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to provide a therapeutic or prophylactic effect.

In some embodiments, TBMs (or derivatives, analogues, or pharmaceutically acceptable salts thereof) or peptide conjugates of the present technology are useful in improving a function of one or more organs selected from the group consisting of: renal, lung, heart, liver, brain, pancreas, and the like. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In a particular embodiment, the improvement in lung function is selected from the group consisting of lower levels of edema, improved histological injury score, and lower levels of inflammation.

In some embodiments, TBMs (or derivatives, analogues, or pharmaceutically acceptable salts thereof) or peptide conjugates of the present technology are useful in the prevention and/or treatment of acute hepatic injury caused by ischemia, drugs (e.g., acetaminophen, alcohol), viruses, obesity (e.g., non-alcoholic steatohepatitis), and obstruction (e.g., bile duct obstruction, tumors). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, TBMs (or derivatives, analogues, or pharmaceutically acceptable salts thereof) or peptide conjugates of the present technology are useful in preventing or treating acute liver failure (ALF) in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. ALF is a clinical condition that results from severe and extensive damage of liver cells leading to failure of the liver to function normally. ALF results from massive necrosis of liver cells leading to hepatic encephalopathy and severe impairment of hepatic function. It has various causes, such as viral hepatitis (A, B, C), drug toxicity, frequent alcohol intoxication, and autoimmune hepatitis. ALF is a very severe clinical condition with high mortality rate. Drug-related hepatotoxicity is the leading cause of ALF in the United States.

In some embodiments, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject prior to or simultaneously with the administration of a drug or agent known or suspected to induced hepatotoxicity, e.g., acetaminophen, in order to provide protection against ALF. For example, the subject may receive the compositions from about 1 to 2 hours, about 1 to 6 hours, about 1 to 12 hours, about 1 to 24 hours, or about 1 to 48 hours prior to receiving the drug or agent. Likewise, the subject may be administered the compositions at about the same time as the drug or agent to provide a prophylactic effect against ALF caused by the drug or agent. Moreover, administration of the compositions to the subject may continue following administration of the drug or agent. In some embodiments, the subject may continue to receive the compositions at intervals of about 1, 2, 3, 4, 5, 6, 7, 8, 12, 24, and 48 hours following administration of the drug or agent, in order to provide a protective or prophylactic effect.

In some embodiments, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject exhibiting one or more signs or symptoms of ALF, including, but not limited to, elevated levels of hepatic enzymes (transaminases, alkaline phosphatase), elevated serum bilirubin, ammonia, glucose, lactate, or creatinine. Administration of the compositions of the present technology improves one or more of these indicators of liver function in the subject compared to a control subject not administered the compositions. The subject may receive TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology from about 1 to 2 hours, about 1 to 6 hours, about 1 to 12 hours, about 1 to 24 hours, about 1 to 48 hours, or about 1 to 72 hours after the first signs or symptoms of ALF.

In some embodiments, TBMs (or derivatives, analogues, or pharmaceutically acceptable salts thereof) or peptide conjugates of the present technology are useful in treating or ameliorating the local and distant pathophysiological effects of burn injury, including, but not limited to, hypermetabolism and organ damage. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2', 6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in treating or preventing burn injuries and systemic conditions associated with a burn injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject following a burn and after the onset of detectable symptoms of systemic injury. Thus, the term "treatment" is used herein in its broadest sense and refers to use of a composition for a partial or complete cure of the burn and/or secondary complications, such as organ dysfunction and hypermetabolism.

In other embodiments, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject following a burn, but before the onset of detectable symptoms of systemic injury in order to protect against or provide prophylaxis for the systemic injury, such as organ damage or hypermetabolism. Thus the term "prevention" is used herein in its broadest sense and refers to a prophylactic use which completely or partially prevents local injury to the skin or systemic injury, such as organ dysfunction or hypermetabolism following burns. It is also contemplated that the compositions may be administered to a subject at risk of receiving burns.

Burns are generally classified according to their severity and extent. First degree burns are the mildest and typically affect only the epidermis. The burn site appears red, and is painful, dry, devoid of blisters, and may be slightly moist due to fluid leakage. Mild sunburn is typical of a first degree burn. In second degree burns, both the epidermis and dermis are affected. Blisters usually appear on the skin, with damage to nerves and sebaceous glands. Third degree burns are the most serious, with damage to all layers of the skin, including subcutaneous tissue. Typically there are no blisters, with the burned surface appearing white or black due to charring, or bright red due to blood in the bottom of the wound. In most cases, the burn penetrates the superficial fascia, extending into the muscle layers where arteries and veins are affected. Because of nerve damage, it is possible for the burn to be painless.

In some embodiments, TBMs (or derivatives, analogues, or pharmaceutically acceptable salts thereof) or peptide conjugates of the present technology are useful in the treatment of burns from any cause, including dry heat or cold burns, scalds, sunburn, electrical burns, chemical agents such as acids and alkalis, including hydrofluoric acid, formic acid, anhydrous ammonia, cement, and phenol, or radiation burns. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Burns resulting from exposure to either high or low temperature are within the scope of the present technology. The severity and extent of the burn may vary, but secondary organ damage or hypermetabolism will usually arise when the burns are very extensive or very severe (second or third degree burns). The development of secondary organ dysfunction or failure is dependent on the extent of the burn, the response of the patient's immune system and other factors, such as infection and sepsis.

In some embodiments, TBMs (or derivatives, analogues, or pharmaceutically acceptable salts thereof) or peptide conjugates of the present technology are useful in treating or preventing organ dysfunction secondary to a burn. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. The chain of physiological processes which lead to organ dysfunction following burns is complex. In subjects with serious burns, release of catecholamines, vasopressin, and angiotensin causes peripheral and splanchnic bed vasoconstriction that can compromise the perfusion of organs remote to the injury. Myocardial contractility also may be reduced by the release of TNF-α. Activated neutrophils are sequestered in dermal and distant organs, such as the lung, within hours following a burn injury, resulting in the release of toxic reactive oxygen species and proteases and producing vascular endothelial cell damage. When the integrity of pulmonary capillary and alveolar epithelia is compromised, plasma and blood leak into the interstitial and intra-alveolar spaces, resulting in pulmonary edema. A decrease in pulmonary function can occur in severely burned patients, as a result of bronchoconstriction caused by humoral factors, such as histamine, serotonin, and thromboxane A2.

Subjects suffering from a burn injury are also at risk for skeletal muscle dysfunction. While not wishing to be limited by theory, burn-induced mitochondrial skeletal muscle dysfunction is thought to result from defects in oxidative phosphorylation (OXPHOS) via stimulation of mitochondrial production of reactive oxygen species (ROS) and the resulting damage to the mitochondrial DNA (mtDNA). In some embodiments, TBMs (or derivatives, analogues, or pharmaceutically acceptable salts thereof) or peptide conjugates of the present technology are useful in inducing ATP synthesis via a recovery of the mitochondrial redox status or via the peroxisome proliferator activated receptor-gamma coactivator-1β, which is down-regulated as early as 6 hours after a burn. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in ameliorating mitochondrial dysfunction caused by a burn injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in treating a wound resulting from a burn injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology may be administered systemically or topically to the wound. Burn wounds are typically uneven in depth and severity. There are typically significant areas around the coagulated tissue where injury may be reversible and damage mediated by the inflammatory and immune cells to the microvasculature of the skin could be prevented. In one embodiment, the administration of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology slows or ameliorates the effects of wound contraction. Wound contraction is the process which diminishes the size of a full-thickness open wound, especially a full-thickness burn. The tensions developed during contracture and the formation of subcutaneous fibrous tissue can result in deformity, and in particular to fixed flexure or fixed extension of a joint where the wound involves an area over the joint. Such complications are especially relevant in burn healing. No wound contraction will occur when there is no injury to the tissue, and maximum contraction will occur when the burn is full thickness and no viable tissue remains in the wound. In some embodiments, TBMs (or derivatives, analogues, or pharmaceutically acceptable salts thereof) or peptide conjugates of the present technology are useful in preventing progression of a burn injury from a second degree burn to a third degree burn. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in decreasing scarring or the formation of scar tissue attendant the healing process at a burn site. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Scarring is the formation of fibrous tissue at sites where normal tissue has been destroyed. The present disclosure thus also includes a method for decreasing scarring following a second or third degree burn. This method comprises treating an animal with a second or third degree burn with an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology.

In some embodiments, TBMs (or derivatives, analogues, or pharmaceutically acceptable salts thereof) or peptide conjugates of the present technology are useful in treating or preventing damage to distant organs or tissues in a subject suffering from a burn. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In particular, dysfunction or failure of the lung, liver, kidneys, and/or bowel following burns to the skin or other sites of the body has a significant impact on morbidity and mortality. While not wishing to be limited by theory, it is believed that systemic inflammatory responses arise in subjects following burn injury, and that it is this generalized inflammation which leads to remote tissue injury which is expressed as the dysfunction and failure of organs remote from the injury site. Systemic injury, including organ dysfunction and hypermetabolism, is typically associated with second and third degree burns. A characteristic of the systemic injury, i.e., organ dysfunction or hypermetabolism, is that the burn which provokes the subsequent injury or condition does not directly affect the organ in question, i.e., the injury is secondary to the burn.

In some embodiments, TBMs (or derivatives, analogues, or pharmaceutically acceptable salts thereof) or peptide conjugates of the present technology are useful in treating or protecting damage to liver tissues secondary to a burn. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Methods for assessing liver function are well known in the art and include, but are not limited to, using blood tests for serum alanine aminotransferase (ALT) levels, alkaline phosphatase (AP), or bilirubin levels. Methods for assessing deterioration of liver structure are also well known. Such methods include liver imaging (e.g., MRT, ultrasound), or histological evaluation of liver biopsy.

In some embodiments, TBMs (or derivatives, analogues, or pharmaceutically acceptable salts thereof) or peptide conjugates of the present technology are useful in treating or protecting damage to kidney tissues secondary to a burn. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Methods for assessing kidney function are well known in the art and include, but are not limited to, using blood tests for serum creatinine, or glomerular filtration rate. Methods for assessing deterioration of kidney structure are also well known. Such methods include kidney imaging (e.g., MRI, ultrasound), or histological evaluation of kidney biopsy.

In some embodiments, TBMs (or derivatives, analogues, or pharmaceutically acceptable salts thereof) or peptide conjugates of the present technology are useful in preventing or treating hypermetabolism associated with a burn injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe- NH$_2$) will show a synergistic effect in this regard. A hypermetabolic state may be associated with hyperglycemia, protein loss, and a significant reduction of lean body mass. Reversal of the hypermetabolic response may be accomplished by administering TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology and by manipulating the subject's physiologic and biochemical environment through the administration of specific nutrients, growth factors, or other agents. As demonstrated in the examples, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology may be administered to a subject suffering from a burn in order to treat or prevent hypermetabolism.

In one aspect, the disclosure provides method for preventing in a subject, a burn injury or a condition associated with a burn injury, by administering TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to the subject. TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology may be administered to a subject at risk of receiving burns. In prophylactic applications, pharmaceutical compositions or medicaments of compositions of the present technology are administered to a subject susceptible to, or otherwise at risk of a burn injury to eliminate or reduce the risk, or delay the onset of the burn injury and its complications.

Another aspect of the disclosure includes methods of treating or preventing burn injuries and associated complications in a subject for therapeutic purposes. In therapeutic applications, compositions or medicaments are administered to a subject already suffering from a burn injury in an amount sufficient to cure, or partially arrest, the symptoms of the injury, including its complications and intermediate pathological phenotypes in development of the disease. TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology may be administered to a subject following a burn, but before the development of detectable symptoms of a systemic injury, such as organ dysfunction or failure, and thus the term "prevention" as used herein in its broadest sense and refers to a prophylactic use which completely or partially prevents systemic injury, such as organ dysfunction or failure or hypermetabolism following burns.

In some embodiments, TBMs (or derivatives, analogues, or pharmaceutically acceptable salts thereof) or peptide conjugates of the present technology can prevent or treat Metabolic Syndrome in mammalian subjects. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some cases, the Metabolic Syndrome may be due to a high-fat diet or, more generally, over-nutrition and lack of exercise. TBMs (or derivatives, analogues, or pharmaceutically acceptable salts thereof) or peptide conjugates of the present technology may reduce one or more signs or symptoms of Metabolic Syndrome, including, but not limited to, dyslipidemia, central obesity, blood fat disorders, and insulin resistance. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

Without wishing to be bound by theory, it is thought that loss of mitochondrial integrity and insulin sensitivity stem from a common metabolic disturbance, i.e., oxidative stress. Over-nutrition, particularly from high-fat diets may increase mitochondrial reactive oxygen species (ROS) production and overall oxidative stress, leading to the development of metabolic syndrome. TBMs (or derivatives, analogues, or pharmaceutically acceptable salts thereof) or peptide conjugates of the present technology mitigate these effects, thereby improving mitochondrial function in various body tissues, and improving one or more of the risk factors associated with Metabolic Syndrome. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

The present disclosure provides for both prophylactic and therapeutic methods of treating a subject at risk of (or susceptible to) Metabolic Syndrome. Metabolic Syndrome is generally associated with type II diabetes, coronary artery disease, renal dysfunction, atherosclerosis, obesity, dyslipidemia, and essential hypertension. Accordingly, the present methods provide for the prevention and/or treatment of Metabolic Syndrome or associated conditions in a subject by administering an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a subject in need thereof. For example, a subject may be administered TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to improve one or more of the factors contributing to Metabolic Syndrome. In some embodiments, TBMs (or derivatives, analogues, or pharmaceutically acceptable salts thereof) or peptide conjugates of the present technology are useful in reducing the symptoms of Metabolic Syndrome. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg- Phe-Lys-NH$_2$, Phe-D-Arg-Phe-Lys-NH$_2$, or D-Arg-2',6'-Dmt-Lys-Phe-NH$_2$) will show a synergistic effect in this regard.

In one aspect, the technology may provide a method of treating or preventing the specific disorders associated with Metabolic Syndrome, such as obesity, diabetes, hypertension, and hyperlipidemia, in a mammal by administering TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology. In certain embodiments, the specific disorder may be obesity. In certain embodiments, the specific disorder may be dyslipidemia (i.e., hyperlipidemia).

In one embodiment, administration of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a subject exhibiting one or more conditions associated with Metabolic Syndrome will cause an improvement in one or more of those conditions (e.g., an improvement in one or more of body weight, LDL cholesterol level, HDL cholesterol level, triglyceride level, oral glucose tolerance). By way of example, but not by way of limitation, in some embodiments, a subject may exhibit at least about 5%, at least about 10%, at least about 20%, or at least about 50% reduction in body weight compared to the subject prior to receiving the TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology. By way of example, but not by way of limitation, in some embodiments, a subject may exhibit at least about 5%, at least about 10%, at least about 20%, or at least about 50% reduction in LDL cholesterol and/or at least about 5%, at least about 10%, at least about 20%, or at least about 50% increase in HDL cholesterol compared to the subject prior to receiving the TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology. By way of example, but not by way of limitation, in some embodiments, a subject may exhibit at least about 5%, at least about 10%, at least about 20%, or at least about 50% reduction in some triglycerides compared to the subject prior to receiving the TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology. By way of example, but not by way of limitation, in some embodiments, a subject may exhibit at least about 5%, at least about 10%, at least about 20%, or at least about 50% improvement in oral glucose tolerance (OGTT) compared to the subject prior to receiving the TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology. In some embodiments, the subject may show observable improvement in more than one condition associated with Metabolic Syndrome.

In one aspect, the present technology provides a method for preventing, in a subject, a disease or condition associated with Metabolic Syndrome in skeletal muscle tissues, by administering to the subject TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology that modulate one or more signs or markers of metabolic syndrome, e.g., body weight, serum triglycerides or cholesterol, fasting glucose/insulin/free fatty acid, oral glucose tolerance (OGTT), in vitro muscle insulin sensitivity, markers of insulin signaling (e.g., Akt-P, IRS-P), mitochondrial function (e.g., respiration or H$_2$O$_2$ production), markers of intracellular oxidative stress (e.g., lipid peroxidation, GSH/GSSG ratio or aconitase activity) or mitochondrial enzyme activity. The fasting glucose/insulin/free fatty acid, oral glucose tolerance (OGTT), cholesterol and triglyceride levels, etc. may be measured using standard clinical laboratory techniques well-known in the art.

Subjects at risk for Metabolic Syndrome can be identified by, e.g., any or a combination of diagnostic or prognostic assays as described herein. In prophylactic applications, pharmaceutical compositions or medicaments of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject susceptible to, or otherwise at risk for a disease or condition in an amount sufficient to eliminate or reduce the risk, or delay the onset of the disease, including biochemical, histologic and/or behavioral symptoms of the disease, its complications and intermediate pathological phenotypes presenting during development of the disease. Administration of the prophylactic compositions of the present technology can occur prior to the manifestation of symptoms characteristic of the aberrancy, such that a disease or disorder is prevented or, alternatively, delayed in its progression. Depending upon the type of aberrancy, TBMs (or derivatives, analogues, or pharmaceutically acceptable salts thereof) or peptide conjugates of the present technology, which act to enhance or improve mitochondrial function, can be used for treating the subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

Another aspect of the technology includes methods of reducing the symptoms associated with Metabolic Syndrome in a subject for therapeutic purposes. In therapeutic applications, compositions or medicaments of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject suspected of, or already suffering from such a disease in an amount sufficient to cure, or partially arrest, the symptoms of the disease, including its complications and intermediate pathological phenotypes in development of the disease. As such, the present technology provides methods of treating an individual afflicted with Metabolic Syndrome or a Metabolic Syndrome-associated disease or disorder.

The present disclosure also contemplates combination therapies of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$), or peptide conjugates of the present technology with one or more agents for the treatment of blood pressure, blood triglyceride levels, or high cholesterol. Treatment for Metabolic Syndrome, obesity, insulin resistance, high blood pressure, dyslipidemia, etc., can also include a variety of other approaches, including weight loss and exercise, and dietary changes. These dietary changes include: maintaining a diet that limits carbohydrates to 50 percent or less of total calories; eating foods defined as complex carbohydrates, such as whole grain bread (instead of white), brown rice (instead of white), sugars that are unrefined, increasing fiber consumption by eating legumes (for example, beans), whole grains, fruits and vegetables, reducing intake of red meats and poultry, consumption of "healthy" fats, such as those in olive oil, flaxseed oil and nuts, limiting alcohol intake, etc. In addition, treatment of blood pressure, and blood triglyceride levels can be controlled by a variety of available drugs (e.g., cholesterol modulating drugs), as can clotting disorders (e.g., via aspirin therapy) and in general, prothrombotic or proinflammatory states. If Metabolic Syndrome leads to diabetes, there are, of course, many treatments available for this disease.

In some embodiments, TBMs (or derivatives, analogues, or pharmaceutically acceptable salts thereof) or peptide conjugates of the present technology are useful in the treatment or prevention of an ophthalmic condition. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. Without wishing to be limited by theory, TBMs (or derivatives, analogues, or pharmaceutically acceptable salts thereof) or peptide conjugates of the present technology may treat or prevent ophthalmic diseases or conditions by reducing the severity or occurrence of oxidative damage in the eye. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In one embodiment, the ophthalmic condition is selected from the group consisting of: dry eye, diabetic retinopathy, cataracts, retinitis pigmentosa, glaucoma, macular degeneration, choroidal neovascularization, retinal degeneration, and oxygen-induced retinopathy.

In some embodiments, TBMs (or derivatives, analogues, or pharmaceutically acceptable salts thereof) or peptide conjugates of the present technology are useful in reducing intracellular reactive oxygen species (ROS) in human retinal epithelial cells (HRECs). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard.

In some embodiments, TBMs (or derivatives, analogues, or pharmaceutically acceptable salts thereof) or peptide conjugates of the present technology are useful in preventing the mitochondrial potential loss of HRECs treated with high-glucose. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. The $\Delta\psi m$ of HRECs can be measured by flow cytometry after JC-1 fluorescent probe staining. High glucose (30 mM) treatment results in a rapid loss of mitochondrial membrane potential of the cultured HRECs. In some embodiments, TBMs (or derivatives, analogues, or pharmaceutically acceptable salts thereof) or peptide conjugates of the present technology are useful in increasing $\Delta\psi m$ in high glucose treated HRECs. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard.

In some embodiments, TBMs (or derivatives, analogues, or pharmaceutically acceptable salts thereof) or peptide conjugates of the present technology are useful in reducing the elevated expression of caspase-3 in high glucose-treated HRECs. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, TBMs (or derivatives, analogues, or pharmaceutically acceptable salts thereof) or peptide conjugates of the present technology are useful in increasing the expression of Trx2 in the high glucose-treated HRECs. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$), or peptide conjugates of the present technology will have no adverse effects on the viability of primary human retinal pigment epithelial (RPE) cells.

In some embodiments, TBMs (or derivatives, analogues, or pharmaceutically acceptable salts thereof) or peptide conjugates of the present technology are useful in both prophylactic and therapeutic methods of treating a subject at risk of (or susceptible to) an ophthalmic disease or condition. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-

Dmt-Lys-Phe-NH$_2$) will show a synergistic effect in this regard. Accordingly, the present methods provide for the prevention and/or treatment of an ophthalmic condition in a subject by administering an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a subject in need thereof. For example, a subject can be administered compositions comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to improve one or more of the factors contributing to an ophthalmic disease or condition.

One aspect of the present technology includes methods of reducing an ophthalmic condition in a subject for therapeutic purposes. In therapeutic applications, compositions or medicaments comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject known to have or suspected of having a disease, in an amount sufficient to cure, or at least partially arrest/reduce, the symptoms of the disease, including complications and intermediate pathological phenotypes in development of the disease. As such, the disclosure provides methods of treating an individual afflicted with an ophthalmic condition. In some embodiments, the technology provides a method of treating or preventing specific ophthalmic disorders, such as diabetic retinopathy, cataracts, retinitis pigmentosa, glaucoma, choroidal neovascularization, retinal degeneration, and oxygen-induced retinopathy, in a mammal by administering TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology.

In some embodiments, TBMs (or derivatives, analogues, or pharmaceutically acceptable salts thereof) or peptide conjugates of the present technology are useful in treating or preventing diabetic retinopathy in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Diabetic retinopathy is characterized by capillary microaneurysms and dot hemorrhaging. Thereafter, microvascular obstructions cause cotton wool patches to form on the retina. Moreover, retinal edema and/or hard exudates may form in individuals with diabetic retinopathy due to increased vascular hyperpermeability. Subsequently, neovascularization appears and retinal detachment is caused by traction of the connective tissue grown in the vitreous body. Iris rubeosis and neovascular glaucoma may also occur which, in turn, can lead to blindness. The symptoms of diabetic retinopathy include, but are not limited to, difficulty reading, blurred vision, sudden loss of vision in one eye, seeing rings around lights, seeing dark spots, and/or seeing flashing lights.

In some embodiments, TBMs (or derivatives, analogues, or pharmaceutically acceptable salts thereof) or peptide conjugates of the present technology are useful in treating or preventing cataracts in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Cataracts are a congenital or acquired disease characterized by a reduction in natural lens clarity. Individuals with cataracts may exhibit one or more symptoms, including, but not limited to, cloudiness on the surface of the lens, cloudiness on the inside of the lens, and/or swelling of the lens. Typical examples of congenital cataract-associated diseases are pseudo-cataracts, membrane cataracts, coronary cataracts, lamellar cataracts, punctuate cataracts, and filamentary cataracts. Typical examples of acquired cataract-associated diseases are geriatric cataracts, secondary cataracts, browning cataracts, complicated cataracts, diabetic cataracts, and traumatic cataracts. Acquired cataracts are also inducible by electric shock, radiation, ultrasound, drugs, systemic diseases, and nutritional disorders. Acquired cataracts further include postoperative cataracts.

In some embodiments, TBMs (or derivatives, analogues, or pharmaceutically acceptable salts thereof) or peptide conjugates of the present technology are useful in treating or preventing retinitis pigmentosa in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Retinitis pigmentosa is a disorder that is characterized by rod and/or cone cell damage. The presence of dark lines in the retina is typical in individuals suffering from retinitis pigmentosa. Individuals with retinitis pigmentosa also present with a variety of symptoms including, but not limited to, headaches, numbness or tingling in the extremities, light flashes, and/or visual changes. See, e.g., Heckenlively, et al., *Am. J. Ophthalmol.* 105(5):504-511 (1988).

In some embodiments, TBMs (or derivatives, analogues, or pharmaceutically acceptable salts thereof) or peptide conjugates of the present technology are useful in treating or preventing glaucoma in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Glaucoma is a genetic disease characterized by an increase in intraocular pressure, which leads to a decrease in vision. Glaucoma may emanate from various ophthalmologic conditions that are already present in an individual, such as, wounds, surgery, and other structural malformations. Although glaucoma can occur at any age, it frequently develops in elderly individuals and leads to blindness. Glaucoma patients typically have an intraocular pressure in excess of 21 mm Hg. However, normal tension glaucoma, where glaucomatous alterations are found in the visual field and optic papilla, can occur in the absence of such increased intraocular pressures, i.e., greater than 21 mm Hg. Symptoms of glaucoma include, but are not limited to, blurred vision, severe eye pain, headache, seeing haloes around lights, nausea, and/or vomiting.

In some embodiments, TBMs (or derivatives, analogues, or pharmaceutically acceptable salts thereof) or peptide conjugates of the present technology are useful in treating or preventing macular degeneration in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Macular degeneration is typically an age-related disease. The general categories of macular degeneration include wet, dry, and non-aged related macular degeneration. Dry macular degeneration, which accounts for about 80-90 percent of all cases, is also known as atrophic, nonexudative, or drusenoid macular degeneration. With dry macular degeneration, drusen typically accumulate beneath the retinal pigment epithelium tissue. Vision loss subsequently occurs when drusen interfere with the function of photoreceptors in the macula. Symptoms of dry macular generation include, but are not limited to, distorted vision, center-vision distortion, light or dark distortion, and/or changes in color perception. Dry macular degeneration can result in the gradual loss of vision.

In some embodiments, TBMs (or derivatives, analogues, or pharmaceutically acceptable salts thereof) or peptide conjugates of the present technology are useful in treating or preventing choroidal neovascularization in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Choroidal neovascularization (CNV) is a disease characterized by the development of new blood vessels in the choroid layer of the eye. The newly formed blood vessels grow in the choroid, through the Bruch membrane, and invade the sub-retinal space. CNV can lead to the impairment of sight or complete loss of vision. Symptoms of CNV include, but are not limited to, seeing flickering, blinking lights, or gray spots in the affected eye or eyes, blurred vision, distorted vision, and/or loss of vision.

In some embodiments, TBMs (or derivatives, analogues, or pharmaceutically acceptable salts thereof) or peptide conjugates of the present technology are useful in treating or preventing retinal degeneration in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Retinal degeneration is a genetic disease that relates to the break-down of the retina. Retinal tissue may degenerate for various reasons, such as, artery or vein occlusion, diabetic retinopathy, retinopathy of prematurity, and/or retrolental fibroplasia. Retinal degradation generally includes retinoschisis, lattice degeneration, and is related to progressive macular degeneration. The symptoms of retina degradation include, but are not limited to, impaired vision, loss of vision, night blindness, tunnel vision, loss of peripheral vision, retinal detachment, and/or light sensitivity.

In some embodiments, TBMs (or derivatives, analogues, or pharmaceutically acceptable salts thereof) or peptide conjugates of the present technology are useful in treating or preventing oxygen-induced retinopathy in a subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Oxygen-induced retinopathy (OIR) is a disease characterized by microvascular degeneration. OIR is an established model for studying retinopathy of prematurity. OIR is associated with vascular cell damage that culminates in abnormal neovascularization. Microvascular degeneration leads to ischemia which contributes to the physical changes associated with OIR. Oxidative stress also plays an important role in the development of OIR where endothelial cells are prone to peroxidative damage. Pericytes, smooth muscle cells, and perivascular astrocytes, however, are generally resistant to peroxidative injury. See, e.g., Beauchamp, et al., *J. Appl. Physiol.* 90:2279-2288 (2001). OIR, including retinopathy of prematurity, is generally asymptomatic. However, abnormal eye movements, crossed eyes, severe nearsightedness, and/or leukocoria, can be a sign of OIR or retinopathy of prematurity.

In one aspect, the present technology provides a method for preventing an ophthalmic condition in a subject by administering to the subject an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology that modulates one or more signs or markers of an ophthalmic condition. Subjects at risk for an ophthalmic condition can be identified by, e.g., any or a combination of diagnostic or prognostic assays as described herein. In prophylactic applications, pharmaceutical compositions or medicaments comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject susceptible to, or otherwise at risk of a disease or condition in an amount sufficient to eliminate or reduce the risk, or delay the onset of the disease, including biochemical, histologic and/or behavioral symptoms of the disease, its complications and intermediate pathological phenotypes presenting during development of the disease. Administration of the prophylactic compositions of the present technology can occur prior to the manifestation of symptoms characteristic of the aberrancy, such that a disease or disorder is prevented or, alternatively, delayed in its progression. Depending upon the type of aberrancy, TBMs (or derivatives, analogues, or pharmaceutically acceptable salts thereof) or peptide conjugates of the present technology act to enhance or improve mitochondrial function or reduce oxidative damage, and can be used for treating the subject. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful for both prophylactic and therapeutic methods of treating a subject having or at risk of (susceptible to) heart failure. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Accordingly, the present methods provide for the prevention and/or treatment of heart failure in a subject by administering an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a subject in need thereof. In particular embodiments, TBMs (or derivatives, analogues, or pharmaceutically acceptable salts thereof) or peptide conjugates of the present technology are used to treat or prevent heart failure by enhancing mitochondrial function in cardiac tissues. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

One aspect of the technology includes methods of treating heart failure in a subject for therapeutic purposes. In therapeutic applications, compositions or medicaments comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject suspected of, or already suffering from such a disease in an amount sufficient to cure, or partially arrest, the symptoms of the disease, including its complications and intermediate pathological phenotypes in development of the disease. As such, the present technology provides methods of treating an individual afflicted with heart failure.

Subjects suffering from heart failure can be identified by any or a combination of diagnostic or prognostic assays known in the art. For example, typical symptoms of heart failure include shortness of breath (dyspnea), fatigue, weakness, difficulty breathing when lying flat, and swelling of the legs, ankles, or abdomen (edema). The subject may also be suffering from other disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. The primary signs of congestive heart failure are: cardiomegaly (enlarged heart), tachypnea (rapid breathing; occurs in the case of left side failure) and hepatomegaly (enlarged liver; occurs in the case of right side failure). Acute myocardial infarction ("AMI") due to obstruction of a coronary artery is a common initiating event that can lead ultimately to heart failure. However, a subject that has AMI does not necessarily develop heart failure. Likewise, subjects that suffer from heart failure do not necessarily suffer from an AMI.

In one aspect, the present technology provides a method of treating hypertensive cardiomyopathy by administering an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a subject in need thereof. As hypertensive cardiomyopathy worsens, it can lead to congestive heart failure. Subjects suffering from hypertensive cardiomyopathy can be identified by any or a combination of diagnostic or prognostic assays known in the art. For example, typical symptoms of hypertensive cardiomyopathy include hypertension (high blood pressure), cough, weakness, and fatigue. Additional symptoms of hypertensive cardiomyopathy include leg swelling, weight gain, difficulty breathing when lying flat, increasing shortness of breath with activity, and waking in the middle of the night short of breath.

In one aspect, the present technology provides a method for preventing heart failure in a subject by administering to the subject TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology that prevent the initiation or progression of the infarction. Subjects at risk for heart failure can be identified by, e.g., any or a combination of diagnostic or prognostic assays as described herein. In prophylactic applications, pharmaceutical compositions or medicaments of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject susceptible to, or otherwise at risk of a disease or condition in an amount sufficient to eliminate or reduce the risk, or delay the onset of the disease, including biochemical, histologic and/or behavioral symptoms of the disease, its complications and intermediate pathological phenotypes presenting during development of the disease. Administration of prophylactic TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology can occur prior to the manifestation of symptoms characteristic of the aberrancy, such that a disease or disorder is prevented or, alternatively, delayed in its progression.

In some embodiments, TBMs (or derivatives, analogues, or pharmaceutically acceptable salts thereof) or peptide conjugates of the present technology are useful in reducing activation of p38 MAPK and apoptosis in response to Ang II. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in ameliorating myocardial performance index (MPI) in Gαq mice. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, TBMs (or derivatives, analogues, or pharmaceutically acceptable salts thereof) or peptide conjugates of the present technology are useful in preventing an increase in normalized heart weight. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, TBMs (or derivatives, analogues, or pharmaceutically acceptable salts thereof) or peptide conjugates of the present technology are useful in promoting normalized lung weight in Gαq mice. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in methods for treating, ameliorating or reversing left ventricular stiffening, ventricular wall thickening, abnormal left ventricular relaxation and filling, LV remodeling, cardiac myocyte hypertrophy, inflammation, other abnormal left ventricular function, myocardial fibrosis, and/or myocardial extracellular matrix accumulation, and preventing progression to diastolic heart failure. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Moreover, it is proposed that these improvements in diastolic heart disease (DHD) pathology will have a resultant positive effect on the health of the individuals by reducing complications of myocardial fibrosis and left ventricular stiffness, including the development of diastolic dysfunction and diastolic heart failure.

In some embodiments, an effective dose of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology, can be administered via a variety of routes including, but not limited to, e.g., parenteral via an intravenous infusion given as repeated bolus infusions or constant infusion, intradermal injection, subcutaneously given as repeated bolus injection or constant infusion, or oral administration.

In certain embodiments, an effective parenteral dose (given intravenously, intraperitoneally, or subcutaneously) of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to an experimental animal is within the range of 2 mg/kg up to 160 mg/kg body weight, or 10 mg/kg, or 30 mg/kg, or 60 mg/kg, or 90 mg/kg, or 120 mg/kg body weight.

In some embodiments, an effective parenteral dose (given intravenously, intraperitoneally, or subcutaneously) of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to an experimental animal can be administered three times weekly, twice weekly, once weekly, once every two weeks, once monthly, or as a constant infusion.

In certain embodiments, an effective parental dose (given intravenously or subcutaneously) of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a human subject is within the range of 0.5 mg/kg up to 25 mg/kg body weight, or 1 mg/kg, or 2 mg/kg, or 5 mg/kg or 7.5 mg/kg, or 10 mg/kg body weight, or 15 mg/kg body weight.

In some embodiments, an effective parental dose (given intravenously or subcutaneously) of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a human subject can be administered three times weekly, twice weekly, once weekly, once every two weeks, once monthly, or as a constant infusion.

In some embodiments, a therapeutically effective dose of TBMs (or derivatives, analogues, or pharmaceutically acceptable salts thereof) or peptide conjugates of the present technology, results in a change in serum biomarkers, e.g., of at least 1-10% in the level of the serum biomarkers of DHD including, but not limited to, e.g., hyaluronic acid, type I collagen carboxyterminal telopeptide (ICTP), and other breakdown products of collagens, titin, troponin I, troponin T and other cytoskeletal cellular proteins, matrix metalloprotease-9, tissue inhibitor of matrix metalloproteases 2 (TIMP2) and other myocardial derived collagen and matrix proteases. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. These compounds and biomarkers may be measured in serum or myocardial tissue using immunoassays and the levels correlated with severity of disease and treatment.

In some embodiments, a therapeutically effective dose of TBMs (or derivatives, analogues, or pharmaceutically acceptable salts thereof) or peptide conjugates of the present technology, results in a change of at least 1-10% in serum biomarkers of DHD including, but not limited to, e.g., reactive oxygen products of lipid or protein origin, coenzyme Q reduced or oxidized forms, and lipid molecules or conjugates. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. These biomarkers can be measured by various means including immunoassays and electrophoresis and their levels correlated with severity of disease and treatment.

In some embodiments, a therapeutically effective dose of TBMs (or derivatives, analogues, or pharmaceutically acceptable salts thereof) or peptide conjugates of the present technology, results in a change of at least 1-10% in serum biomarkers of DHD including, but not limited to, e.g., cytokines that include but are not limited to TNF-α, TGF-β, IL-6, IL-8, or monocyte chemoattractant protein 1 (MCP-1) osteopontin, or a metabolic profile of serum components that is indicative of DHD occurrence or severity (these include serum and urine markers). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. A profile of one or more of these cytokines, as measured by immunoassay or proteomic assessment by LC mass spec, may provide an assessment of activity of the disease and a marker to follow in therapy of the disease.

In some embodiments, a therapeutically effective dose of TBMs (or derivatives, analogues, or pharmaceutically acceptable salts thereof) or peptide conjugates of the present technology, results in a change of at least 1-10% in the clinical manifestations of DHD including, but not limited to, e.g., clinical testing of stage and severity of the disease, clinical signs and symptoms of disease, and medical complications. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Clinical testing of stage and severity of DHD include, but are not limited to, e.g., hematologic testing (including, but not limited to, e.g., red blood cell count and morphology, white blood cell count and differential and morphology, platelet count and morphology), serum or plasma lipids including, but not limited to, e.g., triglycerides, cholesterol, fatty acids, lipoprotein species and lipid peroxidation species, serum or plasma enzymes (including, but not limited to, e.g., aspartate transaminase (AST), creatine kinase (CK-MB), lactate dehydrogenase (LDH) and isoforms, serum or plasma brain natriuretic peptide (BNP), cardiac troponins, and other proteins indicative of heart failure or damage, including ischemia or tissue necrosis, serum or plasma electrolytes (including, but not limited to, e.g., sodium, potassium, chloride, calcium, phosphorous), coagulation profile including, but not limited to, e.g., prothrombin time (PT), partial thromoplastin time (PTT), specific coagulation factor levels, bleeding time and platelet function. Clinical testing also includes but is not limited to non-invasive and invasive testing that assesses the architecture, structural integrity or function of the heart including, but not limited to, e.g., computerized tomography (CT scan), ultrasound (US), ultrasonic elastography (including, but not limited to, e.g., (Time Harmonic Elastography) or other measurements of the elasticity of heart tissue, magnetic resonance scanning or spectroscopy, percutaneous or skinny needle or transjugular liver biopsy and histological assessment (including, but not limited to, e.g., staining for different components using affinity dyes or immunohistochemistry), or other non-invasive or invasive tests that may be developed for assessing severity of DHD in the heart tissue.

In some embodiments, a therapeutically effective dose of TBMs (or derivatives, analogues, or pharmaceutically acceptable salts thereof) or peptide conjugates of the present technology, results in a change of at least 1-10% in the pathophysiologic spectrum of DHD which includes histopathological findings on heart biopsy that include but are not limited to evidence of myocyte hypertrophy, perivascular and interstitial fibrosis, extracellular matrix accumulation, collagen deposition, inflammatory cell infiltrates (including, but not limited to, e.g., lymphocytes and various subsets of lymphocytes and neutrophils), changes in endothelial cells, and methods that combine various sets of observations for grading the severity of DHD. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In certain embodiments, a therapeutically effective dose of TBMs (or derivatives, analogues, or pharmaceutically acceptable salts thereof) or peptide conjugates of the present technology, results in a change of at least 1-10% in the pathophysiologic spectrum of DHD which includes cardiac imaging measurements and analysis, that include but are not limited to Doppler and Tissue Doppler echocardiographic measures of left ventricular isovolumetric relaxation time (IVRT), E/A ratio (transmitral blood flow), pulmonary vein flow, E wave deceleration time, pulmonary vein A-wave reversal velocity, pulmonary artery systolic pressure, left ventricular mass, left atrial volume, and E/E' ratio (ration transmitral blood flow in early diastole with mitral annular velocity during early diastole, which characterizes left ventricular diastolic pressures). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Speckle Tracking and ultrasound imaging methods may also be used.

In some embodiments, a therapeutically effective dose of TBMs (or derivatives, analogues, or pharmaceutically acceptable salts thereof) or peptide conjugates of the present technology, results in a change of at least 1-10% in clinical signs and symptoms of disease include dyspnea, pulmonary congestion, pulmonary edema, flash pulmonary edema, pulmonary hypertension, tachypnea, orthopnea, lung crepitations, coughing, fatigue, sleep disturbance, peripheral edema, and other organ edema. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. The symptoms of diastolic heart failure progress quickly and become sufficiently severe to warrant placement on a heart transplantation list or receiving a heart transplantation.

In certain embodiments, a therapeutically effective dose of TBMs (or derivatives, analogues, or pharmaceutically acceptable salts thereof) or peptide conjugates of the present technology, has an effect on DHD and/or fibrosis in the absence of any effect on whole blood glucose in patients with diabetes or serum lipids in patients with elevated serum lipids. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, a therapeutically effective dose of TBMs (or derivatives, analogues, or pharmaceutically acceptable salts thereof) or peptide conjugates of the present technology, results in a reduction of at least 1-10% in the level of galectin-3 in heart tissue or serum. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in methods of treating a subject having diastolic heart disease, diastolic dysfunction, diastolic heart failure, left ventricular stiffening, ventricular wall thickening, abnormal left ventricular relaxation and filling, LV remodeling, cardiac myocyte hypertrophy, myocardial fibrosis, inflammation, and/or myocardial extracellular matrix accumulation. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, the method comprises the steps of obtaining a composition for parenteral or enteral administration comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates in an acceptable pharmaceutical carrier; administering to a subject an effective dose of the composition for parenteral administration, the subject having diastolic heart disease, diastolic dysfunction, diastolic heart failure, left ventricular stiffening, ventricular wall thickening, abnormal left ventricular relaxation and filling, LV remodeling, cardiac myocyte hypertrophy, myocardial fibrosis, inflammation, and/or myocardial extracellular matrix accumulation.

In some embodiments, administration of a therapeutically effective dose of TBMs (or derivatives, analogues, or pharmaceutically acceptable salts thereof) or peptide conjugates of the present technology to a subject in need thereof, results in the prevention, amelioration, or treatment of diastolic heart disease, diastolic dysfunction, diastolic heart failure, left ventricular stiffening, ventricular wall thickening, abnormal left ventricular relaxation and filling, LV remodeling, cardiac myocyte hypertrophy, myocardial fibrosis, inflammation, and/or myocardial extracellular matrix accumulation. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In certain embodiments, administration of a therapeutically effective dose of TBMs (or derivatives, analogues, or pharmaceutically acceptable salts thereof) or peptide conjugates of the present technology to a subject in need thereof, can result in reduction of at least one grade in severity of diastolic heart disease scoring systems, reduction of the level of serum markers of diastolic heart disease, reduction of diastolic heart disease activity or reduction in the medical consequences of diastolic heart disease. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In certain embodiments, administration of a therapeutically effective dose of TBMs (or derivatives, analogues, or pharmaceutically acceptable salts thereof) or peptide conjugates of the present technology to a subject in need thereof, can result in the reduction of cardiac tissue cell ballooning as determined from cardiac tissue histological section by assessment of swelling of cardiac tissue cells indicating toxicity and inability to regulate cellular volume. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the cardiac tissue cell ballooning is reduced by at least 1-10% compared to the extent of swelling present prior to administration of the composition.

In some embodiments, administration of a therapeutically effective dose of TBMs (or derivatives, analogues, or pharmaceutically acceptable salts thereof) or peptide conjugates of the present technology to a subject in need thereof, can result in the reduction in the infiltration of inflammatory cells in cardiac tissue histological specimens, as assessed by the number of neutrophils and lymphocytes. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the infiltration of inflammatory cells in cardiac tissue histological specimens is reduced by at least 1-10%, compared to the percentage of inflammatory cells observed prior to administration of the composition.

In certain embodiments, administration of a therapeutically effective dose of TBMs (or derivatives, analogues, or pharmaceutically acceptable salts thereof) or peptide conjugates of the present technology to a subject in need thereof, can result in the reduction of accumulation of collagen in the heart as determined by quantitative analysis of Sirius Red staining of cardiac tissue histological sections. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the reduction of accumulation of collagen in the heart is reduced by at least 1-5% compared to the percentage of cardiac tissue staining positive for Sirius red (indicating collagen) prior to administration of the composition.

In certain embodiments, administration of a therapeutically effective dose of TBMs (or derivatives, analogues, or pharmaceutically acceptable salts thereof) or peptide conjugates of the present technology to a subject in need thereof, can result in the reduction in the level of the serum markers of diastolic heart disease activity. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the serum markers of diastolic heart disease activity can include, but are not limited to, serum levels of brain natriuretic peptide (BNP), cardiac troponin T, degraded titan, type I collagen telopeptide, serum levels of coenzyme Q reduced or oxidized, or a combination of other serum markers of diastolic heart disease activity known in the art.

In certain embodiments, administration of a therapeutically effective dose of TBMs (or derivatives, analogues, or pharmaceutically acceptable salts thereof) or peptide conjugates of the present technology to a subject in need thereof, can result in the reduction of cardiac tissue fibrosis, thickening, stiffness, or extracellular matrix accumulation based on evidence comprising a reduction of the level of the biochemical markers of fibrosis, non-invasive testing of cardiac tissue fibrosis, thickening, stiffness, or extracellular matrix accumulation or cardiac tissue histologic grading of fibrosis, thickening, stiffness, or extracellular matrix accumulation. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, administration of a therapeutically effective dose of TBMs (or derivatives, analogues, or pharmaceutically acceptable salts thereof) or peptide conjugates of the present technology to a subject in need thereof, can result in the reduction of at least one grade in severity of diastolic heart disease grading scoring systems including, but not limited to, e.g., the Mayo Clinic Doppler echocardiographic diastolic dysfunction I-IV classification system (Nishimura R A, et al., *J Am Coll Cardiol.* 30:8-18 (1997)), or the Canadian consensus recommendations for echocardiographic measurement of diastolic dysfunction (Rakowski H., et al., *J Am Soc Echocardiogr* 9:736-60 (1996)). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In certain embodiments, administration of a therapeutically effective dose of TBMs (or derivatives, analogues, or pharmaceutically acceptable salts thereof) or peptide conjugates of the present technology to a subject in need thereof, can result in the reduction in the medical consequences of diastolic heart disease such as pulmonary congestion, pulmonary edema, flash pulmonary edema, pulmonary hypertension, tachypnea, dyspnea, orthopnea, lung crepitations, and other edema. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, the efficacy of a composition comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology for parenteral administration can be determined by administering the composition to animal models of diastolic heart disease, including, but not limited to, e.g., mice subjected to aortic constriction or Dahl salt-sensitive hypertensive rats. In some embodiments, administration of the TBMs (or derivatives, analogues, or pharmaceutically acceptable salts thereof) or peptide conjugate composition to animal models of diastolic heart disease can result in at least a 1-5% reduction in heart infiltration by inflammatory cells or at least a 1-5% reduction in heart collagen content as determined by morphometric quantification. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some aspects, the present technology relates to compositions having TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology for the treatment of diastolic heart disease, diastolic dysfunction, diastolic heart failure, left ventricular stiffening, ventricular wall thickening, abnormal left ventricular relaxation and filling, LV remodeling, cardiac myocyte hypertrophy, myocardial fibrosis, inflammation, and/or myocardial extracellular matrix accumulation.

Other aspects of the present technology relate to the use of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology, in the manufacture of a pharmaceutical composition for the treatment of diastolic heart disease, diastolic dysfunction, diastolic heart failure, left ventricular stiffening, ventricular wall thickening, abnormal left ventricular relaxation and filling, LV remodeling, cardiac myocyte hypertrophy, myocardial fibrosis, inflammation, and/or myocardial extracellular matrix accumulation.

In some embodiments, TBMs (or derivatives, analogues, or pharmaceutically acceptable salts thereof) or peptide conjugates of the present technology are useful for both prophylactic and therapeutic methods of treating a subject at risk of (or susceptible to) vessel occlusion injury, ischemia-reperfusion injury, or cardiac ischemia-reperfusion injury. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Accordingly, the present methods provide for the prevention and/or treatment of vessel occlusion injury, ischemia-reperfusion injury, or cardiac ischemia-reperfusion injury in a subject by administering an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a subject in need thereof or of a subject having a coronary artery bypass graft (CABG) procedure.

In one aspect, the present technology provides a method for preventing vessel occlusion injury in a subject by administering to the subject TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology that prevent the initiation or progression of the condition. Subjects at risk for vessel occlusion injury can be identified by, e.g., any or a combination of diagnostic or prognostic assays as described herein. In prophylactic applications, pharmaceutical compositions or medicaments comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject susceptible to, or otherwise at risk of a disease or condition in an amount sufficient to eliminate or reduce the risk, or delay the onset of the disease, including biochemical, histologic and/or behavioral symptoms of the disease, its complications and intermediate pathological phenotypes presenting during development of the disease. Administration of prophylactic TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology can occur prior to the manifestation of symptoms characteristic of the aberrancy, such that a disease or disorder is prevented or, alternatively, delayed in its progression. In some embodiments, the compositions are administered in sufficient amounts to prevent renal or cerebral complications from CABG.

Another aspect of the present technology includes methods of treating vessel occlusion injury or ischemia-reperfusion injury in a subject. In therapeutic applications, compositions or medicaments comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates are administered to a subject suspected of, or already suffering from such a disease in an amount sufficient to cure, or partially arrest, the symptoms of the disease, including its complications and intermediate pathological phenotypes in development of the disease. As such, the technology provides methods of treating an individual afflicted with ischemia-reperfusion injury or treating an individual afflicted with cardiac ischemia-reperfusion injury by administering an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology and performing a CABG procedure.

The present technology also potentially relates to compositions and methods for the treatment or prevention of ischemia-reperfusion injury associated with AMI and organ transplantation in mammals. In general, the methods and compositions include one or more TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2', 6'-Dmt-Lys-Phe-NH$_2$), or peptide conjugates of the present technology or pharmaceutically acceptable salts thereof.

In some aspects, TBMs (or derivatives, analogues, or pharmaceutically acceptable salts thereof) or peptide conjugates of the present technology are used in methods for treating AMI injury in mammals. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some aspects, TBMs (or derivatives, analogues, or pharmaceutically acceptable salts thereof) or peptide conjugates of the present technology are used in methods for ischemia and/or reperfusion injury mammals. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some aspects, TBMs (or derivatives, analogues, or pharmaceutically acceptable salts thereof) or peptide conjugates of the present technology are used in methods for the treatment, prevention or alleviation of symptoms of cyclosporine-induced nephrotoxicity injury in mammals. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some aspects, TBMs (or derivatives, analogues, or pharmaceutically acceptable salts thereof) or peptide conjugates of the present technology are used in methods for performing revascularization procedures in mammals. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In one embodiment, the revascularization procedure is selected from the group consisting of: percutaneous coronary intervention; balloon angioplasty; insertion of a bypass graft; insertion of a stent; and directional coronary atherectomy. In some embodiments, the revascularization procedure comprises removal of the occlusion. In some embodiments, the revascularization procedure comprises administration of one or more thrombolytic agents. In some embodiments, the one or more thrombolytic agents are selected from the group consisting of: tissue plasminogen activator; urokinase; prourokinase; streptokinase; an acylated form of plasminogen; acylated form of plasmin; and acylated streptokinase-plasminogen complex.

In another aspect, the present disclosure provides a method of coronary revascularization comprising: (a) administering simultaneously, separately or sequentially an effective amount of (i) TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys- Phe-NH$_2$), or peptide conjugates of the present technology or a pharmaceutically acceptable salt and (ii) an additional active agent; and (b) performing a coronary artery bypass graft procedure on the subject. In some embodiments, the additional active agent comprises cyclosporine or a cyclosporine derivative or analogue.

In another aspect, the present disclosure provides a method of coronary revascularization comprising: (a) administering to a mammalian subject a therapeutically effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology or a pharmaceutically acceptable salt thereof; (b) administering to the subject a therapeutically effective amount of cyclosporine or a cyclosporine derivative or analogue; and (c) performing a coronary artery bypass graft procedure on the subject.

In one aspect, the present technology provides a method for preventing AMI injury in a subject by administering to the subject TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology and cyclosporine that prevent the initiation or progression of the condition. In prophylactic applications, pharmaceutical compositions or medicaments comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology and cyclosporine are administered to a subject susceptible to, or otherwise at risk of a disease or condition in an amount sufficient to eliminate or reduce the risk, or delay the onset of the disease, including biochemical, histologic and/or behavioral symptoms of the disease, its complications and intermediate pathological phenotypes presenting during development of the disease. Administration of prophylactic TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology and cyclosporine can occur prior to the manifestation of symptoms characteristic of the aberrancy, such that a disease or disorder is prevented or, alternatively, delayed in its progression.

In some embodiments, TBMs (or derivatives, analogues, or pharmaceutically acceptable salts thereof) or peptide conjugates of the present technology, and cyclosporine are useful in protecting kidneys from ARI. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Another aspect of the technology includes methods of treating ischemia in any organ or tissue. Accordingly, in some embodiments, such ischemia can be treated, prevented, ameliorated (e.g., the severity of ischemia is decreased) by the administration of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology or a pharmaceutically acceptable salt thereof, such as acetate, tartrate, or trifluoroacetate salt, and an active agent, such as cyclosporine or a derivative or analogue thereof.

Another aspect of the present technology includes methods for preventing or ameliorating cyclosporine-induced nephrotoxicity. For example, in some embodiments, a pharmaceutical composition or medicament comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology is administered to a subject presenting with or at risk of cyclosporine-induced nephrotoxicity. For example, in some embodiments, a subject receiving cyclosporine, e.g., as an immunosuppressant after an organ or tissue transplant, is also administered a therapeutically effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology. In some embodiments, the composition is administered to the subject prior to organ or tissue transplant, during organ or tissue transplant and/or after an organ or tissue transplant. In some embodiments, the subject would receive a combination of (i) TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2', 6'-Dmt-Lys-Phe-NH$_2$), or (ii) peptide conjugates of the present technology and cyclosporine before, during and/or after an organ or tissue transplant. The composition or medicament including TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology and optionally, cyclosporine, would be administered in an amount sufficient to cure, or partially arrest, the symptoms of nephrotoxicity, including its complications and intermediate pathological phenotypes. For example, in some embodiments, the compositions or medicaments are administered in an amount sufficient to eliminate the risk of, reduce the risk of, or delay the onset of nephrotoxicity, including biochemical, histologic and/or behavioral symptoms of the condition, its complications and intermediate pathological phenotypes. Administration of prophylactic TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology and cyclosporine can occur prior to the manifestation of symptoms characteristic of the aberrancy, such that the condition is prevented or, alternatively, delayed in its progression. Typically, subjects who receive the composition will have a healthier transplanted organ or tissue, and/or are able to maintain a higher and/or more consistent cyclosporine dosage or regimen for longer periods of time compared to subjects who do not receive the composition. In some embodiments, patients receiving TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$), or peptide conjugates of the present technology or pharmaceutically acceptable salt thereof such as an acetate, tartrate, or trifluoroacetate salt, in conjunction with cyclosporine are able to tolerate longer and/or more consistent cyclosporine treatment regimens, and/or higher doses of cyclosporine. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. In some embodiments, patients receiving TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$), or peptide conjugates of the present technology or a pharmaceutically acceptable salt thereof such as an acetate, tartrate, or trifluoroacetate salt, in conjunction with cyclosporine, will have an increased tolerance for cyclosporine as compared to a patient who is not receiving the composition. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard.

In some embodiments, TBMs (or derivatives, analogues, or pharmaceutically acceptable salts thereof) or peptide conjugates of the present technology are useful in decreasing islet cell apoptosis and enhancing viability of islet cells after transplantation. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard.

In some embodiments, TBMs (or derivatives, analogues, or pharmaceutically acceptable salts thereof) or peptide conjugates of the present technology described herein are useful in reducing oxidative damage in a mammal in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$) will show a synergistic effect in this regard. Mammals in need of reducing oxidative damage are those mammals suffering from a disease, condition or treatment associated with oxidative damage. Typically, oxidative damage is caused by free radicals, such as reactive oxygen species (ROS) and/or reactive nitrogen species (RNS). Examples of ROS and RNS include hydroxyl radical, superoxide anion radical, nitric oxide, hydrogen, hypochlorous acid (HOCl) and peroxynitrite anion. Oxidative damage is considered to be "reduced" if the amount of oxidative damage in a mammal, a removed organ, or a cell is decreased after administration of an effective amount of the TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$), or peptide conjugates of the present technology.

In some embodiments, a mammal to be treated can be a mammal with a disease or condition associated with oxidative damage. The oxidative damage can occur in any cell, tissue or organ of the mammal. In humans, oxidative stress is involved in many diseases. Examples include atherosclerosis, Parkinson's disease, heart failure, myocardial infarction, Alzheimer's disease, schizophrenia, bipolar disorder, fragile X syndrome, and chronic fatigue syndrome.

In one embodiment, a mammal may be undergoing a treatment associated with oxidative damage. For example, the mammal may be undergoing reperfusion. Reperfusion refers to the restoration of blood flow to any organ or tissue in which the flow of blood is decreased or blocked. The restoration of blood flow during reperfusion leads to respiratory burst and formation of free radicals.

In one embodiment, the mammal may have decreased or blocked blood flow due to hypoxia or ischemia. The loss or severe reduction in blood supply during hypoxia or ischemia may, for example, be due to thromboembolic stroke, coronary atherosclerosis, or peripheral vascular disease. Numerous organs and tissues are subject to ischemia or hypoxia. Examples of such organs include brain, heart, kidney, intestine and prostate. The tissue affected is typically muscle, such as cardiac, skeletal, or smooth muscle. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

The methods can also be used in reducing oxidative damage associated with any neurodegenerative disease or condition. The neurodegenerative disease can affect any cell, tissue or organ of the central and peripheral nervous system. Examples of such cells, tissues and organs include, the brain, spinal cord, neurons, ganglia, Schwann cells, astrocytes, oligodendrocytes, and microglia. The neurodegenerative condition can be an acute condition, such as a stroke or a traumatic brain or spinal cord injury. In another embodiment, the neurodegenerative disease or condition can be a chronic neurodegenerative condition. In a chronic neurodegenerative condition, the free radicals can, for example, cause damage to a protein. An example of such a protein is amyloid precursor protein. Examples of chronic neurodegenerative diseases associated with damage by free radicals include Parkinson's disease, Alzheimer's disease, Huntington's disease and Amyotrophic Lateral Sclerosis (ALS). Other conditions which can be treated include preeclampsia, diabetes, and symptoms of and conditions associated with aging, such as macular degeneration, wrinkles.

In one aspect, TBMs (or derivatives, analogues, or pharmaceutically acceptable salts thereof) or peptide conjugates of the present technology described herein are useful in treating any disease or condition that is associated with mitochondria permeability transitioning (MPT). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Such diseases and conditions include, but are not limited to, ischemia and/or reperfusion of a tissue or organ, hypoxia and any of a number of neurodegenerative diseases. Mammals in need of inhibiting or preventing of MPT are those mammals suffering from these diseases or conditions.

In some embodiments, TBMs (or derivatives, analogues, or pharmaceutically acceptable salts thereof) or peptide conjugates of the present technology are useful in the treatment or prophylaxis of neurodegenerative diseases associated with MPT. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Neurodegenerative diseases associated with MPT include, for example, Parkinson's disease, Alzheimer's disease, Huntington's disease and Amyotrophic Lateral Sclerosis (ALS). The compositions disclosed herein can be used to delay the onset or slow the progression of these and other neurodegenerative diseases associated with MPT. In certain embodiments, TBMs (or derivatives, analogues, or pharmaceutically acceptable salts thereof) or peptide conjugates of the present technology are particularly useful in the treatment of humans suffering from the early stages of neurodegenerative diseases associated with MPT and in humans predisposed to these diseases. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

Accordingly, the present disclosure describes methods and compositions including TBMs (or derivatives, analogues, or pharmaceutically acceptable salts thereof) or peptide conjugates of the present technology that are capable of reducing mitochondrial ROS production in the diaphragm during prolonged MV, or in other skeletal muscles, e.g., soleus or plantaris muscle, during limb immobilization, or muscle disuse in general. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful as therapeutic and/or prophylactic agents in subjects suffering from, or at risk of suffering from muscle infirmities such as weakness, atrophy, dysfunction, etc. caused by mitochondrial derived ROS. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, TBMs (or derivatives, analogues, or peptide conjugates of the present technology decrease mitochondrial ROS production in muscle. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Additionally or alternatively, in some embodiments, TBMs (or derivatives, analogues, or pharmaceutically acceptable salts thereof) or peptide conjugates of the present technology will selectively concentrate in the mitochondria of skeletal muscle and provide radical scavenging of H$_2$O$_2$, OH—, and ONOO—, and in some embodiments, radical scavenging occurs on a dose-dependent basis. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

In some embodiments, TBMs (or derivatives, analogues, or pharmaceutically acceptable salts thereof) or peptide conjugates of the present technology are useful in methods for treating muscle infirmities (e.g., weakness, atrophy, dysfunction, etc.). In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In such therapeutic applications, compositions or medicaments including TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology or a pharmaceutically acceptable salt thereof, such as acetate, tartrate, or trifluoroacetate salt, can be administered to a subject suspected of, or already suffering from, muscle infirmity, in an amount sufficient to prevent, reduce, alleviate, or partially arrest, the symptoms of muscle infirmity, including its complications and intermediate pathological phenotypes in development of the infirmity. As such, the present technology provides methods of treating an individual afflicted, or suspected of suffering from muscle infirmities described herein by administering TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology or a pharmaceutically acceptable salt thereof, such as acetate, tartrate, or trifluoroacetate salt.

In another aspect, the disclosure provides methods for preventing, or reducing the likelihood of muscle infirmity, as described herein, by administering to the subject TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology that prevent or reduce the likelihood of the initiation or progression of the infirmity. Subjects at risk for developing muscle infirmity can be readily identified, e.g., a subject preparing for or about to undergo MV or related diaphragmatic muscles disuse or any other skeletal muscle disuse that may be envisaged by a medical professional (e.g., casting a limb).

In prophylactic applications, a pharmaceutical composition or medicament comprising one or more TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology or a pharmaceutically acceptable salt thereof, such as acetate, tartrate, or trifluoroacetate salt, are administered to a subject susceptible to, or otherwise at risk of muscle infirmity in an amount sufficient to eliminate or reduce the risk, or delay the onset of muscle infirmity, including biochemical, histologic and/or behavioral symptoms of the infirmity, its complications and intermediate pathological phenotypes presenting during development of the infirmity. Administration of one or more TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology can occur prior to the manifestation of symptoms characteristic of the aberrancy, such that the disorder is prevented or, alternatively, delayed in its progression.

In some embodiments, subjects in need of protection from or treatment of muscle infirmity also include subjects suffering from a disease, condition or treatment associated with oxidative damage. Typically, the oxidative damage is caused by free radicals, such as reactive oxygen species (ROS) and/or reactive nitrogen species (RNS). Examples of ROS and RNS include hydroxyl radical (HO.), superoxide anion radical (O$_2$.$^-$), nitric oxide (NO.), hydrogen peroxide (H$_2$O$_2$), hypochlorous acid (HOCl), and peroxynitrite anion (ONOO$^-$).

A composition comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to treat or prevent muscle infirmity associated with muscle immobilization e.g., due to casting or other disuse, can be administered at any time before, during or after the immobilization or disuse. For example, in some embodiments, one or more doses of a composition comprising TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology can be administered before muscle immobilization or disuse, immediately after muscle immobilization or disuse, during the course of muscle immobilization or disuse, and/or after muscle immobilization or disuse (e.g., after cast removal). By way of example, and not by way of limitation, in some embodiments, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology can be administered once per day, twice per day, three times per day, four times per day six times per day or more, for the duration of the immobilization or disuse. In other embodiments, TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology can be administered daily, every other day, twice, three times, or for times per week, or once, twice three, four, five or six times per month for the duration of the immobilization or disuse.

In some embodiments, TBMs (or derivatives, analogues, or pharmaceutically acceptable salts thereof) or peptide conjugates of the present technology are useful in methods of treating or preventing muscle infirmity due to muscle disuse or disuse atrophy, associated with loss of muscle mass and strength. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. Atrophy is a physiological process relating to the reabsorption and degradation of tissues, e.g., fibrous muscle tissue, which involves apoptosis at the cellular level. When atrophy occurs from loss of trophic support or other disease, it is known as pathological atrophy. Such atrophy or pathological atrophy may result from, or is related to, limb immobilization, prolonged limb immobilization, casting limb immobilization, mechanical ventilation (MV), prolonged MV, extended bed rest cachexia, congestive heart failure, liver disease, sarcopenia, wasting, poor nourishment, poor circulation, hormonal irregularities, loss of nerve function, and the like. Accordingly, the present methods relate to the prevention and/or treatment of muscle infirmities in a subject, including skeletal muscle atrophy, comprising administering an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates to a subject in need thereof.

Additional examples of muscle infirmities which can be treated, prevented, or alleviated by administering the compositions and formulations disclosed herein include, without limitation, age-related muscle infirmities, muscle infirmities associated with prolonged bed rest, muscle infirmities such as weakness and atrophy associated with microgravity, as in space flight, muscle infirmities associated with effects of certain drugs (e.g., statins, antiretrovirals, and thiazolidinediones (TZDs), and muscle infirmities such as cachexia, for example cachexia caused by cancer or other diseases.

In some embodiments, TBMs (or derivatives, analogues, or pharmaceutically acceptable salts thereof) or peptide conjugates of the present technology are useful in the treatment or prevention of an anatomic zone of no re-flow to a subject in need thereof. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In one embodiment, the administration of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys- NH$_2$, or D-Arg-2',6'-Dmt-Lys-Phe-NH$_2$), or peptide conjugates to a subject is done before the formation of the anatomic zone of no re-flow. In another embodiment, the administration of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology to a subject is done after the formation of an anatomic zone of no re-flow. In one embodiment, the method is performed in conjunction with a revascularization procedure. Also provided is a method for the treatment or prevention of cardiac ischemia-reperfusion injury. Also provided is a method of treating a myocardial infarction in a subject to prevent injury to the heart upon reperfusion. In one aspect, the present technology relates to a method of coronary revascularization comprising administering to a mammalian subject a therapeutically effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology and performing a coronary artery bypass graft (CABG) procedure on the subject.

In some embodiments, TBMs (or derivatives, analogues, or pharmaceutically acceptable salts thereof) or peptide conjugates of the present technology are useful in methods of preventing an anatomic zone of no re-flow in a subject, which prevent the initiation or progression of the condition. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

Subjects at risk for an anatomic zone of no re-flow can be identified by, e.g., any or a combination of diagnostic or prognostic assays as described herein. In prophylactic applications, pharmaceutical compositions or medicaments of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject susceptible to, or otherwise at risk of a disease or condition in an amount sufficient to eliminate or reduce the risk, or delay the onset of the disease or condition, including biochemical, histologic and/or behavioral symptoms of the disease or condition, its complications and intermediate pathological phenotypes presenting during development of the disease or condition. Administration of a prophylactic TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology can occur prior to the manifestation of symptoms characteristic of the aberrancy, such that a disease or disorder is prevented or, alternatively, delayed in its progression.

In some embodiments, the aromatic-cationic peptide, TBM, or peptide conjugate of the present technology is administered to a subject in an amount effective to protect the subject from acute renal injury (ARI) or acute liver failure (ALF). Also, the aromatic-cationic peptide, TBM, or peptide conjugate of the present technology may be administered to a subject in an amount effective in treating ARI or ALF.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with ARI or ALF. The amount of a composition of the present technology administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present technology can also be administered in combination with one or more additional therapeutic compounds. In the present methods, aromatic-cationic peptide, TBM, or peptide conjugate of the present technology may be administered to a subject having one or more signs of ARI caused by a disease or condition. Administration of an effective amount of the aromatic-cationic peptide, TBM, or peptide conjugate of the present technology may improve at least one sign or symptom of ARI in the subject, e.g., metabolic acidosis (acidification of the blood), hyperkalemia (elevated potassium levels), oliguria, or anuria (decrease or cessation of urine production), changes in body fluid balance, and effects on other organ systems. For example, a "therapeutically effective amount" of the aromatic-cationic peptide, TBM, or peptide conjugate of the present technology means a level at which the physiological effects of acute renal failure will be kept at a minimum. Typically, the efficacy of the biological effect is measured in comparison to a subject or class of subjects not administered the compounds.

Any method known to those in the art for contacting a cell, organ or tissue with an aromatic-cationic peptide, TBM, or peptide conjugate of the present technology may be employed. Suitable methods include in vitro, ex vivo, or in vivo methods. In vivo methods typically include the administration of aromatic-cationic peptides, TBMs, or peptide conjugates of the present technology, such as those described herein, to a mammal, such as a human. When used in vivo for therapy, an aromatic-cationic peptide, TBM, or peptide conjugate of the present technology is administered to the subject in effective amounts (i.e., amounts that have desired therapeutic effect). Compositions will normally be administered parenteral, topically, or orally. The dose and dosage regimen will depend upon the type and severity of disease or injury, the characteristics of the particular aromatic-cationic peptide, TBM, or peptide conjugate of the present technology e.g., its therapeutic index, the characteristics of the subject, and the subject's medical history.

In some embodiments, the dosage of the aromatic-cationic peptide, TBM, or peptide conjugate of the present technology is provided at a "low," "mid," or "high" dose level. In some embodiments, the low dose is from about 0.001 to about 0.5 mg/kg/h, or from about 0.01 to about 0.1 mg/kg/h. In some embodiments, the mid-dose is from about 0.1 to about 1.0 mg/kg/h, or from about 0.1 to about 0.5 mg/kg/h. In some embodiments, the high dose is from about 0.5 to about 10 mg/kg/h, or from about 0.5 to about 2 mg/kg/h. The skilled artisan will appreciate that certain factors may influence the dosage and timing required to effectively treat a subject, including but not limited to, the severity of the medical disease or condition, previous treatments, the general health and/or age of the subject, and other diseases present. Moreover, treatment of a subject with a therapeutically effective amount of the aromatic-cationic peptides, TBMs, or peptide conjugates described herein can include a single treatment or a series of treatments.

In some embodiments, the aromatic-cationic peptide, TBM, or peptide conjugate of the present technology is administered in combination with another therapeutic agent. By way of example, a patient receiving an aromatic-cationic peptide, TBM, or peptide conjugate of the present technology who experiences inflammation may be co-administered an anti-inflammatory agent. By way of example, the therapeutic effectiveness of the aromatic-cationic peptide, TBM, or peptide conjugate of the present technology may be enhanced by co-administration of an adjuvant. By way of example, the therapeutic benefit to a patient may be increased by administering an aromatic-cationic peptide, TBM, or peptide conjugate of the present technology in combination with another therapeutic agent known or suspected to aid in the prevention or treatment of a particular condition.

Non-limiting examples of combination therapies include use of one or more aromatic-cationic peptides, TBMs, or peptide conjugates of the present technology together with nitric oxide (NO) inducers, statins, negatively charged phospholipids, antioxidants, minerals, anti-inflammatory agents, anti-angiogenic agents, matrix metalloproteinase inhibitors, or carotenoids. In some embodiments, agents used in combination with compositions described herein may fall within multiple categories (for example, lutein is both an antioxidant and a carotenoid). Further, the aromatic-cationic peptide, TBM, or peptide conjugate of the present technology may be administered with additional agents that may provide benefit to the patient, including by way of example only cyclosporin A.

In addition, the aromatic-cationic peptide, TBM, or peptide conjugate of the present technology may also be used in combination with procedures that may provide additional or synergistic benefit to the patient, including, for example, extracorporeal rheopheresis (membrane differential filtration), implantable miniature telescopes, laser photocoagulation of drusen, and microstimulation therapy.

The use of antioxidants has been shown to benefit patients with macular degenerations and dystrophies. See, e.g., *Arch. Ophthalmol.* 119:1417-36 (2001); Sparrow, et al., *J. Biol. Chem.* 278:18207-13 (2003). Non-limiting examples of antioxidants suitable for use in combination with at least one aromatic-cationic peptide, TBM, or peptide conjugate of the present technology include vitamin C, vitamin E, beta-carotene and other carotenoids, coenzyme Q, 4-hydroxy-2,2,6,6-tetramethylpiperidine-1-oxyl (Tempol), lutein, butylated hydroxytoluene, resveratrol, a trolox analogue (PNU-83836-E), and bilberry extract.

The use of certain minerals has also been shown to benefit patients with macular degenerations and dystrophies. See, e.g., *Arch. Ophthalmol.*, 119:1417-36 (2001). Non-limiting examples of minerals for use in combination with at least one aromatic-cationic peptide, TBM, or peptide conjugate of the present technology include copper-containing minerals (e.g., cupric oxide), zinc-containing minerals (e.g., zinc oxide), and selenium-containing compounds.

The use of certain negatively-charged phospholipids has also been shown to benefit patients with macular degenerations and dystrophies. See, e.g., Shaban & Richter, *Biol., Chem.* 383:537-45 (2002); Shaban, et al., *Exp. Eye Res.* 75:99-108 (2002). Non-limiting examples of negatively charged phospholipids suitable for use in combination with at least one aromatic-cationic peptide, TBM, or peptide conjugate of the present technology include cardiolipin and phosphatidylglycerol. Positively-charged and/or neutral phospholipids may also provide benefit for patients with macular degenerations and dystrophies when used in combination with aromatic-cationic peptide, TBM, or peptide conjugate of the present technology.

The use of certain carotenoids has been correlated with the maintenance of photoprotection necessary in photoreceptor cells. Carotenoids are naturally-occurring yellow to red pigments of the terpenoid group that can be found in plants, algae, bacteria, and certain animals, such as birds and shellfish. Carotenoids are a large class of molecules in which more than 600 naturally occurring species have been identified. Carotenoids include hydrocarbons (carotenes) and their oxygenated, alcoholic derivatives (xanthophylls). They include actinioerythrol, astaxanthin, canthaxanthin, capsanthin, capsorubin, $\beta$-8'-apocarotenal (apo-carotenal), $\beta$-12'-apo-carotenal, $\alpha$-carotene, $\beta$-carotene, "carotene" (a mixture of $\alpha$- and $\beta$-carotenes), $\gamma$-carotenes, $\beta$-cryptoxanthin, lutein, lycopene, violerythrin, zeaxanthin, and esters of hydroxyl- or carboxyl-containing members. Many of the carotenoids occur in nature as cis- and trans-isomeric forms, while synthetic compounds frequently exist as racemic mixtures.

In humans, the retina selectively accumulates mainly two carotenoids: zeaxanthin and lutein. These two carotenoids are thought to aid in protecting the retina because they are powerful antioxidants and absorb blue light. Studies with quails have established that animals raised on carotenoid-deficient diets develop retinas with low concentrations of zeaxanthin and suffer severe light damage, as evidenced by a very high number of apoptotic photoreceptor cells. By contrast, animals raised on high-carotenoid diets develop retinas with high zeaxanthin concentrations that sustain minimal light damage. Non-limiting examples of carotenoids suitable for use in combination with at least one aromatic-cationic peptide, TBM, or peptide conjugate of the present technology include lutein and zeaxanthin, as well as any of the aforementioned carotenoids.

Nitric oxide inducers include compounds that stimulate endogenous NO or elevate levels of endogenous endothelium-derived relaxing factor (EDRF) in vivo, or are substrates for nitric oxide synthase. Such compounds include, for example, L-arginine, L-homoarginine, and N-hydroxy-L-arginine, including their nitrosated and nitrosylated analogues (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosine, bradykinin, calreticulin, bisacodyl, and phenolphthalein. EDRF is a vascular relaxing factor secreted by the endothelium, and has been identified as nitric oxide or a closely related derivative thereof (Palmer, et al., *Nature* 327:524-526 (1987); Ignarro, et al., *Proc. Natl. Acad. Sci.* 84:9265-9269 (1987)). In some embodiments, the aromatic-cationic peptides, TBMs, or peptide conjugates of the present technology may also be used in combination with NO inducers.

Statins serve as lipid-lowering agents and/or suitable nitric oxide inducers. In addition, a relationship has been demonstrated between statin use and delayed onset or development of macular degeneration. G. McGwin, et al., *Br. J.*

*Ophthalmol.* 87:1121-25 (2003). Statins can thus provide benefit to a patient suffering from an ophthalmic condition (such as the macular degenerations and dystrophies, and the retinal dystrophies) when administered in combination with aromatic-cationic peptide, TBM, or peptide conjugate of the present technology. Suitable statins include, by way of example only, rosuvastatin, pitivastatin, simvastatin, pravastatin, cerivastatin, mevastatin, vicrostatin, fluvastatin, compactin, lovastatin, dalvastatin, fluindostatin, atorvastatin, atorvastatin calcium (which is the hemicalcium salt of atorvastatin), and dihydrocompactin.

Suitable anti-inflammatory agents for use in combination with the aromatic-cationic peptide, TBM, or peptide conjugate of the present technology may also be used in combination with include, by way of example only, aspirin and other salicylates, cromolyn, nedocromil, theophylline, zileuton, zafirlukast, montelukast, pranlukast, indomethacin, lipoxygenase inhibitors, non-steroidal anti-inflammatory drugs (NSAIDs) (e.g., ibuprofen and naproxin), prednisone, dexamethasone, cyclooxygenase inhibitors (i.e., COX-1 and/or COX-2 inhibitors such as NAPROXEN™, and CELEBREX™), statins (e.g., rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium (hemicalcium salt of atorvastatin), dihydrocompactin), and disassociated steroids.

Matrix metalloproteinase (MMP) inhibitors may also be administered in combination with compositions described herein for the treatment of ophthalmic conditions or symptoms associated with macular or retinal degeneration. MMPs are known to hydrolyze most components of the extracellular matrix. These proteinases play a central role in many biological processes such as normal tissue remodeling, embryogenesis, wound healing, and angiogenesis. However, high levels of MMPs are associated with many disease states, including macular degeneration. Many MMPs have been identified, most of which are multi-domain zinc endopeptidases. A number of metalloproteinase inhibitors are known (see, e.g., Whittaker, et al., *Chem. Rev.* 99(9):2735-2776 (1999)). Representative examples of MMP inhibitors include tissue inhibitors of metalloproteinases (TIMPs) (e.g., TIMP-1, TIMP-2, TIMP-3, TIMP-4), α-2-macroglobulin, tetracyclines (e.g., tetracycline, minocycline, doxycycline), hydroxamates (e.g., BATIMASTAT™, MARIMISTAT™ and TROCADE™), chelators (e.g., EDTA, cysteine, acetylcysteine, D-penicillamine, gold salts), synthetic MMP fragments, succinyl mercaptopurines, phosphonamidates, and hydroxaminic acids. Non-limiting examples of MMP inhibitors suitable for use in combination with compositions described herein include any of the aforementioned inhibitors.

The use of anti-angiogenic or anti-VEGF drugs has also been shown to provide benefit for patients with macular degenerations and dystrophies. Examples of suitable anti-angiogenic or anti-VEGF drugs for use in combination with at least one aromatic-cationic peptide, TBM, or peptide conjugate of the present technology may also be used in combination with include rhufab V2 (LUCCNTIS™), Tryptophanyl-tRNA synthetase (TrpRS), eye001 (anti-VEGF pegylated aptamer), squalamine, RETAANE™ (anecortave acetate for depot suspension), combretastatin A4 prodrug (CA4P), MACUGEN™ MIFEPREX™ (mifepristone-ru486), subtenon triamcinolone acetonide, intravitreal crystalline triamcinolone acetonide, prinomastat (AG3340), fluocinolone acetonide (including fluocinolone intraocular implant), VEGFR inhibitors, and VEGF-Trap.

Other pharmaceutical therapies that have been used to relieve visual impairment can be used in combination with at least one aromatic-cationic peptide, TBM, or peptide conjugate of the present technology may also be used in combination with. Such treatments include but are not limited to agents such as VISUDYNC™ with use of a non-thermal laser, PKC 412, endovion, neurotrophic factors (e.g., glial derived neurotrophic factor, ciliary neurotrophic factor), diatazem, dorzolamide, phototrop, 9-cis-retinal, eye medication (including Echo Therapy) including phospholine iodide or echothiophate or carbonic anhydrase inhibitors, AE-941, Sima-027, pegaptanib, neurotrophins (e.g., NT-4/5), cand5, ranibizumab, INS-37217, integrin antagonists, EG-3306, BDM-E, thalidomide, cardiotrophin-1, 2-methoxyestradiol, DL8234, NTC-200, tetrathiomolybdate, LYN-002, microalgal compound, D-9120, ATX-S10, TGF-beta 2, tyrosine kinase inhibitors, NX-278-L, Opt-24, retinal cell ganglion neuroprotectants, N-nitropyrazole derivatives, KP-I02, and cyclosporin A.

Multiple therapeutic agents may be administered in any order or simultaneously. If simultaneously, the agents may be provided in a single, unified form, or in multiple forms (i.e. as a single solution or as two separate solutions). One of the therapeutic agents may be given in multiple doses, or both may be given as multiple doses. If not simultaneous, the timing between the multiple doses may vary from more than zero weeks to less than about four weeks, less than about six weeks, less than about 2 months, less than about 4 months, less than about 6 months, or less than about one year. In addition, the combination methods, compositions, and formulations are not limited to the use of only two agents. By way of example, an aromatic-cationic peptide, TBM, or peptide conjugate of the present technology may be provided with at least one antioxidant and at least one negatively charged phospholipid. By way of example, an aromatic-cationic peptide, TBM, or peptide conjugate of the present technology may be provided with at least one antioxidant and at least one inducer of nitric oxide production. By way of example, an aromatic-cationic peptide, TBM, or peptide conjugate of the present technology may be provided with at least one inducer of nitric oxide productions and at least one negatively charged phospholipid.

In addition, an aromatic-cationic peptide, TBM, or peptide conjugate of the present technology may be used in combination with procedures that may provide additional or synergistic benefits to the patient. For example, procedures known, proposed, or considered to relieve visual impairment include but are not limited to "limited retinal translocation," photodynamic therapy (e.g., receptor-targeted PDT, porfimer sodium for injection with PDT, verteporfin, rostaporfin with PDT, talaporfin sodium with PDT, motexafin lutetium), antisense oligonucleotides (e.g., products of Novagali Pharma SA, ISIS-13650), laser photocoagulation, drusen lasering, macular hole surgery, macular translocation surgery, implantable miniature telescopes, phi-motion angiography (micro-laser therapy and feeder vessel treatment), proton beam therapy, microstimulation therapy, retinal detachment and vitreous surgery, scleral buckle, submacular surgery, transpupillary thermotherapy, photosystem I therapy, use of RNA interference (RNAi), extracorporeal rheopheresis (membrane differential filtration and rheotherapy), microchip implantation, stem cell therapy, gene replacement therapy, ribozyme gene therapy (including gene therapy for hypoxia response element, LENTIPAC™, PDEF gene therapy), photoreceptor/retinal cell transplantation (including transplantable retinal epithelial cells, retinal cell transplant), and acupuncture.

Further combinations that may be used to benefit an individual include using genetic testing to determine whether that individual is a carrier of a mutant gene that is known to be correlated with certain ophthalmic conditions. By way of example only, defects in the human ABCA4 gene are thought to be associated with five distinct retinal phenotypes including Stargardt disease, cone-rod dystrophy, age-related macular degeneration and retinitis pigmentosa. See e.g., Allikmets, et al., *Science* 277:1805-07 (1997); Lewis, et al., *Am. Hum. Genet.* 64:422-34 (1999); Stone, et al., *Nature Genetics* 20:328-29 (1998); Allikmets, *Am. J Hum. Gen.* 67:793-799 (2000); Klevering, et al., *Ophthalmology* 11 1:546-553 (2004). In addition, an autosomal dominant form of Stargardt Disease is caused by mutations in the ELOV4 gene. See Karan, et al., *Proc. Natl. Acad. Sci.* (2005). Patients possessing any of these mutations are expected to benefit from the therapeutic and/or prophylactic methods described herein.

In some embodiments, aromatic-cationic peptides, TBMs, or peptide conjugates of the present technology are combined with one or more additional agents for the prevention or treatment of heart failure. Drug treatment for heart failure typically involves diuretics, angiotensin-converting-enzyme (ACE) inhibitors, digoxin (digitalis), calcium channel blockers, and beta-blockers. In mild cases, thiazide diuretics, such as hydrochlorothiazide at 25-50 mg/day or chlorothiazide at 250-500 mg/day, are useful. However, supplemental potassium chloride may be needed, since chronic diuresis causes hypokalemis alkalosis. Moreover, thiazide diuretics usually are not effective in patients with advanced symptoms of heart failure. Typical doses of ACE inhibitors include captopril at 2550 mg/day and quinapril at 10 mg/day.

In one embodiment, an aromatic-cationic peptide, TBM, or peptide conjugate of the present technology is combined with an adrenergic beta-2 agonist. An "adrenergic beta-2 agonist" refers to adrenergic beta-2 agonists and analogues and derivatives thereof, including, for example, natural or synthetic functional variants which have adrenergic beta-2 agonist biological activity, as well as fragments of an adrenergic beta-2 agonist having adrenergic beta-2 agonist biological activity. The term "adrenergic beta-2 agonist biological activity" refers to activity that mimics the effects of adrenaline and noradrenaline in a subject and which improves myocardial contractility in a patient having heart failure. Commonly known adrenergic beta-2 agonists include, but are not limited to, clenbuterol, albuterol, formeoterol, levalbuterol, metaproterenol, pirbuterol, salmeterol, and terbutaline.

In one embodiment, an aromatic-cationic peptide, TBM, or peptide conjugate of the present technology is combined with an adrenergic beta-1 antagonist. Adrenergic beta-1 antagonists and adrenergic beta-1 blockers refer to adrenergic beta-1 antagonists and analogues and derivatives thereof, including, for example, natural or synthetic functional variants which have adrenergic beta-1 antagonist biological activity, as well as fragments of an adrenergic beta-1 antagonist having adrenergic beta-1 antagonist biological activity. Adrenergic beta-1 antagonist biological activity refers to activity that blocks the effects of adrenaline on beta receptors. Commonly known adrenergic beta-1 antagonists include, but are not limited to, acebutolol, atenolol, betaxolol, bisoprolol, esmolol, and metoprolol.

Clenbuterol, for example, is available under numerous brand names including Spiropent, BRONCODIL®, BRONEOTEROL®, Cesbron, and Clenbuter. Similarly, methods of preparing adrenergic beta-1 antagonists such as metoprolol and their analogues and derivatives are well-known in the art. Metoprolol, in particular, is commercially available under the brand names LOPRESSOR® (metoprolol tartate) manufactured by Novartis Pharmaceuticals Corporation (East Hanover, N.J., USA). Generic versions of LOPRESSOR® are also available from Mylan Laboratories Inc. (Canonsburg, Pa., USA); and Watson Pharmaceuticals, Inc. (Morristown, N.J., USA). Metoprolol is also commercially available under the brand name Toprol XL®, manufactured by Astra Zeneca, LP (London, G.B.).

In one embodiment, an additional therapeutic agent is administered to a subject in combination with an aromatic-cationic peptide, TBM, or peptide conjugate of the present technology, such that a synergistic therapeutic effect is produced.

In one embodiment, the subject is administered a composition described herein prior to ischemia. In one embodiment, the subject is administered the composition prior to the reperfusion of ischemic tissue. In one embodiment, the subject is administered the composition at about the time of reperfusion of ischemic tissue. In one embodiment, the subject is administered the composition after reperfusion of ischemic tissue.

In one embodiment, the subject is administered a composition described herein prior to the CABG or revascularization procedure. In another embodiment, the subject is administered the composition after the CABG or revascularization procedure. In another embodiment, the subject is administered the composition during and after the CABG or revascularization procedure. In another embodiment, the subject is administered the composition continuously before, during, and after the CABG or revascularization procedure.

In one embodiment, the subject is administered a composition described herein starting at least 5 minutes, at least 10 minutes, at least 30 minutes, at least 1 hour, at least 3 hours, at least 5 hours, at least 8 hours, at least 12 hours, or at least 24 hours prior to CABG or revascularization, i.e., reperfusion of ischemic tissue. In one embodiment, the subject is administered the composition from about 5-30 minutes, from about 10-60 minutes, from about 10-90 minutes, or from about 10-120 minutes prior to the CABG or revascularization procedure. In one embodiment, the subject is administered the composition until about 5-30 minutes, until about 10-60 minutes, until about 10-90 minutes, until about 10-120 minutes, or until about 10-180 minutes after the CABG or revascularization procedure.

In one embodiment, the subject is administered the composition for at least 30 min, at least 1 hour, at least 3 hours, at least 5 hours, at least 8 hours, at least 12 hours, or at least 24 hours after the CABG procedure or revascularization procedure, i.e., reperfusion of ischemic tissue. In one embodiment, the composition is administered until about 30 minutes, about 1 hour, about 2 hours, about 3 hours, about 4 hours, about 5 hours, about 8 hours, about 12 hours, or about 24 hours after the CABG procedure or revascularization procedure i.e., reperfusion of ischemic tissue.

In one embodiment, the subject is administered the composition as an IV infusion starting at about 1 minute to 30 minutes prior to reperfusion (i.e. about 5 minutes, about 10 minutes, about 20 minutes, or about 30 minutes prior to reperfusion) and continuing for about 1 hour to about 24 hours after reperfusion (i.e., about 1 hour, about 2 hours, about 3 hours, about 4 hours, etc. after reperfusion). In one embodiment, the subject receives an IV bolus injection prior to reperfusion of the tissue. In one embodiment, the subject continues to receive the composition chronically after the reperfusion period, i.e., for about 1-7 days, about 1-14 days, or about 1-30 days after the reperfusion period. During this period, the composition may be administered by any route, e.g., subcutaneously or intravenously.

In one embodiment, the composition is administered by a systemic intravenous infusion commencing about 5-60 minutes, about 10-45 minutes, or about 30 minutes before the induction of anesthesia. In one embodiment, the composition is administered in conjunction with a cardioplegic solution. In one embodiment, the composition is administered as part of the priming solution in a heart lung machine during cardiopulmonary bypass.

In various embodiments, the subject is suffering from a myocardial infarction, a stroke, or is in need of angioplasty. In one embodiment, a revascularization procedure is selected from the group consisting of balloon angioplasty, insertion of a stent, percutaneous coronary intervention (PCI), percutaneous transluminal coronary angioplasty, or directional coronary atherectomy. In one embodiment, the revascularization procedure comprises the removal of the occlusion. In one embodiment, the revascularization procedure comprises the administration of one or more thrombolytic agents. In one embodiment, the one or more thrombolytic agents is selected from the group consisting of: tissue plasminogen activator, urokinase, prourokinase, streptokinase, acylated form of plasminogen, acylated form of plasmin, and acylated streptokinase-plasminogen complex.

In one embodiment the vessel occlusion comprises a cardiac vessel occlusion. In another embodiment, the vessel occlusion is an intracranial vessel occlusion. In yet other embodiments, the vessel occlusion is selected from the group consisting of: deep venous thrombosis; peripheral thrombosis; embolic thrombosis; hepatic vein thrombosis; sinus thrombosis: venous thrombosis; an occluded arteriovenal shunt; and an occluded catheter device.

In one aspect, the present technology relates to the treatment of atherosclerotic vascular disease (ARVD) comprising administering to a subject in need thereof therapeutically effective amounts of aromatic-cationic peptides, TBMs, or peptide conjugates of the present technology. In some embodiments, the treatment is chronic treatment, administered for a period of greater than 1 week.

In another aspect, the present technology relates to the treatment or prevention of ischemic injury in the absence of tissue reperfusion. For example, compositions may be administered to patients experiencing acute ischemia in one or more tissues or organs who, for example, are not suitable candidates for revascularization procedures or for whom revascularization procedures are not readily available. Additionally or alternatively, the compositions may be administered to patients with chronic ischemia in one or more tissues in order to forestall the need for a revascularization procedure. Patients administered compositions for the treatment or prevention of ischemic injury in the absence of tissue reperfusion may additionally be administered compositions prior to, during, and subsequent to revascularization procedures according to the methods described herein.

In one embodiment, the treatment of renal reperfusion injury includes increasing the amount or area of tissue perfusion in a subject compared to a similar subject not administered the composition. In one embodiment, the prevention of renal reperfusion injury includes reducing the amount or area of microvascular damage caused by reperfusion in a subject compared to a similar subject not administered the composition. In some embodiments, treatment or prevention of renal reperfusion injury includes reducing injury to the affected vessel upon reperfusion, reducing the effect of plugging by blood cells, and/or reducing endothelial cell swelling in a subject compared to a similar subject not administered the composition. The extent of the prevention or treatment can be measured by any technique known in the art, including but not limited to measurement of renal volume, renal arterial pressure, renal blood flow (RBF), and glomerular filtration rate (GFR), as well as by imaging techniques known in the art, including, but not limited to CT and micro-CT. Successful prevention or treatment can be determined by comparing the extent of renal reperfusion injury in the subject observed by any of these imaging techniques compared to a control subject or a population of control subjects that are not administered the composition.

In one embodiment, the administration of the composition to a subject is before the occurrence of renal reperfusion injury. For example, in some embodiments, the composition is administered to inhibit, prevent or treat ischemic injury in a subject in need thereof, and/or to forestall reperfusion treatment and/or alleviate or ameliorate reperfusion injury. Additionally or alternatively, in some embodiments, the administration of the composition to a subject is after the occurrence of renal reperfusion injury. In one embodiment, the method is performed in conjunction with a revascularization procedure. In one embodiment, the revascularization procedure is percutaneous transluminal renal angioplasty (PTRA). In one aspect, the present technology relates to a method of renal revascularization comprising administering to a mammalian subject a therapeutically effective amount of the composition and performing PTRA on the subject.

In one embodiment, the subject is administered an aromatic-cationic peptide, TBM, or peptide conjugate of the present technology, prior to a revascularization procedure. In another embodiment, the subject is administered the aromatic-cationic peptide, TBM, and/or peptide conjugate of the present technology after the revascularization procedure. In another embodiment, the subject is administered the aromatic-cationic peptide, TBM, and/or peptide conjugate of the present technology during and after the revascularization procedure. In yet another embodiment, the subject is administered the aromatic-cationic peptide, TBM, and/or peptide conjugate of the present technology continuously before, during, and after the revascularization procedure. In another embodiment, the subject is administered the aromatic-cationic peptide, TBM, or peptide conjugate of the present technology regularly (i.e., chronically) following renal artery stenosis and/or a renal revascularization procedure.

In some embodiments, the subject is administered the aromatic-cationic peptide, TBM, and/or peptide conjugate of the present technology after the revascularization procedure. In one embodiment, the subject is administered the aromatic-cationic peptide, TBM, and/or peptide conjugate of the present technology for at least 3 hours, at least 5 hours, at least 8 hours, at least 12 hours, or at least 24 hours after the revascularization procedure. In some embodiments, the subject is administered the aromatic-cationic peptide, TBM, and/or peptide conjugate of the present technology prior to the revascularization procedure. In one embodiment, the subject is administered the aromatic-cationic peptide, TBM, and/or peptide conjugate of the present technology starting at least 8 hours, at least 4 hours, at least 2 hours, at least 1 hour, or at least 10 minutes prior to the revascularization procedure. In one embodiment, the subject is administered the aromatic-cationic peptide, TBM, and/or peptide conjugate of the present technology for at least one week, at least one month or at least one year after the revascularization procedure. In some embodiments, the subject is administered the aromatic-cationic peptide, TBM, and/or peptide conjugate of the present technology prior to and after the revascularization procedure. In some embodiments, the subject is administered the aromatic-cationic peptide, TBM, and/or peptide conjugate of the present technology as an infusion over a specified period of time. In some embodiments, the aromatic-cationic peptide, TBM, or peptide conjugate of the present technology is administered to the subject as a bolus.

In some embodiments, the present methods comprise administration of aromatic-cationic peptide, TBM, and/or peptide conjugate of the present technology in conjunction with one or more thrombolytic agents. In some embodiments, the one or more thrombolytic agents are selected from the group consisting of: tissue plasminogen activator, urokinase, prourokinase, streptokinase, acylated form of plasminogen, acylated form of plasmin, and acylated streptokinase-plasminogen complex.

In some embodiments, TBMs, (or derivatives, analogues, or pharmaceutically acceptable salts thereof) or peptide conjugates of the present technology are useful in methods of treating vessel occlusion injury, an anatomic zone of no re-flow, or cardiac ischemia-reperfusion injury in a subject for therapeutic purposes. In other embodiments, TBMs, (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In therapeutic applications, compositions or medicaments comprising TBMs, (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or peptide conjugates of the present technology are administered to a subject suspected of, or already suffering from such a disease or condition in an amount sufficient to cure, or partially arrest, the symptoms of the disease or condition, including its complications and intermediate pathological phenotypes in development of the disease or condition. As such, the present technology provides methods of treating an individual afflicted with an anatomic zone of no re-flow.

Pain Management/Analgesia

In one aspect, the present disclosure provides a method for stimulating a mu-opioid receptor in a mammal in need thereof. The method comprises administering systemically to the mammal an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) or peptide conjugates of the present technology. In one embodiment, the method comprises inhibiting norepinephrine in the mammal.

As used herein, "neuropathy" or "peripheral neuropathy" refers generally to damage to nerves of the peripheral nervous system. The term encompasses neuropathy of various etiologies, including but not limited to acquired neuropathies, hereditary neuropathies, and idiopathic neuropathies. Illustrative neuropathies include but are not limited to neuropathies caused by, resulting from, or otherwise associated with trauma, genetic disorders, metabolic/endocrine complications, inflammatory diseases, infectious diseases, vitamin deficiencies, malignant diseases, and toxicity, such as alcohol, organic metal, heavy metal, radiation, and drug toxicity. As used herein, the term encompasses motor, sensory, mixed sensorimotor, chronic, and acute neuropathy. As used herein the term encompasses mononeuropathy, multiple mononeuropathy, and polyneuropathy.

Drug toxicity causes multiple forms of peripheral neuropathy, with the most common being axonal degeneration. A notable exception is that of perhexiline, a prophylactic anti-anginal agent that can cause segmental demyelination, a localized degeneration of the insulating layer around some nerves.

Peripheral neuropathies usually present sensory symptoms initially, and often progress to motor disorders. Most drug-induced peripheral neuropathies are purely sensory or mixed sensorimotor defects. A notable exception here is that of Dapzone, which causes an almost exclusively motor neuropathy.

Drug-induced peripheral neuropathy, including, for example, chemotherapy-induced peripheral neuropathy can cause a variety of dose-limiting neuropathic conditions, including 1) myalgias, 2) painful burning paresthesis, 3) glove-and-stocking sensory neuropathy, and 4) hyperalgia and allodynia. Hyperalgia refers to hypersensitivity and pain caused by stimuli that is normally only mildly painful or irritating. Allodynia refers to hypersensitivity and pain caused by stimuli that is normally not painful or irritating.

In some embodiments, TBMs (or derivatives, analogues, or pharmaceutically acceptable salts thereof) or peptide conjugates of the present technology (e.g., those including D-Arg-2'6'-Dmt-Lys-Phe-NH$_2$) are useful for the treatment or prevention of peripheral neuropathy or the symptoms of peripheral neuropathy. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the peripheral neuropathy is drug-induced peripheral neuropathy. In some embodiments, the peripheral neuropathy is induced by a chemotherapeutic agent. In some embodiments, the chemotherapeutic agent is a vinca alkaloid. In some embodiments, the vinca alkaloid is vincristine. In some embodiments, the symptoms of peripheral neuropathy include hyperalgesia.

As used herein, "hyperalgesia" refers to an increased sensitivity to pain, which may be caused by damage to nociceptors or peripheral nerves (i.e. neuropathy). The term refers to temporary and permanent hyperalgesia, and encompasses both primary hyperalgesia (i.e. pain sensitivity occurring directly in damaged tissues) and secondary hyperalgesia (i.e. pain sensitivity occurring in undamaged tissues surrounding damaged tissues). The term encompasses hyperalgesia caused by but not limited to neuropathy caused by, resulting from, or otherwise associated with genetic disorders, metabolic/endocrine complications, inflammatory diseases, vitamin deficiencies, malignant diseases, and toxicity, such as alcohol, organic metal, heavy metal, radiation, and drug toxicity. In some embodiments hyperalgesia is caused by drug-induced peripheral neuropathy.

In some embodiments, TBMs (or derivatives, analogues, or pharmaceutically acceptable salts thereof) or peptide conjugates of the present technology are useful for the treatment or prevention of hyperalgesia. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard. In some embodiments, the hyperalgesia is drug-induced. In some embodiments, the hyperalgesia is induced by a chemotherapeutic agent. In some embodiments, the chemotherapeutic agent is a vinca alkaloid. In some embodiments, the vinca alkaloid is vincristine.

A wide variety of pharmaceuticals are known to cause drug-induced neuropathy, including but not limited to anti-microbials, anti-neoplastic agents, cardiovascular drugs, hypnotics and psychotropics, anti-rheumatics, and anti-convulsants.

Illustrative anti-microbials known to cause neuropathy include but are not limited to isoniazid, ethambutol, ethionamide, nitrofurantoin, metronidazole, ciprofloxacin, chloramphenicol, thiamphenicol, diamines, colistin, streptomycin, nalidixic acid, clioquinol, sulphonamides, amphotericin, and penicillin.

Illustrative anti-neoplastic agents known to cause neuropathy include but are not limited to procarbazine, nitrofurazone, podophyllum, mustine, ethoglucid, cisplatin, suramin, paclitaxel, chlorambucil, altretamine, carboplatin, cytarabine, docetaxel, dacarbazine, etoposide, ifosfamide with mesna, fludarabine, tamoxifen, teniposide, and thioguanine. Vinca alkaloids, such as vincristine, are known to be particularly neurotoxic.

Illustrative cardiovascular drugs known to cause neuropathy include but are not limited to propranolol, perhexiline, hydrallazine, amiodarone, disopyramide, and clofibrate.

Illustrative hypnotics and psychotropics known to cause neuropathy include but are not limited to phenelzine, thalidomide, methaqualone, glutethimide, amitriptyline, and imipramine.

Illustrative anti-rheumatics known to cause neuropathy include but are not limited to gold, indomethacin, colchicine, chloroquine, and phenyl butazone.

Illustrative anti-convulsants known to cause neuropathy include but are not limited to phenytoin.

Other drugs known to cause neuropathy include but are not limited to calcium carbimide, sulfoxone, ergotamine, propylthiouracil, sulthiame, chlorpropamide, methysergide, phenytoin, disulfiram, carbutamide, tolbutamide, methimazole, dapsone, and anti-coagulants.

The present disclosure contemplates combination therapies comprising the administration of TBMs (alone or in combination with one or more aromatic-cationic peptides such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) with one or more additional therapeutic regimens. The present disclosure also provides combination therapies comprising the administration of peptide conjugates of the present technology with one or more additional therapeutic regimens. In some embodiments, the additional therapeutic regimens are directed to the treatment or prevention of neuropathy or hyperalgesia or symptoms associated with neuropathy or hyperalgesia. In some embodiments, the additional therapeutic regimens are directed to the treatment or prevention of diseases or conditions unrelated to neuropathy or hyperalgesia. In some embodiments, the additional therapeutic regimens include regimens directed to the treatment or prevention of neuropathy or hyperalgesia or symptoms associated with neuropathy or hyperalgesia, in addition to diseases, conditions, or symptoms unrelated to neuropathy or hyperalgesia or symptoms associated with neuropathy or hyperalgesia. In some embodiments, the additional therapeutic regimens comprise administration of one or more drugs, including but not limited to anti-microbials, anti-neoplastic agents, cardiovascular drugs, hypnotics and psychotropics, anti-rheumatics, and anti-convulsants. In embodiments, the additional therapeutic regimens comprise non-pharmaceutical therapies, including but not limited to dietary and lifestyle management.

In one aspect, the present disclosure provides a method for inhibiting or suppressing pain in a subject in need thereof, comprising administering to the subject an effective amount of TBMs (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$). In another aspect, the present disclosure provides a method for inhibiting or suppressing pain in a subject in need thereof, comprising administering to the subject an effective amount of peptide conjugates of the present technology.

In some embodiments, TBMs (or derivatives, analogues, or pharmaceutically acceptable salts thereof) or peptide conjugates of the present technology (e.g., those including D-Arg-2'6'-Dmt-Lys-Phe-NH$_2$) are useful in suppressing pain through the binding and inhibition of mu-opioid receptors. In other embodiments, TBMs (or derivatives, analogues, or pharmaceutically acceptable salts thereof) in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) will show a synergistic effect in this regard.

Determination of the Biological Effect of Therapeutic Biological Molecules (TBMs) or Peptide Conjugates of the Present Technology In various embodiments, suitable in vitro or in vivo assays are performed to determine the effect of a specific composition of the present technology and whether its administration is indicated for treatment. In various embodiments, in vitro assays can be performed with representative animal models, to determine if a given TBM (or derivatives, analogues, or pharmaceutically acceptable salts thereof) alone or in combination with one or more active agents (e.g., an aromatic-cationic peptide such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$), or a peptide conjugate-based therapeutic exerts the desired effect in treating a disease or condition. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

IV. Synthesis of Compositions of the Present Technology

The compounds useful in the methods of the present disclosure (e.g., TBMs, or derivatives, analogues, or pharmaceutically acceptable salts thereof) may be synthesized by any method known in the art.

The aromatic-cationic peptides disclosed herein (such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$) may be synthesized by any method known in the art. Exemplary, non-limiting methods for chemically synthesizing the protein include those described by Stuart and Young in "*Solid Phase Peptide Synthesis*," Second Edition, Pierce Chemical Company (1984), and in "*Solid Phase Peptide Synthesis*," Methods Enzymol. 289, Academic Press, Inc, New York (1997).

Recombinant peptides may be generated using conventional techniques in molecular biology, protein biochemistry, cell biology, and microbiology, such as those described in *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis, Gait, Ed.* (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, Meth. Enzymol., (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

Aromatic-cationic peptide precursors may be made by either chemical (e.g., using solution and solid phase chemical peptide synthesis) or recombinant syntheses known in the art. Precursors of e.g., amidated aromatic-cationic peptides of the present technology may be made in like manner. In some embodiments, recombinant production is believed significantly more cost effective. In some embodiments, precursors are converted to active peptides by amidation reactions that are also known in the art. For example, enzymatic amidation is described in U.S. Pat. No. 4,708,934 and European Patent Publications 0 308 067 and 0 382 403. Recombinant production can be used for both the precursor and the enzyme that catalyzes the conversion of the precursor to the desired active form of the aromatic-cationic peptide. Such recombinant production is discussed in Biotechnology, Vol. 11 (1993) pp. 64-70, which further describes a conversion of a precursor to an amidated product. During amidation, a keto-acid such as an alpha-keto acid, or salt or ester thereof, wherein the alpha-keto acid has the molecular structure RC(O)C(O)OH, and wherein R is selected from the group consisting of aryl, a $C_1$-$C_4$ hydrocarbon moiety, a halogenated or hydroxylated $C_1$-$C_4$ hydrocarbon moiety, and a $C_1$-$C_4$ carboxylic acid, may be used in place of a catalase co-factor. Examples of these keto acids include, but are not limited to, ethyl pyruvate, pyruvic acid and salts thereof, methyl pyruvate, benzoyl formic acid and salts thereof, 2-ketobutyric acid and salts thereof, 3-methyl-2-oxobutanoic acid and salts thereof, and 2-keto glutaric acid and salts thereof.

In some embodiments, the production of the recombinant aromatic-cationic peptide may proceed, for example, by producing glycine-extended precursor in *E. coli* as a soluble fusion protein with glutathione-S-transferase. An α-amidating enzyme catalyzes conversion of precursors to active aromatic-cationic peptide. That enzyme is recombinantly produced, for example, in Chinese Hamster Ovary (CHO) cells as described in the Biotechnology article cited above. Other precursors to other amidated peptides may be produced in like manner. Peptides that do not require amidation or other additional functionalities may also be produced in like manner. Other peptide active agents are commercially available or may be produced by techniques known in the art.

V. Preparation of the Peptide Conjugates of the Present Technology

In some embodiments, at least one TBM and at least one aromatic-cationic peptide as described herein, associate to form a peptide conjugate of the present technology. The TBM and aromatic-cationic peptide can associate by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

For a chemical bond or physical bond, a functional group on the TBM typically associates with a functional group on the aromatic-cationic peptide. Alternatively, a functional group on the aromatic-cationic peptide associates with a functional group on the TBM.

The functional groups on the TBM and aromatic-cationic peptide can associate directly. For example, a functional group (e.g., a sulfhydryl group) on a TBM can associate with a functional group (e.g., sulfhydryl group) on an aromatic-cationic peptide to form a disulfide.

Alternatively, the functional groups can associate through a cross-linking agent (i.e., linker). Some examples of cross-linking agents are described below. The cross-linker can be attached to either the TBM or the aromatic-cationic peptide.

The linker may and may not affect the number of net charges of the aromatic-cationic peptide. Typically, the linker will not contribute to the net charge of the aromatic-cationic peptide. Each amino group, if any, present in the linker will contribute to the net positive charge of the aromatic-cationic peptide. Each carboxyl group, if any, present in the linker will contribute to the net negative charge of the aromatic-cationic peptide.

The number of TBMs or aromatic-cationic peptides in the peptide conjugate is limited by the capacity of the peptide to accommodate multiple TBMs or the capacity of the TBM to accommodate multiple peptides. For example, steric hindrance may hinder the capacity of the peptide to accommodate especially large molecules. Alternatively, steric hindrance may hinder the capacity of the molecule to accommodate a relatively large (e.g., seven, eight, nine or ten amino acids in length) aromatic-cationic peptide.

The number of TBMs or aromatic-cationic peptides in the peptide conjugate is also limited by the number of functional groups present on the other. For example, the maximum number of TBMs associated with a peptide conjugate depends on the number of functional groups present on the aromatic-cationic peptide. Alternatively, the maximum number of aromatic-cationic peptides associated with a TBM depends on the number of functional groups present on the TBM.

In one embodiment, the peptide conjugate comprises at least one TBM, and in some embodiments, at least two TBMs, associated with an aromatic-cationic peptide. A relatively large peptide (e.g., eight, ten amino acids in length) containing several (e.g., 3, 4, 5 or more) functional groups can be associated with several (e.g., 3, 4, 5 or more) TBMs.

In another embodiment, the peptide conjugate comprises at least one aromatic-cationic peptide, and, in some embodiments, at least two aromatic-cationic peptides, associated with a TBM. For example, a TBM containing several functional groups (e.g., 3, 4, 5 or more) can be associated with several (e.g., 3, 4, or 5 or more) peptides.

In yet another embodiment, the peptide conjugate comprises one aromatic-cationic peptide associated to one TBM.

In one embodiment, a peptide conjugate comprises at least one TBM chemically bonded (e.g., conjugated) to at least one aromatic-cationic peptide. The molecule can be chemically bonded to an aromatic-cationic peptide by any method known to those in the art. For example, a functional group on the TBM may be directly attached to a functional group on the aromatic-cationic peptide. Some examples of suitable functional groups include, for example, amino, carboxyl, sulfhydryl, maleimide, isocyanate, isothiocyanate and hydroxyl.

The TBM may also be chemically bonded to the aromatic-cationic peptide by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; 5,985,566; and 6,133,038 of Kreatech Biotechnology, B.V., Amsterdam, The Netherlands.

The functional group on the TBM may be different from the functional group on the peptide. For example, if a sulfhydryl group is present on the TBM, the TBM can be cross-linked to the peptide, e.g., [Dmt$^1$]DALDA, through the 4-amino group of lysine by using the cross-linking reagent SMCC (i.e., succinimidyl 4-(N-maleimidomethyl) cyclohexane-1-carboxylate) from Pierce Biotechnology. In another example, the 4-amino group of lysine of DALDA can be conjugated directly to an alpha-phosphate group on a TBM by using the crosslinking reagent EDC (i.e., (N-[3-dimethylaminopropyl-N'-ethylcarboiimide]) from Pierce Biotechnology.

Alternatively, the functional group on the TBM and peptide can be the same. Homobifunctional cross-linkers are typically used to cross-link identical functional groups. Examples of homobifunctional cross-linkers include EGS (i.e., ethylene glycol bis[succinimidylsuccinate]), DSS (i.e., disuccinimidyl suberate), DMA (i.e., dimethyl adipimidate.2HC1), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

To chemically bond the TBMs and the peptides, the TBMs, peptides, and cross-linker are typically mixed together. The order of addition of the TBMs, peptides, and cross-linker is not important. For example, the peptide can be mixed with the cross-linker, followed by addition of the TBM. Alternatively, the TBM can be mixed with the cross-linker, followed by addition of the peptide. Optimally, the TBM and the peptides are mixed, followed by addition of the cross-linker.

The chemically bonded peptide conjugates deliver the TBM and/or aromatic-cationic peptide to a cell. In some instances, the TBM functions in the cell without being cleaved from the aromatic-cationic peptide. For example, if the aromatic-cationic peptide does not block the catalytic site of the molecule, then cleavage of the molecule from the aromatic-cationic peptide is not necessary.

In other instances, it may be beneficial to cleave the TBM from the aromatic-cationic peptide. The web-site of Pierce Biotechnology, Inc. described above can also provide assistance to one skilled in the art in choosing suitable cross-linkers which can be cleaved by, for example, enzymes in the cell. Thus the molecule can be separated from the aromatic-cationic peptide. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid HCl).

In another embodiment, a peptide conjugate comprises at least one TBM physically bonded with at least one aromatic-cationic peptide. Any method known to those in the art can be employed to physically bond the molecules with the aromatic-cationic peptides.

For example, the aromatic-cationic peptides and TBMs can be mixed together by any method known to those in the art. The order of mixing is not important. For instance, TBMs can be physically mixed with modified or unmodified aromatic-cationic peptides by any method known to those in the art. Alternatively, the modified or unmodified aromatic-cationic peptides can be physically mixed with the molecules by any method known to those in the art.

For example, the aromatic-cationic peptides and TBMs can be placed in a container and agitated, by for example, shaking the container, to mix the aromatic-cationic peptides and TBMs.

The aromatic-cationic peptides can be modified by any method known to those in the art. For instance, the aromatic-cationic peptide may be modified by means of cross-linking agents or functional groups, as described above. The linker may and may not affect the number of net charges of the aromatic-cationic peptide. Typically, the linker will not contribute to the net charge of the aromatic-cationic peptide. Each amino group, if any, present in the linker contributes to the net positive charge of the aromatic-cationic peptide. Each carboxyl group, if any, present in the linker contributes to the net negative charge of the aromatic-cationic peptide.

For example, [Dmt$_1$]DALDA can be modified, through the 4-amino group of lysine by using the cross-linking reagent SMCC (i.e., succinimidyl 4-(N-maleimidomethyl) cyclohexane-1-carboxylate) from Pierce Biotechnology. To form a peptide conjugate, the modified aromatic-cationic peptide is usually formed first and then mixed with the TBM.

One advantage of the physically bonded peptide conjugates, is that the TBM functions in a cell without the need for removing an aromatic-cationic peptide, such as those peptide conjugates in which the TBM is chemically bonded to an aromatic-cationic peptide. Furthermore, if the aromatic-cationic peptide does not block the catalytic site of the molecule, then dissociation of the complex is also not necessary.

In some embodiments, at least one TBM and at least one aromatic-cationic peptide as described above (e.g., 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$ or a pharmaceutically acceptable salt thereof), are associated to form a conjugate. The TBM and aromatic-cationic peptide can associate by any method known to those in the art. The following examples of peptide-TBM linkages are provided by way of illustration only, and are not intended to be limiting. In general, TBMs can be linked to an aromatic-cationic peptide of the present disclosure by any suitable technique, with appropriate consideration of the need for pharmokinetic stability and reduced overall toxicity to the subject. A TBM can be coupled to an aromatic-cationic peptide either directly or indirectly (e.g., via a linker group).

Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking. In some embodiments, bonds between the compounds are rapidly degraded or dissolved;

in some embodiments, bonds are cleaved by drug metabolizing or excretory chemistry and/or enzymes.

For a chemical bond or physical bond, a functional group on the TBM typically associates with a functional group on the aromatic-cationic peptide. For example, TBMs may contain carboxyl functional groups, or hydroxyl functional groups. The free amine group of an aromatic-cationic peptide may be cross-linked directly to the carboxyl group of a TBM using 1-Ethyl-3-[3-dimethylaminopropyl]carbodiimide hydrochloride (EDC or EDAC) or dicyclohexylcarbodiimide (DCC). Cross-linking agents can, for example, be obtained from Pierce Biotechnology, Inc., Rockford, Ill. The Pierce Biotechnology, Inc. website can provide assistance.

In some embodiments, a direct reaction between an additional active agent (e.g., a TBM) and an aromatic-cationic peptide (e.g., 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$ or a pharmaceutically acceptable salt thereof), is formed when each possesses a functional group capable of reacting with the other. Additionally or alternatively, a suitable chemical linker group can be used. A linker group can function as a spacer to distance the peptide and the TBM in order to avoid interference with, for example, binding capabilities. A linker group can also serve to increase the chemical reactivity of a substituent, and thus increase the coupling efficiency.

In exemplary embodiments, suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups can be designed into recombinant immunoglobulin molecules. It will be evident to those skilled in the art that a variety of bifunctional or polyfunctional reagents, both homo- and hetero-functional (such as those described in the catalogue of the Pierce Chemical Co., Rockford, Ill.), can be employed as a linker group. Coupling can be affected, e.g., through amino groups, carboxyl groups, sulfhydryl groups or oxidized carbohydrate residues (see, e.g., U.S. Pat. No. 4,671,958).

As an additional or alternative coupling method, a TBM can be coupled to the aromatic-cationic peptides disclosed herein, e.g., through an oxidized carbohydrate group at a glycosylation site, for example, as described in U.S. Pat. Nos. 5,057,313 and 5,156,840. Yet another alternative method of coupling an aromatic-cationic peptide to an additional active agent is by the use of a non-covalent binding pair, such as streptavidin/biotin, or avidin/biotin. In these embodiments, one member of the pair is covalently coupled to the aromatic-cationic peptide, and the other member of the binding pair is covalently coupled to the TBM.

In some embodiments, a TBM may be more potent when free from the aromatic-cationic peptide, and it may be desirable to use a linker group which is cleavable during or upon internalization into a cell, or which is gradually cleavable over time in the extracellular environment. A number of different cleavable linker groups have been described. Examples of the intracellular release of active agents from these linker groups include, e.g., but are not limited to, cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

In some embodiments the aromatic-cationic peptide, such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$, is chemically linked to at least one TBM. In some embodiments, the peptide is linked to the TBM using a labile bond such that hydrolysis in vivo releases the two pharmaceutically active agents. A schematic diagram illustrating exemplary embodiments is shown in FIG. 1. In some embodiments, the linkage comprises an ester, a carbonate, a carbamate or other labile linkage.

In some embodiments, an aromatic-cationic peptide as disclosed herein is coupled to more than one TBM. For example, in some embodiments, aromatic-cationic peptide is coupled to a mixture of at least two TBMs. That is, more than one type of TBM can be coupled to one aromatic-cationic peptide. For instance, a TBM can be conjugated to an aromatic-cationic peptide to increase the effectiveness of the therapy, as well as lowering the required dosage necessary to obtain the desired therapeutic effect. Regardless of the particular embodiment, formulations with more than one moiety can be prepared in a variety of ways. For example, more than one moiety can be coupled directly to an aromatic-cationic peptide, or linkers that provide multiple sites for attachment (e.g., dendrimers) can be used. Alternatively, a carrier with the capacity to hold more than one TBM can be used.

In some embodiments, linkers that that are cleaved within a cell may also be used. For example, heterocyclic "self-immolating" linker moieties can be used to link aromatic-cationic peptides of the present technology to TBMs (see, for example U.S. Pat. Nos. 7,989,434 and 8,039,273, herein incorporated by reference in its entirety).

In some embodiments, the linker moiety comprises a heterocyclic "self-immolating moiety" bound to the aromatic-cationic peptide (e.g., D-Arg, 2'6'-Dmt-Lys-Phe-NH$_2$) and a TBM and incorporates an amide group or beta-glucuronide group that, upon hydrolysis by an intracellular protease or beta-glucuronidase, initiates a reaction that ultimately cleaves the self-immolative moiety from the aromatic-cationic peptide such that the TBM is released from the peptide in an active form.

Figure 2:
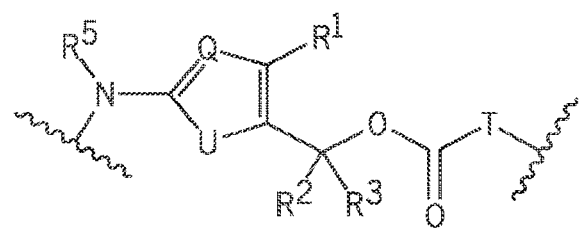
FIG. 2 shows illustrative examples of aromatic-cationic peptides of the present disclosure linked by covalent attachment to self-immolating moieties.
Figure 2:
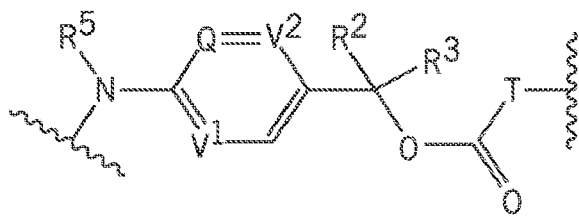
Figure 2:
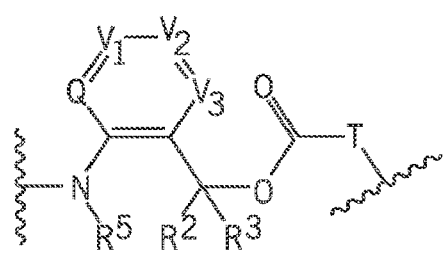

Exemplary self-immolating moieties include those of Formulas presented in FIG. 2. In FIG. 2, the wavy lines indicate the covalent attachment sites to the aromatic-cationic peptide and the TBM, wherein:

U is O, S or NR$^6$;

Q is CR$^4$ or N;

V$^1$, V$^2$ and V$^3$ are independently CR$^4$ or N provided that for Formula Q and R of FIG. 2 at least one of Q, V$^1$ and V$^2$ is N;

T is NH, NR$^6$, O or S pending from said drug moiety;

R$^1$, R$^2$, R$^3$ and R$^4$ are independently selected from H, F, Cl, Br, I, OH, —N(R$^5$)$_2$, N(R$^5$)$_3^+$, C$_1$-C$_8$ alkylhalide, carboxylate, sulfate, sulfamate, sulfonate, —SO$_2$R$^5$, —S(=O)R$^5$, —SR$^5$, —SO$_2$N(R$^5$)$_2$, —C(=O)R$^5$, —CO$_2$R$^5$, —C(=O)N(R$^5$)$_2$, —CN, —N$_3$, —NO$_2$, C$_1$-C$_8$ alkoxy, C$_1$-C$_8$halosubstituted alkyl, polyethyleneoxy, phosphonate, phosphate, C$_1$-C$_8$ alkyl, C$_1$-C$_8$ substituted alkyl, C$_2$-C$_8$ alkenyl, C$_2$-C$_8$ substituted alkenyl, C$_2$-C$_8$ alkynyl, C$_2$-C$_8$ substituted alkynyl, C$_6$-C$_{20}$ aryl, C$_6$-C$_{20}$ substituted aryl, C$_1$-C$_{20}$ heterocycle, and C$_1$-C$_{20}$ substituted heterocycle; or when taken together, R$^2$ and R$^3$ form a carbonyl (=O), or spiro carbocyclic ring of 3 to 7 carbon atoms; and R$^5$ and R$^6$ are independently selected from H, C$_1$-C$_8$ alkyl, C$_1$-C$_8$ substituted alkyl, C$_2$-C$_8$ alkenyl, C$_2$-C$_8$ substituted alkenyl, C$_2$-C$_8$ alkynyl, C$_2$-C$_8$ substituted alkynyl, C$_6$-C$_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from F, $C_1$, Br, I, OH, —N($R^5$)$_2$, —N($R^5$)$_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2$R$^5$, S(=O)R$^5$, —SO$_2$N(R$^5$)$_2$, —C(=O)R$^5$, —CO$_2$R$^5$, —C(=O)N(R$^5$)$_2$, —CN, —N$_3$, NO$_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, and phosphate.

The linker moiety may further include a cleavable peptide sequence adjacent to the self-immolative moiety that is a substrate for an intracellular enzyme, for example a cathepsin such as cathepsin B, that cleaves the cleavable peptide at the amide bond shared with the self-immolative moiety (e.g., Phe-Lys, Ala-Phe, or Val-Cit). In some embodiments, the amino acid residue chain length of the cleavable peptide sequence ranges from that of a single amino acid to about eight amino acid residues. The following are exemplary enzymatically-cleavable peptide sequences: Gly-Gly, Phe-Lys, Val-Lys, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Ala-Phe, Gly-Gly-Gly, Gly-Ala-Phe, Gly-Val-Cit, Gly-Phe-Leu-Gly, Ala-Leu-Ala-Leu, Phe-N 9-tosyl-Arg, and Phe-N 9-Nitro-Arg, in either orientation. Numerous specific cleavable peptide sequences suitable for use in the present formulations can be designed and optimized in their selectivity for enzymatic cleavage by a particular intracellular enzyme, e.g., liver cell enzymes.

Figure 3A:
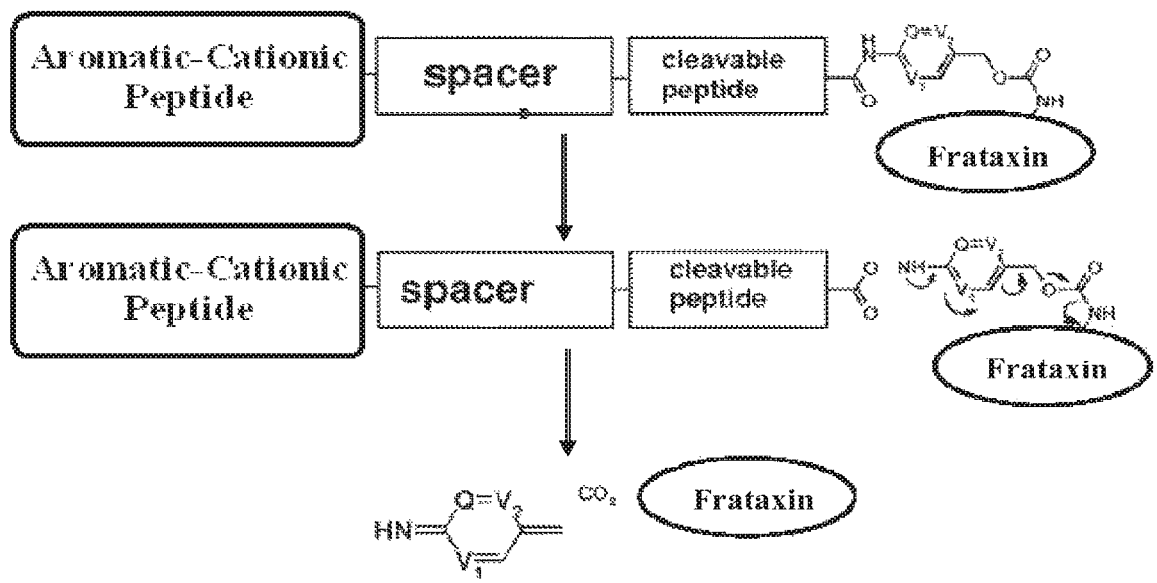
FIGS. 3A, B, and C show illustrative examples of aromatic-cationic peptides of the present disclosure incorporating spacer units to link the additional moieties to the peptide.
Figure 3B:
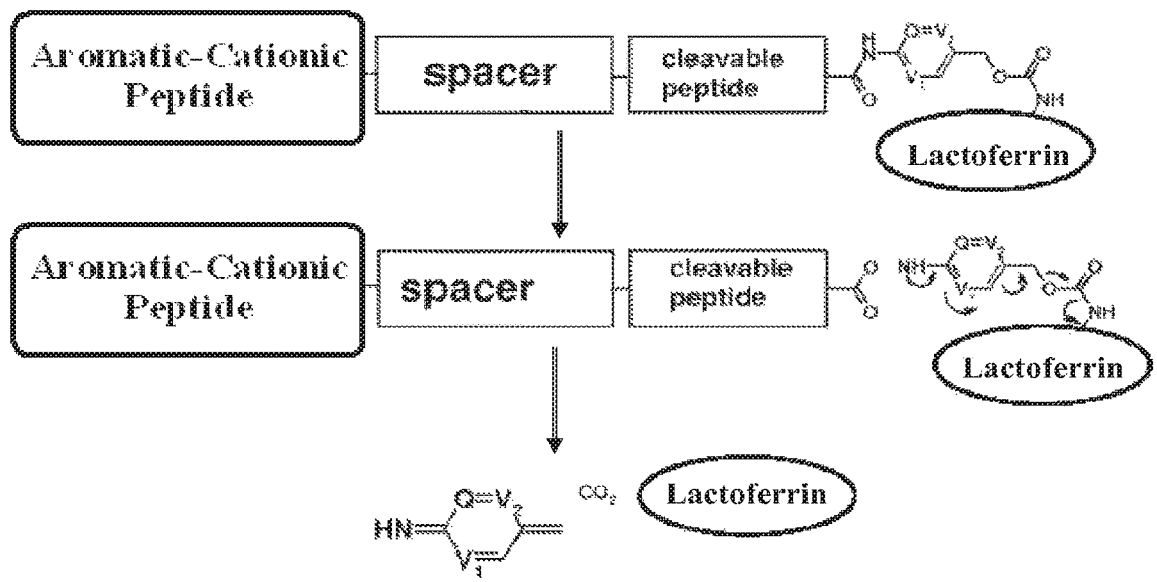
Figure 3C:
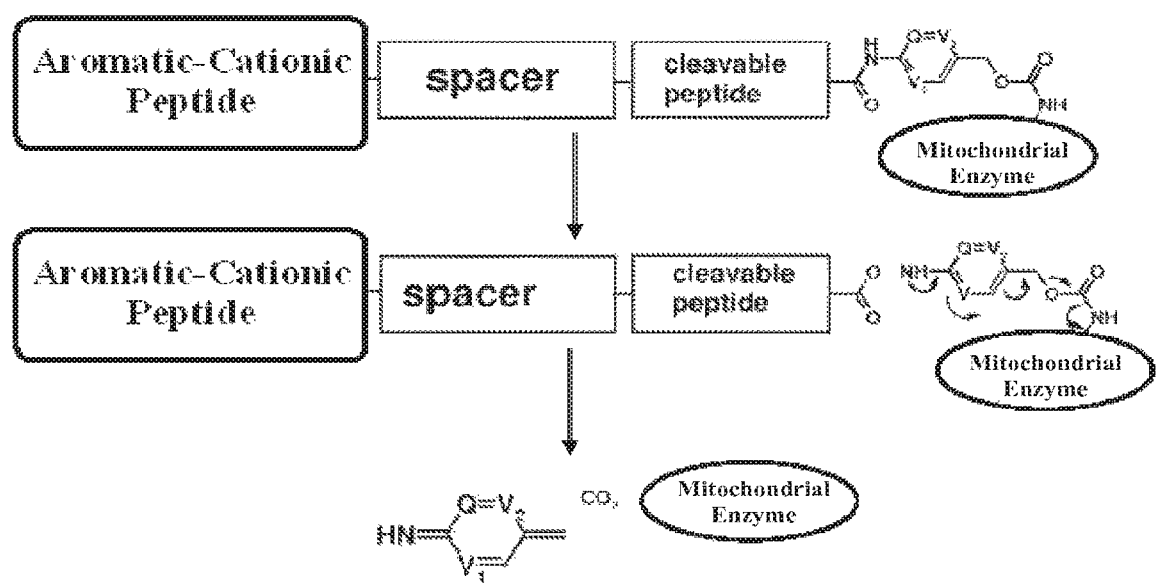

A spacer unit may be linked to the aromatic-cationic peptide via an amide, amine or thioether bond. In some embodiments, the TBM may be connected to the self-immolative moiety of the linker via a chemically reactive functional group pending from the TBM. Exemplary schematics of illustrative embodiments of such formulations are shown in FIG. 3.

In some embodiments, once the aromatic-cationic peptide-TBM conjugate enters the cell or blood stream, the linker is cleaved releasing the peptide from the TBM. The formulations are not intended to be limited by linkers or cleavage means. For example, in some embodiments, linkers are cleaved in the body (e.g., in the blood stream, interstitial tissue, gastrointestinal tract, etc.), releasing the peptide from the TBM via enzymes (e.g., esterases) or other chemical reactions.

As explained above, an aromatic-cationic peptide can be linked to TBMs in a variety of ways, including covalent bonding either directly or via a linker group, and non-covalent associations. For example, in some embodiments, the aromatic-cationic peptide and TBMs can be combined with encapsulation carriers. In some embodiments, this is especially useful to allow the therapeutic compositions to gradually release the aromatic-cationic peptide and TBM over time while concentrating it in the vicinity of the target cells.

In some embodiments, an aromatic-cationic peptide of the present technology, e.g., 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$, can be linked to a TBM of the present technology using an ester linkage. In some embodiments, the ester linkage is formed by coupling the pendant hydroxyl group of a TBM to a linker group bearing the formula:

D-Arg-2'6'-Dmt-Lys-Phe-NH—(C=O)-(linker)-COOH where linker may contain two or more carbon atoms.

As noted above, in some embodiments, the aromatic-cationic peptide-TBM conjugate is generated using a cleavable linker to facilitate release of the peptide in vivo. In some embodiments, the cleavable linker is an acid-labile linker, peptidase-sensitive linker, photolabile linker, a dimethyl linker, or a disulfide-containing linker. In some embodiments, the linker is a labile linkage that is hydrolyzed in vivo to release the TBM and peptide. In some embodiments, the labile linkage comprises an ester linkage, a carbonate linkage, or a carbamate linkage.

In some embodiments, the peptide aromatic-cationic peptide of the present technology, e.g., 2',6'-dimethyl-Tyr-D-Arg-Phe-Lys-NH$_2$, Phe-D-Arg-Phe-Lys-NH$_2$, or D-Arg-2', 6'-Dmt-Lys-Phe-NH$_2$, is chemically linked to a TBM of the present technology using a labile linkage to form a pro-drug that upon hydrolysis in vivo releases the peptide and the TBM as active agents. In some embodiments, the labile linkage comprises an ester linkage, a carbonate linkage, or a carbamate linkage.

As noted above, in one aspect, the present disclosure provides combination therapies for the treatment of disease or disorders comprising administering an effective amount of aromatic-cationic peptide-TBM conjugates that are linked via chemically labile bonds. In some embodiments, the aromatic-cationic peptide-TBM conjugates will be created by linking the aromatic-cationic peptide and the TBM via a linker group bearing the formula:

HOOC-(linker)-COOH; or

HOOC-(linker)-OH; or

HOOC-(linker)-SH where linker consists of one or more carbon atoms. In other embodiments, the linker consists of two or more carbon atoms.

Figure 4:
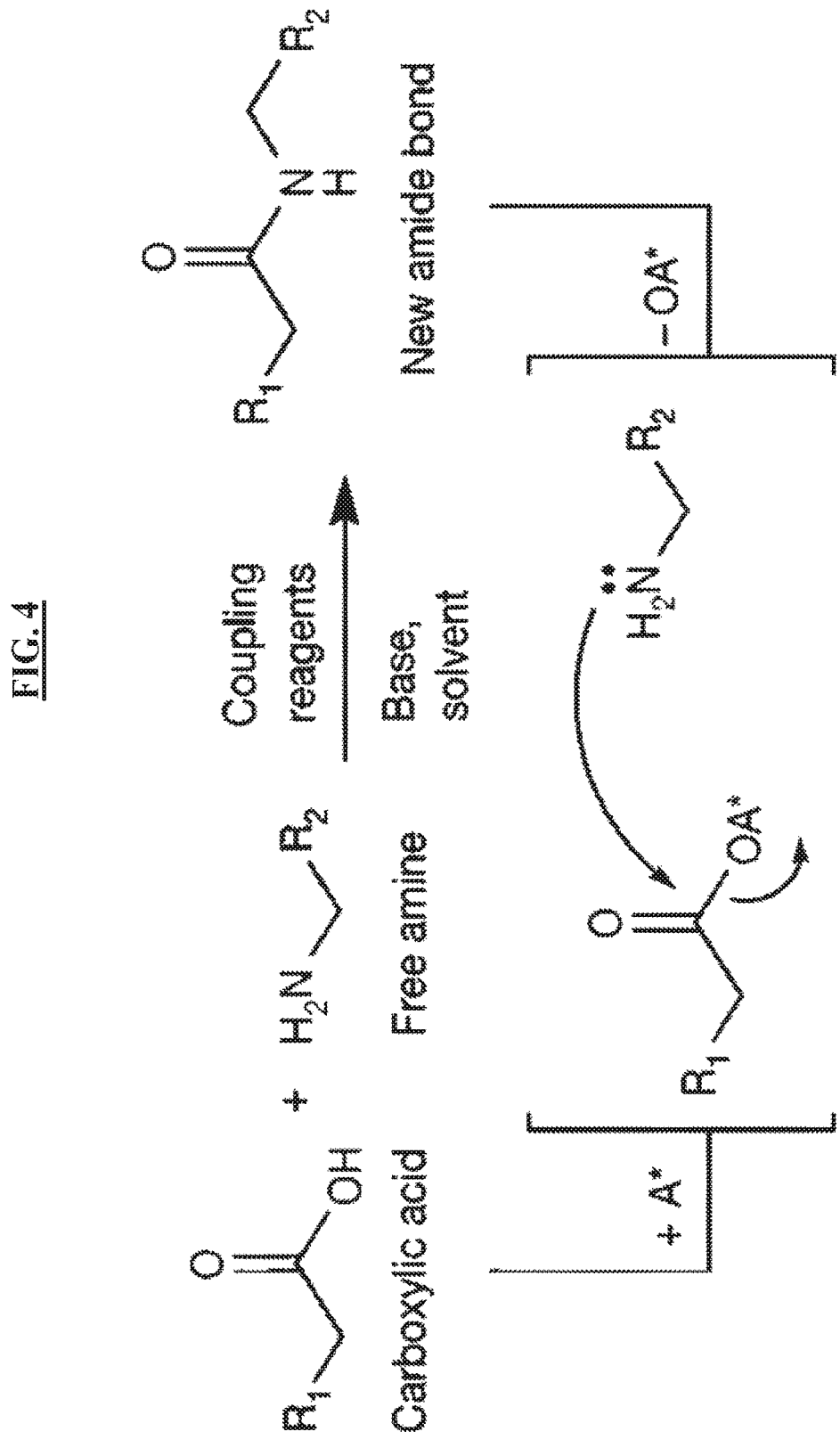
FIG. 4 shows illustrative peptide chemistry to form amide bonds, where the $R_2$ free amine is 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$ and $R_1$ is selected from a linker bearing the formula: -(linker)-COOH; or where linker consists of one or more carbon atoms. In some embodiments, the linker consists of two or more carbon atoms.

By way of example, but not by way of limitation, FIG. 4 illustrates how standard peptide chemistry can be used to form amide bonds between an aromatic-cationic peptide, such as 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$, and the linker groups described herein. Coupling between the aromatic-cationic peptide and the linker can be performed by any of the methods well-known in the art, including the use of carbodiimide coupling chemistry.

Figure 5A:
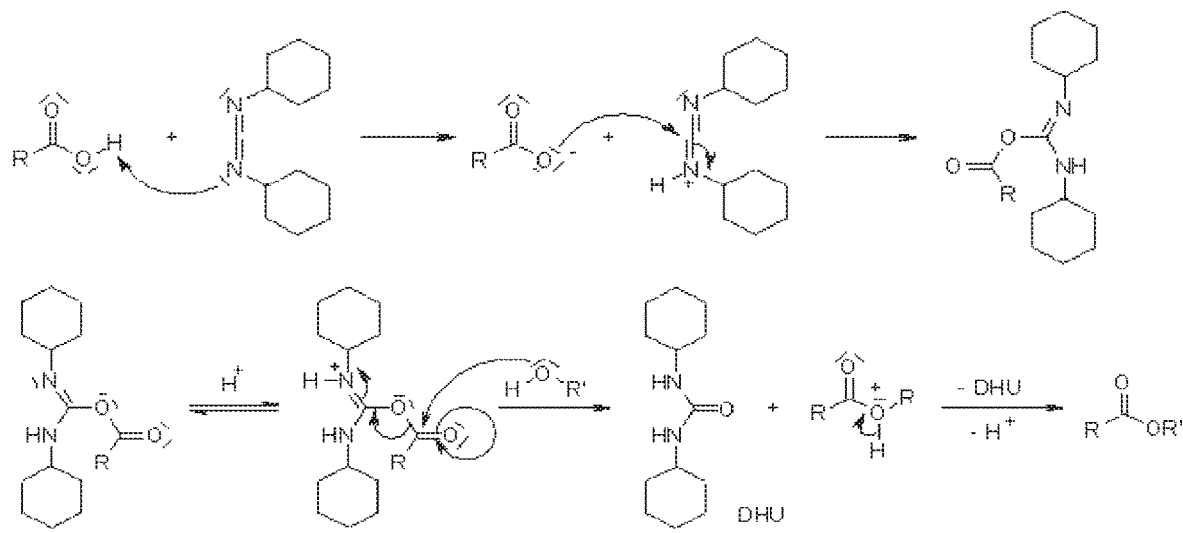
FIGS. 5A and 5B show exemplary linking chemistry of the present disclosure.
Figure 5B:
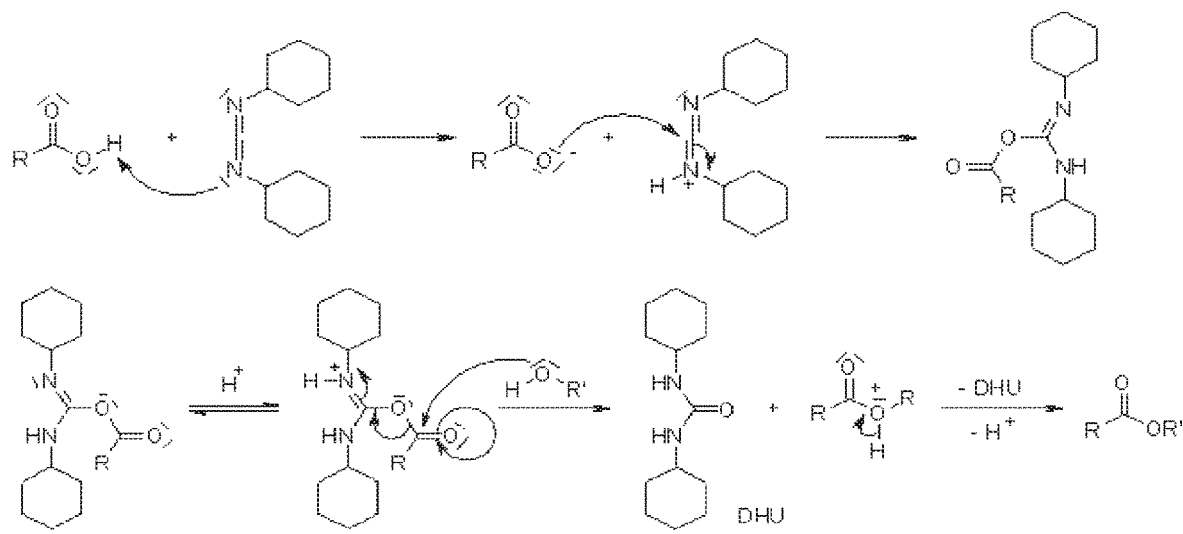

By way of example, but not by way of limitation, FIGS. 5A and 5B illustrate how standard esterification chemistry can be used to couple a TBM and a linker group using a labile ester linkage. Coupling between the TBM and the linker can be performed by any of the methods well known in the art, including the use of carbodiimide coupling chemistry.

Encapsulated Therapeutic Biological Molecules (TBMs) Linked to Aromatic-Cationic Peptides In some embodiments, at least one TBM is encapsulated before being linked to at least one aromatic-cationic peptide. By way of example, but not by limitation, in some embodiments, at least one TBM is encapsulated by a liposome or by polysaccharides, e.g., pectin or chitosan.

In some embodiments, at least one TBM is encapsulated by a liposome and the aromatic-cationic peptide is linked to the outer surface of the liposome. In some embodiments, the liposome is modified to prolong circulation, i.e., coated with polyethylene glycol (PEG). In some embodiments, the liposome is modified to improve targeting of the liposome, e.g., antibody conjugated liposomes.

Encapsulation of a TBM by liposomes can be performed by any methods known in the art. (See Nii, T. and Ishii, F., *International Journal of Pharmaceutics*, 298(11): 198-205 (2005)).

In some embodiments, at least one TBM is encapsulated by a polysaccharide and the aromatic-cationic peptide is linked to the outer surface of the polysaccharide. Examples of encapsulating polysaccharides include, but are not limited to, pectin and chitosan.

Encapsulation of the TBM by polysaccharides can be performed by any methods known in the art. (See Gan, Q. and Wang, T., *Colloids and Surfaces B: Biointerfaces*, 59(1): 24-34 (2007)).

In some embodiments, the TBM is encapsulated but not linked to the aromatic-cationic peptide.

VI. Modes of Administration

Any method known to those in the art for contacting a cell, organ or tissue with compositions such as peptide conjugates, TBMs, and/or an aromatic-cationic peptide such as 2',6'-dimethyl-Tyr-D-Arg-Phe-Lys-$NH_2$, Phe-D-Arg-Phe-Lys-$NH_2$, or D-Arg-2',6'-Dmt-Lys-Phe-$NH_2$, or pharmaceutically acceptable salt thereof, may be employed. Suitable methods include in vitro, ex vivo, or in vivo methods.

In vitro methods typically include cultured samples. For example, a cell can be placed in a reservoir (e.g., tissue culture plate), and incubated with a compound under appropriate conditions suitable for obtaining the desired result. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are typically returned to the donor, placed in a recipient, or stored for future use. Thus, the compound is generally in a pharmaceutically acceptable carrier.

In vivo methods typically include the administration of a TBM, aromatic-cationic peptide or peptide conjugate such as those described herein, to a mammal such as a human. When used in vivo for therapy, an aromatic-cationic peptide, TBM, or peptide conjugate of the present technology are administered to a mammal in an amount effective in obtaining the desired result or treating the mammal. The effective amount is determined during pre-clinical trials and clinical trials by methods familiar to physicians and clinicians. The dose and dosage regimen will depend upon the degree of the infection in the subject, the characteristics of the particular aromatic-cationic peptide, TBM, or peptide conjugate of the present technology used, e.g., its therapeutic index, the subject, and the subject's history.

An effective amount of an aromatic-cationic peptide, TBM, or peptide conjugate of the present technology useful in the present methods, such as in a pharmaceutical composition or medicament, may be administered to a mammal in need thereof by any of a number of well-known methods for administering pharmaceutical compositions or medicaments. The aromatic-cationic peptide, TBM, or peptide conjugate of the present technology may be administered systemically or locally.

The aromatic-cationic peptide, TBM, or peptide conjugate of the present technology may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regimen). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when an aromatic-cationic peptide, TBM, or peptide conjugate of the present technology contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N' dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine, and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic, and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic, and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, acetate, tartrate, trifluoroacetate, and the like.

The aromatic-cationic peptide, TBM, or peptide conjugate of the present technology described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with the intended route of administration. Routes of administration include, for example, parenteral (e.g., intravenous, intradermal, intraperitoneal or subcutaneous), oral, respiratory (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity, such as sodium chloride or dextrose. The pH can be adjusted with acids or bases, such as hydrochloric acid or sodium hydroxide. The preparation can be enclosed in ampoules, disposable syringes or multiple-dose vials made of glass or plastic. For convenience of the patient or treating physician, the dosing formulation can be provided in a kit containing all necessary equipment (e.g., vials of drug, vials of diluent, syringes and needles) for a course of treatment (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J., USA) or phosphate buffered saline (PBS). In all cases, a composition for parenteral administration must be sterile and should be formulated for ease of syringeability. The composition should be stable under the conditions of manufacture and storage, and must be shielded from contamination by microorganisms such as bacteria and fungi.

In one embodiment, the aromatic-cationic peptide, TBM, or peptide conjugate of the present technology are administered intravenously. For example, an aromatic-cationic peptide, TBM, or peptide conjugate of the present technology may be administered via rapid intravenous bolus injection. In some embodiments, the aromatic-cationic peptide, TBM, or peptide conjugate of the present technology is administered as a constant-rate intravenous infusion.

The aromatic-cationic peptide, TBM, or peptide conjugate of the present technology may also be administered orally, topically, intranasally, intramuscularly, subcutaneously, or transdermally. In one embodiment, transdermal administration is by iontophoresis, in which the charged composition is delivered across the skin by an electric current.

Other routes of administration include intracerebroventricularly or intrathecally. Intracerebroventricularly refers to administration into the ventricular system of the brain. Intrathecally refers to administration into the space under the arachnoid membrane of the spinal cord. Thus, in some embodiments, intracerebroventricular or intrathecal administration is used for those diseases and conditions which affect the organs or tissues of the central nervous system.

The aromatic-cationic peptide, TBM, or peptide conjugate of the present technology may also be administered to mammals by sustained release, as is known in the art. Sustained release administration is a method of drug delivery to achieve a certain level of the drug over a particular period of time. The level is typically measured by serum or plasma concentration. A description of methods for delivering a compound by controlled release can be found in international PCT Application No. WO 02/083106, which is incorporated herein by reference in its entirety.

Any formulation known in the art of pharmacy is suitable for administration of the aromatic-cationic peptide, TBM, or peptide conjugate of the present technology. For oral administration, liquid or solid formulations may be used. Examples of formulations include tablets, gelatin capsules, pills, troches, elixirs, suspensions, syrups, wafers, chewing gum and the like. The aromatic-cationic peptides, TBMs, or peptide conjugates of the present technology can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the aromatic-cationic peptides, TBMs, or peptide conjugates of the present technology may utilize conventional diluents, carriers, or excipients etc., such as those known in the art to deliver the aromatic-cationic peptides, TBMs, or peptide conjugates of the present technology. For example, the formulations may comprise one or more of the following: a stabilizer, a surfactant, such as a nonionic surfactant, and optionally a salt and/or a buffering agent. The aromatic-cationic peptide, TBM, or peptide conjugate of the present technology may be delivered in the form of an aqueous solution, or in a lyophilized form.

The stabilizer may comprise, for example, an amino acid, such as for instance, glycine; an oligosaccharide, such as, sucrose, tetralose, lactose; or a dextran. Alternatively, the stabilizer may comprise a sugar alcohol, such as, mannitol. In some embodiments, the stabilizer or combination of stabilizers constitutes from about 0.1% to about 10% weight for weight of the formulated composition.

In some embodiments, the surfactant is a nonionic surfactant, such as a polysorbate. Examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. In some embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

Formulations of aromatic-cationic peptides, TBMs, or peptide conjugates of the present technology may additionally contain one or more conventional additives. Examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; an anesthetic agent such as for example a morphine derivative; and an isotonic agent etc., such as described herein. As a further precaution against oxidation or other spoilage, the pharmaceutical compositions may be stored under nitrogen gas in vials sealed with impermeable stoppers.

The mammal treated in accordance with the present technology may be any mammal, including, for example, farm animals, such as sheep, pigs, cows, and horses; pet animals, such as dogs and cats; and laboratory animals, such as rats, mice and rabbits. In one embodiment, the mammal is a human.

In some embodiments, aromatic-cationic peptides, TBMs, or peptide conjugates of the present technology are administered to a mammal in an amount effective in reducing the number of mitochondria undergoing, or preventing, MPT. The effective amount is determined during pre-clinical trials and clinical trials by methods familiar to physicians and clinicians.

The aromatic-cationic peptide, TBM, or peptide conjugate of the present technology may be administered systemically or locally. In one embodiment, the aromatic-cationic peptide, TBM, or peptide conjugate of the present technology are administered intravenously. For example, aromatic-cationic peptide, TBM, or peptide conjugate of the present technology may be administered via rapid intravenous bolus injection. In one embodiment, the aromatic-cationic peptide, TBM, or peptide conjugate of the present technology is administered as a constant-rate intravenous infusion.

The aromatic-cationic peptide, TBM, or peptide conjugate of the present technology can be injected directly into a coronary artery during, for example, angioplasty or coronary bypass surgery, or applied onto coronary stents.

The aromatic-cationic peptide, TBM, or peptide conjugate of the present technology may include a carrier, which can be a solvent or dispersion medium containing, for example, water, ethanol, polyol (for example, glycerol, propylene glycol, and liquid polyethylene glycol, and the like), or suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included in the composition to prevent oxidation. In many cases, it is desirable to include isotonic agents, for example, sugars, polyalcohols such as mannitol, sorbitol, or sodium chloride. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials may be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the aromatic-cationic peptide, TBM, or peptide conjugate of the present technology can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of an aromatic-cationic peptide, TBM, or peptide conjugate of the present technology as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

An aromatic-cationic peptide, TBM, or peptide conjugate of the present technology can be formulated in a carrier system. The carrier can be a colloidal system. The colloidal system can be a liposome, a phospholipid bilayer vehicle. In one embodiment, the therapeutic aromatic-cationic peptide, TBM, or peptide conjugate of the present technology is encapsulated in a liposome while maintaining protein integrity. As one skilled in the art will appreciate, there are a variety of methods to prepare liposomes. (See Lichtenberg, et al., *Methods Biochem. Anal.* 33:337-462 (1988); Anselem, et al., *Liposome Technology*, CRC Press (1993)). Liposomal formulations can delay clearance and increase cellular uptake (See Reddy, *Ann. Pharmacother.* 34 (78):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic aromatic-cationic peptide, TBM, or peptide conjugate of the present technology can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect.

(See Reddy, *Ann. Pharmacother.* 34:915-923 (2000)). A polymer formulation for human growth hormone (hGH) has been used in clinical trials. (See Kozarich and Rich, *Chemical Biology* 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the aromatic-cationic peptides, TBMs, or peptide conjugates of the present technology are prepared with carriers that will protect the aromatic-cationic peptides, TBMs, or peptide conjugates of the present technology against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation (Mountain View, Calif., USA) and Nova Pharmaceuticals, Inc. (Sydney, AU). Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The aromatic-cationic peptide, TBM, or peptide conjugate of the present technology can also be formulated to enhance intracellular delivery. For example, liposomal delivery systems are known in the art. See, e.g., Chonn and Cullis, *Curr. Opin. Biotech.* 6:698-708 (1995); Weiner, *Immunometh.* 4(3):201-9 (1994); Gregoriadis, *Trends Biotechnol.* 13(12):527-37 (1995). Mizguchi, et al., *Cancer Lett.* 100:63-69 (1996), describes the use of fusogenic liposomes to deliver a protein to cells both in vivo and in vitro Dosage, toxicity and therapeutic efficacy of the aromatic-cationic peptide, TBM, or peptide conjugate of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the aromatic-cationic peptides, TBMs, or peptide conjugates of the present technology exhibit high therapeutic indices. While aromatic-cationic peptides, TBMs, or peptide conjugates of the present technology that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any aromatic-cationic peptide, TBM, or peptide conjugate of the present technology used in the methods described herein, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptide, TBM, or peptide conjugate of the present technology, sufficient for achieving a therapeutic or prophylactic effect, range from about 0.000001 mg per kilogram body weight per day to about 10,000 mg per kilogram body weight per day. In some embodiments, the dosage ranges will be from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of aromatic-cationic peptide, TBM, or peptide conjugate of the present technology ranges from 0.1-10,000 micrograms per kg body weight. In one embodiment, aromatic-cationic peptide, TBM, or peptide conjugate concentrations in a carrier range from 0.2 to 2000 micrograms per delivered milliliter. An exemplary treatment regimen entails administration once per day or once a week. Intervals can also be irregular as indicated by measuring blood levels of glucose or insulin in the subject and adjusting dosage or administration accordingly. In some methods, dosage is adjusted to achieve a desired fasting glucose or fasting insulin concentration. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

In some embodiments, a therapeutically effective amount of aromatic-cationic peptide, TBM, or peptide conjugate of the present technology is defined as a concentration of the aromatic-cationic peptide, TBM, or peptide conjugate of the present technology at the target tissue of $10^{-11}$ to $10^{-6}$ molar, e.g., approximately $10^{-7}$ molar. This concentration may be delivered by systemic doses of 0.01 to 100 mg/kg or equivalent dose by body surface area. The schedule of doses is optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and the presence of other diseases. Moreover, treatment of a subject with a therapeutically effective amount of the therapeutic compositions described herein can include a single treatment or a series of treatments.

Therapeutic Peptide Analogues

In some aspects, the present disclosure provides compositions including TBMs or peptide conjugates of the present technology in combination with one or more active agents. In some embodiments, the active agents include any one or more of the aromatic-cationic peptides shown in Section II. In some embodiments, the aromatic-cationic peptide is 2',6'-dimethyl-Tyr-D-Arg-Phe-Lys-NH$_2$, Phe-D-Arg-Phe-Lys-NH$_2$, or D-Arg-2',6'-Dmt-Lys-Phe-NH$_2$.

In some embodiments, the TBMs and aromatic-cationic peptides are modified so as to increase resistance to enzymatic degradation. One way of stabilizing peptides against enzymatic degradation is the replacement of an L-amino acid with a D-amino acid at the peptide bond undergoing cleavage. Peptide analogues are prepared containing one or more D-amino acid residues. Another way to prevent enzymatic degradation is N-methylation of the α-amino group at one or more amino acid residues of the peptides. This will prevent peptide bond cleavage by any peptidase. Examples include: H-D-Arg-Dmt-Lys(N$^\alpha$Me)-Phe-NH$_2$; H-D-Arg-Dmt-Lys-Phe(NMe)-NH$_2$; H-D-Arg-Dmt-Lys(N$^\alpha$Me)-Phe(NMe)-NH$_2$; and H-D-Arg(N$^\alpha$Me)-Dmt(NMe)-Lys(N$^\alpha$Me)-Phe(NMe)-NH$_2$. N$^\alpha$-methylated analogues have lower hydrogen bonding capacity and can be expected to have improved intestinal permeability. In some embodiments, the therapeutic peptide is modified by N-methylation of the α-amino group at one or more amino acid residues of the peptide.

An alternative way to stabilize a peptide amide bond (—CO—NH—) against enzymatic degradation is its replacement with a reduced amide bond (Ψ[CH$_2$—NH]). This can be achieved with a reductive alkylation reaction between a Boc-amino acid-aldehyde and the amino group of the N-terminal amino acid residue of the growing peptide chain in solid-phase peptide synthesis. The reduced peptide bond is predicted to result in improved cellular permeability because of reduced hydrogen-bonding capacity. Examples include: H-D-Arg-Ψ[CH$_2$—NH]Dmt-Lys-Phe-NH$_2$, H-D-Arg-Dmt-Ψ[CH$_2$—NH]Lys-Phe-NH$_2$, H-D-Arg-Dmt-LysΨ[CH$_2$—NH]Phe-NH$_2$, H-D-Arg-Dmt-Ψ[CH$_2$—NH]Lys-Ψ[CH$_2$—NH]Phe-NH$_2$, etc. In some embodiments, the therapeutic peptide is modified to include a reduced amide bond (Ψ[CH$_2$—NH]).

Stabilized peptide analogues may be screened for stability in plasma, simulated gastric fluid (SGF) and simulated intestinal fluid (SIF). An amount of peptide is added to 10 ml of SGF with pepsin (COLE-PALMER®, Vernon Hills, Ill.) or SIF with pancreatin (COLE-PALMER®, Vernon Hills, Ill.), mixed and incubated for 0, 30, 60, 90 and 120 min. The samples are analyzed by HPLC following solid-phase extraction. New analogues that are stable in both SGF and SIF are then be evaluated for their distribution across the Caco-2 monolayer. Analogues with apparent permeability coefficient determined to be >10$^{-6}$ cm/s (predictable of good intestinal absorption) will then have their activity in reducing mitochondrial oxidative stress determined in cell cultures. Mitochondrial ROS is quantified by FACS using MitoSox for superoxide, and HyPer-mito (a genetically encoded fluorescent indicator targeted to mitochondria for sensing H$_2$O$_2$). Mitochondrial oxidative stressors can include t-butylhydroperoxide, antimycin and angiotensin. Therapeutic peptide analogues that satisfy all these criteria can then undergo large-scale synthesis.

It is predicted that the proposed strategies will produce a therapeutic peptide analog that would have oral bioavailability. The Caco-2 model is regarded as a good predictor of intestinal absorption by the drug industry.

VII. Formulations

In some aspects, the present disclosure provide pharmaceutical formulations for the delivery of aromatic-cationic peptides, TBMs, or peptide conjugates of the present technology.

In one aspect, the present technology relates to a finished pharmaceutical product adapted for oral delivery of TBM compositions or peptide conjugates of the present technology, the product comprising: (a) a therapeutically effective amount of the active agent; (b) at least one pharmaceutically acceptable pH-lowering agent; and (c) at least one absorption enhancer effective to promote bioavailability of the active agent, wherein the pH-lowering agent is present in the finished pharmaceutical product in a quantity which, if the product were added to 10 milliliters of 0.1M aqueous sodium bicarbonate solution, would be sufficient to lower the pH of the solution to no higher than 5.5, and wherein an outer surface of the product is substantially free of an acid-resistant protective vehicle.

In some embodiments, the pH-lowering agent is present in a quantity which, if the product were added to 10 milliliters of 0.1M sodium bicarbonate solution, would be sufficient to lower the pH of the solution to no higher than 3.5. In some embodiments, the absorption enhancer is an absorbable or biodegradable surface active agent. In some embodiments, the surface active agent is selected from the group consisting of acylcarnitines, phospholipids, bile acids and sucrose esters. In some embodiments, the absorption enhancer is a surface active agent selected from the group consisting of: (a) an anionic agent that is a cholesterol derivative, (b) a mixture of a negative charge neutralizer and an anionic surface active agent, (c) non-ionic surface active agents, and (d) cationic surface active agents.

In some embodiments, the finished pharmaceutical product further comprises an amount of an additional peptide that is not a physiologically active peptide effective to enhance bioavailability of the aromatic-cationic peptides, TBMs, or peptide conjugates of the present technology. In some embodiments, the finished pharmaceutical product comprises at least one pH-lowering agent with a solubility in water of at least 30 grams per 100 milliliters of water at room temperature. In some embodiments, the finished pharmaceutical product comprises granules containing a pharmaceutical binder and, uniformly dispersed in the binder, the pH-lowering agent, the absorption enhancer and the aromatic-cationic peptides, TBMs, and/or peptide conjugates of the present technology.

In some embodiments, the finished pharmaceutical product comprises a lamination having a first layer comprising at least one pharmaceutically acceptable pH-lowering agent and a second layer comprising the therapeutically effective amount of the active agent (e.g., TBMs with or without aromatic-cationic peptides, or peptide conjugates); the product further comprising the at least one absorption enhancer effective to promote bioavailability of the active agent, wherein the first and second layers are united with each other, but the at least one pH-lowering agent and the active agent are substantially separated within the lamination such that less than about 0.1% of the active agent contacts the pH-lowering agent to prevent substantial mixing between the first layer material and the second layer material and thus to avoid interaction in the lamination between the pH-lowering agent and the active agent.

In some embodiments, the finished pharmaceutical product comprises a pH-lowering agent selected from the group consisting of citric acid, tartaric acid and an acid salt of an amino acid. In some embodiments, the pH-lowering agent is selected from the group consisting of dicarboxylic acids and tricarboxylic acids. In some embodiments, the pH-lowering agent is present in an amount not less than 300 milligrams.

VIII. Combination Therapy with Therapeutic Biological Molecule (TBM) Compositions and other Therapeutic Agents In some embodiments, TBMs, aromatic-cationic peptides, peptide conjugates of the present technology or a combination thereof, may be combined with one or more additional therapeutic agents for the prevention, amelioration or treatment of a medical disease or condition.

In one embodiment, an additional therapeutic agent is administered to a subject in combination with a TBM, aromatic-cationic peptide, peptide conjugate of the present technology or a combination thereof, such that a synergistic therapeutic effect is produced.

The multiple therapeutic agents (including, but not limited to TBMs, aromatic-cationic peptides, or peptide conjugates of the present technology) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

IX. Examples

The present technology is further illustrated by the following examples, which should not be construed as limiting in any way. For each of the examples below, any aromatic-cationic peptide described herein could be used. By way of example, but not by limitation, the aromatic-cationic peptide used in the examples below could be 2'6'-Dmt-D-Arg-Phe-Lys-NH$_2$, Phe-D-Arg-Phe-Lys-NH$_2$, or D-Arg-2'6'-Dmt-Lys-Phe-NH$_2$ or any one or more of the peptides shown in Section II and TBM is any compound shown in Section I.

Example 1: Compositions of the Present Technology Suppress Oxidized Low-Density Lipoprotein (oxLDL)-Induced CD36 Expression and Foam Cell Formation in Mouse Peritoneal Macrophages Atherosclerosis is thought to develop as a result of lipid uptake by vascular-wall macrophages leading to the development of foam cells and the elaboration of cytokines and chemokines resulting in smooth muscle-cell proliferation. CD36 is a scavenger receptor that mediates uptake of oxLDL into macrophages and subsequent foam-cell development. CD36 knockout mice showed reduced uptake of oxLDL and reduced atherosclerosis. CD36 expression is regulated at the transcriptional level by various cellular stimuli, including glucose and oxLDL.

Macrophages are harvested from mice peritoneal cavity cultured overnight in the absence or presence of oxLDL (50 µg/mL) for 48 hours. Incubation with oxLDL is anticipated to significantly increase CD36 mRNA. Inclusion of peptide conjugates (e.g., 10 nM-1 aromatic-cationic peptides (e.g., an equivalent molar dose of aromatic-cationic peptide based on the concentration of aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) to the culture medium is anticipated to abolish the up-regulation of CD36.

Expression of CD36 protein, as determined by western blot, is also anticipated to significantly increase after a 48 hour incubation with 25 µg/mL of oxLDL (oxLDL) when compared to vehicle control (V). Other controls will include CD36 expression from mouse heart (H) and macrophages obtained from CD36 knockout mice (KO). The amount of CD36 protein will be normalized to β-actin. Incubation with peptide conjugates, aromatic-cationic peptides, and TBMs alone or in combination with aromatic-cationic peptides is anticipated to significantly reduce CD36 protein levels compared to macrophages exposed to vehicle control (V). Incubation with peptide conjugates, aromatic-cationic peptides, or TBMs alone or in combination with aromatic-cationic peptides is anticipated to also significantly inhibit the up-regulation of CD36 protein levels in macrophages exposed to 25 µg/mL oxLDL for 48 hours (oxLDL/S). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

Incubation of macrophages with oxLDL for 48 hours is also anticipated to increase foam cell formation. Foam cell will be visualized by oil red O, which stains lipid droplets red. Inclusion of peptide conjugates, aromatic-cationic peptides, or TBMs alone or in combination with aromatic-cationic peptides is anticipated to prevent oxLDL-induced foam cell formation. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

Incubation of macrophages with oxLDL is anticipated to increase the percentage of apoptotic cells. Treatment with peptide conjugates, aromatic-cationic peptides, or TBMs alone or in combination with aromatic-cationic peptides is anticipated to significantly reduce the percentage of apoptotic cells induced by oxLDL. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBM (with or without aromatic-cationic peptides) or peptide conjugates of the present technology or pharmaceutically acceptable salts thereof, such as acetate, tartrate, or trifluoroacetate salts, are useful in methods for treating or preventing atherosclerosis in mammalian subjects.

Example 2: Compositions of the Present Technology Protect from the Effects of Acute Cerebral Ischemia Cerebral ischemia initiates a cascade of cellular and molecular events that lead to brain damage. One such event is post-ischemic inflammation. Using a mouse model of cerebral ischemia-reperfusion (20 minute occlusion of the middle cerebral artery), it has been found that CD36 is up-regulated in microglia and macrophages in the post-ischemic brain, with increased reactive oxygen species production. CD36 knockout mice have a profound reduction in reactive oxygen species after ischemia and improved neurological function compared to wild type mice.

Cerebral ischemia will be induced by occlusion of the right middle cerebral artery for 30 min. Wild-type (WT) mice will be given either saline vehicle (Veh) (i.p., n=9), peptide conjugates (2 mg/kg or 5 mg/kg, i.p., n=6), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) at 0, 6, 24 and 48 hours after ischemia. Mice will be sacrificed 3 days after ischemia. Brains will be frozen, sectioned, and stained using Nissl stain. Infarct volume and hemispheric swelling will be determined using an image analyzer. Data will be analyzed by one-way ANOVA with posthoc analysis.

It is anticipated that treatment of wild type mice with peptide conjugates, aromatic-cationic peptides, or TBMs (with or without aromatic-cationic peptides) at 0, 6, 24 and 48 hours after a 30 minute occlusion of the middle cerebral artery will result in a significant reduction in infarct volume and hemispheric swelling compared to saline controls. It has previously been shown that thirty minutes of cerebral ischemia in WT mice results in significant depletion in reduced glutathione (GSH) in the ipsilateral cortex and striatum compared to the contralateral side in vehicle-treated animals. The depletion of GSH in the ipsilateral cortex is anticipated to significantly be reduced when the mice are treated with peptide conjugates, aromatic-cationic peptides, or TBMs (with or without aromatic-cationic peptides) (2 mg/kg i.p. at 0, 6, 24 and 48 hours).

It is anticipated that administration of peptide conjugates of the present technology will have synergistic effects with respect to protecting subjects from the effects of acute cerebral ischemia compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for treating or preventing the effects of acute cerebral ischemia in mammalian subjects.

Example 3: Compositions of the Present Technology Protect Against CD36-Mediated Acute Cerebral Ischemia CD36 knockout (CD36 KO) mice will be subjected to acute cerebral ischemia as described in Example 2. CD36 KO mice will be given either saline vehicle (Veh) (i.p., n=5), peptide conjugates (2 mg/kg or 5 mg/kg, i.p., n=6), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) at 0, 6, 24 and 48 hours following a 30 minute period of ischemia. Infarct volume and hemispheric swelling in CD36 KO mice are expected to be similar in subjects receiving saline, TBMs (alone or in combination with aromatic-cationic peptides), aromatic-cationic peptides and peptide conjugates. It is expected that treatment of CD36 KO mice with peptide conjugates, aromatic-cationic peptides, or TBMs (with or without aromatic-cationic peptides) will fail to further prevent GSH depletion in the ipsilateral cortex caused by the ischemia. The data will show that the protective action of peptide conjugates, aromatic-cationic peptides, or TBMs (with or without aromatic-cationic peptides) in acute cerebral ischemia is a function of inhibition of CD36 up-regulation.

These results will show that TBMs (with or without aromatic-cationic peptides) or peptide conjugates of the present technology or pharmaceutically acceptable salts thereof, such as acetate, tartrate, or trifluoroacetate salts, are useful in methods for preventing or treating the effects of CD36-mediated acute cerebral ischemia in mammalian subjects.

Example 4: Compositions of the Present Technology Suppress CD36 Expression in Post-Ischemic Brain Transient occlusion of the middle cerebral artery has been shown to significantly increase the expression of CD36 mRNA in microglia and macrophages in the post-ischemic brain. Wild-type mice will be given saline vehicle (Veh, i.p., n=6), peptide conjugates (5 mg/kg, i.p., n=6), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) at 0 and 6 hours after a 30 minute period of ischemia. Levels of CD36 mRNA in post-ischemic brain will be determined using real time PCR. It is anticipated that CD36 expression will be up-regulated as much as 6-fold in the ipsilateral brain compared to the contralateral brain of mice receiving saline, with CD36 mRNA significantly reduced in the ipsilateral brain of mice receiving peptide conjugates, aromatic-cationic peptides, or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for suppressing CD36 expression in post-ischemic brain in mammalian subjects.

Example 5: Compositions of the Present Technology Suppress CD36 Up-Regulation in Renal Tubular Cells Following Unilateral Ureteral Obstruction Unilateral ureteral obstruction (UUO) is a common clinical disorder associated with tubular cell apoptosis, macrophage infiltration, and interstitial fibrosis. Interstitial fibrosis leads to a hypoxic environment and contributes to progressive decline in renal function despite surgical correction. CD36 has been shown to be expressed in renal tubular cells.

UUO will be induced in Sprague-Dawley rats. The rats will be treated with saline (i.p., n=6), peptide conjugates (1 mg/kg i.p., n=6), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) one day prior to induction of UUO, and once daily for 14 days after UUO induction. Rats will be sacrificed and the kidneys removed, embedded in paraffin, and sectioned. The sections will be treated with an anti-CD36 polyclonal IgG (Santa Cruz, sc-9154; diluted 1:100 with blocking serum) at room temperature for 1.5 hours. The slides will then be incubated with the second antibody conjugated with biotin (anti-rabbit IgG-B1; ABC kit, PK-6101) at room temperature for 30 min. The slides will then be treated with avidin, developed with DAB and counterstained with 10% hematoxylin. The contralateral unobstructed kidney will serve as the control for each animal.

It is anticipated that UUO will result in tubular dilation and significant increase in expression of CD36 in the tubular cells of saline-treated subjects. Tubular dilation is also anticipated in rats treated with peptide conjugates, aromatic-cationic peptides, or TBMs (with or without aromatic-cationic peptides). But it is anticipated that treatment with peptide conjugates, aromatic-cationic peptides, or TBMs (with or without aromatic-cationic peptides) will result in a significant reduction in CD36 expression. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

To demonstrate that peptide conjugates reduce lipid peroxidation in kidney after UUO, rats will be treated with either saline (n=6), peptide conjugates (1 mg/kg i.p., n=6), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) one day prior to induction of UUO, and once daily for 14 days after UUO. Rats will then be sacrificed, kidneys removed, embedded in paraffin and sectioned. Slides will be incubated with anti-HNE rabbit IgG and a biotin-linked anti-rabbit IgG will be used as secondary antibody. The slides will be developed with DAB. Lipid peroxidation, which is increased by UUO, is anticipated to be reduced by treatment with peptide conjugates, aromatic-cationic peptides, or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

It is anticipated that HNE stain (brown) will be significantly increased in tubular cells in the obstructed kidney compared to the contralateral control. It is anticipated that obstructed kidneys from rats treated with peptide conjugates, aromatic-cationic peptides, or TBMs (with or without aromatic-cationic peptides) will show significantly less HNE staining compared to saline-treated rats. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

To demonstrate that peptide conjugates reduce tubular cell apoptosis in obstructed kidney after UUO, rats will be treated with either saline (n=6), peptide conjugates (1 mg/kg i.p., n=6), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) one day prior to induction of UUO, and once daily for 14 days after UUO. Rats will then be sacrificed, kidneys removed, embedded in paraffin and sectioned. To quantify nuclei with fragmented DNA, TUNEL assay will be performed with in situ TUNEL kit. Slides will be developed with DAB and counterstained with 10% hematoxylin. The up-regulation of CD36 in saline-treated controls associated with tubular cell apoptosis is anticipated to be significantly inhibited by treatment with peptide conjugates, aromatic-cationic peptides, or TBMs (with or without aromatic-cationic peptides). It is anticipated that there will be a significant increase in apoptotic cells observed in the obstructed kidney from saline-treated animals when compared to the contralateral unobstructed control. The number of apoptotic cells is anticipated to be significantly reduced in obstructed kidney from animals treated with peptide conjugates, aromatic-cationic peptides, or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

Macrophage infiltration and interstitial fibrosis are anticipated to be prevented by treatment with peptide conjugates, aromatic-cationic peptides, or TBMs (alone or in combination with aromatic-cationic peptides). Rats will be treated with either saline (n=6), peptide conjugates (1 mg/kg i.p., n=6), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group) or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) one day prior to induction of UUO, and once daily for 14 days after UUO. Rats will then be sacrificed, the kidneys removed, embedded in paraffin and sectioned. Slides will be treated with monoclonal antibody for ED1 macrophage (1:75; Serotec). Horseradish peroxidase-linked rabbit anti-mouse secondary antibody (Dako) will be used for macrophage detection. Sections will then be counterstained with 10% hematoxylin. The number of macrophages in the obstructed kidney in saline-treated rats is anticipated to be significantly increased compared to the contralateral unobstructed control. Macrophage infiltration is anticipated to be significantly reduced in rats treated with peptide conjugates, aromatic-cationic peptides, or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

Rats will be treated with either saline (n=6), peptide conjugates (1 mg/kg i.p., n=6), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) one day prior to induction of UUO, and once daily for 14 days after UUO. Rats will then be sacrificed, kidneys removed, embedded in paraffin and sectioned. Slides will be stained with hematoxylin and eosin and Masson's trichrome for interstitial fibrosis (blue stain). It is anticipated that obstructed kidneys from saline-treated rats will show increased fibrosis compared to the contralateral unobstructed control, while obstructed kidneys from rats treated with peptide conjugates, aromatic-cationic peptides, or TBMs (with or without aromatic-cationic peptides) will show significantly less fibrosis. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that peptide conjugates, aromatic-cationic peptides, or TBMs (with or without aromatic-cationic peptides) suppress the up-regulation of CD36 in renal tubular cells induced by UUO. These results will further show that TBMs (with or without aromatic-cationic peptides) or peptide conjugates of the present technology or pharmaceutically acceptable salts thereof, such as acetate, tartrate, or trifluoroacetate salts, are useful in methods for suppressing the up-regulation of CD36 in renal tubular cells induced by UUO in mammalian subjects.

Example 6: Compositions of the Present Technology Suppress CD36 Up-Regulation in Isolated Hearts Upon Reperfusion after Prolonged Cold Ischemic Storage Organ transplantation requires hypothermic storage of the isolated organ for transport to the recipient. Currently, cardiac transplantation is limited by the short time of cold ischemic storage that can be tolerated before coronary blood flow is severely compromised (<4 hours). The expression of CD36 in coronary endothelium and cardiac muscles is up-regulated in isolated hearts subjected to prolonged cold ischemic storage and warm reperfusion.

Isolated guinea pig hearts will be perfused with St. Thomas solution alone or St. Thomas solution containing peptide conjugates (1-100 nM), aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 3 minutes and then stored in the same solution at 4° C. for 18 hours. After ischemic storage, hearts will be re-perfused with 34° C. Krebs-Henseleit solution for 90 min. Hearts freshly isolated from guinea pigs will be used as controls.

The hearts will be fixed in paraffin and sliced for immunostaining with an anti-CD36 rabbit polyclonal antibody. It is anticipated that the sections from a representative heart stored in St. Thomas solution for 18 hours at 4° C. will show increased CD36 staining compared to freshly isolated controls. CD36 staining is anticipated to be significantly reduced in hearts stored with peptide conjugates, aromatic-cationic peptides, or TBMs (with or without aromatic-cationic peptides) in St. Thomas solution for 18 hours. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

It is also anticipated that there will be a decrease in lipid peroxidation in the hearts treated with peptide conjugates, aromatic-cationic peptides, or TBMs (with or without aromatic-cationic peptides). Guinea pig hearts will be perfused with a cardioplegic solution (St. Thomas solution) alone or St. Thomas solution containing 1-100 nM peptide conjugates, aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 3 minutes and then subjected to 18 hours of cold ischemia (4° C.). The hearts will be then re-perfused with Krebs Henseleit buffer at 34° C. for 90 minutes. Immunohistochemical analysis of 4-hydroxynonenol (HNE)-modified proteins in paraffin sections from tissue slices will be performed by incubation with an anti-HNE antibody (Santa Cruz) and a fluorescent secondary antibody. HNE staining is anticipated to significantly increase in hearts subjected to 18 hours of cold storage in St. Thomas solution compared to non-ischemic hearts. HNE staining is anticipated to be reduced in hearts stored in peptide conjugates, aromatic-cationic peptides, or TBMs (with or without aromatic-cationic peptides) compared to controls stored in St. Thomas solution alone. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

Further, it is anticipated that peptide conjugates, aromatic-cationic peptides, or TBMs (with or without aromatic-cationic peptides) will dramatically reduce endothelial apoptosis. Guinea pig hearts will be perfused with St. Thomas solution alone or St. Thomas solution containing peptide conjugates, aromatic-cationic peptides (e.g., an equivalent molar dose of aromatic-cationic peptide based on the concentration of the aromatic-cationic peptide administered in the peptide conjugate treatment group), TBMs (e.g., an equivalent molar dose of TBM based on the concentration of TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 3 minutes and then subjected to 18 hours of cold ischemia (4° C.). The hearts will then be re-perfused with Krebs-Henseleit buffer at 34° C. for 90 min. After deparaffinization, sections will be incubated with deoxynucleotidyl transferase (Tdt) with digoxigenin-dNTP for 1 hour. The reaction will be stopped with terminating buffer. A fluorescent anti-digoxigenin antibody will then be applied.

It is anticipated that hearts subjected to 18 hours of cold storage in St. Thomas solution will show prominent endothelial apoptosis, whereas no endothelial apoptosis will be observed in non-ischemic control hearts. It is anticipated that apoptotic cells will not be observed in hearts stored in peptide conjugates, aromatic-cationic peptides, or TBMs (with or without aromatic-cationic peptides). It is anticipated that a significant improvement of coronary blood flow after prolonged cold ischemic storage and warm reperfusion will occur when hearts are preserved in peptide conjugates, aromatic-cationic peptides, or TBMs (with or without aromatic-cationic peptides).

It is anticipated that administration of peptide conjugates of the present technology will have synergistic effects with respect to suppressing CD36 up-regulation in isolated organs upon reperfusion following prolonged cold ischemic storage compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for suppressing CD36 up-regulation in isolated organs upon reperfusion following prolonged cold ischemic storage.

Example 7: Compositions of the Present Technology Prevent Renal Damage in Diabetic Mice CD36 expression is up-regulated in a variety of tissues of diabetic patients, including monocytes, heart, kidneys, and blood. High glucose is known to up-regulate the expression of CD36 by improving the translational efficiency of CD36 mRNA. Diabetic nephropathy is a common complication of type 1 and type 2 diabetes, and is associated with tubular epithelial degeneration and interstitial fibrosis. CD36 has been identified as a mediator of tubular epithelial apoptosis in diabetic nephropathy. High glucose stimulates CD36 expression and apoptosis in proximal tubular epithelial cells.

Streptozotocin (STZ) will be used to induce diabetes in mice. Five groups of CD-1 mice will be studied: Group I—no STZ treatment; Group II—STZ (50 mg/kg, i.p.) will be given once daily for 5 days; Group III—STZ (50 mg/kg, i.p.) will be given once daily for 5 days, + peptide conjugates (3 mg/kg, i.p.) will be given once daily for 16 days; Group IV—STZ (50 mg/kg, i.p.) will be given once daily for 5 days, + aromatic-cationic peptides (an equivalent molar dose of aromatic-cationic peptide based on the concentration of the aromatic-cationic peptide administered in the peptide conjugate treatment group) will be given once daily for 16 days; Group V—STZ (50 mg/kg, i.p.) will be given once daily for 5 days, + TBM (an equivalent molar dose of TBM based on the concentration of the TBM administered in the peptide conjugate treatment group) will be given once daily for 16 days; Group VI—STZ (50 mg/kg, i.p.) will be given once daily for 5 days, + TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be given once daily for 16 days. It is anticipated that STZ treatment will result in a progressive increase in blood glucose. Animals will be sacrificed after 3 weeks and kidney tissues preserved for histopathology. Kidney sections will be examined by Periodic Schiff (PAS) staining for renal tubular brush border.

It is anticipated that STZ treatment will cause a dramatic loss of brush border in proximal tubules of the renal cortex, with tubular epithelial cells showing small condensed nuclei. It is anticipated that daily treatment with peptide conjugates, aromatic-cationic peptides, or TBMs (with or without aromatic-cationic peptides) will prevent the loss of brush border in the STZ-treated mice, and the tubular epithelial nuclei will appear normal. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

It is anticipated that STZ treatment will induce significant apoptosis in tubular epithelial cells. Kidney sections will be examined for apoptosis using a TUNEL assay as described herein. It is anticipated that kidney sections from mice treated with STZ will show a large number of apoptotic nuclei in the proximal tubules, compared to non-STZ treated controls. It is anticipated that treatment with peptide conjugates, aromatic-cationic peptides, or TBMs (with or without aromatic-cationic peptides) will dramatically reduce apoptotic cells in the proximal tubule CD36 expression in proximal tubular epithelial cells. It is anticipated that by reducing CD36 expression, peptide conjugates, aromatic-cationic peptides, or TBMs (with or without aromatic-cationic peptides) will inhibit tubular cell apoptosis and the loss of brush border in mice treated with STZ, without affecting blood glucose levels. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for treating or preventing renal damage in diabetic mammals.

Example 8: Penetration of Cell Membranes by Compositions of the Present Technology The cellular uptake of [$^3$H] TBMs (with or without aromatic-cationic peptides) or [$^3$H] peptide conjugates will be studied using Caco-2 cells (human intestinal epithelial cells), and confirmed using SH-SY5Y (human neuroblastoma), HEK293 (human embryonic kidney) and CRFK (kidney epithelial) cells. Monolayers of cells will be cultured in 12-well plates ($5\times10^5$ cells/well) coated with collagen for 3 days. On day 4, the cells will be washed twice with pre-warmed HBSS, and incubated with 0.2 mL of HBSS containing 250 nM [$^3$H] peptide conjugates; [$^3$H] aromatic-cationic peptides (an equivalent molar dose of aromatic-cationic peptide based on the concentration of the aromatic-cationic peptide administered in the peptide conjugate treatment group); [$^3$H] TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) at 37° C. or 4° C. for various times up to 1 hour.

It is anticipated that [$^3$H] TBMs (with or without aromatic-cationic peptides) or [$^3$H] peptide conjugates will be observed in cell lysate and steady state levels will be achieved within 1 hour. It is anticipated that the rate of [$^3$H] TBMs (with or without aromatic-cationic peptides) or [$^3$H] peptide conjugate uptake will be slower at 4° C. compared to 37° C., but that uptake will reach a high level of saturation by 45 minutes (e.g., 76.5%) and a higher level of saturation by 1 hour (e.g., 86.3%). It is anticipated that the internalization of [$^3$H] TBMs (with or without aromatic-cationic peptides) or [$^3$H] peptide conjugates will not be limited to Caco-2 cells, and that similar results will be achieved with SH-SY5Y, HEK293 and CRFK cells. The intracellular concentration of TBMs (with or without aromatic-cationic peptides) or peptide conjugates is anticipated to be approximately 50 times higher than the extracellular concentration following 1 hour of incubation. It is anticipated that administration of peptide conjugates of the present technology will have synergistic effects with respect to cell membrane permeability compared to treatment with aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

In a separate experiment, cells will be incubated with a range of peptide conjugate concentrations (1 μM-3 mM); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 1 hour at 37° C. At the end of the incubation period, cells will be washed 4 times with HBSS, and 0.2 mL of 0.1N NaOH with 1% SDS will be added to each well. The cell lysates will then be transferred to scintillation vials and radioactivity will be counted. To distinguish between internalized radioactivity and surface-associated radioactivity, an acid-wash step will be included. Prior to cell lysis, cells will be incubated with 0.2 mL of 0.2 M acetic acid/0.05 M NaCl for 5 minutes on ice.

The uptake of TBMs (with or without aromatic-cationic peptides) or peptide conjugates into Caco-2 cells will be confirmed by confocal laser scanning microscopy (CLSM) using a fluorescent analog of TBMs (with or without aromatic-cationic peptides) or peptide conjugates. Cells will be grown as described above and will be plated on (35 mm) glass dishes (MatTek Corp., Ashland, Mass.) for 2 days. The medium will then be removed and cells will be incubated with 1 mL of HBSS containing 0.1 μM to 1.0 μM of the fluorescent analog of TBMs (with or without aromatic-cationic peptides) or peptide conjugates at 37° C. for 1 hour. Cells will be washed three times with ice-cold HBSS and covered with 200 μL of PBS. Microscopy will be performed within 10 minutes at room temperature using a Nikon confocal laser scanning microscope with a C-Apochromat 63×/1.2 W corr objective. Excitation will be performed at 340 nm by means of a UV laser, and emission will be measured at 520 nm. For optical sectioning in z-direction, 5-10 frames with 2.0μ z-steps will be collected.

CLSM will be used to confirm the uptake of fluorescent TBMs (with or without aromatic-cationic peptides) or peptide conjugates into Caco-2 cells after incubation with 0.1 μM fluorescent analog for 1 h at 37° C. It is anticipated that the uptake of the fluorescent analog will be similar at 37° C. and 4° C. It is anticipated that the fluorescence will appear diffuse throughout the cytoplasm but will be completely excluded from the nucleus.

These results will show that TBMs (with or without aromatic-cationic peptides) or peptide conjugates of the present technology or pharmaceutically acceptable salts thereof, such as acetate, tartrate, or trifluoroacetate salts, are useful in methods for penetrating cell membranes.

Example 9: Targeting of Compositions of the Present Technology to Mitochondria In Vivo A fluorescent analog of TBMs (with or without aromatic-cationic peptides) or peptide conjugates will be prepared. The cells will be grown as described above and will be plated on (35 mm) glass dishes (MatTek Corp., Ashland, Mass.) for 2 days. The medium will be then removed and cells will be incubated with 1 mL of HBSS containing 0.1 μM fluorescent analog at 37° C. for 15 minutes to 1 hour.

Cells will also be incubated with tetramethylrhodamine methyl ester (TMRM, 25 nM), a dye for staining mitochondria, for 15 minutes at 37° C. Cells will be washed three times with ice-cold HBSS and covered with 200 μL of PBS. Microscopy will be performed within 10 minutes at room temperature using a Nikon confocal laser scanning microscope with a C-Apochromat 63×/1.2 W corr objective.

For fluorescent analog, excitation will be performed at 350 nm using a UV laser, and emission will be measured at 520 nm. For TMRM, excitation will be performed at 536 nm, and emission will be measured at 560 nm.

It is anticipated that CLSM will show the uptake of fluorescent analog into Caco-2 cells after incubation for as little as 15 minutes at 37° C., and that staining will be excluded from the nucleus. Mitochondrial localization of fluorescent analog will be demonstrated by the overlap of the fluorescent analog and TMRM.

These results will show that TBMs (with or without aromatic-cationic peptides) or peptide conjugates of the present technology or pharmaceutically acceptable salts thereof, such as acetate, tartrate, or trifluoroacetate salts, are useful in methods comprising the targeting of the compound to mitochondria in vivo.

Example 10: Targeting of Compositions of the Present Technology to Isolated Mitochondria To isolate mitochondria from mouse liver, mice will be sacrificed by decapitation. The liver will be removed and rapidly placed into chilled liver homogenization medium. The liver will be finely minced using scissors and then homogenized by hand using a glass homogenizer.

The homogenate will be centrifuged for 10 minutes at 1000×g at 4° C. The supernatant will be aspirated and transferred to polycarbonate tubes and centrifuged again for 10 minutes at 3000×g, 4° C. The resulting supernatant will be removed, and the fatty lipids on the side-wall of the tube will be removed.

The pellet will be resuspended in liver homogenate medium and the homogenization repeated twice. The final purified mitochondrial pellet will be resuspended in medium. Protein concentration in the mitochondrial preparation will be determined by the Bradford procedure.

Approximately 1.5 mg mitochondria in 400 μL buffer will be incubated with [$^3$H] peptide conjugates; [$^3$H] aromatic-cationic peptides (an equivalent molar dose of aromatic-cationic peptide based on the concentration of the aromatic-cationic peptide administered in the peptide conjugate treatment group); [$^3$H] TBMs (an equivalent molar dose of TBM based on the concentration of the TBM administered in the peptide conjugate treatment group); or [$^3$H] TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 5-30 minutes at 37° C. The mitochondria will then be centrifuged and the amount of radioactivity will be determined in the mitochondrial fraction and buffer fraction. Assuming a mitochondrial matrix volume of 0.7 μL/mg protein (Lim, et al., J. Physiol. 545:961-974 (2002)), it is anticipated that the concentration of [$^3$H] TBMs (with or without aromatic-cationic peptides) or [$^3$H] peptide conjugates in mitochondria will be higher than in the buffer, indicating that TBMs (with or without aromatic-cationic peptides) or peptide conjugates are concentrated in mitochondria.

To demonstrate that TBMs (with or without aromatic-cationic peptides) or peptide conjugates are selectively distributed to mitochondria, we will examine the uptake of fluorescent TBMs (with or without aromatic-cationic peptides) or fluorescent peptide conjugates and [$^3$H] TBMs (with or without aromatic-cationic peptides) or [$^3$H] peptide conjugates into isolated mouse liver mitochondria. The rapid uptake of fluorescent TBMs (with or without aromatic-cationic peptides) or fluorescent peptide conjugates is anticipated. Pre-treatment of mitochondria with carbonyl cyanide p-(trifluoromethoxy)-phenylhydrazone (FCCP), an uncoupler that results in immediate depolarization of mitochondria, is anticipated to reduce the uptake of fluorescent TBMs (with or without aromatic-cationic peptides) or fluorescent peptide conjugates, demonstrating that the uptake is membrane potential-dependent.

To demonstrate that the mitochondrial targeting is not an artifact of the fluorophore, we will also examine mitochondrial uptake of [$^3$H] peptide conjugates or [$^3$H] TBMs (with or without aromatic-cationic peptides). Isolated mitochondria will be incubated with [$^3$H] peptide conjugates or [$^3$H] TBMs (with or without aromatic-cationic peptides) and radioactivity will be determined in the mitochondrial pellet and supernatant. It is anticipated that the amount of radioactivity in the pellet will not change from 2 minutes to 8 minutes, and that treatment of mitochondria with FCCP will decrease the amount of [$^3$H] peptide conjugates or [$^3$H] TBMs (with or without aromatic-cationic peptides) associated with the mitochondrial pellet.

The minimal effect of FCCP on mitochondrial uptake of TBMs (with or without aromatic-cationic peptides) or peptide conjugates will show that [$^3$H] TBMs (with or without aromatic-cationic peptides) or [$^3$H] peptide conjugates are likely associated with mitochondrial membranes or in the inter-membrane, space rather than in the mitochondrial matrix. We will also demonstrate the effect of mitochondrial swelling on the mitochondrial localization of fluorescent TBMs (with or without aromatic-cationic peptides) or fluorescent peptide conjugates using alamethicin to induce swelling and rupture of the outer mitochondrial membrane. It is anticipated that the uptake of fluorescent TBMs (with or without aromatic-cationic peptides) or fluorescent peptide conjugates will be only partially reversed by mitochondrial swelling. This result will confirm that TBMs (with or without aromatic-cationic peptides) or peptide conjugates are associated with mitochondrial membranes.

It is further anticipated that treatment with the peptide conjugate will show a synergistic effect with respect to mitochondrial targeting compared to treatment with aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods comprising the targeting of the TBMs (with or without aromatic-cationic peptides) or peptide conjugates to isolated mitochondria.

Example 11: Compositions of the Present Technology do not Alter Mitochondrial Respiration or Membrane Potential This Example will demonstrate that TBMs (with or without aromatic-cationic peptides) or peptide conjugates do not alter mitochondrial function, as measured by oxygen consumption and mitochondrial membrane potential.

Isolated mouse liver mitochondria will be incubated with 100 pM of TBMs (with or without aromatic-cationic peptides) or peptide conjugates, and oxygen consumption will be measured. It is anticipated that TBMs (with or without aromatic-cationic peptides) or peptide conjugates will not alter oxygen consumption during state 3 or state 4, or the respiratory ratio (state 3/state 4) (6.2 versus 6.0). Mitochondrial membrane potential will be measured using TMRM. It is anticipated that addition of mitochondria will result in immediate quenching of the TMRM signal, which will be readily reversible by the addition of FCCP, indicating mitochondrial depolarization. It is anticipated that the addition of $Ca^{2+}$ (150 µM) will result in immediate mitochondrial depolarization followed by progressive loss of quenching indicative of MPT. It is anticipated that the addition of TBMs (with or without aromatic-cationic peptides) or peptide conjugates alone, even at 200 µM, will not cause mitochondrial depolarization or MPT.

These results will show that TBMs (with or without aromatic-cationic peptides) or peptide conjugates of the present technology or pharmaceutically acceptable salts thereof, such as acetate, tartrate, or trifluoroacetate salts, do not alter mitochondrial function, as measured by oxygen consumption and mitochondrial membrane potential.

Example 12: Compositions of the Present Technology Protect Against MPT Induced by $Ca^{2+}$ and 3NP This Example will demonstrate that peptide conjugates, aromatic-cationic peptides, or TBMs (with or without aromatic-cationic peptides) protect against MPT induced by $Ca^{2+}$ overload and 3-nitropropionic acid (3NP).

It is anticipated that the pre-treatment of isolated mitochondria with 10 µM peptide conjugates, aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 2 minutes prior to addition of $Ca^{2+}$ will result only in transient depolarization and will prevent the onset of MPT. It is further anticipated that peptide conjugates, aromatic-cationic peptides, or TBMs (with or without aromatic-cationic peptides) will dose-dependently increase the tolerance of mitochondria to cumulative $Ca^{2+}$ challenges. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

3-Nitropropionic acid (3NP) is an irreversible inhibitor of succinate dehydrogenase in complex II of the electron transport chain. It is anticipated that the addition of 3NP (1 mM) to isolated mitochondria will cause the loss of mitochondrial membrane potential and the onset of MPT. It is further anticipated that the pre-treatment of mitochondria with peptide conjugates, aromatic-cationic peptides, or TBMs (with or without aromatic-cationic peptides) will dose-dependently delay the onset of MPT induced by 3NP. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

Caco-2 cells will be treated with 3NP (10 mM) alone or in the presence of peptide conjugates (0.1 μM); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 4 hours, and then incubated with TMRM and examined by CLSM. It is expected that 3NP-treated cells will display reduced fluorescence compared to control cells, which indicates mitochondrial depolarization. By contrast, it is anticipated that concurrent treatment with peptide conjugates, aromatic-cationic peptides, or TBMs (with or without aromatic-cationic peptides) will protect against mitochondrial depolarization caused by 3NP. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for protecting mitochondria against MPT in vitro or in vivo.

Example 13: Compositions of the Present Technology Protect Against Mitochondrial Swelling and Cytochrome c Release MPT pore opening results in mitochondrial swelling. We will demonstrate the effects of peptide conjugates, aromatic-cationic peptides, or TBMs alone or in combination with aromatic-cationic peptides on mitochondrial swelling by measuring reduction in absorbance at 540 nm (A540). Mitochondrial suspensions will be centrifuged and the amount of cytochrome c in the pellet and supernatant will be determined using a commercially available ELISA kit. It is anticipated that the pre-treatment of isolated mitochondria with peptide conjugates, aromatic-cationic peptides, or TBMs (with or without aromatic-cationic peptides) will inhibit swelling and cytochrome c release induced by $Ca^{2+}$ overload. It is further anticipated that in addition to preventing MPT induced by $Ca^{2+}$ overload, peptide conjugates, aromatic-cationic peptides, or TBMs (with or without aromatic-cationic peptides) will also prevent mitochondrial swelling induced by 1-methyl-4-phenylpyridium ions ($MPP^+$), an inhibitor of complex I of the mitochondrial electron transport chain. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for protecting mitochondria against mitochondrial swelling and cytochrome c release in vitro or in vivo.

Example 14: Compositions of the Present Technology Protect Against Ischemia-Reperfusion-Induced Myocardial Stunning Guinea pig hearts will be rapidly isolated, and the aorta will be cannulated in situ and perfused in a retrograde fashion with an oxygenated Krebs-Henseleit at constant pressure (40 cm $H_2O$). Contractile force will be measured with a small hook inserted into the apex of the left ventricle and a silk ligature connected to a force-displacement transducer. Coronary flow will be measured by timing the collection of pulmonary artery effluent.

Hearts will be perfused with peptide conjugates (1-100 nM); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 30 minutes and then subjected to 30 minutes of global ischemia. Reperfusion will not be performed using perfusion buffer lacking both peptide conjugates and TBMs (with or without aromatic-cationic peptides).

It is anticipated that two-way ANOVA will demonstrate significant differences in contractile force, heart rate, and coronary flow in hearts treated with peptide conjugates, aromatic-cationic peptides, or TBMs (with or without aromatic-cationic peptides) compared to untreated ischemic controls. In control hearts, it is anticipated that contractile force will be significantly lower during the reperfusion period compared to the pre-ischemic period. In hearts treated with peptide conjugates, aromatic-cationic peptides, or TBMs (with or without aromatic-cationic peptides), it is anticipated that contractile force during the reperfusion period will be improved compared to untreated controls. It is further anticipated that peptide conjugates, aromatic-cationic peptides, or TBMs (with or without aromatic-cationic peptides) will provide complete inhibition of cardiac stunning. In addition, it is anticipated that coronary flow will be well-sustained throughout the reperfusion period and that there will be no decrease in heart rate in hearts treated with peptide conjugates, aromatic-cationic peptides, or TBMs (with or without aromatic-cationic peptides).

It is anticipated that administration of peptide conjugates of the present technology will have synergistic effects with respect to treating or preventing the effects of ischemia-reperfusion induced myocardial stunning compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology, or pharmaceutically acceptable salts thereof, such as acetate, tartrate, or trifluoroacetate salts, are useful in methods for treating or preventing the effects of ischemia-reperfusion induced myocardial stunning.

Example 15: Compositions of the Present Technology Enhance Organ Preservation

For transplantation, the donor hearts are preserved in a cardioplegic solution during transport. The preservation solution contains high potassium which effectively stops the heart from beating and conserves energy. However, the survival time of the isolated heart is quite limited.

This Example will demonstrate that peptide conjugates, aromatic-cationic peptides, or TBMs alone or in combination with aromatic-cationic peptides prolong survival of organs stored for transplant. Isolated guinea pig hearts will be perfused in a retrograde fashion with an oxygenated Krebs-Henseleit solution at 34° C. After 30 minutes of stabilization, the hearts will be perfused with a cardioplegic solution (CPS; St. Thomas) alone or in the presence of peptide conjugates (100 nM); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 3 minutes. Global ischemia will then be induced by complete interruption of coronary flow and maintained for 90 minutes. Reperfusion will be performed for 60 minutes with oxygenated Krebs-Henseleit solution. Contractile force, heart rate, and coronary flow will be monitored continuously throughout the procedure.

It is anticipated that the addition of peptide conjugates, aromatic-cationic peptides, or TBMs (with or without aromatic-cationic peptides) to cardioplegic solution will significantly enhance contractile function after prolonged ischemia. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for enhancing organ preservation.

Example 16: Compositions of the Present Technology Scavenge Hydrogen Peroxide

The effect of peptide conjugates, aromatic-cationic peptides, or TBMs (with or without aromatic-cationic peptides) on $H_2O_2$ will be measured by luminol-induced chemiluminescence. Luminol (25 µM) and horseradish peroxidase (0.7 IU) will be added to a solution of $H_2O_2$ (4.4 nmol) followed by peptide conjugates; aromatic-cationic peptides; or TBMs alone or in combination with aromatic-cationic peptides. Chemiluminescence will be monitored with a Chronolog Model 560 aggregometer (Havertown, Pa.) for 20 minutes at 37° C.

It is anticipated that peptide conjugates, aromatic-cationic peptides, or TBMs (with or without aromatic-cationic peptides) will dose-dependently inhibit the luminol response, demonstrating the ability to scavenge $H_2O_2$. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for $H_2O_2$ scavenging.

Example 17: Compositions of the Present Technology Inhibit Lipid Peroxidation

Linoleic acid peroxidation will be induced using the water-soluble initiator 2,2'-azobis(2-amidinopropane) (ABAP), and lipid peroxidation will be detected by the formation of conjugated dienes, monitored spectrophotometrically at 236 nm (E. Longoni, W. A. Pryor, P. Marchiafava, *Biochem. Biophys. Res. Commun.* 233, 778-780 (1997)).

5 mL of 0.5 M ABAP and varying concentrations of peptide conjugates; aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be incubated in 2.4 mL linoleic acid suspension until autoxidation rate becomes constant. It is anticipated that peptide conjugates, aromatic-cationic peptides, or TBMs (with or without aromatic-cationic peptides) will dose-dependently inhibit the peroxidation of linoleic acid.

It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for inhibiting lipid peroxidation.

Example 18: Compositions of the Present Technology Inhibit LDL Oxidation

Human low density lipoprotein (LDL) will be prepared fresh from stored plasma. LDL oxidation will be induced catalytically by the addition of 10 mM $Cu_8O_4$, and the formation of conjugated dienes will be monitored at 234 nm for 5 hours at 37° C. (B. Moosmann and C. Behl, *Mol. Pharmacol.* 61:260-268 (2002).

It is anticipated that peptide conjugates, aromatic-cationic peptides, or TBMs (with or without aromatic-cationic peptides) will dose-dependently inhibit the rate of LDL oxidation. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for inhibiting LDL oxidation.

Example 19: Compositions of the Present Technology Suppress Hydrogen Peroxide Production by Isolated Mouse Liver Mitochondria This Example will demonstrate the effect of peptide conjugates, aromatic-cationic peptides, or TBMs alone or in combination with aromatic-cationic peptides on $H_2O_2$ formation in isolated mitochondria. Livers will be harvested from mice, homogenized in ice-cold buffer, and centrifuged at 13800×g for 10 min. The pellet will be washed once, re-suspended in 0.3 mL of wash buffer, and placed on ice until use. $H_2O_2$ will be measured using luminol chemiluminescence as described previously (Li, et al., *Biochim. Biophys. Acta* 1428:1-12 (1999). 0.1 mg mitochondrial protein will be added to 0.5 mL potassium phosphate buffer (100 mM, pH 8.0) in the presence of vehicle, peptide conjugates, TBMs alone or in combination with aromatic-cationic peptides, or aromatic-cationic peptides. 25 mM luminol and 0.7 IU horseradish peroxidase will be added, and chemiluminescence will be monitored with a Chronolog Model 560 aggregometer (Havertown, Pa.) for 20 minutes at 37° C. The amount of $H_2O_2$ produced will be quantified as the area under the curve (AUC) over 20 min, and all data will be normalized to AUC produced by mitochondria alone.

It is anticipated that the amount of $H_2O_2$ production will be significantly reduced in the presence of peptide conjugates, aromatic-cationic peptides, or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for suppressing $H_2O_2$ production in mitochondria.

Example 20: Compositions of the Present Technology Suppress Antimycin-Induced Hydrogen Peroxide Production by Isolated Mouse Liver Mitochondria Livers will be harvested from mice, homogenized in ice-cold buffer, and centrifuged at 13800×g for 10 min. The pellet will be washed once, re-suspended in 0.3 mL of wash buffer, and placed on ice until use. $H_2O_2$ will be measured using luminol chemiluminescence as described previously (Li, et al., *Biochim. Biophys. Acta* 1428, 1-12 (1999). 0.1 mg mitochondrial protein will be added to 0.5 mL potassium phosphate buffer (100 mM, pH 8.0) in the presence of vehicle, peptide conjugates, aromatic-cationic peptides, or TBMs with or without aromatic-cationic peptides. 25 mM luminol and 0.7 IU horseradish peroxidase will be added, and chemiluminescence will be monitored with a Chronolog Model 560 aggregometer (Havertown, Pa.) for 20 minutes at 37° C. The amount of $H_2O_2$ produced will be quantified as the area under the curve (AUC) over 20 min, and all data will be normalized to AUC produced by mitochondria alone.

It is anticipated that peptide conjugates, aromatic-cationic peptides, or TBMs (with or without aromatic-cationic peptides) will dose-dependently reduce the spontaneous production of $H_2O_2$ by isolated mitochondria. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

It is anticipated that peptide conjugates, aromatic-cationic peptides, or TBMs (with or without aromatic-cationic peptides) will dose-dependently reduce the production of $H_2O_2$ induced by antimycin in isolated mitochondria. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for suppressing antimycin-induced $H_2O_2$ production in mitochondria.

Example 21: Compositions of the Present Technology Reduce Intracellular Reactive Oxygen Species (ROS) and Increases Cell Survival To demonstrate that compounds described herein are effective when applied to whole cells, neuronal N2A cells will be plated in 96-well plates at a density of $1\times10^4$/well and allowed to grow for 2 days before treatment with t-BHP (0.5 or 1 mM) for 40 min. Cells will be washed twice and incubated in medium alone or medium containing varying concentrations of peptide conjugates, aromatic-cationic peptides or TBMs with or without aromatic-cationic peptides for 4 hours. Intracellular ROS will be measured using carboxy-H2DCFDA (Molecular Probes, Portland, Oreg., U.S.A.). Cell death will be measured using an MTS cell proliferation assay (Promega, Madison, Wis.).

It is anticipated that incubation with t-BHP will result in a dose-dependent increase in intracellular ROS and a decrease in cell viability. It is anticipated that incubation with peptide conjugates, aromatic-cationic peptides, or TBMs (with or without aromatic-cationic peptides) will dose-dependently reduce intracellular ROS and increase cell survival with an $EC_{50}$ in the nM range. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology, or pharmaceutically acceptable salts thereof, such as acetate, tartrate, or trifluoroacetate salts, are useful in methods comprising reducing intracellular ROS levels/production and increasing cell survival.

Example 22: Compositions of the Present Technology Prevent Loss of Cell Viability Neuronal N2A and SH-SY5Y cells will be plated in 96-well plate at a density of $1\times10^4$/well and allowed to grow for 2 days before treatment with t-butyl hydroperoxide (t-BHP) (0.05-0.1 mM) alone or in the presence of peptide conjugates, aromatic-cationic peptides or TBMs with or without aromatic-cationic peptides for 24 hours. Cell death will be assessed using an MTS cell proliferation assay (Promega, Madison, Wis.).

It is anticipated that treatment of N2A and SH-SY5Y cells with low doses of t-BHP (0.05-0.1 mM) for 24 hours will result in a decrease in cell viability. It is anticipated that treatment of cells with peptide conjugates, aromatic-cationic peptides, or TBMs (with or without aromatic-cationic peptides) will result in a dose-dependent reduction of t-BHP-induced cytotoxicity. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for reducing the loss of cell viability.

Example 23: Compositions of the Present Technology Decrease Caspase Activity

N2A cells will be grown on 96-well plates, treated with t-BHP (0.05 mM) in the presence of vehicle, peptide conjugates, aromatic-cationic peptides, or TBMs with or without aromatic-cationic peptides at 37° C. for 12-24 hours. All treatments will be carried out in quadruplicate. N2A cells will be incubated with t-BHP (50 mM) alone or in the presence of peptide conjugates, aromatic-cationic peptides, or TBMs with or without aromatic-cationic peptides at 37° C. for 12 hours. Cells will be gently lifted from the plates with a cell detachment solution (Accutase, Innovative Cell Technologies, Inc., San Diego, Calif., U.S.A.) and will be washed twice in PBS. Caspase activity will be assayed using a FLICA kit (Immunochemistry Technologies LLC, Bloomington, Minn.). According to the manufacturer's recommendation, cells will be resuspended (approx. $5\times10^6$ cells/mL) in PBS and labeled with pan-caspase inhibitor FAM-VAD-FMK for 1 hour at 37° C. under 5% $CO_2$ while protected from light. Cells will then be rinsed to remove the unbound reagent and fixed. Fluorescence intensity in the cells will be measured by a laser scanning cytometer (Beckman-Coulter XL, Beckman Coulter, Inc., Fullerton, Calif., U.S.A.) using the standard emission filters for green (FL1). For each run, 10,000 individual events will be collected and stored in list-mode files for off-line analysis.

Caspase activation is the initiating trigger of the apoptotic cascade, and it is anticipated that there will be a significant increase in caspase activity after incubation of the cells with 50 mM t-BHP for 12 hours, which will be dose-dependently inhibited by peptide conjugates, aromatic-cationic peptides, or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for decreasing caspase activity.

Example 24: Compositions of the Present Technology Inhibit Lipid Peroxidation in Cells Exposed to Oxidative Damage Lipid peroxidation will be evaluated by measuring 4-HNE Michael adducts. 4-HNE is one of the major products of the peroxidation of membrane polyunsaturated fatty acids. N2A cells will be seeded on a glass dish 1 day before t-BHP treatment (1 mM, 3 hours, 37° C., 5% $CO_2$) alone or in the presence of peptide conjugates ($10^{-8}$ to $10^{-10}$ M), aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group). Cells will be washed twice with PBS, fixed 30 minutes with 4% paraformaldehyde in PBS at RT, and washed 3 additional times with PBS. Cells will then be permeabilized and treated with rabbit anti-HNE antibody followed by a secondary antibody (goat anti-rabbit IgG conjugated to biotin). Cells will be mounted in Vectashield and imaged using a Zeiss fluorescence microscope using an excitation wavelength of 460±20 nm and a longpass filter of 505 nm for emission.

It is anticipated that peptide conjugates, aromatic-cationic peptides, or TBMs (with or without aromatic-cationic peptides) will inhibit lipid peroxidation in N2A cells treated with t-BHP. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for inhibiting lipid peroxidation in cells exposed to oxidative damage.

Example 25: Compositions of the Present Technology Inhibit Loss of Mitochondrial Membrane Potential in Cells Exposed to Hydrogen Peroxide Caco-2 cells will be treated with t-BHP (1 mM) alone or in the presence of peptide conjugates (0.1 µM); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 4 hours, and then incubated with TMRM and examined under CLSM. In cells treated with t-BHP, it is anticipated that TMRM fluorescence will be much reduced compared to control cells, suggesting generalized mitochondrial depolarization. In contrast, it is anticipated that treatment with peptide conjugates, aromatic-cationic peptides, or TBMs (with or without aromatic-cationic peptides) will protect against mitochondrial depolarization caused by t-BHP. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for inhibiting the loss of mitochondrial membrane potential in cells exposed to hydrogen peroxide.

Example 26: Compositions of the Present Technology Prevent Loss of Mitochondrial Membrane Potential and Increased ROS Accumulation in N2A Cells Exposed to t-BHP N2A cells cultured in a glass dish will be treated with 0.1 mM t-BHP alone or in the presence of peptide conjugates (1 nM); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group) or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) for 6 hours. Cells will then be loaded with 10 µM dichlorofluorescin (DCF) (ex/em=485/530) for 30 minutes at 37° C., 5% $CO_2$. Cells will be washed 3 times with HBSS, stained with 20 nM of Mitotracker TMRM (ex/em=550/575 nm) for 15 minutes at 37° C., and examined by confocal laser scanning microscopy.

It is anticipated that the treatment of N2A cells with t-BHP will result in a loss of TMRM fluorescence, indicating mitochondrial depolarization, and a concomitant increase in DCF fluorescence, indicating an increase in intracellular ROS. It is further anticipated that treatment with peptide conjugates, aromatic-cationic peptides, or TBMs (with or without aromatic-cationic peptides) will prevent mitochondrial depolarization and reduce ROS accumulation. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for inhibiting the loss of mitochondrial membrane potential and increased ROS accumulation in cells exposed to t-BHP.

Example 27: Compositions of the Present Technology Prevent Apoptosis Caused by Oxidative Stress SH-SY5Y cells will be grown in 96-well plates and treated with t-BHP (0.025 mM) alone or in the presence of peptide conjugates, aromatic-cationic peptides, or TBMs with or without aromatic-cationic peptides at 37° C. for 24 hours. All treatments will be carried out in quadruplicate. Cells will then be stained with 2 mg/mL Hoechst 33342 for 20 minutes, fixed with 4% paraformaldehyde, and imaged using a Zeiss fluorescent microscope (Axiovert 200M) equipped with the Zeiss Acroplan 20× objective. Nuclear morphology will be evaluated using an excitation wavelength of 350±100 m and a longpass filter of 400 nm for emission. All images will be processed and analyzed using MetaMorph software (Universal Imaging Corp., West Chester, Pa., U.S.A.). Uniformly stained nuclei will be scored as healthy, viable neurons. Cells with condensed or fragmented nuclei will be scored as apoptotic. It is anticipated that peptide conjugates, aromatic-cationic peptides, or TBMs with or without aromatic-cationic peptides will prevent SH-SY5Y cell apoptosis induced by 0.025 mM t-BHP. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for preventing apoptosis caused by oxidative stress.

Example 28: Compositions of the Present Technology Prevent Lipid Peroxidation in Hearts Subjected to Ischemia and Reperfusion Isolated guinea pig hearts will be perfused in a retrograde manner in a Langendorff apparatus and subjected to various intervals of ischemia-reperfusion. Hearts will be fixed immediately, embedded in paraffin, and sectioned. Immunohistochemical analysis of 4-hydroxy-2-nonenol (HNE)-modified proteins will be carried out using an anti-HNE antibody.

It is anticipated that treatment with peptide conjugates, aromatic-cationic peptides, or TBMs with or without aromatic-cationic peptides will prevent lipid peroxidation in hearts subjected to brief intervals of ischemia and reperfusion compared to untreated controls. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for preventing lipid peroxidation in organs subjected to ischemia and reperfusion.

Example 29: Compositions of the Present Technology Improve Viability of Isolated Pancreatic Islet Cells Islet cells will be isolated from mouse pancreas according to standard procedures. Peptide conjugates, aromatic-cationic peptides, TBMs with or without aromatic-cationic peptides or control vehicle will be added to isolation buffers used throughout the isolation procedure. Mitochondrial membrane potential will be measured using TMRM (red) and visualized by confocal microscopy, and apoptosis will be measured by flow cytometry using annexin V and necrosis by propidium iodide.

It is anticipated that peptide conjugates, aromatic-cationic peptides, or TBMs (with or without aromatic-cationic peptides) will reduce apoptosis and increase islet cell viability, as measured by mitochondrial membrane potential. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for improving the viability of isolated pancreatic islet cells.

Example 30: Compositions of the Present Technology Protect Against Oxidative Damage in Pancreatic Islet Cells Isolated mouse pancreatic islet cells will be treated with 25 μM t-BHP alone or in the presence of peptide conjugates, aromatic-cationic peptides, or TBMs with or without aromatic-cationic peptides. Mitochondrial membrane potential will be measured by TMRM (red) and reactive oxygen species will be measured by DCF (green) using confocal microscopy. It is anticipated that peptide conjugates, aromatic-cationic peptides, or TBMs (with or without aromatic-cationic peptides) will protect against oxidative damage in isolated pancreatic islet cells. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for preventing oxidative damage in pancreatic islet cells.

Example 31: Compositions of the Present Technology Protect Against Parkinson's Disease 1-methyl-4-phenyl-1,2,3,6-tetrahydropyridine ($M_{tox}$) is a neurotoxin that selectively destroys striatal dopaminergic neurons and is an accepted animal model of Parkinson's Disease. 1-methyl-4-phenylpyridinium ($MPP^+$), a metabolite of $M_{tox}$, targets mitochondria, inhibits complex I of the electron transport chain, and increases ROS production. $MPP^+$ is used for in vitro studies because cells are unable to metabolize $M_{tox}$ to the active metabolite, while $M_{tox}$ is used for in vivo (i.e., animal) studies.

SN-4741 cells will be treated with buffer; 50 µM $MPP^+$; 50 µM $MPP^+$ and peptide conjugates; 50 µM $MPP^+$ and aromatic-cationic peptides; or 50 µM $MPP^+$ and TBMs; or 50 µM $MPP^+$ and TBMs with aromatic-cationic peptides for 48 hours. Apoptosis will be measured by fluorescent microscopy with Hoechst 33342. It is anticipated that the number of condensed, fragmented nuclei will be significantly increased by $MPP^+$ treatment in control cells, and that treatment with peptide conjugates, aromatic-cationic peptides, or TBMs (with or without aromatic-cationic peptides) will reduce the number of apoptotic cells. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is further anticipated that peptide conjugates, aromatic-cationic peptides, or TBMs with or without aromatic-cationic peptides will dose-dependently prevent the loss of dopaminergic neurons in mice treated with $M_{tox}$. Three doses of $M_{tox}$ (10 mg/kg) will be given to mice (n=12) 2 hours apart. Peptide conjugates, aromatic-cationic peptides, or TBMs with or without aromatic-cationic peptides will be administered 30 minutes before each $M_{tox}$ injection, and at 1 and 12 hours after the last $M_{tox}$ injection. Animals will be sacrificed one week later and striatal brain regions will be immunostained for tyrosine hydroxylase activity. Levels of dopamine, DOPAC and HVA levels will be quantified by high pressure liquid chromatography.

It is anticipated that dopamine, DOPAC (3,4 dihydroxyphenylacetic acid) and HVA (homovanillic acid) levels will be significantly reduced by $M_{tox}$ exposure in untreated control mice. It is anticipated that peptide conjugates, aromatic-cationic peptides, or TBMs with or without aromatic-cationic peptides will dose-dependently increase striatal dopamine, DOPAC, and HVA levels in mice treated with $M_{tox}$. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for treating or preventing Parkinson's disease in mammalian subjects.

Example 32: Compositions of the Present Technology Reduce Mitochondrial Dysfunction in Rats Fed a High-Fat Diet To determine the potential impact of diet-induced obesity on the control of cellular redox balance in skeletal muscle, a novel approach to measure the rate of mitochondrial $H_2O_2$ production in permeabilized skeletal muscle fiber bundles will be developed. See Anderson, et al., *J. Clin. Invest.* (doi: 10.1 172/JC137048). During basal (state 4) respiration supported by NADH-linked complex I substrates, the rate of superoxide formation is low, representing 0.1-0.5% of total $O_2$ utilization (Anderson & Neufer, Am. *J. Physiol. Cell Physiol.* 290: C844-851 (2006); St-Pierre, et al., *J. Biol. Chem.* 277:44784-44790 (2002)). However, respiration supported exclusively by succinate, an FADH-linked complex II substrate, promotes high rates of superoxide production by generating reverse electron flow back into complex I (Anderson & Neufer, *Am J Physiol Cell Physiol* 290:C844-851 (2006); St-Pierre, et al., *J. Biol. Chem.* 277:44784-44790 (2002); Liu, et al., *J. Neurochem.* 80:780-787 (2002); Turrens, et al., *Biochem.* 1 191:421-427 (1980)). This Example describes methods for measuring mitochondrial function in permeabilized muscle tissues and examines the effects of a high-fat diet on mitochondrial function.

Animals and Reagents.

Thirty male Sprague-Dawley rats will be obtained from Charles River Laboratory (Wilmington, Mass.) and housed in a temperature (22° C.) and light controlled room with free access to food and water. Twenty of the animals will be maintained on a high (60%) fat diet (Research Dyets, Bethlehem, Pa.). Skeletal muscle will be obtained from anesthetized animals (100 mg/kg i.p. ketamine-xylazine). After surgery, animals will be sacrificed by cervical dislocation while anesthetized. Amplex Red Ultra reagent will be obtained from Molecular Probes (Eugene, Oreg.). Stigmatellin and horseradish peroxidase (HRP) will be obtained from Fluka Biochemika (Buchs, Switzerland). All other chemicals will be purchased from Sigma-Aldrich (St. Louis, Mo.). All animal studies will be approved by the East Carolina University Institutional Animal Care and Use Committee.

Preparation of Permeabilized Muscle Fiber Bundles.

Briefly, small portions (25 mg) of soleus, red gastrocnemius (RG), and white gastrocnemius (WG) muscle will be dissected and placed in ice-cold buffer X, containing 60 mM K-MES, 35 mM KCl, 7.23 mM $K_2EGTA$, 2.77 mM $CaK_2EGTA$, 20 mM imidazole, 0.5 mM DTT, 20 mM taurine, 5.7 mM ATP, 15 mM PCr, and 6.56 mM $MgCl_2.6H_2O$ (pH 7.1, 295 mosmol/kg $H_2O$). The muscle will be trimmed of connective tissue and cut down to fiber bundles (2×7 mm, 4-8 mg wet wt). Using a pair of needle-tipped forceps under a dissecting microscope, fibers will be gently separated from one another to maximize surface area of the fiber bundle, leaving only small regions of contact. To permeabilize the myofibers, each fiber bundle will be placed in ice-cold buffer X containing 50 µg/mL saponin and incubated on a rotator for 30 minutes at 4° C. Permeabilized fiber bundles (PmFBs) will be washed in ice-cold buffer Z containing 110 mM K-MES, 35 mM KCl, 1 mM EGTA, 10 mM $K_2HPO_4$, 3 mM $MgCl_2.6H_2O$, 5 mg/mL BSA, 0.1 mM glutamate, and 0.05 mM malate (pH 7.4, 295 mOsm), and incubated in buffer Z on a rotator at 4° C. until analysis (<2 hours).

Mitochondrial Respiration and $H_2O_2$ Production Measurements.

High resolution respirometric measurements will be obtained at 30° C. in buffer Z using the Oroboros $O_2K$ Oxygraph (Innsbruck, Austria). Mitochondrial $H_2O_2$ production will be measured at 30° C. during state 4 respiration in buffer Z (10 µg/mL oligomycin) by continuously monitoring oxidation of Amplex Red using a Spex Fluoromax 3 (Jobin Yvon, Ltd.) spectrofluorometer with temperature control and magnetic stirring at >1000 rpm. Amplex Red reagent reacts with $H_2O_2$ in a 1:1 stoichiometry catalyzed by HRP to yield the fluorescent compound resorufin and molar equivalent $O_2$. Resorufin has excitation/emission characteristics of 563 nm/587 nm and is extremely stable once formed. After baseline fluorescence (reactants only) is established, the reaction will be initiated by addition of a permeabilized fiber bundle to 300 µL of buffer Z containing 5 µM Amplex Red and 0.5 U/mL HRP, with succinate at 37° C. For the succinate experiments, the fiber bundle will be washed briefly in buffer Z without substrate to eliminate residual pyruvate and malate. Where indicated, 10 µg/mL oligomycin will be included in the reaction buffer to block ATP synthase and ensure state 4 respiration. At the conclusion of each experiment, PmFBs will be washed in double-distilled (dd) $H_2O$ to remove salts, and freeze-dried in a lyophilizer (LabConco). The rate of respiration will be expressed as pmol per second per mg dry weight, and mitochondrial $H_2O_2$ production expressed as pmol per minute per dry weight.

Statistical Analyses.

Data will be presented as means±SE. Statistical analyses will be performed using a one-way ANOVA with Student-Newman-Keuls method for analysis of significance among groups. The level of significance will be set at $p<0.05$.

It is anticipated that maintaining animals on a 60% fat diet for a period of 3 weeks will cause an increase in the maximal rate of mitochondrial $H_2O_2$ production. It is anticipated that the addition of rotenone at the conclusion of succinate titration will eliminate $H_2O_2$ production, confirming complex I as the source of superoxide production in both control animals and those fed high-fat diets. Mitochondrial $H_2O_2$ production will also be measured by titrating pyruvate/malate in the presence of antimycin (complex III inhibitor), with the expectation that animals fed a high-fat diet will have a higher maximal rate of $H_2O_2$ production than control animals.

It is anticipated that peptide conjugates, aromatic-cationic peptides, or TBMs with or without aromatic-cationic peptides will reduce mitochondrial dysfunction in mammalian subjects exposed to a high-fat diet. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology, or pharmaceutically acceptable salts thereof, such as acetate, tartrate, or trifluoroacetate salts, are useful in methods for reducing mitochondrial dysfunction in mammalian subjects exposed to a high-fat diet.

Example 33: Compositions of the Present Technology Reduce ROS Production in Rats Fed a High-Fat Diet Superoxide production is higher during basal respiration supported by fatty acid versus carbohydrate metabolism, raising the possibility that the increase in mitochondrial $H_2O_2$ production caused by a high-fat diet may be a result of elevations in cellular $H_2O_2$ levels (e.g., ROS by a ROS-induced ROS release mechanism). To test this hypothesis, the effects of the peptide conjugates, aromatic-cationic peptides, or TBMs with or without aromatic-cationic peptides on mitochondrial function in high-fat fed rats will be examined. Some antioxidants have been shown to effectively reduce ROS in hearts subjected to myocardial stunning, in pancreatic islet cells after transplantation, and in animal models of Parkinson's disease and amyotrophic lateral sclerosis (Zhao, et al., *J. Biol. Chem.* 279:34682-34690 (2004); Thomas, et al., *J. Am. Soc. Nephr.* 16, TH-FC067 (2005); Petri, et al., *J. Neurochem.* 98, 1141-1148 (2006); Szeto, et al., *AAPS J.* 8: E521-531 (2006)).

Ten rats maintained on a high-fat diet will receive daily intraperitoneal injections of peptide conjugates (1.5 mg/kg); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) dissolved in phosphate-buffered saline. Dose response curves for peptide conjugates, aromatic-cationic peptides and TBMs with or without aromatic-cationic peptides will be established in vitro and in vivo. Mitochondrial function will be measured according to the methods described herein. It is anticipated that both dose response curves will reflect a reduction in mitochondrial $H_2O_2$ production during succinate-supported respiration.

Next, rats will be placed on a high-fat diet (60%) for six weeks with daily administration of vehicle, peptide conjugates, aromatic-cationic peptides, or TBMs with or without aromatic-cationic peptides. It is anticipated that succinate titration experiments conducted on permeabilized fibers will reveal an increase in the maximal rate of $H_2O_2$ production in high-fat fed rats. It is further anticipated that permeabilized fibers from high-fat fed rats will display a higher rate of $H_2O_2$ production during basal respiration supported by palmitoyl-carnitine. It is anticipated that high-fat fed rats treated with peptide conjugates, aromatic-cationic peptides, or TBMs with or without aromatic-cationic peptides, will show a reduction in mitochondrial $H_2O_2$ production during both succinate and palmitoyl-carnitine supported respiration. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is further anticipated that basal respiration supported by pyruvate/malate will be slightly increased in fibers from high-fat fed rats, suggesting some degree of uncoupling. However, it is also anticipated that in high-fat fed rats, basal rates of pyruvate/malate- or palmitoyl-carnitine-supported respiration will be unaffected by TBM- (with or without aromatic-cationic peptides) or peptide conjugate-treatment, indicating that the normalization of $H_2O_2$ production with TBM- (with or without aromatic-cationic peptides) or peptide conjugate-treatment is not mediated by an increase in proton leak. It is also anticipated that treatment with TBMs (with or without aromatic-cationic peptides) or peptide conjugates will not affect body weight gain in high-fat fed rats.

Collectively, these findings will demonstrate that administration of a mitochondrial targeted antioxidant, such as the TBMs (with or without aromatic-cationic peptides) or peptide conjugates of the present technology, prevents or compensates for the increase in mitochondrial $H_2O_2$ production induced by a high-fat diet. As such, the TBMs (with or without aromatic-cationic peptides) or peptide conjugates of the present technology are useful in methods for preventing or treating insulin resistance caused by mitochondrial dysfunction in mammalian subjects with high fat diets.

It is increasingly recognized that the intracellular localization and activity of many proteins (e.g., receptors, kinases/phosphatases, transcription factors, etc.) is controlled by the oxidation state of thiol (—SH)-containing residues, suggesting that shifts in the intracellular redox environment can affect a wide variety of cellular functions (Schafer and Buetner, *Free Radic Biol Med* 30, 1191-1212 (2001). Glutathione (GSH), the most abundant redox buffer in cells, is reversibly oxidized to GSSG by glutathione peroxidase in the presence of $H_2O_2$, and reduced to GSH by glutathione reductase with electrons donated by NADPH. The ratio of GSH/GSSG is typically very dynamic, and reflects the overall redox environment of the cell.

Protein homogenates will be prepared by homogenizing 100 mg of frozen muscle in a buffer containing 10 mM Tris, 1 mM EDTA, 1 mM EGTA, 2 mM NaOrthovanadate, 2 mM NaPyrophosphate, 5 mM NaF, and protease inhibitor cocktail (Complete), at pH 7.2. After homogenization, 1% Triton X-100 will be added to the protein suspension, which will be vortexed and incubated on ice for 5 minutes. Samples will be centrifuged at 10,000 rpm for 10 minutes to pellet the insoluble debris. For GSSG measurement, tissue will be homogenized in a solution containing 20 mM Methyl-2-vinylpyridinium triflate to scavenge all reduced thiols in the sample. Total GSH and GSSG will be measured using a commercially available GSH/GSSG assay (Oxis Research Products, Percipio Biosciences, Foster City, Calif., U.S.A).

It is anticipated that high-fat feeding will cause a reduction in total cellular glutathione content ($GSH_t$) irrespective of treatment with peptide conjugates, aromatic-cationic peptides, or TBMs with or without aromatic-cationic peptides, demonstrating that high-fat intake compromises GSH-mediated redox buffering capacity in skeletal muscle. To establish a link between the increased mitochondrial $H_2O_2$ production brought about by high-fat diet and its effect on overall redox environment of skeletal muscle, both GSH and GSSG will be measured in skeletal muscle from standard chow-fed and high-fat fed rats 1) following a 10 hour fast, and 2) 1 hour after administration of a standard glucose load (oral gavage, 10 hour fasted). In standard chow-fed controls, it is anticipated that glucose ingestion will cause a reduction in the GSH/GSSG ratio (normalized to $GSH_t$), presumably reflecting a shift to a more oxidized state in response to the increase in insulin-stimulated glucose metabolism. In high-fat fed rats, it is anticipated that the GSH/GSSG ratio will be reduced in the 10 hour fasted state relative to standard chow-fed controls and will decrease further in response to the glucose ingestion. It is anticipated that treatment with peptide conjugates, aromatic-cationic peptides, or TBMs (with or without aromatic-cationic peptides) will preserve the GSH/GSSG ratio near control levels, even following glucose ingestion. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These findings will demonstrate that a high-fat diet shifts the intracellular redox environment in skeletal muscle to a more oxidized state, as compared to controls. It is anticipated that treatment with peptide conjugates, aromatic-cationic peptides, or TBMs with or without aromatic-cationic peptides will preserve the intracellular redox state in skeletal muscle, presumably by scavenging primary oxidants, thereby compensating for the reduction in total GSH-mediated redox buffering capacity induced by a high-fat diet. Thus, it is anticipated that the administration of a mitochondrial-targeted antioxidant, such as the TBMs (with or without aromatic-cationic peptides) or peptide conjugates of the present technology, will prevent or compensate for the metabolic dysfunction that develops in rats fed a high-fat diet.

These results will show that TBMs (with or without aromatic-cationic peptides) or peptide conjugates of the present technology or pharmaceutically acceptable salts thereof, such as acetate, tartrate, or trifluoroacetate salts, are useful in methods for reducing ROS production in mammalian subjects exposed to a high-fat diet.

Example 34: Compositions of the Present Technology Prevent Insulin Resistance in Rats Fed a High-Fat Diet To demonstrate that mitochondria-driven changes in the intracellular redox environment may be linked to the etiology of high-fat diet-induced insulin resistance, oral glucose tolerance tests will be performed in rats following six weeks of a high-fat diet. On the day of testing, food will be removed 10 hours prior to administration of a 2 g/kg glucose solution via oral gavage. Glucose levels will be determined on whole blood samples (Lifescan, Milpitas, Calif., U.S.A.). Serum insulin levels will be determined using a rat/mouse ELISA kit (Linco Research, St. Charles, Mo., U.S.A.). Fasting data will be used to determine homeostatic model assessment (HOMA)-calculated as fasting insulin (mU/mL)×fasting glucose (mM)/22.5.

Blood glucose and insulin responses to the oral glucose challenge are anticipated to be higher and more sustained in high-fat fed rats compared with standard chow-fed rats. Treatment of high-fat fed rats with peptide conjugates, aromatic-cationic peptides, or TBMs with or without aromatic-cationic peptides is expected to normalize blood glucose and insulin responses to the oral glucose challenge. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is anticipated that homeostatic model assessment (HOMA) will confirm the development of insulin resistance in high-fat fed rats, and that treatment of high-fat fed rats with peptide conjugates, aromatic-cationic peptides, or TBMs with or without aromatic-cationic peptides will suppress the development of insulin resistance. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

To further assess insulin sensitivity, the phosphorylation state of the insulin signaling protein Akt in skeletal muscle will be measured 1) following a 10 hour fast, and 2) 1 hour after receiving an oral glucose load. It is anticipated that in response to glucose ingestion, Akt phosphorylation will increase in skeletal muscle of standard chow-fed controls but will remain essentially unchanged in high-fat fed rats, confirming the presence of insulin resistance at the level of insulin signaling. It is further anticipated that the treatment of high-fat fed rats with peptide conjugates, aromatic-cationic peptides, or TBMs with or without aromatic-cationic peptides will increase Akt phosphorylation in response to glucose ingestion, which, indicates insulin sensitivity. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that administration of a mitochondrial-targeted antioxidant, such as the TBMs (with or without aromatic-cationic peptides) or peptide conjugates of the present technology, prevents insulin resistance that develops in rats fed a high-fat diet. As such, the TBMs (with or without aromatic-cationic peptides) or peptide conjugates of the present technology or pharmaceutically acceptable salts thereof, such as acetate, tartrate, or trifluoroacetate salts, are useful in methods of preventing or treating insulin resistance in mammalian subjects.

Example 35: Compositions of the Present Technology Prevent Mitochondria-Driven Changes in the Intracellular Redox Environment and Insulin Resistance in Human Subjects This Example will illustrate the link between mitochondria-driven changes in the intracellular redox environment and insulin resistance in human subjects.

Mitochondrial $H_2O_2$ production and respiration in permeabilized skeletal myofiber bundles from lean, insulin sensitive (BMI=21.6±1.2 kg·m$^{-2}$, HOMA=1.2±0.4), and obese/insulin resistant (BMI=43.0±4.1 kg·m$^{-2}$, HOMA=2.5±0.7) male subjects will be measured. On the day of the experiment, subjects will report to the laboratory following an overnight fast (approximately 12 hours). A fasting blood sample will be obtained for determination of glucose and insulin. Height and body weight will be recorded and skeletal muscle biopsies will be obtained from lateral aspect of vastus lateralis by the percutaneous needle biopsy technique under local subcutaneous anesthesia (1% lidocaine). A portion of the biopsy samples will be flash frozen in liquid N2 for protein analysis, and another portion will be used to prepare permeabilized fiber bundles.

Mitochondrial $H_2O_2$ production is anticipated to be higher in obese subjects than in lean subjects in response to titration of succinate, and to be higher during basal respiration supported by fatty acid. Basal $O_2$ utilization is anticipated to be similar in lean and obese subjects, with the rate of mitochondrial free radical leak higher during glutamate/malate/succinate and palmitoyl-carnitine supported basal respiration higher in obese subjects. Finally, it is anticipated that both total cellular GSH content and the GSH/GSSG ratio will be lower in the skeletal muscle of obese subjects, indicating an overall lower redox buffer capacity and a more oxidized intracellular redox environment.

These results will show that mitochondrial ROS production and the resulting shift to a more oxidized skeletal muscle redox environment is an underlying cause of high-fat diet-induced insulin resistance. The anticipated increase in mitochondrial $H_2O_2$ production is expected to be a primary factor contributing to the shift in overall cellular redox environment. Thus, administration of a mitochondrial-targeted antioxidant, such as the peptide conjugates of the present technology, aromatic-cationic peptides or TBMs with or without aromatic-cationic peptides is expected to prevent or compensate for the metabolic dysfunction caused by a high-fat diet. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

As such, the TBMs (with or without aromatic-cationic peptides) or peptide conjugates of the present technology or pharmaceutically acceptable salts thereof, such as acetate, tartrate, or trifluoroacetate salts, are useful in methods for preventing or treating insulin resistance in human subjects.

Example 36: Compositions of the Present Technology in the Prevention and Treatment of Insulin Resistance To demonstrate the prevention and treatment of insulin resistance, the TBMs (with or without aromatic-cationic peptides) or peptide conjugates of the present technology will be administered to fatty (fa/fa) Zucker rats, which are an accepted model of diet-induced insulin resistance. As compared to high-fat fed Sprague-Dawley rats (as used in Examples 32-34), fatty Zucker rats are anticipated to develop a greater degree of obesity and insulin resistance under similar conditions. As in Examples 32-34, it is anticipated that mitochondrial dysfunction (e.g., increased $H_2O_2$ production) will be evident in permeabilized fibers from the Zucker rats.

To demonstrate the effects of TBMs (with or without aromatic-cationic peptides) or peptide conjugates on the prevention of insulin resistance, young Zucker rats (~3-4 weeks of age) will be administered peptide conjugates, aromatic-cationic peptides, or TBMs with or without aromatic-cationic peptides for approximately 6 weeks. As these young rats do not yet exhibit signs or symptoms of insulin resistance, they provide a useful model for assessing the efficacy of methods of preventing insulin resistance. Peptide conjugates (1.0-5.0 mg/kg body wt); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be administered to the rats intraperitoneally (i.p.) or orally (drinking water or oral gavage).

It is predicted that administration of peptide conjugates, aromatic-cationic peptides, or TBM (with or without aromatic-cationic peptides) will attenuate or prevent the development of whole body and muscle insulin resistance that normally develops in fatty Zucker rats. Physiological parameters measured will include body weight, fasting glucose/insulin/free fatty acid, oral glucose tolerance (OGTT), in vitro muscle insulin sensitivity (in vitro incubation), biomarkers of insulin signaling (Akt-P, IRS-P), mitochondrial function studies on permeabilized fibers (respiration, $H_2O_2$ production), biomarkers of intracellular oxidative stress (lipid peroxidation, GSH/GSSG ratio, aconitase activity), and mitochondrial enzyme activity. Control animals will include wild-type and untreated fatty rats. Successful prevention of insulin resistance by the peptide conjugates of the present technology, aromatic-cationic peptides, or TBM (with or without aromatic-cationic peptides) will be indicated by a reduction in one or more of the markers associated with insulin resistance or mitochondrial dysfunction enumerated above. It is anticipated that administration of peptide conjugates of the present technology will have synergistic effects in this regard compared to that observed with either aromatic-cationic peptides or TBM (alone or in combination with aromatic-cationic peptides). It is anticipated that administration of TBMs in combination with aromatic-cationic peptides will have synergistic effects in this regard compared to that observed with either aromatic-cationic peptides or TBMs alone.

To demonstrate the effects of the peptide conjugates on treatment of insulin resistance, Zucker rats (~12 weeks of age) will be administered peptide conjugates, aromatic-cationic peptides, or TBMs with or without aromatic-cationic peptides for approximately 6 weeks. As these rats show signs of obesity and insulin resistance, they will provide a useful model for assessing the efficacy of methods of treating insulin resistance. Peptide conjugates (1.0-5.0 mg/kg body wt); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be administered to the rats intraperitoneally (i.p.) or orally (drinking water or oral gavage).

It is predicted that administration of peptide conjugates, aromatic-cationic peptides, or TBMs with or without aromatic-cationic peptides will reduce the whole body and muscle insulin resistance that normally develops in fatty Zucker rats. Parameters measured will include body weight, fasting glucose/insulin/free fatty acid, oral glucose tolerance (OGTT), in vitro muscle insulin sensitivity (in vitro incubation), biomarkers of insulin signaling (Akt-P, IRS-P), mitochondrial function studies on permeabilized fibers (respiration, $H_2O_2$ production), biomarkers of intracellular oxidative stress (lipid peroxidation, GSH/GSSG ratio, aconitase activity), and mitochondrial enzyme activity. Controls will include wild-type and untreated fatty rats. Successful treatment of insulin resistance by the peptide conjugates of the present technology, aromatic-cationic peptides, or TBMs with or without aromatic-cationic peptides will be indicated by a reduction in one or more of the markers associated with insulin resistance or mitochondrial dysfunction enumerated above. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for treating or preventing insulin resistance in mammalian subjects.

Example 37: Compositions of the Present Technology Protect Against Prerenal ARI Caused by Ischemia-Reperfusion This Example will demonstrate the effects of TBMs (with or without aromatic-cationic peptides) or peptide conjugates of the present technology in protecting a subject from acute renal injury (ARI) caused by ischemia-reperfusion (FR).

Eight Sprague Dawley rats (250-300 g) will be assigned to one of the following groups: (1) sham surgery (no I/R); (2) I/R+saline vehicle; (3) I/R+peptide conjugates; (4) I/R+ aromatic-cationic peptides; (5) I/R+TBMs; (6) I/R+TBMs and aromatic-cationic peptides. Peptide conjugates (3 mg/kg in saline); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group) or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be administered 30 minutes before ischemia and immediately before reperfusion. Control animals will be given saline alone according to the same schedule.

Rats will be anesthetized with a mixture of ketamine (90 mg/kg, i.p.) and xylazine (4 mg/kg, i.p.). The left renal vascular pedicle will be occluded using a micro-clamp for 30-45 min. At the end of the ischemic period, reperfusion will be established by removing the clamp. At that time, the contralateral kidney will be removed. After 24 hours of reperfusion, animals will be sacrificed and blood samples will be obtained by cardiac puncture. Renal function will be determined by measuring levels of blood urea nitrogen (BUN) and serum creatinine (BioAssay Systems DIUR-500 and DICT-500).

Renal Morphologic Examination:

Kidneys will be fixed in 10% neutral-buffered formalin and embedded in paraffin wax for sectioning. Three-micron sections will be stained with hematoxylin-eosin (H&E) and periodic acid-Schiff (PAS), and analyzed by light microscopy. Lesions will be scored based on 1) mitosis and necrosis of individual cells, 2) necrosis of all cells in adjacent proximal convoluted tubules with survival of surrounding tubules, 3) necrosis confined to the distal third of the proximal convoluted tubule with a band of necrosis extending across the inner cortex, and 4) necrosis affecting all three segments of the proximal convoluted tubule.

TUNEL Assay for Apoptosis:

Renal tissue sections will be deparaffinized and rehydrated with xylenes, a graded alcohol series, and deionized $H_2O$, and incubated in 20 μg/mL proteinase K for 20 minutes at RT An in situ cell death detection POD kit (Roche, Ind., USA) will be used according to the manufacturer's instructions. Briefly, endogenous peroxidase activity in the kidney sections will be blocked by incubation for 10 minutes with 0.3% $H_2O_2$ in methanol. The sections will be then incubated in a humidified chamber in the dark for 30 minutes at 37° C. with TUNEL reaction mixture. After washing, the slides will be incubated with 50-100 μL Converter-POD in a humidified chamber for 30 minutes at RT. The slides will be incubated in DAB solution (1-3 min), counterstained with hemotoxylin, dehydrated through a graded series of alcohol, and mounted in Permount for microscopy.

Immunohistochemistry:

Renal sections will be cut from paraffin blocks and mounted on slides. After removal of paraffin with xylene, the slides will be rehydrated using graded alcohol series and deionized $H_2O$. Slides will be heated in citrate buffer (10 mM Citric Acid, 0.05% Tween 20, pH 6.0) for antigen retrieval. Endogenous peroxidase will be blocked with hydrogen peroxide 0.3% in methanol. Immunohistochemistry will be then performed using a primary antibody against heme oxygenase-I (HO-1) (rat anti-HO-1/HMOX1/HSP32 monoclonal antibody (R&D Systems, MN, USA) at 1:200 dilution, and secondary antibody (HRP conjugated goat anti-rat IgG, VECTASTAIN ABC (VECTOR Lab Inc. MI, USA)). Substrate reagent 3-amino-9-ethylcarbazole (AEC, Sigma, Mo., USA) will be used to develop the slides, with hematoxylin used for counterstaining.

Western Blotting:

Kidney tissue will be homogenized in 2 mL of RIPA lysis buffer (Santa Cruz, Calif., USA) on ice and centrifuged at 500×g for 30 minutes to remove cell debris. Aliquots of the supernatants will be stored at −80° C. An aliquot comprising 30 μg of protein from each sample will be suspended in loading buffer, boiled for 5 minutes, and subjected to 10% SDS-PAGE gel electrophoresis. Proteins will be transferred to a PVDF membrane, blocked in 5% non-fat dry milk with 1% bovine serum albumin for 1 hour, and incubated with a 1:2000 dilution of anti-HO1/HMOXUHSP32 or a 1:1000 diluted anti-AMPKα-1, monoclonal antibody (R&D Systems, MN, USA). Specific binding will be detected using horseradish peroxidase-conjugated secondary antibodies, which will be developed using Enhanced Chemi Luminescence detection system (Cell Signaling, Mass., USA).

ATP Content Assay:

Immediately following harvesting, kidney tissue will be placed into 10 mL 5% trichloroacetic acid with 10 mM DTT, 2 mM EDTA, homogenized on ice, incubated on ice for 10 min, centrifuged for 10 minutes at 2000×g, and neutralized with pH 7.6 using 10 N KOH. Following centrifugation for 10 minutes at 2000×g, aliquots of the resulting supernatant will be stored at −80° C. ATP will be measured by bioluminescence using a commercially available kit (ATP bioluminescent kit, Sigma, Mo., USA).

Mitochondrial Function:

Renal mitochondria will be isolated and oxygen consumption measured in accordance with the procedures described herein.

It is anticipated that treatment with peptide conjugates, aromatic-cationic peptides, or TBMs (with or without aromatic-cationic peptides) will improve BUN and serum creatinine values in rats after ischemia and reperfusion compared to untreated ischemic controls, and will prevent tubular cell apoptosis after ischemia and reperfusion. It is further anticipated that peptide conjugates, aromatic-cationic peptides, or TBMs (with or without aromatic-cationic peptides) will prevent tubular cell injury after ischemia and reperfusion. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology are effective in reducing the incidence of ARI caused by ischemia-reperfusion. These results will show that TBMs (with or without aromatic-cationic peptides) or peptide conjugates of the present technology or pharmaceutically acceptable salts thereof, such as acetate, tartrate, or trifluoroacetate salts, are useful in methods for protecting a subject from ARI caused by ischemia.

Example 38: Compositions of the Present Technology Protect Against Postrenal ARI Caused by Ureteral Obstruction The effects of the TBMs (with or without aromatic-cationic peptides) or peptide conjugates of the present technology in protecting a subject from ARI caused by ureteral obstruction will be demonstrated in an animal model of unilateral ureteral obstruction (UUO).

Sprague-Dawley rats will undergo unilateral ureteral ligation with a 4-0 silk suture through a midline abdominal incision under sterile conditions. Ureteral obstruction will be carried out by ligating the lower end of the left ureter, just above the ureterovesical junction. Peptide conjugates (1 mg/kg or 3 mg/kg; n=16); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group); or control vehicle (n=16) will be administered intraperitoneally, one day prior to UUO and continuing for 14 days following UUO.

Renal Histology:

Trichrome sections of paraffin embedded specimens will be examined by a board-certified pathologist (SVS, renal pathology specialist), and fibrosis scored on a scale of 0-+++.

Immunohistochemical Analysis:

Immunohistochemical staining for macrophages will be carried out using a monoclonal antibody to ED-1 as previously described. Macrophages will be counted in 10 high-power fields (×400) by two independent investigators in a blinded fashion. Apoptosis will be measured by TUNEL assay as described in Example 37. The presence of fibroblasts will be examined using immunohistochemistry, as described above, using the DAKO #S100-A4 antibody (1:100 dilution). Antigen will be retrieved by incubating cells with Proteinase K for 20 minutes. The remaining immunoperoxidase protocol will be carried out according to routine procedures.

It is expected that S100-A4 staining will be present in spindle-shaped interstitial cells and round, inflammatory cells. Only spindle-shaped cells will be quantified. Staining for 8-OH dG will be done using Proteinase K for antigen retrieval and an antibody provided by the Japan Institute Control of Aging at a dilution of 1:200-1:500.

Polymerase Chain Reaction Analysis:

Renal expression of heme oxygenase-1 (HO-1) will be measured by RT-PCR according to the following: Rat kidneys will be harvested and stored at −80° C. until use. Total RNA will be extracted using the Trizol (R)-Chloroform extraction procedure, and mRNA will be purified using the Oligotex mRNA extraction kit (Qiagen, Valencia, Calif., U.S.A.) according to manufacturer instructions. mRNA concentration and purity will be determined by measuring absorbance at 260 nm. RT-PCR will be performed using Qiagen One-step PCR kit (Qiagen, Valencia, Calif., U.S.A.) and an automated thermal cycler (ThermoHybrid, PX2). Thermal cycling will be carried out as follows: initial activation step for 15 minutes at 95° C. followed by 35 cycles of denaturation for 45 seconds at 94° C., annealing for 30 seconds at 60° C., extension for 60 seconds at 72° C. Amplification products will be separated on a 2% agarose gel electrophoresis, visualized by ethidium bromide staining, and quantified using Image J densitometric analysis software. GAPDH will be used as an internal control.

It is anticipated that the unobstructed contralateral kidneys will show very little, if any, inflammation or fibrosis in tubules, glomeruli or interstitium, and that obstructed kidneys of control animals will show moderate (1-2+) medullary trichrome staining and areas of focal peripelvic 1+ staining. It is anticipated that the cortex will show less fibrosis than the medulla. It is also anticipated that control obstructed kidneys will show moderate inflammation, generally scored as 1+ in the cortex and 2+ in the medulla. Peptide conjugate-, aromatic-cationic peptide-, or TBM- (with or without aromatic-cationic peptides) treated obstructed kidneys are expected to show significantly less trichrome staining, with 0-trace in the cortex and tr-1+ in the medulla. Thus, it is anticipated that treatment with peptide conjugates, aromatic-cationic peptides, or TBMs (with or without aromatic-cationic peptides) will decrease medullary fibrosis in a UUO model. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

Fibroblasts will be visualized by immunoperoxidase for fibroblast-specific protein (FSP-1; aka S100-A4). It is anticipated that increased expression of FSP-1 will be found in obstructed kidneys. It is also anticipated that peptide conjugates (1 mg/kg), aromatic-cationic peptides (an equivalent molar dose of aromatic-cationic peptide based on the concentration of the aromatic-cationic peptide administered in the peptide conjugate treatment group), TBMs (an equivalent molar dose of TBM based on the concentration of the TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will significantly decrease the amount of fibroblast infiltration in obstructed kidneys. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. Thus, it anticipated that peptide conjugates, aromatic-cationic peptides, or TBMs (with or without aromatic-cationic peptides) will decrease fibroblast expression in a UUO model.

It is anticipated that in untreated kidneys, 2 weeks of UUO will result in a significant increase in apoptotic tubular cells as compared to the contralateral kidneys. It is further anticipated that peptide conjugates (1 mg/kg), aromatic-cationic peptides (an equivalent molar dose of aromatic-cationic peptide based on the concentration of the aromatic-cationic peptide administered in the peptide conjugate treatment group), TBMs (an equivalent molar dose of TBM based on the concentration of the TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will significantly decrease tubular apoptosis in obstructed kidneys. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. Thus, it is anticipated that peptide conjugates, aromatic-cationic peptides, or TBMs (with or without aromatic-cationic peptides) will decrease tubular apoptosis in a UUO model.

It is anticipated that there will be a significant increase in macrophage infiltration into obstructed kidneys as compared to contralateral kidneys after 2 weeks of UUO. It is further expected that treatment with 1 mg/kg or 3 mg/kg of peptide conjugates, aromatic-cationic peptides (an equivalent molar dose of aromatic-cationic peptide based on the concentration of the aromatic-cationic peptide administered in the peptide conjugate treatment group), TBMs (an equivalent molar dose of TBM based on the concentration of the TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will significantly decrease macrophage infiltration in obstructed kidneys. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. Thus, it is anticipated that peptide conjugates, aromatic-cationic peptides, or TBMs (with or without aromatic-cationic peptides) will decrease macrophage infiltration in a UUO model.

It is anticipated that obstructed kidneys will be associated with increased proliferation of renal tubular cells, as visualized by immunoperoxidase for PCNA. It is anticipated that peptide conjugates, aromatic-cationic peptides, or TBMs (with or without aromatic-cationic peptides) will cause a significant decrease in renal tubular proliferation in the obstructed kidneys. It is anticipated that tubular cell proliferation will be decreased by TBMs (with or without aromatic-cationic peptides), aromatic-cationic peptides or peptide conjugates at the 1 mg/kg dose, and will be further decreased at the 3 mg/kg dose. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone. Thus, it is anticipated that peptide conjugates, aromatic-cationic peptides, or TBMs (with or without aromatic-cationic peptides) will suppress renal tubular cell proliferation in a UUO model.

It is anticipated that obstructed kidneys will show elevated oxidative damage compared to contralateral kidneys, as measured by increased expression of heme oxygenase-1 (HO-1) and 8-OH dG. It is anticipated that treatment with peptide conjugates, aromatic-cationic peptides, or TBMs (with or without aromatic-cationic peptides) will decrease HO-1 expression in the obstructed kidney. It is anticipated that 8-OH dG staining will be detected in both tubular and interstitial compartments of the obstructed kidney, that the number of 8-OH dG positive cells will be significantly increased in obstructed kidneys compared to contralateral kidneys, and that the number of 8-OH dG positive cells will be significantly reduced by treatment with peptide conjugates, aromatic-cationic peptides, or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. Thus, it is anticipated that peptide conjugates, aromatic-cationic peptides, or TBMs (with or without aromatic-cationic peptides) will decrease oxidative damage in a UUO model.

These results will show that peptide conjugates, aromatic-cationic peptides, or TBMs (with or without aromatic-cationic peptides) are effective in reducing interstitial fibrosis, tubular apoptosis, macrophage infiltration, and tubular proliferation in an animal model of ARI caused by UUO. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. As such, the TBMs (with or without aromatic-cationic peptides) or peptide conjugates of the present technology or pharmaceutically acceptable salts thereof, such as acetate, tartrate, or trifluoroacetate salts, are useful in methods for protecting a subject from ARI caused by ureteral obstruction.

Example 39: Compositions of the Present Technology in the Prevention and Treatment of Contrast-Induced Nephropathy (CIN)

This Example will demonstrate the use of TBMs (with or without aromatic-cationic peptides) or peptide conjugates of the present technology in the prevention and treatment of contrast-induced nephropathy (CIN) in an animal model of ARI.

Animal Model:

A rat model of radiocontrast dye-induced renal failure as described by Agmon, et al., *J. Clin. Invest.* 94:1069-1075 (1994) will be used. As in humans, radiocontrast dyes are generally non-toxic when administered to animals with normal renal function. However, radiocontrast dyes can induce ARI in animals with impaired renal function. In this model, impaired renal function will be induced by the administration of indomethacin (10 mg/kg) and L-NAME (10 mg/kg). Animals will be assigned to one of the following groups:

1. Control (n=8)
2. Indomethcin and L-NAME administered 15 minutes apart, followed by iothalamate (6 mL/kg) (n=7)
3. peptide conjugates (3 mg/kg, i.p.) administered 15 minutes prior to indomethacin/L-NAME/iothalamate administration as described in Group 2; second dose of peptide conjugates (3 mg/kg) administered immediately after drug exposure (n=9).
4. aromatic-cationic peptides (an equivalent molar dose of aromatic-cationic peptide based on the concentration of the aromatic-cationic peptide administered in the peptide conjugate treatment group) administered 15 minutes prior to indomethacin/L-NAME/iothalamate administration as described in Group 2; second dose of aromatic-cationic peptides (an equivalent molar dose of aromatic-cationic peptide based on the concentration of the aromatic-cationic peptide administered in the peptide conjugate treatment group) administered immediately after drug exposure (n=9).
5. TBMs (an equivalent molar dose of TBM based on the concentration of the TBM administered in the peptide conjugate treatment group) administered 15 minutes prior to indomethacin/L-NAME/iothalamate administration as described in Group 2; second dose of TBMs (an equivalent molar dose of TBM based on the concentration of the TBM administered in the peptide conjugate treatment group) administered immediately after drug exposure (n=9).
6. TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) administered 15 minutes prior to indomethacin/L-NAME/iothalamate administration as described in Group 2; second dose of TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) administered immediately after drug exposure (n=9).

Renal Function:

Renal function will be assessed by determining GFR at baseline and 24 hours following dye administration. GFR will be determined by creatinine clearance which will be estimated over a 24 hour interval before and after dye administration. Creatinine clearance will be analyzed by measuring plasma and urinary creatinine levels (Bioassay Systems; DICT-500) and urine volume.

Renal Histology:

Kidneys will be fixed in 10% neutral-buffered formalin and embedded in paraffin wax for sectioning. Three-micron sections will be stained with hematoxylin-eosin (H&E) and periodic acid-Schiff (PAS) and analyzed by light microscopy by a board certified pathologist. Apoptosis will be visualized by TUNEL labeling.

It is anticipated that control animals will not display a significant difference in GFR between the first 24 hour period (approx. 235.0±30.5 µL/min/g) and the second 24 hour period (approx. 223.7±44.0 µL/min/g). It is anticipated that when contrast dye is administered to animals pre-treated with indomethacin and L-NAME, GFR will decline within 24 hours, and that treatment with peptide conjugates, aromatic-cationic peptides, or TBMs (with or without aromatic-cationic peptides) before and after dye administration will reduce the decline in renal function. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is anticipated that PAS staining will illustrate normal morphology in control kidneys, and a loss of renal brush border and vacuolization in contrast dye-exposed kidneys. It is further anticipated that the defects in contrast dye-exposed kidneys will be attenuated by treatment with peptide conjugates, aromatic-cationic peptides, or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. Thus, it is anticipated that peptide conjugates, aromatic-cationic peptides, or TBMs (with or without aromatic-cationic peptides) will prevent renal injury in subjects exposed to radiocontrast dyes.

It is anticipated that control kidneys will show few apoptotic cells, while contrast dye-exposed kidneys will have numerous apoptotic cells. It is further anticipated that treatment with peptide conjugates, aromatic-cationic peptides, or TBMs (with or without aromatic-cationic peptides) will reduce the number of apoptotic cells in contrast dye-exposed kidneys. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology are effective in reducing renal injury induced by radiocontrast dye exposure. As such, the TBMs (with or without aromatic-cationic peptides) or peptide conjugates of the present technology or pharmaceutically acceptable salts thereof, such as acetate, tartrate, or trifluoroacetate salts, are useful in methods for treating or preventing acute renal injury caused by contrast dye exposure.

Example 40: Compositions of the Present Technology in the Prevention and Treatment of CIN in Diabetic Subjects This Example will demonstrate the use of TBMs (with or without aromatic-cationic peptides) or peptide conjugates of the present technology in the prevention and treatment of contrast-induced nephropathy (CIN) in diabetic subjects.

Animal Model:

Impaired renal function caused by diabetes is one of the major predisposing factors for contrast induced nephropathy (McCullough, et al., *J. Am. Coll. Cardio.*, 2008, 51, 1419-1428). In this experiment, a total of 57 Sprague-Dawley rats will be fed a high-fat diet for 6 weeks, followed by the administration of low-dose streptozotocin (30 mg/kg) for a period of 9 weeks. Blood glucose, serum creatinine and Cystatin C will be measured. Animals meeting the following criteria (n=20) will advance to CIN studies: Scr>250 µM, Cystatin C >750 ng/mL and blood glucose >=16.7 µM.

Animals will be administered iohexol and a saline control vehicle; iohexol and peptide conjugates; iohexol and aromatic-cationic peptides; iohexol and TBMs; or iohexol and TBMs+aromatic-cationic peptides.

On day 1, serum samples will be collected and total urine protein will be measured using a Bradford assay. On days 2 and 3, ~3 mg/kg peptide conjugates, aromatic-cationic peptides (an equivalent molar dose of aromatic-cationic peptide based on the concentration of the aromatic-cationic peptide administered in the peptide conjugate treatment group), TBMs (an equivalent molar dose of TBM based on the concentration of the TBM administered in the peptide conjugate treatment group), TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group), or control vehicle will be administered subcutaneously (s.c.) 30 minutes prior to contrast dye injection (6 mL/kg i.v. tail vein). Peptide conjugate, aromatic-cationic peptide, TBM with or without aromatic-cationic peptide or vehicle administration will be repeated at 2 and 24 hours post-dye administration. Serum and urine samples will be collected at days 4 and 5. Animals will be euthanized on day 5, and the vital organs harvested. Samples will be analyzed by Student's t-test and differences will be considered significant at $p<0.05$.

Renal Function:

Renal function will be assessed by determining serum and urinary creatinine at baseline, 48 hours and 72 hours following dye administration. The creatinine clearance will be calculated based on the serum and urinary creatinine and urinary volume. Urinary protein concentration will be determined by Bradford Protein Assay kit (Sigma, St. Louis, Mo., U.S.A.), and Cystatin C will be measured using a Westang Rat Cystatin C kit (Shanghai, P.R.C.).

It is anticipated that control animals will display elevated levels of serum Cystatin C (an AKI biomarker) and reduced creatinine clearance following contrast dye exposure, and that treatment with peptide conjugates, aromatic-cationic peptides, or TBMs with or without aromatic-cationic peptides will attenuate these effects. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

Thus, it is anticipated that TBMs (with or without aromatic-cationic peptides) or peptide conjugates of the present technology reduce renal dysfunction caused by radiocontrast dye in a diabetic animal model. As such, the TBMs (with or without aromatic-cationic peptides) or peptide conjugates of the present technology, or pharmaceutically acceptable salts thereof, such as acetate, tartrate, or trifluoroacetate salts, are useful in methods for protecting a diabetic subject from acute renal injury caused by contrast agents.

Example 41: Compositions of the Present Technology in the Prevention and Treatment of CIN in a Glycerol-Induced Rhabdomyolysis Animal Model This Example demonstrates the use of TBMs (with or without aromatic-cationic peptides) or peptide conjugates of the present technology in the prevention and treatment of CIN in a glycerol-induced rhabdomyolysis animal model.

Animal Model:

This Example will utilize animals subjected to glycerol-induced rhabdomyolysis, as previously described. Parvez, et al., *Invest. Radiol.*, 24:698-702 (1989); Duan, et al., *Acta Radiologica*, 41:503-507(2000). Sprague-Dawley rats with body weight of 300-400 g will be dehydrated for 24 hours followed by intramuscular (i.m.) injection of 25% glycerol solution (v/v) at the dose of 10 mL/kg. Twenty-four hours later, the animals will be administered a contrast dye with peptide conjugates, aromatic-cationic peptides, TBMs with or without aromatic-cationic peptides, or control vehicle according to the following: 1) 25% glycerin+Saline+PBS (n=6), 2) 25% glycerin+diatrizoate+PBS (n=7), 3) 25% glycerin+diatrizoate+peptide conjugates (n=7), 4) 25% glycerin+diatrizoate+aromatic-cationic peptides (n=7), 5) 25% glycerin+diatrizoate+TBMs, and 6) 25% glycerin+diatrizoate+TBMs+aromatic-cationic peptides. The effects of TBMs (with or without aromatic-cationic peptides) or peptide conjugates on ARI will be demonstrated by comparing the renal functions in animals from each group. Samples will be analyzed by Student's t-test and differences will be considered significant at $p<0.05$.

Renal Function:

Renal function will be assessed by determining serum and urinary creatinine at baseline, 24 hours after dehydration, and 48 hours following contrast dye administration. Creatinine clearance will be calculated based on serum and urinary creatinine levels and urinary volume. Urinary albumin concentration will be determined using a competition ELISA assay.

It is anticipated that creatinine clearance will be reduced when contrast dye is administered to subjects having glycerol-induced rhabdomyolysis. It is further anticipated that treatment with peptide conjugates, aromatic-cationic peptides, or TBMs (with or without aromatic-cationic peptides) will attenuate or prevent reduced creatinine clearance. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

Albuminuria is an indicator of increased permeability of the glomerular membrane, and can result from exposure to contrast dye. It is anticipated that albuminuria will increase when contrast dye is administered to subjects having glycerol-induced rhabdomyolysis. It is further anticipated that treatment with peptide conjugates, aromatic-cationic peptides, or TBMs (with or without aromatic-cationic peptides) will attenuate or prevent albuminuria in such subjects, suggesting that they have a protective effect on the permeability of the glomerular basement membrane in this model. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is anticipated that PAS staining will illustrate a loss of proximal tubule brush border following administration of contrast dye to subjects having glycerol-induced rhabdomyolysis, as well as glomerular swelling and tubular protein cast deposition. It is further anticipated that treatment with peptide conjugates, aromatic-cationic peptides, or TBMs (with or without aromatic-cationic peptides) will attenuate or prevent these effects in such subjects. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for the prevention and treatment of CIN in subjects having rhabdomyolysis.

Example 42: Compositions of the Present Technology in the Prevention and Treatment of Nephrotoxicity ($CCl_4$-induced Chronic Kidney Injury)

This Example demonstrates the use of TBMs (with or without aromatic-cationic peptides) or peptide conjugates of the present technology for the prevention and treatment of carbon tetrachloride ($CCl_4$)-induced chronic nephrotoxicity.

Animal Model:

Generation of reactive radicals has been implicated in carbon tetrachloride-induced nephrotoxicity, in which is characterized by lipid peroxidation and accumulation of dysfunctional proteins. Ozturk, et al., *Urology*, 62:353-356 (2003). This Example describes the effect of administration of TBMs (with or without aromatic-cationic peptides) or peptide conjugates for the prevention of carbon tetrachloride ($CCl_4$)-induced chronic nephrotoxicity.

Study Design and Experimental Protocol:

Sprague-Dawley rats with body weight of 250 g will be fed a 0.35 g/L phenobarbital solution (Luminal water) for two weeks, and assigned to one of the following groups: 1) luminal water+olive oil, intragastrointestinal (i.g.), 1 mL/kg, twice per week; PBS subcutaneously (s.c.) 5 days per week; 2) luminal water+50% $CCl_4$ .i.g., 2 mL/kg, twice per week; and PBS s.c 5 days per week; 3) luminal water+50% $CCl_4$ .i.g., 2 mL/kg, twice per week; peptide conjugates (10 mg/kg) s.c. 5 days per week; 4) luminal water+50% $CCl_4$ .i.g., 2 mL/kg, twice per week; aromatic-cationic peptides (an equivalent molar dose of aromatic-cationic peptide based on the concentration of the aromatic-cationic peptide administered in the peptide conjugate treatment group) s.c. 5 days per week; 5) luminal water+50% $CCl_4$ .i.g., 2 mL/kg, twice per week; TBMs (an equivalent molar dose of TBM based on the concentration of the TBM administered in the peptide conjugate treatment group) s.c. 5 days per week; 6) luminal water+50% $CCl_4$ .i.g., 2 mL/kg, twice per week; TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) s.c. 5 days per week. Trials will run for a total of 7 weeks.

At the end of fifth week, four subjects from each group will be sacrificed for liver histopathological sectioning and fibrosis examination. At the end of seventh week, all remaining subjects will be sacrificed, and kidney and liver tissues harvested for histopathological examination.

Renal Histology:

Kidneys will be fixed in 10% neutral-buffered formalin and embedded in paraffin wax for sectioning. Three-micron sections will be stained with hematoxylin-eosin (H&E) and analyzed by light microscopy by a certified pathologist.

It is anticipated that peptide conjugates, aromatic-cationic peptides, or TBMs (with or without aromatic-cationic peptides) will protect renal tubules from $CCl_4$ nephrotoxicity. H&E staining is anticipated to illustrate that $CCl_4$ exposure results in tubular epithelial cell degeneration and necrosis. It is also anticipated that animals treated with peptide conjugates, aromatic-cationic peptides, or TBMs (with or without aromatic-cationic peptides) will show no significant histopathological changes compared to untreated control animals of Group (1). It is anticipated that administration of peptide conjugates of the present technology will have synergistic effects with respect to preventing or treating $CCl_4$-induced nephrotoxicity compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

Thus, TBMs (with or without aromatic-cationic peptides) or peptide conjugates of the present technology are useful in methods for preventing or treating $CCl_4$-induced nephrotoxicity.

Example 43: Compositions of the Present Technology in the Prevention of Cisplatin-Induced ARI This Example will demonstrate the use of TBMs (with or without aromatic-cationic peptides) or peptide conjugates of the present technology, or pharmaceutically acceptable salts thereof, such as acetate, tartrate, or trifluoroacetate salts, in the prevention of cisplatin-induced ARI.

Experimental Protocol:

Sprague-Dawley rats (350-400 g) will be given a single dose of cisplatin (7 mg/kg) intraperitoneally (i.p.) on Day 1. Subjects will receive peptide conjugates (3 mg/kg) (n=8), aromatic-cationic peptides (an equivalent molar dose of aromatic-cationic peptide based on the concentration of the aromatic-cationic peptide administered in the peptide conjugate treatment group) (n=8), TBMs (an equivalent molar dose of TBM based on the concentration of the TBM administered in the peptide conjugate treatment group) (n=8), TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) (n=8) or saline vehicle (n=8) subcutaneously just prior to cisplatin administration, and once daily for 3 additional days. Subjects will be placed in metabolic cages for the final 24 hours of the trial for urine collection. At the end of the trial, blood samples will be withdrawn from tail veins and the kidneys harvested.

Renal Function:

Renal function will be assessed by measuring blood urea nitrogen (BUN), serum creatinine, urine creatinine, and urine protein. GFR will be estimated from creatinine clearance, which will be determined from serum and urinary creatinine, and urinary volume.

Renal Histology:

Kidneys will be fixed in 10% neutral-buffered formalin and embedded in paraffin wax for sectioning. Three-micron sections will be stained with periodic acid-Schiff (PAS) and analyzed by light microscopy.

It is anticipated that vehicle control subjects will display a significant reduction in body weight after cisplatin administration, as compared to body weights prior to cisplatin administration, and that treatment with peptide conjugates, aromatic-cationic peptides, or TBMs (with or without aromatic-cationic peptides) will attenuate or prevent this effect. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is further anticipated that serum creatinine will substantially increase in vehicle control subjects, and that treatment with peptide conjugates, aromatic-cationic peptides, or TBMs (with or without aromatic-cationic peptides) will attenuate or prevent this effect. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is anticipated that vehicle control subjects will display a significant increase in BUN after cisplatin treatment, and that treatment with peptide conjugates, aromatic-cationic peptides, or TBMs (with or without aromatic-cationic peptides) will attenuate or prevent this effect. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. These results will show that TBMs (with or without aromatic-cationic peptides) or peptide conjugates protect kidneys from cisplatin-induced nephropathy.

As such, the TBMs (with or without aromatic-cationic peptides) or peptide conjugates of the present technology or pharmaceutically acceptable salts thereof, such as acetate, tartrate, or trifluoroacetate salts, are useful in methods for protecting a subject from acute renal injury caused by cisplatin or similar nephrotoxic agents.

Example 44: Compositions of the Present Technology in the Prevention and Treatment of Acute Liver Failure (ALF)

This Example demonstrates the use of TBMs (with or without aromatic-cationic peptides) or peptide conjugates of the present technology in the prevention and treatment of acute liver failure (ALF).

Suitable animal models of ALF utilize surgical procedures, toxic liver injury, or a combination thereof. See Belanger & Butterworth, Metabolic Brain Disease, 20:409-423 (2005). Peptide conjugates, aromatic-cationic peptides, TBMs with or without aromatic-cationic peptides or control vehicle will be administered prior to or simultaneously with a toxic or surgical insult. Hepatic function will be assessed by measuring serum hepatic enzymes (transaminases, alkaline phosphatase), serum bilirubin, serum ammonia, serum glucose, serum lactate, or serum creatinine. Efficacy of the TBMs (with or without aromatic-cationic peptides) or peptide conjugates of the present technology in preventing ALF will be indicated by a reduction in the occurrence or severity of the ALF as indicated by the above markers, as compared to control subjects.

It is anticipated that toxic or surgical liver insult will cause reduced liver function, and that treatment with peptide conjugates, aromatic-cationic peptides, or TBMs (with or without aromatic-cationic peptides) will attenuate or prevent these effects. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology or pharmaceutically acceptable salts thereof, such as acetate, tartrate, or trifluoroacetate salts, are useful in methods for preventing or treating ALF.

Example 45: Compositions of the Present Technology in the Prevention or Treatment of Hypermetabolism After Burn Injury Hypermetabolism (HYPM) is a hallmark feature of metabolic disturbance after burn injury. Increased energy expenditure (EE) is associated with accelerated substrate oxidation and shifts of fuel utilization, with an increased contribution of lipid oxidation to total energy production. Mitochondria dysfunction is closely related to the development of HYPM. This Example will demonstrate the use of TBMs (with or without aromatic-cationic peptides) or peptide conjugates of the present technology in the prevention and treatment of HYPM.

Sprague Dawley rats will be randomized into the following groups; sham-burn (SB), burn with saline treatment (B), burn with peptide conjugate-treatment (BP), burn with aromatic-cationic peptides (BP2), burn with TBMs (BP3), burn with TBMs+aromatic-cationic peptides (BP4). Catheters will be surgically placed into jugular vein and carotid artery. Band BP, BP2, BP3 and BP4 animals will receive 30% total body surface area full thickness burns by immersing the dorsal part into 100° C. water for 12 seconds with immediate fluid resuscitation. BP, BP2, BP3 and BP4 animals will receive IV injection of peptide conjugates (2 mg/kg every 12 hours), aromatic-cationic peptides (an equivalent molar dose of aromatic-cationic peptide based on the concentration of the aromatic-cationic peptide administered in the peptide conjugate treatment group every 12 hours), TBMs (an equivalent molar dose of TBM based on the concentration of the TBM administered in the peptide conjugate treatment group every 12 hours), and TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group every 12 hours) respectively for three days. The EE of the animals will be monitored for 12 hours in a TSE Indirect calorimetry System (TSE Co., Germany).

It is anticipated that animals in the B group will show a significant increase in EE compared to animals in the SB group, and that treatment with peptide conjugates, aromatic-cationic peptides, or TBMs (with or without aromatic-cationic peptides) will attenuate or prevent this effect. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. These results will show that treatment with peptide conjugates, aromatic-cationic peptides, or TBMs (with or without aromatic-cationic peptides) prevents or attenuates burn-induced HYPM.

As such, TBMs (with or without aromatic-cationic peptides) or peptide conjugates of the present technology, or pharmaceutically acceptable salts thereof, such as acetate, tartrate, or trifluoroacetate salts, are useful in methods for treating burn injuries and secondary complications in subjects in need thereof.

Example 46: Compositions of the Present Technology Protect Against Burn-Induced Liver Apoptosis Systemic inflammatory response syndrome (SIRS) and multiple organ failure (MOF) are leading causes of morbidity and mortality in severe burn patients. This Example demonstrates the use of TBMs (with or without aromatic-cationic peptides) or peptide conjugates in preventing these effects.

Six-to-eight week old male C57BL mice will be subjected to 30% total body surface (TBSA) burn injury and subsequently injected daily with saline vehicle; peptide conjugates (5 mg/kg body weight); aromatic-cationic peptides (an equivalent molar dose of aromatic-cationic peptide based on the concentration of the aromatic-cationic peptide administered in the peptide conjugate treatment group); TBMs (an equivalent molar dose of TBM based on the concentration of the TBM administered in the peptide conjugate treatment group); or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group). A weight- and time-matched sham-burn group exposed to lukewarm (~37° C.) will serve as controls. Liver tissues will be collected 1, 3, and 7 days after burn injury treatment and analyzed for apoptosis (TUNEL), activated caspase levels (Western blot), and caspase activity (enzymatic assay).

It is anticipated that burn injury will increase the rate of apoptosis in the liver of burned subjects on all days examined, with the most dramatic increase predicted to occur on day 7 post-burn injury. It is further anticipated that treatment with peptide conjugates, aromatic-cationic peptides, or TBMs (with or without aromatic-cationic peptides) will attenuate or prevent this effect. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is anticipated that Western blot analysis will reveal a progressive increase in activated caspase-3 following burn injury, as compared to sham control group. It is further anticipated that treatment with peptide conjugates, aromatic-cationic peptides, or TBMs (with or without aromatic-cationic peptides) will attenuate or suppress caspase-3 activation on days 3 and 7 post-burn, resulting in activated caspase-3 levels similar to those of sham control animals. It is anticipated that the caspase activity will increase significantly on post-burn day 7, and the treatment with peptide conjugates, aromatic-cationic peptides, or TBMs (with or without aromatic-cationic peptides) will reduce caspase activity to a level not statistically different from that of sham control group. It is further anticipated that there will be a decrease in protein oxidation following burn injury in mice treated with the peptide conjugates, aromatic-cationic peptides, or TBMs (with or without aromatic-cationic peptides), as compared to burn control subjects. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that TBMs (with or without aromatic-cationic peptides) or peptide conjugates prevent burn-induced activation of apoptotic signaling pathways and subsequent liver apoptosis. As such, TBMs (with or without aromatic-cationic peptides) or peptide conjugates of the present technology or pharmaceutically acceptable salts thereof, such as acetate, tartrate, or trifluoroacetate salts, are useful in methods for preventing or treating systemic organ damage, such as liver damage, secondary to a burn.

Example 47: Compositions of the Present Technology in the Prevention of Wound Contraction After Burn Injury This Example will demonstrate the use of TBMs (with or without aromatic-cationic peptides) or peptide conjugates of the present technology in the prevention of wound contraction.

Burn wounds are typically uneven in depth and severity, with significant areas around coagulated tissue where the injury may be reversible, and inflammatory tissue damage could be prevented. Wound contraction is a process which diminishes the size of a full-thickness open wound, and especially of a full-thickness burn. Tensions developed during contraction and the formation of subcutaneous fibrous tissue can result in tissue deformity, fixed flexure, or fixed extension of a joint (where the wound involves an area over the joint). Such complications are especially relevant in burn healing. No wound contraction will occur when there is no injury to the tissue; and maximum contraction will occur when the burn is full thickness with no viable tissue remaining in the wound.

Sprague-Dawley rats (male, 300-350 g) will be pretreated with (1 mg) peptide conjugates administered i.p. (approx. 3 mg/kg) 1 hour prior to burn (65° C. water, 25 seconds, lower back), followed by the topical application of peptide conjugates to the wound (1 mg), and 1 mg peptide conjugates administered i.p. once every 12 hours for 72 hours. Wounds will be observed for up to 3 weeks post-burn. A similar treatment regimen is followed for the groups treated with aromatic-cationic peptides (an equivalent molar dose of aromatic-cationic peptide based on the concentration of the aromatic-cationic peptide administered in the peptide conjugate treatment group), TBMs (an equivalent molar dose of TBM based on the concentration of the TBM administered in the peptide conjugate treatment group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group).

It is anticipated that the wounds will take on the appearance of a hard scab, which will be quantified as a measure of wound size. It is anticipated that a slower rate of wound contraction will be observed in the group treated with peptide conjugates, aromatic-cationic peptides, or TBMs (with or without aromatic-cationic peptides) as compared to burn control subjects, such that the burn injury will be less severe in these subjects compared to controls. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology or pharmaceutically acceptable salts thereof, such as acetate, tartrate, or trifluoroacetate salts, are useful in methods for treating wounds associated with a burn injury.

Example 48: Compositions of the Present Technology Alleviate Skeletal Muscle Dysfunction after Burn Injury This Example will demonstrate the use of TBMs (with or without aromatic-cationic peptides) or peptide conjugates in the prevention and treatment of post-burn complications.

It is thought that a major cause of skeletal muscle mitochondrial dysfunction in burns is the result of defects in oxidative phosphorylation (OXPHOS) via stimulation of mitochondrial production of reactive oxygen species (ROS) and the oxidative damage to the mitochondrial DNA (mtDNA). This hypothesis is supported by data indicating that the ATP synthesis rate significantly decreases and ROS production increases in skeletal muscle in response to burn injury. This progression underlies the burn pathophysiology, which includes skeletal muscle wasting and cachexia.

A clinically relevant murine burn injury model will be used to demonstrate the effects of TBMs (with or without aromatic-cationic peptides) or peptide conjugates on burn-induced mitochondrial dysfunction and endoplasmic reticulum (ER) stress. The redox state of the gastrocnemius muscle immediately below a local cutaneous burn (90° C. for 3 sec) will be evaluated by nitroxide EPR. It is anticipated that the redox state in the muscle will be compromised by burn injury, with the most dramatic effect at 6 hours post-burn.

Peptide conjugates (3 mg/kg), aromatic-cationic peptides (an equivalent molar dose of aromatic-cationic peptide based on the concentration of the aromatic-cationic peptide administered in the peptide conjugate treatment group), TBMs (an equivalent molar dose of TBM based on the concentration of the TBM administered in the peptide conjugate treatment group) or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be administered i.p. 30 minutes before burn, and immediately after burn. It is anticipated that at the 6-hour time point, treatment with peptide conjugates, aromatic-cationic peptides, or TBMs (with or without aromatic-cationic peptides) will significantly increase the rate of nitroxide reduction, demonstrating that a decrease in oxidative stress in muscle beneath the burn. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology, or pharmaceutically acceptable salts thereof, such as acetate, tartrate, or trifluoroacetate salts, are useful in methods of preventing or treating secondary complications of a burn injury, such as skeletal muscle dysfunction.

Example 49: Compositions of the Present Technology Attenuate the Progression of Tissue Damage Following a Burn This Example will demonstrate the use of TBMs (with or without aromatic-cationic peptides) or peptide conjugates in the prevention of tissue damage progression following burn injuries. The results will show that TBMs (with or without aromatic-cationic peptides) or peptide conjugates improve wound healing (i.e., accelerates healing or leads to less scarring) in a partial thickness burn wound.

Sprague Dawley rats will be randomized into the following groups; sham-burn (SB), burn with saline treatment (B), burn with peptide conjugate-treatment (BP), burn with aromatic-cationic peptides (BP2), burn with TBMs (BP3), and burn with TBMs+aromatic-cationic peptides (BP4). Band BP, BP2, BP3 and BP4 animals will receive a 30% total body surface area full thickness burns by immersing the dorsal body into 100° C. water for 12 seconds with immediate fluid resuscitation. BP, BP2, BP3 and BP4 animals will receive IV injection of peptide conjugates (2 mg/kg every 12 hours), aromatic-cationic peptides (an equivalent molar dose of aromatic-cationic peptide based on the concentration of the aromatic-cationic peptide administered in the peptide conjugate treatment group every 12 hours), TBMs (an equivalent molar dose of TBM based on the concentration of the TBM administered in the peptide conjugate treatment group every 12 hours) and TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group every 12 hours) respectively for three days. Wound re-epithelialization, contraction, and depth will be assessed via gross morphology and histologically over a period of 21 days. For this purpose, immediately after wounding, dark marks will be applied onto the skin of the animals at the wound edges as well as 1 cm away from the edges. Wounds will be digitally photographed over 21 days, and image analysis software will be used to measure the area of the wound (defined as the scab). Distances of the marks from the wound site will be used to assess wound contraction.

At selected time points, wounds will be harvested from the animals. Because the progression from a second to a third degree wound is expected to occur primarily in the first 48 hours post-burn, samples will be harvested at 12, 24, and 48 hours. To monitor the long-term impact on the wound healing process, samples will be harvested at 2, 7, 14, and 21 days. The tissues will be fixed and embedded, and sections across the center of the wounds collected for H&E and trichrome staining.

Apoptosis of hair follicles of the skin will be measured using TUNEL labeling and activated caspase-3 immunostaining using skin samples obtained between 0 and 48 hours post-burn. Quantification of TUNEL and caspase-3 staining will be done on digitally acquired images at high power. The number of positive cells per high power field will be determined, and compared among the groups.

Luminescence mapping will be performed using Doppler imaging to assess wound blood flow. Two hours post-burn, the dorsum of the animal will be imaged on a scanning laser Doppler apparatus to quantify the superficial blood flow distribution in the skin within and outside of the burn area. For luminescence mapping, 100 male Sprague-Dawley rats will be used. Eighty animals will receive a large (covering 30% of the total body surface area) full-thickness burn injury on the dorsum. This is a well-established model. They will be divided into several groups: one treated with peptide conjugates, one treated with aromatic-cationic peptides, one treated with TBMs, one treated with TBMs+aromatic-cationic peptides and the other with placebo (saline) treatment. Each group will be further divided into 4 subgroups consisting of 4 time points where animals will be sacrificed for further analysis. Prior to sacrifice, luminescence imaging will be carried out, followed by euthanasia and skin tissue sampling for subsequent histology. Another 20 animals will receive a "sham burn" and will be treated with peptide conjugates, aromatic-cationic peptides, TBMs with or without aromatic-cationic peptides or saline. Euthanasia will be performed on two animals in each of the corresponding 4 time points. On average, each animal will be housed for 10 days (including the pre-burn days in the animal farm) in separate cages.

It is predicted that administration of peptide conjugates, aromatic-cationic peptides, or TBMs (with or without aromatic-cationic peptides) will accelerate wound healing and attenuate the progression of burn injuries in this model. It is further predicted that treatment with peptide conjugates, aromatic-cationic peptides, or TBMs (with or without aromatic-cationic peptides) will reduce burn-induced apoptosis and blood flow. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology, or pharmaceutically acceptable salts thereof, such as acetate, tartrate, or trifluoroacetate salts, are useful in methods for attenuating the progression of tissue damage following a burn injury, as in the progression of a partial thickness burn injury to a full-thickness burn injury.

Example 50: Compositions of the Present Technology Protect Against Sunburn and Attenuates Progression of Tissue Damage Following Sunburn This Example will demonstrate the use of TBMs (with or without aromatic-cationic peptides) or peptide conjugates to protect against sunburn and attenuate the progression of tissue damage following sunburn in a murine model.

Hairless mice, with skin characteristics similar to humans, will be exposed to excessive UV radiation over the course of a week. Subjects will be randomly divided into the following groups: 1) burn; saline vehicle; 2) burn, peptide conjugates (4 mg/kg per day, low-dose group); 3) burn, peptide conjugates (40 mg/kg per day, high-dose group), 4) burn, aromatic-cationic peptides (an equivalent molar dose of aromatic-cationic peptide based on the concentration of the aromatic-cationic peptide administered in the peptide conjugate low-dose group); 5) burn, aromatic-cationic peptides (an equivalent molar dose of aromatic-cationic peptide based on the concentration of the aromatic-cationic peptide administered in the peptide conjugate high-dose group); 6) burn, TBMs (an equivalent molar dose of TBM based on the concentration of the TBM administered in the peptide conjugate high-dose group); 7) burn, TBMs (an equivalent molar dose of TBM based on the concentration of the TBM administered in the peptide conjugate low-dose group); 8) burn, TBMs in combination with aromatic-cationic peptides (e.g., an equivalent molar dose of TBM based on the concentration of TBM administered in the peptide conjugate high-dose group and an equivalent molar dose of aromatic-cationic peptide based on the concentration of aromatic-cationic peptide administered in the peptide conjugate high-dose group); 9) burn, TBMs in combination with aromatic-cationic peptides (e.g., an equivalent molar dose of TBM based on the concentration of TBM administered in the peptide conjugate low-dose group and an equivalent molar dose of aromatic-cationic peptide based on the concentration of aromatic-cationic peptide administered in the peptide conjugate low-dose group). Peptide conjugates, aromatic-cationic peptides, or TBMs with or without aromatic-cationic peptides will be administered intravenously twice per day for seven days. Parameters measured will include wound contraction, re-epithelialization distance, cellularity, and collagen organization. Ki67 proliferation antigen will be assessed, as well as TUNEL and caspase-3 activation. Blood flow will be measured by luminescence mapping.

It is predicted that administration of peptide conjugates, aromatic-cationic peptides, or TBMs (with or without aromatic-cationic peptides) will accelerate wound healing and attenuate the progression of sunburn injuries in this model. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology, or pharmaceutically acceptable salts thereof, such as acetate, tartrate, or trifluoroacetate salts, are useful in methods for protecting against sunburn and attenuating the progression of tissue damage following sunburn.

Example 51: Compositions of the Present Technology Attenuate Burn-Induced Hypermetabolism by Down-Regulating UCP-1 Expression in Brown Adipose Tissue Hypermetabolism is the hallmark feature of metabolic disturbance after burn injury. Mitochondrial dysfunction occurs after burns, and is closely related to the development of hypermetabolism (and altered substrate oxidation). Uncoupling protein 1 (UCP-1) is expressed in the brown adipose tissue, and plays a key role in producing heat. This Example will show that the TBMs (with or without aromatic-cationic peptides) or peptide conjugates of the present technology down-regulate UCP-1 expression following burn injury.

Methods.

Sprague Dawley rats will be randomly divided into the following groups; sham (S), sham with saline vehicle (SSal), sham with peptide conjugate-treatment (SC), sham with aromatic-cationic peptides (SC2), sham with TBMs (SC3), sham with TBMs+aromatic-cationic peptides (SC4), burn with saline vehicle (BSal), burn with peptide conjugate-treatment (BC), burn with aromatic-cationic peptides (BC2), burn with TBMs (BC3) and burn with TBMs+aromatic-cationic peptides (BC4). The dorsal aspect of burn subjects will be immersed into 100° C. water for 12 seconds to produce third degree 30% TBSA burns under general anesthesia. Sham burn will be produced by immersion in lukewarm water. Subjects will receive 40 mL/kg intraperitoneal saline injection for the resuscitation following the injury. A venous catheter will be placed surgically into the right jugular vein subsequent to sham or burn injury. Peptide conjugates (2 mg/kg), aromatic-cationic peptides (an equivalent molar dose of aromatic-cationic peptide based on the concentration of the aromatic-cationic peptide administered in the peptide conjugate group), TBMs (an equivalent molar dose of TBM based on the concentration of the TBM administered in the peptide conjugate group), TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) or saline vehicle will be infused for 7 days (4 mg/kg/day) using osmotic pumps (Durect, Calif.). Indirect calorimetry will be performed for 24 hours at 6 days after burn injury in a TSE Indirect calorimetry System (TSE Co., Germany), and VO2, VCO2 and energy expenditure will be recorded every six minutes. Interscapullar brown adipose tissue will be collected after the indirect calorimetry, and UCP-1 expression in the brown adipose tissue will be evaluated by Western blot.

It is anticipated that VO2, VCO2, and energy expenditure will be significantly increased in the BSal group, as compared to the SSal group, and that treatment with peptide conjugates, aromatic-cationic peptides, or TBMs (with or without aromatic-cationic peptides) will significantly attenuate this effect. It is further anticipated that UCP-1 expression in the BSal group will be higher than in the SSal group, with UCP-1 levels in the BC, BC2, BC3 and BC4 groups lower than in the BSal group. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that TBMs (with or without aromatic-cationic peptides) or peptide conjugates attenuate burn-induced hypermetabolism by the down regulation of UCP-1 expression in brown adipose tissue. As such, the TBMs (with or without aromatic-cationic peptides) or peptide conjugates of the present technology, or pharmaceutically acceptable salts thereof, such as acetate, tartrate, or trifluoroacetate salts, are useful in methods for treating a subject suffering from a burn injury.

Example 52: Compositions of the Present Technology Induce ATP Synthesis Following a Burn Injury This Example will demonstrate that TBMs (with or without aromatic-cationic peptides) or peptide conjugates increase the rate of ATP synthesis following a burn injury using $^{31}$P NMR and electron paramagnetic resonance (EPR) in vivo.

It is thought that a major cause of skeletal muscle mitochondrial dysfunction in burns is the result of defects in oxidative phosphorylation (OXPHOS) via stimulation of mitochondrial production of reactive oxygen species (ROS) and the oxidative damage to the mitochondrial DNA (mtDNA). This hypothesis is supported by data indicating that the ATP synthesis rate significantly decreases and ROS production increases in skeletal muscle in response to burn injury. This progression underlies the burn pathophysiology, which includes skeletal muscle wasting and cachexia.

Material and Methods.

Male 6-week-old CD1 mice weighing 20-25 g will be anesthetized by intraperitoneal (i.p.) injection of 40 mg/kg pentobarbital sodium. The left hind limb of all mice in all groups will be shaved. Burn subjects will be subjected to a nonlethal scald injury of 3-5% total body surface area (TBSA) by immersing the left hind limb in 90° C. water for 3 seconds.

NMR spectroscopy is described in detail in Padfield, et al., Proc. Natl. Acad. Sci., 102:5368-5373 (2005). Briefly, mice will be randomized into 1) burn+control vehicle, 2) burn+peptide conjugate, 3) non-burn+control vehicle, 4) non-burn+peptide conjugate, 5) burn+aromatic-cationic peptides, 6) non-burn+aromatic-cationic peptides, 7) burn+ TBM, 8) non-burn+TBM, 9) burn+TBM+aromatic-cationic peptides, and 10) non-burn+TBM+aromatic-cationic peptides groups. The peptide conjugates (3 mg/kg), aromatic-cationic peptides (an equivalent molar dose of aromatic-cationic peptide based on the concentration of the aromatic-cationic peptide administered in the peptide conjugate group), TBMs (an equivalent molar dose of TBM based on the concentration of the TBM administered in the peptide conjugate group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be injected intraperitoneally 30 minutes prior to the burn and immediately after the burn. NMR experiments will be performed in a horizontal bore magnet (proton frequency 400 MHz, 21 cm diameter, Magnex Scientific) using a Bruker Avanee console. A 90° pulse will be optimized for detection of phosphorus spectra (repetition time 2 s, 400 averages, 4K data points). Saturation 90°-selective pulse trains (duration 36.534 ms, bandwidth 75 Hz) followed by crushing gradients will be used to saturate the $\gamma$-ATP peak. The same saturation pulse train will be also applied downfield of the inorganic phosphate (Pi) resonance, symmetrically to the $\gamma$-ATP resonance. T1 relaxation times of Pi and phosphocreatine (PCr) will be measured using an inversion recovery pulse sequence in the presence of $\gamma$-ATP saturation. An adiabatic pulse (400 scans, sweep with 10 KHz, 4K data) will be used to invert Pi and PCr, with an inversion time between 152 ms and 7651 ms.

EPR spectroscopy is described in detail in Khan, et al., *Mol. Med. Rep.* 1:813-819 (2008). Briefly, mice will be randomized into 1) burn+control vehicle, 2) burn+peptide conjugate, 3) non-burn+control vehicle, 4) non-burn+peptide conjugate, 5) burn+aromatic-cationic peptide, 6) non-burn+aromatic-cationic peptides, 7) burn+TBM, 8) non-burn+TBM, 9) burn+TBM+aromatic-cationic peptides, and 10) non-burn+TBM+aromatic-cationic peptides groups. The peptide conjugates (3 mg/kg), aromatic-cationic peptides (an equivalent molar dose of aromatic-cationic peptide based on the concentration of the aromatic-cationic peptide administered in the peptide conjugate group), TBMs (an equivalent molar dose of TBM based on the concentration of the TBM administered in the peptide conjugate group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be injected intraperitoneally at 0, 3, 6, 24, and 48 hours post-burn. EPR measurements will be carried out with an I.2-GHz EPR spectrometer equipped with a microwave bridge and external loop resonator designed for in vivo experiments. The optimal spectrometer parameters will be: incident microwave power, 10 mW; magnetic field center, 400 gauss; modulation frequency, 27 kHz. The decay kinetics of intravenously-injected nitroxide (150 mg/kg) will be measured at the various time points, to assess the mitochondrial redox status of the muscle.

It is anticipated that control subjects will display a significantly elevated redox status after a burn injury, and a significant reduction of the ATP synthesis rate. It is further anticipated that treatment with peptide conjugates, aromatic-cationic peptides, or TBMs (with or without aromatic-cationic peptides) will induce a significant increase in the ATP synthesis rate in burned mice, as compared to burn controls. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that treatment with peptide conjugates, aromatic-cationic peptides, or TBMs (with or without aromatic-cationic peptides) induces ATP synthesis rate possibly via a recovery of the mitochondrial redox status or via the peroxisome proliferator activated receptor-gamma coactivator-1$\beta$ (PGC-1$\beta$). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. Thus, it is predicted that the mitochondrial dysfunction caused by burn injury is attenuated by administration of the peptide conjugates, aromatic-cationic peptides, or TBMs (with or without aromatic-cationic peptides).

It is also predicted that administration of the peptide conjugates, aromatic-cationic peptides, or TBMs (with or without aromatic-cationic peptides) will increase ATP synthesis rate substantially even in control healthy mice. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology, or pharmaceutically acceptable salts thereof, such as acetate, tartrate, or trifluoroacetate salts, are useful in methods of preventing or treating secondary complications of a burn injury, such as skeletal muscle dysfunction.

Example 53: Compositions of the Present Technology Reduce Mitochondrial Aconitase Activity in Burn Injury Mitochondrial aconitase is part of the TCA cycle and its activity has been directly correlated with the TCA flux. Moreover, its activity is inhibited by ROS, such that it is considered an index of oxidative stress. This Example will demonstrate the effects of TBMs (with or without aromatic-cationic peptides) or peptide conjugates of the present technology on mitochondrial aconitase activity.

Murine subjects will be subjected to burn injury or sham and administered peptide conjugates, aromatic-cationic peptides, TBMs alone or in combination with aromatic-cationic peptides, or control vehicle as described above. Mitochondria will be isolated from burned and control tissues and mitochondrial aconitase activity assessed using a commercially available kit.

It is anticipated that mitochondrial aconitase activity will be increased in both burned (local burn effect) and contralateral to burned leg (systemic burn effect), most probably due to the hypermetabolism induced by burn injury. Thus, the increased ROS production known to occur in burn injury, which could inhibit mitochondrial aconitase activity, will likely not overcome the hypermetabolic effect with respect to mitochondrial aconitase activity and TCA flux. A similar result has been also shown in the case of exercise/repeated contractions in intact human and isolated mouse skeletal muscle, although an increase in ROS is also observed in this situation.

Thus, it is further anticipated that treatment with peptide conjugates, aromatic-cationic peptides or TBMs (with or without aromatic-cationic peptides) will reduce mitochondrial aconitase activity to sham control levels in subjects receiving a burn injury. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology, or pharmaceutically acceptable salts thereof, such as acetate, tartrate, or trifluoroacetate salts, are useful in methods for reducing mitochondrial aconitase activity following a burn injury.

Example 54: Compositions of the Present Technology in the Prevention or Treatment of Metabolic Syndrome This Example will demonstrate the use of TBMs (with or without aromatic-cationic peptides) or peptide conjugates of the present technology in the prevention and treatment of Metabolic Syndrome.

Sprague Dawley rats will be fed with a high-fat diet (HFD) for 6 weeks and then administered a single dose of STZ (30 mg/kg). The rats will be maintained on HFD until 14 weeks after STZ administration. Control subjects fed normal rat chow (NRC) for 6 weeks will be administered citrate buffer without STZ. After 5 months, diabetic subjects will be treated with peptide conjugates (10 mg/kg, 3 mg/kg, or 1 mg/kg s.c.q.d. (subcutaneously, once daily)), aromatic-cationic peptides (an equivalent molar dose of aromatic-cationic peptide based on the concentration of the aromatic-cationic peptide administered in the peptide conjugate group), TBMs (an equivalent molar dose of TBM based on the concentration of the TBM administered in the peptide conjugate group), TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) or control vehicle (saline) 5 days per week for 10 weeks. The study groups will be as follows:

Group A: HFD/STZ+peptide conjugates 10 mg/kg s.c.q.d. (Mon-Fri.), n=12;

Group B: HFD/STZ+peptide conjugates 3 mg/kg s.c.q.d. (Mon-Fri.), n=12;

Group C: HFD/STZ+peptide conjugates 1 mg/kg s.c.q.d. (Mon-Fri.), n=10;

Group D: HFD/STZ+control vehicle s.c.q.d. (Mon-Fri.), n=10;

Group E: NRC+control vehicle s.c.q.d. (Mon-Fri.), n=10;

Group F: HFD/STZ+aromatic-cationic peptide (an equivalent molar dose of aromatic-cationic peptide based on concentration of the aromatic-cationic peptide administered in the 10 mg/kg s.c.q.d. peptide conjugate group), n=12

Group G: HFD/STZ+aromatic-cationic peptide (an equivalent molar dose of aromatic-cationic peptide based on concentration of the aromatic-cationic peptide administered in the 3 mg/kg s.c.q.d. peptide conjugate group), n=12

Group H: HFD/STZ+aromatic-cationic peptide (an equivalent molar dose of aromatic-cationic peptide based on concentration of the aromatic-cationic peptide administered in the 1 mg/kg s.c.q.d. peptide conjugate group), n=12

Group I: HFD/STZ+TBM (an equivalent molar dose of TBM based on concentration of the TBM administered in the 10 mg/kg s.c.q.d. peptide conjugate group), n=12

Group J: HFD/STZ+TBM (an equivalent molar dose of TBM based on concentration of the TBM administered in the 3 mg/kg s.c.q.d. peptide conjugate group), n=12

Group K: HFD/STZ+TBM (an equivalent molar dose of TBM based on concentration of the TBM administered in the 1 mg/kg s.c.q.d. peptide conjugate group), n=12.

Group L: HFD/STZ+TBMs in combination with aromatic-cationic peptides (e.g., an equivalent molar dose of TBM based on the concentration of TBM administered in the 10 mg/kg s.c.q.d. peptide conjugate treatment group and an equivalent molar dose of aromatic-cationic peptide based on the concentration of aromatic-cationic peptide administered in the 10 mg/kg s.c.q.d. peptide conjugate treatment group), n=12

Group M: HFD/STZ+TBMs in combination with aromatic-cationic peptides (e.g., an equivalent molar dose of TBM based on the concentration of TBM administered in the 3 mg/kg s.c.q.d. peptide conjugate treatment group and an equivalent molar dose of aromatic-cationic peptide based on the concentration of aromatic-cationic peptide administered in the 3 mg/kg s.c.q.d. peptide conjugate treatment group), n=12

Group N: HFD/STZ+TBMs in combination with aromatic-cationic peptides (e.g., an equivalent molar dose of TBM based on the concentration of TBM administered in the 1 mg/kg s.c.q.d. peptide conjugate treatment group and an equivalent molar dose of aromatic-cationic peptide based on the concentration of aromatic-cationic peptide administered in the 1 mg/kg s.c.q.d. peptide conjugate treatment group), n=12

It is anticipated that HFD feeding for 6 weeks will produce obvious body weight gain, and that STZ administration will increase blood glucose and hyperlipidemia, indicating a metabolic syndrome-like disorder in these subjects. Hence, the protocol will have induced metabolic syndrome in these subjects.

During the 10-week period of treatment, no obvious changes in body weight or blood glucose level are expected in subjects receiving peptide conjugates, aromatic-cationic peptides or TBMs (with or without aromatic-cationic peptides). The blood glucose of NRC group is expected to stay in normal range, while that of STZ treatment groups is predicted to remain higher than throughout the 10-week period trial period.

It is anticipated that the blood triglyceride level of HFD/STZ rats will be much higher than in NRC rats before treatment with peptide conjugates, aromatic-cationic peptides or TBMs (with or without aromatic-cationic peptides), and will be reduced to normal levels following 10 weeks of peptide conjugate-, aromatic-cationic peptide- or TBM- (with or without aromatic-cationic peptides) administration, demonstrating beneficial effects on lipid metabolism. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology, or pharmaceutically acceptable salts thereof, such as acetate, tartrate, or trifluoroacetate salts, are useful in methods for preventing or treating metabolic syndrome.

Example 55: Compositions of the Present Technology Prevent High Glucose-Induced Injury to Human Retinal Epithelial Cells This Example will demonstrate the use of TBMs (with or without aromatic-cationic peptides) or peptide conjugates for the prevention of high glucose-induced injury to human retinal epithelial cells (HREC).

Methods of HREC culture useful in the studies of the present technology are known. See generally, Li, et al., *Clin. Ophthal. Res.* 23:20-2 (2005); Premanand, et al., *Invest. Ophthalmol. Vis. Sci.* 47:2179-84 (2006). Briefly, HREC cells will be cultured under one of these conditions: 1) normal control; 2) 30 mM glucose; 3) 30 mM glucose+peptide conjugates; 4) 30 mM glucose+an aromatic-cationic peptide; 5) 30 mM glucose+TBM; 6) 30 mM glucose+TBM+aromatic-cationic peptides. Survival of HRECs in high glucose co-treated with various concentrations of peptide conjugates (10 nM, 100 nM, 1 µM, 10 µM) will be measured by flow cytometry using Annexin V. See generally, Koopman, et al., *Blood* 84:1415 (1994); Homburg, et al., *Blood* X5: 532 (1995); Vermes, et al. *J. Immunol. Meth.* 184:39 (1995); Fadok, et al., *J. Immunol.* 148:2207 (1992).

The survival of HRECs in high glucose co-treated with peptide conjugates, aromatic-cationic peptides, or TBMs with or without aromatic-cationic peptides will be tested at 24 hours and 48 hours. It is predicted that survival of HRECs will be significantly improved with the administration of peptide conjugates, aromatic-cationic peptides, or TBMs (with or without aromatic-cationic peptides) as compared to controls, with a reduction in apoptotic and necrotic cells. Treatment with peptide conjugates, aromatic-cationic peptides, or TBMs (with or without aromatic-cationic peptides) is also anticipated to reduce the production of ROS. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

To demonstrate that a mitochondrial-mediated pathway will be important in TBM-(with or without aromatic-cationic peptides) or peptide conjugate-mediated protection against high glucose-induced cell death, mitochondrial membrane potential will be measured by flow cytometry using TMRM. It is anticipated that incubating the HRECs with high-glucose for 24 or 48 hours will lead to a rapid loss of mitochondrial membrane potential, and that concurrent treatment with peptide conjugates, aromatic-cationic peptides, or TBMs (with or without aromatic-cationic peptides) will prevent or attenuate this effect. These results will show that peptide conjugates, aromatic-cationic peptides, or TBMs (with or without aromatic-cationic peptides) prevent the mitochondrial membrane potential loss caused by exposure to a high glucose environment. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is expected that glucose (30 mmol/L) will induce cytochrome c release from the mitochondria of HRECs. Fixed HRECs will be immunolabeled with a cytochrome c antibody and a mitochondrial specific protein antibody (HSP60). It is predicted that confocal microscopic analysis will show that HRECs in normal culture and in cultures containing peptide conjugates, aromatic-cationic peptides, or TBMs with or without aromatic-cationic peptides co-treated with glucose have overlapping cytochrome c staining and mitochondria staining, indicating colocalization of cytochrome c and mitochondria. It is anticipated that after treatment with 30 mmol/L glucose for 24 or 48 hours, cytochrome c will be observed in the cytoplasm of HRECs, indicating that glucose induces the release of cytochrome c from the mitochondria to cytoplasm in HREC cells, and that treatment with peptide conjugates, aromatic-cationic peptides, or TBMs (with or without aromatic-cationic peptides) will prevent or attenuate this effect. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that TBMs (with or without aromatic-cationic peptides) or peptide conjugates promote the survival of HREC cells in a high glucose environment. As such, the TBMs (with or without aromatic-cationic peptides) or peptide conjugates of the present technology, or pharmaceutically acceptable salts thereof, such as acetate, tartrate, or trifluoroacetate salts, are useful in methods for the prevention of diabetic retinopathy.

Example 56: Compositions of the Present Technology Prevent Diabetic Retinopathy in Rats Fed a High-Fat Diet This Example will demonstrate use of TBMs (with or without aromatic-cationic peptides) or peptide conjugates in the prevention of diabetic retinopathy in rats fed a high-fat diet (HFD).

A rat model of diabetes will be established by combination of 6-week HFD and either 1) a low-dose STZ (30 mg/kg) injection, or 2) a single high dose of STZ (65 mg/kg) in Sprague-Dawley rats. See generally, Srinivasan, et al., *Pharm. Res.* 52(4):313-320 (2005). Controls will be maintained on normal rat chow (NRC). Treatment groups will be as follows:

Group A: 12 HFD/STZ peptide conjugates 10 mg/kg s.c
Group B: 12 HFD/STZ peptide conjugates 3 mg/kg s.c.
Group C: 12 HFD/STZ peptide conjugates 1 mg/kg s.c.
Group D: 10 HFD/STZ control vehicle. s.c.
Group E: 10 NRC control vehicle. s.c.

Group F: 12 HFD/STZ aromatic-cationic peptide (an equivalent molar dose of aromatic-cationic peptide based on concentration of the aromatic-cationic peptide administered in the 10 mg/kg s.c.q.d. peptide conjugate group)

Group G: 12 HFD/STZ aromatic-cationic peptide (an equivalent molar dose of aromatic-cationic peptide based on concentration of the aromatic-cationic peptide administered in the 3 mg/kg s.c.q.d. peptide conjugate group)

Group H: 12 HFD/STZ aromatic-cationic peptide (an equivalent molar dose of aromatic-cationic peptide based on concentration of the aromatic-cationic peptide administered in the 1 mg/kg s.c.q.d. peptide conjugate group)

Group I: 12 HFD/STZ TBM (an equivalent molar dose of TBM based on concentration of the TBM administered in the 10 mg/kg s.c.q.d. peptide conjugate group)

Group J: 12 HFD/STZ TBM (an equivalent molar dose of TBM based on concentration of the TBM administered in the 3 mg/kg s.c.q.d. peptide conjugate group)

Group K: 12 HFD/STZ TBM (an equivalent molar dose of TBM based on concentration of the TBM administered in the 1 mg/kg s.c.q.d. peptide conjugate group).

Group L: TBMs in combination with aromatic-cationic peptides (e.g., an equivalent molar dose of TBM based on the concentration of TBM administered in the 10 mg/kg s.c.q.d. peptide conjugate treatment group and an equivalent molar dose of aromatic-cationic peptide based on the concentration of aromatic-cationic peptide administered in the 10 mg/kg s.c.q.d. peptide conjugate treatment group)

Group M: TBMs in combination with aromatic-cationic peptides (e.g., an equivalent molar dose of TBM based on the concentration of TBM administered in the 3 mg/kg s.c.q.d. peptide conjugate treatment group and an equivalent molar dose of aromatic-cationic peptide based on the concentration of aromatic-cationic peptide administered in the 3 mg/kg s.c.q.d. peptide conjugate treatment group)

Group N: TBMs in combination with aromatic-cationic peptides (e.g., an equivalent molar dose of TBM based on the concentration of TBM administered in the 1 mg/kg s.c.q.d. peptide conjugate treatment group and an equivalent molar dose of aromatic-cationic peptide based on the concentration of aromatic-cationic peptide administered in the 1 mg/kg s.c.q.d. peptide conjugate treatment group)

Eyes will be harvested and subjects assessed for cataract formation, epithelial changes, integrity of the blood-retinal barrier, retinal microvascular structure, and retinal tight junction structure using methods known in the art.

It is anticipated that administration of peptide conjugates, aromatic-cationic peptides, or TBMs (with or without aromatic-cationic peptides) will result in a prevention or reversal of cataract formation in the lenses of diabetic rats. It is further anticipated that administration of peptide conjugates, aromatic-cationic peptides or TBMs (with or without aromatic-cationic peptides) will reduce epithelial cellular changes in both STZ rat model and HFD/STZ rat model, and result in improved inner blood-retinal barrier function compared to control subjects. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

It is anticipated that administration of peptide conjugates, aromatic-cationic peptides or TBMs (with or without aromatic-cationic peptides) will reduce retinal microvascular changes observed in STZ or HFD/STZ rats. It is further anticipated that the tight junctions, as visualized by claudin-5 localization, will be uniformly distributed along the retinal vessels in control subjects, and non-uniformly in HFD/STZ subjects. It is further anticipated that treatment with peptide conjugates, aromatic-cationic peptides or TBMs (with or without aromatic-cationic peptides) will prevent, reverse, or attenuate this effect. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will collectively establish that peptide conjugates, aromatic-cationic peptides or TBMs (with or without aromatic-cationic peptides) prevent/compensate for the negative effects of diabetes in the eye, e.g., cataracts and microvasculature damage. As such, the TBMs (with or without aromatic-cationic peptides) or peptide conjugates of the present technology, or pharmaceutically acceptable salts thereof, such as acetate, tartrate, or trifluoroacetate salts, are useful in methods for preventing or treating ophthalmic conditions associated with diabetes in human subjects.

Example 57: Compositions of the Present Technology in the Prevention and Treatment of Heart Failure This Example will demonstrate the use of TBMs (with or without aromatic-cationic peptides) or peptide conjugates in the prevention and treatment of hypertensive cardiomyopathy and heart failure. This Example will further demonstrate the role of NADPH and mitochondria in angiotensin II (Ang II)-induced cardiomyopathy, and in cardiomyopathic mice overexpressing the α subunit of the heterotrimeric Gq protein (Gαq).

Ventricles from mouse neonates younger than 72 hours will be dissected, minced, and enzymatically digested with Blendzyme 4 (45 mg/mL, Roche). After enzymatic digestion, cardiomyocytes will be enriched using differential pre-plating for 2 hours, and seeded on fibronectin-coated culture dishes for 24 hours in DMEM (Gibco) with 20% Fetal Bovine Serum (Sigma) and 25 µM Arabinosylcytosine (Sigma). Cardiomyocytes will be stimulated with Angiotensin II (1 µM) for 3 hours in serum-free DMEM containing 0.5% insulin transferrin-selenium (Sigma), 2 mM glutamine, and 1 mg/mL BSA. Cardiomyocytes are simultaneously treated with one of the following: peptide conjugates (1 nM), aromatic-cationic peptides (an equivalent molar dose of aromatic-cationic peptide based on concentration of the aromatic-cationic peptide administered in the peptide conjugate group), TBMs (an equivalent molar dose of TBM based on concentration of the TBM administered in the peptide conjugate group), TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group), N-acetyl cysteine (NAC: 0.5 mM), or PBS control. To measure mitochondrial superoxide concentration, Mitosox (5 pM) will be incubated for 30 minutes at 37° C. to load cardiomyocytes, followed by 2 washes with Hanks Balanced Salt Solution. Samples will be analyzed using excitation/emission of 488/625 nm by flow cytometry. Flow data will be analyzed using FCS Express (De Novo Software, Los Angeles, Calif., U.S.A.), and presented as histogram distributions of Mitosox fluorescence intensity.

Mouse Experiments, Drug Delivery, Echocardiography and Blood Pressure Measurement.

Six to ten mice will be included in each experimental group (Saline, Ang II, Ang II+peptide conjugate, Ang II+aromatic-cationic peptide, Ang II+TBM, Ang II+TBM+aromatic-cationic peptide, WT, G$\alpha$q, G$\alpha$q+peptide conjugate, G$\alpha$q+aromatic-cationic peptide, G$\alpha$q+TBM, G$\alpha$q+TBM+aromatic-cationic peptide). A pressor dose of Ang II (1.1 mg/kg/d) will be continuously administered for 4 weeks using subcutaneous Alzet 1004 osmotic minipumps, either alone or in the presence of with peptide conjugates (3 mg/kg/d), aromatic-cationic peptides (an equivalent molar dose of aromatic-cationic peptide based on concentration of the aromatic-cationic peptide administered in the peptide conjugate group), TBMs (an equivalent molar dose of TBM based on concentration of the TBM administered in the peptide conjugate group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group). Echocardiography will be performed at baseline and 4 weeks after pump implantation using a Siemens Acuson CV-70 equipped with a 13 MHz probe. Under 0.5% isoflurane to reduce agitation, standard M-mode, conventional and Tissue Doppler images will be taken, and functional calculations will be performed according to American Society of Echocardiography guidelines. MTI will be calculated as the ratio of the sum of isovolemic contraction and relaxation time to LV ejection time. An increase in MPI is an indication that a greater fraction of systole is spent to cope with the pressure changes during the isovolemic phases. As a reference for the effect of the TBM (with or without aromatic-cationic peptides) or peptide conjugate in Ang II treated mice, a genetic mouse model of Rosa-26 inducible-mCAT will be included, in which mitochondrial catalase will be overexpressed for two weeks before Ang II treatment.

Blood pressure will be measured in a separate group of mice by telemetry using an intravascular catheter PA-C 10 (DSI, MN), in which measurement will be performed every three hours starting from 2 days before pump placement until 2 days after Ang pump placement. After this time, a new pump loaded with Ang II+peptide conjugate/TBM (with or without aromatic-cationic peptides)/aromatic-cationic peptide will be inserted, followed by another 2 days of recording to see if the peptide conjugate, TBM (with or without aromatic-cationic peptides) or aromatic-cationic peptide has an effect on blood pressure.

Quantitative Pathology.

Ventricular tissues will be cut into transverse slices, and subsequently embedded with paraffin, sectioned, and subjected to Masson Trichrome staining. Quantitative analysis of fibrosis will be performed by measuring the percentage of blue-staining fibrotic tissue relative to the total cross-sectional area of the ventricles.

Measurement of Mitochondrial Protein Carbonyl Groups.

For mitochondrial protein extraction, ventricular tissues will be homogenized in mitochondrial isolation buffer (1 mM EGTA, 10 mM HEPES, 250 mM sucrose, 10 mM Tris-HCl, pH 7.4). The lysates will be centrifuged for 7 minutes at 800 g in 4° C. The supernatants will be then centrifuged for 30 minutes at 4000 g in 4° C. The crude mitochondria pellets will be resuspended in small volume of mitochondrial isolation buffer, sonicated on ice to disrupt the membrane, and treated with 1% streptomycin sulfate to precipitate mitochondrial nucleic acids. The OXISELECT™ Protein Carbonyl ELISA Kit (Cell Biolabs) will be used to analyze 1 µg of protein sample per assay. The ELISA will be performed according to the instruction manual, with slight modification. Briefly, protein samples will be reacted with dinitrophenylhydrazine (DNPH) and probed with anti-DNPH antibody, followed by HRP conjugated secondary antibody. The anti-DNPH antibody and HRP conjugated secondary antibody concentrations will be 1:2500 and 1:4000, respectively.

Quantitative PCR.

Gene expression will be quantified by quantitative real-time PCR using an Applied Biosystems 7900 thermocycler with Taqman Gene Expression Assays on Demand, which includes: PGC1-$\alpha$ (Mm00731216), TFAM (Mm004474X5), NRF-1 (Mm00447996), NRF-2 (Mm00487471), Collagen 1a2 (Mm00483937), and ANP (Mm01255747). Expression assays will be normalized to 18S RNA.

NADPH Oxidase Activity.

The NADPH oxidase assay will be performed as described elsewhere. In brief, 10 µg of ventricular protein extract will be incubated with dihydroethidium (DHE, 10 µM), sperm DNA (1.25 µg/mL), and NADPH (50 µM) in PBS/DTPA (containing 100 µM DTPA). The assay will be incubated at 37° C. in the dark for 30 minutes and the fluorescence will be detected using excitation/emission of 490/580 nm.

Western Immunoblots.

Cardiac protein extracts will be prepared by homogenization in lysis buffer containing protease and phosphatase inhibitors on ice (1.5 mM KCl, 50 mM Tris HCl, 0.125% Sodium deoxycholate, 0.375% Triton X 100, 0.15% NP40, 3 mM EDTA). The samples will be sonicated and centrifuged at 10,000×g for 15 minutes at 4° C. The supernatant will be collected and the protein concentration determined using a BCA assay (Pierce Thermo Scientific, Rockford, Ill., U.S.A.). Total protein (25 µg) will be separated on NuPAGE 4-12% Bis-Tris gel (Invitrogen) and transferred to 0.45 µm PVDF membrane (Millipore), and then blocked in 5% non-fat dry milk in Tris-buffer solution with 0.1% Tween-20 for 1 hour. Primary antibodies will be incubated overnight, and secondary antibodies will be incubated for 1 hour. The primary antibodies include: rabbit monoclonal anti-cleaved caspase-3 (Cell Signaling), mouse monoclonal anti-GAPDH (Millipore), rabbit polyclonal phospho-p3X MAP kinase (Cell Signaling), and mouse monoclonal anti-p38 (Santa Cruz Biotechnology). The enhanced chemiluminescence method (Thermo Scientific) will be used for detection. Image Quant ver.2.0 will be used to quantified the relative band density as a ratio to GAPDH (internal control). All samples will be normalized to the same cardiac protein sample.

It is anticipated that Ang-II will increase mitochondrial ROS in neonatal cardiomyocytes, which will be alleviated by treatment with peptide conjugates, aromatic-cationic peptides or TBMs (with or without aromatic-cationic peptides). It is predicted that flow cytometry analysis will demonstrate that Angiotensin II increased Mitosox fluorescence (an indicator of mitochondrial superoxide) in neonatal cardiomyocytes. It is predicted that treatment with N-acetyl cysteine (NAC), a non-targeted antioxidant drug, will not show any effect on the level of mitochondrial ROS after Ang II. In contrast, it is anticipated that peptide conjugates, aromatic-cationic peptides or TBMs (with or without aromatic-cationic peptides) will reduce Ang II-induced fluorescence to the level similar to that of saline-treated control cardiomyocytes. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. These anticipated results will indicate that Ang II induced mitochondrial oxidative stress in cardiomyocytes can be alleviated by a mitochondrial targeted antioxidant.

Treatment with peptide conjugates, aromatic-cationic peptides or TBMs (with or without aromatic-cationic peptides) is anticipated to ameliorate Ang II-induced cardiomyopathy despite the absence of blood pressure lowering effect. To recapitulate hypertensive cardiomyopathy, a pressor dose of Ang II (1.1 mg/kg/d) will be administered for 4 weeks via subcutaneous continuous delivery with Alzet 1004 osmotic minipumps. It is predicted that intravascular telemetry will reveal that this dose of Ang II will significantly increase systolic and diastolic blood pressure by 25-28 mm Hg above baseline. It is predicted that the simultaneous administration of peptide conjugates (3 mg/kg/d), aromatic-cationic peptides (an equivalent molar dose of aromatic-cationic peptide based on concentration of the aromatic-cationic peptide administered in the peptide conjugate group) TBMs (an equivalent molar dose of TBM based on concentration of the TBM administered in the peptide conjugate group) or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will not have any effect on blood pressure.

The cardiac pathology will be examined by Masson trichrome staining, which demonstrated perivascular fibrosis and interstitial fibrosis after 4 weeks of Ang II. It is anticipated that quantitative image analysis of ventricular fibrosis (blue staining on trichrome) will show that Ang II significantly increases ventricular fibrosis, which is anticipated to be fully attenuated by peptide conjugates, aromatic-cationic peptides or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. The increase in cardiac fibrosis will be confirmed by quantitative PCR of the procollagen 1a2 gene, the main component of fibrosis.

Consistent with the expectation that Ang II will induce mitochondrial ROS in cardiomyocytes, it is predicted that chronic administration of Ang II for 4 weeks will significantly increase ventricular mitochondrial protein carbonyl content, which is an indicator of protein oxidative damage. It is anticipated that mitochondrial targeted antioxidant peptide conjugates, aromatic-cationic peptides or TBMs (with or without aromatic-cationic peptides) will significantly reduce cardiac mitochondrial protein carbonyls. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is anticipated that TBMs (with or without aromatic-cationic peptides) or peptide conjugates act downstream of NADPH oxidase and will reduce activation of p38 MAPK and apoptosis in response to Ang II. It is anticipated that consistent with previous reports, 4 weeks of Ang II will significantly increase cardiac NADPH oxidase activity, however, it is predicted this will not be changed by administration of peptide conjugates or TBMs (with or without aromatic-cationic peptides), which suggests that TBMs or peptide conjugate protection acts downstream of NADPH oxidase.

Ang II has been shown to activate several mitogen activated protein kinase (MAPK), such as p38. It is anticipated that administration of Ang II for 4 weeks will increase phosphorylation of p38 MAPK, and this phosphorylation will be significantly and nearly fully attenuated by peptide conjugates, aromatic-cationic peptides or TBMs (with or without aromatic-cationic peptides), which suggests that MAP kinase is activated through mitochondrial —ROS sensitive mechanisms. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

Mitochondrial ROS, either directly, or indirectly by activating apoptosis signal regulating kinase, may induce apoptosis. It is anticipated that Ang II will induce cardiac apoptosis, which will be shown through an increase in cleaved caspase-3. It is also anticipated that peptide conjugates, aromatic-cationic peptides or TBMs (with or without aromatic-cationic peptides) will completely prevent the activation of caspase-3 caused by Ang II. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is anticipated that peptide conjugates, aromatic-cationic peptides or TBMs (with or without aromatic-cationic peptides) will partially rescue G$\alpha$q overexpression-induced heart failure. G$\alpha$q protein is coupled to receptors for catecholamines and Ang II, all of which are known to be key mediators in hypertensive cardiovascular diseases. To extend these observations to a model of chronic catecholamine/Ang II stimulation, a genetic mouse model with cardiac specific overexpression of G$\alpha$q will be used, which causes heart failure in mice by 14-16 weeks of age. The G$\alpha$q mice in this study will have impairment of systolic function at 16 weeks age, which will be shown by a substantial decline in FS, with enlargement of the LV chamber, impairment of diastolic function indicated by decreased Ea/Aa, and worsening of myocardial performance index (MPI). Peptide conjugates (3 mg/kg/d), aromatic-cationic peptides (an equivalent molar dose of aromatic-cationic peptide based on concentration of the aromatic-cationic peptide administered in the peptide conjugate group), TBMs (an equivalent molar dose of TBM based on concentration of the TBM administered in the peptide conjugate group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be administered from 12 to 16 weeks of age, and it is predicted that these compounds will significantly ameliorate systolic function and improve myocardial performance. LV chamber enlargement is anticipated to be slightly reduced from treatment with peptide conjugates, aromatic-cationic peptides or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

It is anticipated that administration of peptide conjugates of the present technology will have synergistic effects with respect to preventing or treating hypertensive cardiomyopathy or heart failure in mammalian subjects compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology, or pharmaceutically acceptable salts thereof, such as acetate, tartrate, or trifluoroacetate salts, are useful in methods for preventing or treating cardiomyopathy or heart failure in mammalian subjects.

Example 58: Compositions of the Present Technology Protect Against Vessel Occlusion Injuries This Example will demonstrate that the administration of TBMs (with or without aromatic-cationic peptides) or peptide conjugates at the time of revascularization limits the size of the infarct during acute myocardial infarction.

Men and women, 18 years of age or older, who present after the onset of chest pain, and for whom the clinical decision is made to treat with a revascularization procedure (e.g., PCI or thrombolytics) will be eligible for enrollment. Patients may be STEMI (ST-Elevation Myocardial Infarction) or Non-STEMI. A STEMI patient will present with symptoms suggestive or a cutting off of the blood supply to the myocardium and also if the patient's ECG shows the typical heart attack pattern of ST elevation. The diagnosis is made therefore purely on the basis of symptoms, clinical examination and ECG changes. In the case of a Non-ST elevation heart attack, the symptoms of chest pain can be identical to that of a STEMI but the important difference is that the patient's ECG does not show the typical ST elevation changes traditionally associated with a heart attack. The patient often has a history of having experienced angina, but the ECG at the time of the suspected attack may show no abnormality at all. The diagnosis will be suspected on the history and symptoms and will be confirmed by a blood test which shows a rise in the concentration of substances called cardiac enzymes in the blood.

Left ventricular and coronary angiography will be performed with the use of standard techniques, just before revascularization. Revascularization will be performed by PCI with the use of direct stenting. Alternative revascularization procedures include, but are not limited to, balloon angioplasty; percutaneous transluminal coronary angioplasty; and directional coronary atherectomy.

After coronary angiography is performed but before the stent is implanted, patients who meet the enrollment criteria are randomly assigned to either the control group or the experimental group. Randomization is performed with the use of a computer-generated randomization sequence. Less than 10 minutes before direct stenting, the patients in the experimental group receive an intravenous bolus injection of the peptide conjugate, aromatic-cationic peptide or TBMs (with or without aromatic-cationic peptides). Patients will be equally randomized into any of the following treatment arms (for example, 0, 0.001, 0.005, 0.01, 0.025, 0.05, 0.10, 0.25, 0.5, and 1.0 mg/kg/hour for peptide conjugates and equivalent molar doses of aromatic-cationic peptide, TBM, or TBM+aromatic-cationic peptides based on concentration of the aromatic-cationic peptide and/or TBM administered in the peptide conjugate group). The compound will be administered as an IV infusion from about 10 minutes prior to reperfusion to about 3 hours post-PCL. Following the reperfusion period, the subject may be administered the compound chronically by any means of administration, e.g., subcutaneous or IV injection.

The primary end point is the size of the infarct as assessed by measurements of cardiac biomarkers. Blood samples will be obtained at admission and repeatedly over the next 3 days. Coronary biomarkers will be measured in each patient. For example, the area under the curve (AUC) (expressed in arbitrary units) for creatine kinase and troponin I release (Beckman kit) may be measured in each patient by computerized planimetry. The principal secondary end point is the size of the infarct as measured by the area of delayed hyperenhancement that is seen on cardiac magnetic resonance imaging (MRI), assessed on day 5 after infarction. For the late-enhancement analysis, 0.2 mmol of gadolinium-tetrazacyclododecanetetraacetic acid (Gd.DOTA) per kilogram will be injected at a rate of 4 mL per second and will be flushed with 15 mL of saline. Delayed hyperenhancement is evaluated 10 minutes after the injection of gadolinium Gd.DOTA with the use of a three dimensional inversion-recovery gradient-echo sequence. The images are analyzed in short axis slices covering the entire left ventricle.

Myocardial infarction will be identified by delayed hyperenhancement within the myocardium, defined quantitatively by an intensity of the myocardial postcontrast signal that is more than 2 SD above that in a reference region of remote, non-infarcted myocardium within the same slice. For all slices, the absolute mass of the infarcted area will be calculated according to the following formula: infarct mass (in grams of tissue)=(hyperenhanced area [in square centimeters]) x slice thickness (in centimeters) x myocardial specific density (1.05 g per cubic centimeter).

It is predicted that administration of peptide conjugates, aromatic-cationic peptides or TBMs (with or without aromatic-cationic peptides) at the time of reperfusion will be associated with a smaller infarct by some measures than that seen with placebo. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone. These results will show that the TBMs (with or without aromatic-cationic peptides) or peptide conjugates of the present technology, or pharmaceutically acceptable salts thereof, such as acetate, tartrate, or trifluoroacetate salts, are useful for limiting infarct size during acute myocardial infarction.

Example 59: Compositions of the Present Technology Protect Against Acute Myocardial Infarction Injury in a Rabbit Model This Example will demonstrate the use of TBMs (with or without aromatic-cationic peptides) or peptide conjugates in protecting against an acute myocardial infarction injury in a rabbit model.

New Zealand white rabbits will be used in this study. The rabbits will be males and >10 weeks in age. Environmental controls in the animal rooms will be set to maintain temperatures of 61° to 72° F. and relative humidity between 30% and 70%. Room temperature and humidity will be recorded hourly, and monitored daily. There will be approximately 10-15 air exchanges per hour in the animal rooms. Photoperiod will be 12-hr light/12-hr dark (via fluorescent lighting) with exceptions as necessary to accommodate dosing and data collection. Routine daily observations will be performed. Harlan Teklad, Certified Diet (2030C), rabbit diet will be provided approximately 180 grams per day from arrival to the facility. In addition, fresh fruits and vegetables will be given to the rabbit 3 times a week.

Peptide conjugates, aromatic-cationic peptides or TBMs (with or without aromatic-cationic peptides) will be used as the test article. Dosing solutions will be formulated and will be delivered via continuous infusion (IV) at a constant rate (e.g., 50 μL/kg/min for peptide conjugates and equivalent molar doses of aromatic-cationic peptide, TBM or TBM+aromatic-cationic peptide based on concentration of the aromatic-cationic peptide and/or TBM administered in the peptide conjugate group). Normal saline (0.9% NaCl) will be used as a control.

The test/vehicle articles will be given intravenously, under general anesthesia, in order to mimic the expected route of administration in the clinical setting of AMI and PTCA. Intravenous infusion will be administered via a peripheral vein using a Kd Scientific infusion pump (Holliston, Mass. 01746) at a constant volume (e.g., 50 μL/kg/min for peptide conjugates and equivalent molar doses of aromatic-cationic peptide, TBM or TBM+aromatic-cationic peptide based on concentration of the aromatic-cationic peptide and/or TBM administered in the peptide conjugate group).

The study followed a predetermined placebo and sham controlled design. In short, 10-20 healthy, acclimatized, male rabbits will be assigned to one of these study arms (approximately 2-10 animals per group). Arm A (n=4, CTRL/PLAC) includes animals treated with vehicle (vehicle; VEH, IV); Arm B (n=7, treated) includes animals treated with the compound (peptide conjugates, aromatic-cationic peptides or TBMs (with or without aromatic-cationic peptides)); Arm C (n=2, SHAM) includes sham operated time-controls treated with vehicle (vehicle; VEH, IV) or compound.

In all cases, treatments will be started approximately 30 minutes after the onset of a 30-minute ischemic insult (coronary occlusion) and continued for up to 3 hours following reperfusion. In all cases, cardiovascular function will be monitored both prior to and during ischemia, as well as for up to 180 minutes (3 hours) post-reperfusion. The experiments will be terminated 3 hours post-reperfusion (end of study); irreversible myocardial injury (infarct size by histomorphometry) at this time-point will be evaluated, and will be the primary-end-point of the study.

It is anticipated that administration of peptide conjugates, aromatic-cationic peptides or TBMs (with or without aromatic-cationic peptides) will result in decreased infarct size compared to the vehicle control group. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBMs in combination with aromatic-cationic peptides will have synergistic effects in this regard compared to that observed with either aromatic-cationic peptides or TBMs alone. These results will show that TBMs (with or without aromatic-cationic peptides) or peptide conjugates of the present technology, or pharmaceutically acceptable salts thereof, such as acetate, tartrate, or trifluoroacetate salts, are useful in methods for preventing and treating acute myocardial infarction injury in mammalian subjects.

Example 60: Compositions of the Present Technology and Cyclosporine in the Treatment of Acute Myocardial Infarction Injury This Example will demonstrate that the administration of a TBM (with or without aromatic-cationic peptides) or peptide conjugate, or a pharmaceutically acceptable salt thereof such as acetate, tartrate, or trifluoroacetate salt, and cyclosporine at the time of revascularization limits the size of the infarct during acute myocardial infarction.

Study Group.

Men and women, 18 years of age or older, who present within 6 hours after the onset of chest pain, who have ST-segment elevation of more than 0.1 mV in two contiguous leads, and for whom the clinical decision is made to treat with percutaneous coronary intervention (PCI) will be eligible for enrollment. Patients are eligible for the study whether they are undergoing primary PCI or rescue PCI. Occlusion of the affected coronary artery (Thrombolysis in Myocardial Infarction (TIMI) flow grade 0) at the time of admission is also a criterion for inclusion.

Angiography and Revascularization.

Left ventricular and coronary angiography will be performed with the use of standard techniques, just before revascularization. Revascularization will be performed by PCI with the use of direct stenting. Alternative revascularization procedures include, but are not limited to, balloon angioplasty; insertion of a bypass graft; percutaneous transluminal coronary angioplasty; and directional coronary atherectomy.

Experimental Protocol.

After coronary angiography is performed but before the stent is implanted, patients who meet the enrollment criteria are randomly assigned to either the control group or the experimental group. Randomization will be performed with the use of a computer-generated randomization sequence. Less than 10 minutes before direct stenting, the patients in the experimental group will receive an intravenous bolus injection of the peptide conjugate/aromatic-cationic peptide/ TBM (with or without aromatic-cationic peptides) and cyclosporine. The peptide conjugate, aromatic-cationic peptide or TBM (with or without aromatic-cationic peptides) will be dissolved in normal saline (final concentration, 25 mg/mL for peptide conjugate and equivalent molar doses of aromatic-cationic peptide, TBM, or TBM and aromatic-cationic peptide based on concentration of the aromatic-cationic peptide and/or TBM administered in the peptide conjugate group) and will be injected through a catheter that is positioned within an antecubital vein. Either separately or simultaneously, cyclosporine (final concentration, 25 mg per milliliter will be injected through the catheter. Normal saline (0.9% NaCl) will be used as a control. The patients in the control group receive an equivalent volume of normal saline.

Infarct Size.

The primary end point will be the size of the infarct as assessed by measurements of cardiac biomarkers. Blood samples are obtained at admission and repeatedly over the next 3 days. The area under the curve (AUC) (expressed in arbitrary units) for creatine kinase and troponin I release (Beckman kit) will be measured in each patient by computerized planimetry. The principal secondary end point will be the size of the infarct as measured by the area of delayed hyperenhancement that is seen on cardiac magnetic resonance imaging (MRI), assessed on day 5 after infarction. For the late-enhancement analysis, 0.2 mmol of gadolinium-tetrazacyclododecanetetraacetic acid (Gd.DOTA) per kilogram is injected at a rate of 4 mL per second and will be flushed with 15 mL of saline. Delayed hyperenhancement will be evaluated 10 minutes after the injection of Gd.DOTA with the use of a three dimensional inversion-recovery gradient-echo sequence. The images are analyzed in short axis slices covering the entire left ventricle.

Myocardial infarction will be identified by delayed hyperenhancement within the myocardium, defined quantitatively by an intensity of the myocardial postcontrast signal that is more than 2 SD above that in a reference region of remote, non-infarcted myocardium within the same slice. For all slices, the absolute mass of the infracted area will be calculated according to the following formula: infarct mass (in grams of tissue)=E (hyperenhanced area [in square centimeters]) x slice thickness (in centimeters) x myocardial specific density (1.05 g per cubic centimeter).

Other End Points.

The whole-blood concentration of the TBM (with or without aromatic-cationic peptides) or peptide conjugate is measured immediately prior to PCI as well as at 1, 2, 4, 8 and 12 hours post PCI. Blood pressure and serum concentrations of creatinine and potassium will be measured on admission and 24, 48, and 72 hours after PCI. Serum concentrations of bilirubin, glutamyltransferase, and alkaline phosphatase, as well as white-cell counts, will be measured on admission and 24 hours after PCI.

The cumulative incidence of major adverse events that occur within the first 48 hours after reperfusion are recorded, including death, heart failure, acute myocardial infarction, stroke, recurrent ischemia, the need for repeat revascularization, renal or hepatic insufficiency, vascular complications, and bleeding. The infarct-related adverse events will be assessed, including heart failure and ventricular fibrillation. In addition, 3 months after acute myocardial infarction, cardiac events are recorded, and global left ventricular function will be assessed by echocardiography (Vivid 7 systems; GE Vingmed).

It is predicted that administration of the peptide conjugate, aromatic-cationic peptide, or TBMs (with or without aromatic-cationic peptides) along with cyclosporine at the time of reperfusion will be associated with a smaller infarct by some measures than that seen with placebo. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone. These results will show that TBMs (with or without aromatic-cationic peptides) or peptide conjugates of the present technology, or pharmaceutically acceptable salts thereof, such as acetate, tartrate, or trifluoroacetate salts, are useful in combination with cyclosporine useful in methods for the treatment of myocardial infarction.

Example 61: Compositions of the Present Technology and Cyclosporine in the Treatment of Nephrotoxicity in Transplant Patients This Example will demonstrate the use of cyclosporine and (i) TBMs (with or without aromatic-cationic peptides) or (ii) peptide conjugates along to treat nephrotoxicity in transplant patients.

To prevent organ or tissue rejection after transplant, patients often receive a regimen of the immunosuppressive drug cyclosporine. Cyclosporine levels are established and maintained in the subject at levels to effectively suppress the immune system. However, nephrotoxicity is a concern for these subjects, and the level of the drug in the subject's blood is monitored carefully. Cyclosporine doses are adjusted accordingly in order to not only prevent rejection, but also to deter these potentially damaging side effects. Typically, an adult transplant patient receives cyclosporine as follows: IV: 2 to 4 mg/kg/day IV infusion once daily over 4 to 6 hours, or 1 to 2 mg/kg IV infusion twice a day over 4 to 6 hours, or 2 to 4 mg/kg/day as a continuous IV infusion over 24 hours. Capsules: 8 to 12 mg/kg/day orally in 2 divided doses. Solution: 8 to 12 mg/kg orally once daily. In some patients, doses can be titrated downward with time to maintenance doses as low as 3 to 5 mg/kg/day. In some patients, the tolerance for cyclosporine is poor, and cyclosporine therapy must be discontinued, the dosage lowered, or the dosage regimen cycled so as to prevent destruction of the subject's kidney.

This Example demonstrates the effects of a TBM (with or without aromatic-cationic peptides) or peptide conjugate, or a pharmaceutically acceptable salt thereof, such as acetate, tartrate, or trifluoroacetate salt, together with cyclosporine on post-transplant organ health (e.g., ischemia-reperfusion injury post transplant and organ rejection), as well as kidney health (e.g., nephrotoxic effects of cyclosporine). It is anticipated that administering a TBM (with or without aromatic-cationic peptides) or peptide conjugate will have a protective effect on the transplant organ or tissue, and on kidney health during cyclosporine treatment.

Transplant subjects receiving cyclosporine pursuant to standard pre- and post-transplant procedures will be divided into groups. A therapeutically effective amount of a peptide conjugate or pharmaceutically acceptable salt thereof such as acetate, tartrate, or trifluoroacetate salt; aromatic-cationic peptide; or TBMs (with or without aromatic-cationic peptides) will be administered to subjects prior to, during and/or after transplant. Subjects will be monitored for health and function of the transplanted tissue or organ, as well as the incidence and severity of nephrotoxicity often seen with prolonged cyclosporine administration.

It is predicted that subjects who receive the peptide conjugate, aromatic-cationic peptide or TBMs (with or without aromatic-cationic peptides) will have a healthier transplanted organ or tissue, and/or will be able to maintain a higher and/or more consistent cyclosporine dosage for longer periods of time compared to subjects who do not receive the compounds. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone. These results will show that TBMs (with or without aromatic-cationic peptides) or peptide conjugates of the present technology, or pharmaceutically acceptable salts thereof, such as acetate, tartrate, or trifluoroacetate salts, are useful in combination with cyclosporine is useful in methods for treating nephrotoxicity in transplant patients.

Example 62: Compositions of the Present Technology Facilitate Electron Transfer

ATP synthesis in the electron transport chain (ETC) is driven by electron flow through the protein complexes of the ETC which can be described as a series of oxidation/reduction processes. Rapid shunting of electrons through the ETC is important for preventing short-circuiting that would lead to electron escape and generation of free radical intermediates. The rate of electron transfer (ET) between an electron donor and electron acceptor decreases exponentially with the distance between them, and superexchange ET is limited to 20 angstrom. Long-range ET can be achieved in a multi-step electron hopping process, where the overall distance between donor and acceptor is split into a series of shorter, and therefore faster, ET steps. In the ETC, efficient ET over long distances is assisted by cofactors that are strategically localized along the inner mitochondrial membrane, including FMN, FeS clusters, and hemes. Aromatic amino acids such as Phe, Tyr and Trp can also facilitate electron transfer to heme through overlapping π clouds, and this was specifically shown for cytochrome c. Amino acids with suitable oxidation potential (Tyr, Trp, Cys, Met) can act as stepping stones by serving as intermediate electron carriers. In addition, the hydroxyl group of Tyr can lose a proton when it conveys an electron, and the presence of a basic group nearby, such as Lys, can result in proton-coupled ET which is even more efficient.

It is hypothesized that the distribution of TBMs or peptide conjugates among the protein complexes in the IMM allows it to serve as additional an relay station to facilitate ET. This will be demonstrated using the kinetics of cytochrome c reduction (monitored by absorbance spectroscopy) as a model system, with the TBMs or peptide conjugate facilitating ET. Addition of N-acetylcysteine (NAC) as a reducing agent is anticipated to result in time-dependent increase in absorbance at 550 nm. It is further anticipated that the addition of the TBM (with or without aromatic-cationic peptides) or peptide conjugate alone at 100 µM concentrations will not reduce cytochrome c, but will dose-dependently increase the rate of NAC-induced cytochrome c reduction, suggesting that the compound does not donate an electron but increases the speed of electron transfer.

This Example will further demonstrate the effect of TBMs (with or without aromatic-cationic peptides) or peptide conjugates on the restoration of mitochondrial respiration and ATP synthesis following ischemia-reperfusion (IR) injury in rats. Animals will be subjected to bilateral occlusion of renal artery for 45 minutes followed by 20 minutes or 1 hour of reperfusion. Subjects will receive saline vehicle, a peptide conjugate (2.0 mg/kg s.c.), an aromatic-cationic peptide (an equivalent molar dose of aromatic-cationic peptide based on concentration of the aromatic-cationic peptide administered in the peptide conjugate group) TBM (an equivalent molar dose of TBM based on concentration of the TBM administered in the peptide conjugate group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) 30 minutes before ischemia and again at the time of reperfusion (n=4-5 in each group). It is anticipated that the peptide conjugate, aromatic-cationic peptide or TBMs (with or without aromatic-cationic peptides) will improve oxygen consumption and ATP synthesis. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology, or pharmaceutically acceptable salts thereof, such as acetate, tartrate, or trifluoroacetate salts, are useful in methods comprising electron scavenging electron transfer.

Example 63: Compositions of the Present Technology Enhance Mitochondrial Reduction Potential The redox environment of a cell depends on its reduction potential and reducing capacity. Redox potential is highly compartmentalized within the cell, and the redox couples in the mitochondrial compartment are more reduced than in the other cell compartments and are more susceptible to oxidation. Glutathione (GSH) is present in mM concentrations in mitochondria and is considered the major redox couple. The reduced thiol group —SH can reduce disulfide S—S groups in proteins and restore function. The redox potential of the GSH/GSSG couple is dependent upon two factors: the amounts of GSH and GSSG, and the ratio between GSH and GSSG. As GSH is compartmentalized in the cell and the ratio of GSH/GSSG is regulated independently in each compartment, mitochondrial GSH (mGSH) is the primary defense against mitochondrial oxidative stress. Mitochondrial GSH redox potential becomes more oxidizing with aging, and this is primarily due to increase in GSSG content and decrease in GSH content.

It is anticipated that TBMs (with or without aromatic-cationic peptides) and peptide conjugates of the present technology will enhance mitochondrial reduction potential in vitro in isolated mitochondrial and in vivo in cultured cells and animal subjects. These results will show that TBMs (with or without aromatic-cationic peptides) or peptide conjugates of the present technology, or pharmaceutically acceptable salts thereof, such as acetate, tartrate, or trifluoroacetate salts, are useful in methods for enhancing mitochondrial reduction potential.

Example 64: Compositions of the Present Technology Reduce MV-Induced Mitochondrial Oxidation This Example will show that TBMs (with or without aromatic-cationic peptides) or peptide conjugates of the present technology reduce mechanical ventilation (MV)-induced mitochondrial oxidation.

Experimental Design:

Murine subjects will be treated as follows:
1. Normal, mobile mice: Normal, mobile mice will be randomly divided into four groups, A-E, with 8 mice per group. Group A mice will receive an injection of saline vehicle; Group B mice will receive an i.p. injection of the peptide conjugate; Group C mice will receive an i.p. injection of aromatic-cationic peptide; Group D mice will receive an i.p. injection of TBM; Group E mice will receive an i.p. injection of TBM+ aromatic-cationic peptide.
2. Hind limb casted mice: Mouse hind limbs will be immobilized by casting for 14 days, thereby inducing hind limb muscle atrophy. Casted mice will receive an i.p. injection of saline vehicle (0.3 mL), peptide conjugate, aromatic-cationic peptide, TBM, or TBM with aromatic-cationic peptides. A control group of untreated mice will be also used in this experiment.

To demonstrate that mitochondrial ROS production plays a role in immobilization-induced skeletal muscle atrophy, mice will be randomly assigned to one of three experimental groups (n=24/group): 1) no treatment (control) group; 2) 14 days of hind limb immobilization group (cast); and 3) 14 days of hind-limb immobilization group treated with the mitochondrial-targeted antioxidant peptide conjugate, aromatic-cationic peptide, TBM, or TBM+aromatic-cationic peptides (CasHSS). Subjects will receive s.c. injections of saline vehicle (0.3 mL) or the peptide conjugate, aromatic-cationic peptide or TBM (alone or in combination with aromatic-cationic peptides) (1.5 mg/kg for the peptide conjugate and equivalent molar doses of aromatic-cationic peptide and/or TBM based on concentration of the aromatic-cationic peptide or TBM administered in the peptide conjugate group) administered once daily during the immobilization period.

Immobilization.

Mice will be anesthetized with gaseous isoflurane (3% induction, 0.5-2.5%) maintenance). Anesthetized animals will be cast-immobilized bilaterally with the ankle joint in the plantar-flexed position to induce maximal atrophy of the soleus and plantaris muscle. Both hind limbs and the caudal fourth of the body will be encompassed by a plaster cast. A thin layer of padding will be placed underneath the cast in order to prevent abrasions. In addition, to prevent the animals from chewing on the cast, one strip of fiberglass material will be applied over the plaster. The mice will be monitored on a daily basis for chewed plaster, abrasions, venous occlusion, and problems with ambulation.

Preparation of Permeabilized Muscle Fibers.

Permeabilized muscle fibers will be prepared as previously described. Korshunov, et al., *FEBS Lett* 416:15-18, 1997; Tonkonogi, et al., *Pflügers Arch* 446:261-269, 2003. Briefly, the muscle will be trimmed of connective tissue and cut down to fiber bundles (4-8 mg wet wt). Under a microscope and using a pair of extra-sharp forceps, the muscle fibers will be gently separated in ice-cold buffer X containing 60 mM K-MES, 35 mM KCl, 7.23 mM $K_2$EGTA, 2.77 mM $CaK_2$EGTA, 20 mM imidazole, 0.5 mM DTT, 20 mM taurine, 5.7 mM ATP, 15 mM PCr, and 6.56 mM $MgCl_2·6H_2O$ (pH 7.1, 295 mosmol/kg $H_2O$) to maximize surface area of the fiber bundle. To permeabilize the myofibers, each fiber bundle will be incubated in ice-cold buffer X containing 50 µg/mL saponin on a rotator for 30 minutes at 4° C. The permeabilized bundles will be washed in ice-cold buffer Z, containing 110 mM K-MES, 35 mM KCl, 1 mM EGTA, 5 mM $K_2HPO_4$, and 3 mM $MgCl_2$, 0.005 mM glutamate, and 0.02 mM malate and 0.5 mg/mL BSA, pH 7.1.

Mitochondrial Respiration in Permeabilized Fibers.

Respiration will be measured polarographically in a respiration chamber maintained at 37° C. (Hansatech Instruments, United Kingdom). After the respiration chamber will be calibrated, permeabilized fiber bundles will be incubated with 1 mL of respiration buffer Z containing 20 mM creatine to saturate creatine kinase (Saks, et al., *Mol. Cell Biochem.* 184:81-100, 1998; Walsh, et al., *J. Physiol.* 537:971-978, 2001). Flux through complex I will be measured using 5 mM pyruvate and 2 mM malate. The maximal respiration (state 3), defined as the rate of respiration in the presence of ADP, will be initiated by adding 0.25 mM ADP to the respiration chamber. Basal respiration (state 4) will be determined in the presence of 10 µg/mL oligomycin to inhibit ATP synthesis. The respiratory control ratio (RCR) will be calculated by dividing state 3 by state 4 respiration.

Mitochondrial ROS Production.

Mitochondrial ROS production will be determined using AMPLEX™ Red (Molecular Probes, Eugene, Oreg., U.S.A.). The assay will be performed at 37° C. in 96-well plates using succinate as the substrate. Superoxide dismutase (SOD) will be added at 40 units/mL to convert all superoxide into $H_2O_2$. Resorufin formation (AIVIPLEX™ Red oxidation by $H_2O_2$) will be monitored at an excitation wavelength of 545 nm and an emission wavelength of 590 nm using a multi-well plate reader fluorometer (SpectraMax, Molecular Devices, Sunnyvale, Calif., U.S.A.). The level of Resorufin formation will be recorded every 5 minutes for 15 minutes, and $H_2O_2$ production will be calculated with a standard curve.

It is anticipated that the peptide conjugate, aromatic-cationic peptide or TBMs (with or without aromatic-cationic peptides) will have no effect on normal skeletal muscle size or mitochondrial function, and that the peptide conjugate, aromatic-cationic peptide or TBMs (with or without aromatic-cationic peptides) will prevent oxidative damage and associated muscle weakness induced by hind limb immobilization (e.g., atrophy, contractile dysfunction, etc.). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

It is anticipated that the peptide conjugate, aromatic-cationic peptide or TBMs (with or without aromatic-cationic peptides) will have no effect on normal soleus muscle weight, the respiratory coupling ratio (RCR), mitochondrial state 3 respiration, or mitochondrial state 4 respiration, in mobile mice. RCR is the respiratory quotient ratio of state 3 to state 4 respiration, as measured by oxygen consumption. Likewise, it is anticipated that the peptide conjugate, aromatic-cationic peptide or TBMs (with or without aromatic-cationic peptides) will not cause variable effects on muscle fibers of different size in a normal soleus muscle, or on plantaris muscle weight, the respiratory coupling ratio (RCR), mitochondrial state 3 respiration, or mitochondrial state 4 respiration. Similarly, it is anticipated that the peptide conjugate, aromatic-cationic peptide or TBMs (with or without aromatic-cationic peptides) will not have any variable effects to the muscle fibers of different size in normal plantaris muscle fiber tissue.

It is anticipated that hind limb casting for 7 days will cause a significant decrease in soleus muscle weight and mitochondrial state 3 respiration, both of which are anticipated to be reversed by administration of the peptide conjugate, aromatic-cationic peptide or TBMs (with or without aromatic-cationic peptides). It is anticipated that casting for 7 days will significantly increase $H_2O_2$ production by mitochondria isolated from soleus muscle, which is anticipated to be prevented by the peptide conjugate, aromatic-cationic peptide or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

Casting is also anticipated to significantly increase oxidative damage in soleus muscle, as measured by lipid peroxidation via 4-hydroxynonenal (4-HNE). It is anticipated that this effect will be overcome by administration of the peptide conjugate, aromatic-cationic peptide or TBMs (with or without aromatic-cationic peptides). Moreover, it is anticipated that casting will significantly increase protease activity in the soleus muscle, promoting muscle degradation and atrophy, and that this effect will be attenuated or prevented by administration of the peptide conjugate, aromatic-cationic peptide or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

It is anticipated that calpain-1, caspase-3 and caspase-12 proteolytic degradation of muscle, respectively, will be all prevented by treatment with the peptide conjugate, aromatic-cationic peptide or TBMs (with or without aromatic-cationic peptides). It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that administering peptide conjugates, aromatic-cationic peptides or TBMs (with or without aromatic-cationic peptides) to subjects with MV-induced or disuse-induced increases in mitochondrial ROS production reduces protease activity and attenuates skeletal muscle atrophy and contractile dysfunction. The results will further show that treatment of animals with the mitochondrial-targeted antioxidant peptide conjugate, aromatic-cationic peptide or TBMs (with or without aromatic-cationic peptides) is useful in preventing the atrophy of type I, IIa, and IIx/b skeletal muscle fibers, and that prevention of MV-induced and disuse-induced increases in mitochondrial ROS production protects the diaphragm from MV-induced decreases in diaphragmatic specific force production at both sub-maximal and maximal stimulation frequencies. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

As such, TBMs (with or without aromatic-cationic peptides) or peptide conjugates of the present technology, or pharmaceutically acceptable salts thereof, such as acetate, tartrate, or trifluoroacetate salts, are useful in methods for treating or preventing MV-induced and disuse-induced mitochondrial ROS production in the diaphragm and other skeletal muscles.

Example 65: Compositions of the Present Technology Reduce the Anatomic Zone of No-Reflow Following Ischemia/Reperfusion in the Brain This Example will demonstrate the use of TBMs (with or without aromatic-cationic peptides) or peptide conjugates of the present technology in protecting a subject from an anatomic zone of no-reflow caused by ischemia-reperfusion in the brain.

Cerebral ischemia initiates a cascade of cellular and molecular events that lead to brain damage. One such event is an anatomic zone of no-reflow. Cerebral ischemia will be induced by occlusion of the right middle cerebral artery for 30 minutes. Wild-type (WT) mice will be given either saline vehicle (Veh), peptide conjugate, aromatic-cationic peptide, TBM, TBM and aromatic-cationic peptide (2-5 mg/kg for the peptide conjugate and equivalent molar doses of aromatic-cationic peptide and/or TBM based on concentration of the aromatic-cationic peptide or TBM administered in the peptide conjugate group) i.p. at 0, 6, 24 and 48 hours after ischemia. Mice will be sacrificed 3 days after ischemia, and the brains sliced transversely into 6-8 sections. Sections will be photographed under ultraviolet light to identify the region of no-reflow. The areas of no-reflow in each slice will be digitized using Image J (supplier Rasband WS, Image J, National Institutes of Health, http://rsb.info.nih.gov/ij/). The areas in each slice will be multiplied by the weight of the slice and the results will be summed in order to obtain the mass of the no-reflow areas.

It is predicted that treatment of wild type mice with the peptide conjugate, aromatic-cationic peptide or TBMs (with or without aromatic-cationic peptides) will result in a significant reduction in infarct volume and prevent or reduce the anatomic zone of no-reflow. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone. These results will show that the TBMs (with or without aromatic-cationic peptides) or peptide conjugates of the present technology, or pharmaceutically acceptable salts thereof, such as acetate, tartrate, or trifluoroacetate salts, are useful in methods for reducing the incidence of no-reflow caused by ischemia-reperfusion in the brain.

Example 66: Compositions of the Present Technology Reduce the Anatomic Zone of No-Reflow Following Ischemia/Reperfusion in the Kidney This Example will demonstrate the use of TBMs (with or without aromatic-cationic peptides) or peptide conjugates of the present technology in protecting a subject from an anatomic zone of no-reflow caused by ischemia-reperfusion in the kidney.

Sprague Dawley rats (250-300 g) will be assigned to the following groups: (1) sham surgery group without I/R; (2) I/R+saline vehicle treatment; (3) FR+peptide conjugate treatment; (4) I/R+aromatic-cationic peptide treatment; (5) I/R+TBM treatment; (6) I/R+TBM+aromatic-cationic peptides. The peptide conjugate (3 mg/kg, dissolved in saline), aromatic-cationic peptide (an equivalent molar dose of aromatic-cationic peptide based on the concentration of the aromatic-cationic peptide administered in the peptide conjugate group), TBM (an equivalent molar dose of TBM based on the concentration of the TBM administered in the peptide conjugate group), or TBMs in combination with aromatic-cationic peptides (e.g., an equivalent molar dose of TBM based on the concentration of TBM administered in the peptide conjugate treatment group and an equivalent molar dose of aromatic-cationic peptide based on the concentration of aromatic-cationic peptide administered in the peptide conjugate treatment group) will be administered to rats 30 minutes before ischemia and immediately before onset of reperfusion. The control rats will be given saline vehicle on the same schedule. Rats will be anesthetized with a mixture of ketamine (90 mg/kg, i.p.) and xylazine (4 mg/kg, i.p.). The left renal vascular pedicle will be occluded temporarily using a micro-clamp for 30 or 45 min. At the end of the ischemic period, reperfusion will be established by removing of the clamp. At that time, the contralateral right kidney will be removed. After 24 hours reperfusion, animals will be sacrificed and blood samples will be obtained by cardiac puncture. Renal function will be determined by blood urea nitrogen (BUN) and serum creatinine (BioAssay Systems DIUR-500 and DICT-500).

Analysis of No-reflow Zones, and Necrosis. The kidneys will be sliced transversely into 6-8 sections. Sections will be photographed under ultraviolet light to identify the region of no-reflow. The areas of no-reflow in each slice are digitized using Image J (supplier Rasband WS, Image J, National Institutes of Health, http://rsb.info.nih.gov/ij/). The areas in each slice will be multiplied by the weight of the slice and the results will be summed in order to obtain the mass of the no-reflow areas.

It is predicted that treatment with the peptide conjugate, aromatic-cationic peptide or TBMs (with or without aromatic-cationic peptides) will prevent or reduce the anatomic zone of no-reflow in the kidney. It is further predicted that one or more of BUN, serum creatinine, and glomerular filtration rate will improve in subjects treated with the peptide conjugate, aromatic-cationic peptide or TBMs (with or without aromatic-cationic peptides) as compared to untreated control subjects. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone. As such, the TBMs (with or without aromatic-cationic peptides) or peptide conjugates of the present technology, or pharmaceutically acceptable salts thereof, such as acetate, tartrate, or trifluoroacetate salts, are useful in methods for reducing the incidence of no-reflow caused by ischemia-reperfusion in the kidney.

Example 67: Compositions of the Present Technology Protect Against the No Re-Flow Phenomenon in Humans This Example will demonstrate the use of TBMs (with or without aromatic-cationic peptides) or peptide conjugates of the present technology at the time of revascularization of ischemic tissue to limit the size of the anatomic zone of no-reflow in human subjects.

For treatment of acute myocardial infarction (AMI), the use of mechanical recanalization of the affected artery restores epicardial coronary blood flow to ischemic myocardium (TIMI Flow Grade 3) in more than 90% of patients. However, these reperfusion methods do not address the important ancillary problem of restoration of blood flow downstream at the level of the capillary bed. During or following primary percutaneous coronary intervention (PCI), microcirculatory dysfunction is observed in 20-40% of patients. The lack of ST-segment elevation resolution after angioplasty with stenting is a marker of microvascular problems and is associated with a poor clinical prognosis. In STEMI, failure to achieve myocardial reperfusion despite the presence of a patent coronary artery has been called the "no-reflow" phenomenon.

Study Group.

Men and women, 18 years of age or older, who present within 6 hours after the onset of chest pain, who have ST-segment elevation of more than 0.1 mV in two contiguous leads, and for whom the clinical decision is made to treat with PCI will be eligible for enrollment. Patients will be eligible for the study whether they are undergoing primary PCI or rescue PCI. Occlusion of the affected coronary artery (Thrombolysis in Myocardial Infarction [TIMI] flow grade 0) at the time of admission will also be a criterion for inclusion.

Angiography and Revascularization.

Left ventricular and coronary angiography will be performed with the use of standard techniques, just before revascularization. Revascularization will be performed by PCI with the use of direct stenting. Alternative revascularization procedures include, but are not limited to, balloon angioplasty; insertion of a bypass graft; percutaneous transluminal coronary angioplasty; and directional coronary atherectomy Experimental Protocol.

After coronary angiography is performed but before the stent is implanted, patients who meet the enrollment criteria will be randomly assigned to the control group; the peptide conjugate treatment group; the aromatic-cationic peptide group; the TBM treatment group; TBM+aromatic-cationic peptide treatment group. Randomization will be performed with the use of a computer-generated randomization sequence. Less than 10 minutes before direct stenting, the patients in the experimental group receive an intravenous bolus injection of the peptide conjugate, aromatic-cationic peptide or TBM (alone or in combination with aromatic-cationic peptide). The compound will be dissolved in normal saline (final concentration, 25 mg per milliliter for peptide conjugate and equivalent molar doses of aromatic-cationic peptide and/or TBM based on concentration of the aromatic-cationic peptide or TBM administered in the peptide conjugate group) and will be injected through a catheter that is positioned within an antecubital vein. The patients in the control group receive an equivalent volume of normal saline.

No Re-Flow Zone.

The primary end point will be the size of the anatomic zone of no-reflow. No re-flow will be assessed by one or more imaging techniques. Re-flow phenomenon will be assessed using myocardial contrast echocardiography, coronary angiography, myocardial blush, coronary doppler imaging, electrocardiography, nuclear imaging single-photon emission CT, using thallium or technetium-99m, or PET. A 1.5-T body MRI scanner will be used to perform cardiac MRI in order to assess ventricular function, myocardial edema (area at risk), microvascular obstruction and infarct size. Post-contrast delayed enhancement will be used on day 4±1, day 30±3 and 6+1.5 months after successful PCI and stenting to quantify infracted myocardium. This will be defined quantitatively by an intensity of the myocardial post-contrast signal that is more than 2 SD above that in a reference region of remote, non-infarcted myocardium within the same slice. Standard extracellular gadolinium-based contrast agents will be used at a dose of 0.2 mmol/kg. The 2D inversion recovery prepared fast gradient echo sequences will be used at the following time points: (1) early (approximately 2 minutes after contrast injection) for evaluation of microvascular obstruction. Single shot techniques may be considered if available and (2) late (approximately 10 minutes after contrast injection) for evaluation of infarct size.

It is predicted that administration of the peptide conjugate, aromatic-cationic peptide or TBMs (with or without aromatic-cationic peptides) at the time of reperfusion will be associated with a smaller anatomic zone of no-reflow than that seen with placebo. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone. As such, the TBMs (with or without aromatic-cationic peptides) or peptide conjugates of the present technology, or pharmaceutically acceptable salts thereof, such as acetate, tartrate, or trifluoroacetate salts, are useful in methods for reducing the incidence of no-reflow caused by ischemia-reperfusion in the heart.

Example 68—Use of Compositions of the Present Technology in the Treatment of Drug-Induced Hyperalgesia in Humans This Example will demonstrate use of TBMs (with or without aromatic-cationic peptides) or peptide conjugates of the present technology in the treatment of hyperalgesia in human subjects.

Patients will be recruited to the study as they present in clinic with chronic (>6 months' duration), spontaneous, ongoing, vincristine-related pain. Those enrolled will rate their daily maximum level of pain at 4 or greater on a visual analog scale (VAS). The patients will be screened for their willingness to enroll in the study, and informed consent will be obtained. Healthy subjects will also be recruited for collection of comparison data. No subjects in either the patient or comparison group will have known risk factors for any other cause of peripheral neuropathy, including diabetes, AIDS, chronic alcoholism, or previous radiation exposure.

After a focused interview about the history of the patient's cancer and treatment, the patient will be asked to describe sensory symptoms by choosing from a list of ideal type word descriptors. Ongoing and daily maximum pain intensity will be rated on a VAS with prompts of "no pain" at the bottom and "most imaginable" at the top. The areas of pain and sensory disturbances will be drawn by each patient on a standardized body map. Similar to previous observations in patients treated with paclitaxel, subjects with vincristine-induced peripheral neuropathy are predicted to identify the following three zones of sensation:

a) The painful area: The zone of ongoing pain located on the tips of the fingers and/or toes. The tip of the index finger is expected to be involved in all patients and will be used as the test site in this zone.

b) The border area: Adjacent and proximal to, but distinct from the painful area, represented by nonpainful sensory disturbances and located in the palms and/or soles of the feet. The thenar eminence is expected to be involved in all patients and will be used as the test site in this zone.

c) The nonpainful area: Adjacent and proximal to, but distinct from the border area, reported by the patient to feel "normal." This site is expected to be always proximal to the wrists and/or ankles. Sensory testing will be conducted on the volar surface of the arm.

The tip of the index finger, thenar eminence, and volar forearm, will be tested in normal subjects for comparison. Patients will be specifically queried about the stimuli that provoked pain or caused an exacerbation of ongoing pain in these regions, including the effects that clothing, bed linens, bathing, and normal activities of daily living cause. Each zone will be examined for any physical changes, such as scaling, finger clubbing, and erythema, which will be documented. The areas of sensory disturbance will be physically probed by light touch with a camel hair brush and by manual massage to screen for the presence of allodynia or hyperalgesia.

Touch and Sharpness Detection Thresholds—

Touch detection thresholds will be determined with von Frey monofilaments using the up/down method as previously reported. Starting with a bending force of 0.02 g, each monofilament will be applied to a spot on the skin less than 2 mm in diameter for approximately one second. The force of the filament detected four consecutive times will be assigned as the touch detection threshold. Sharpness detection will be determined using weighted 30-gauge metal cylinders. Briefly, the tip of 30-gauge needles (200 mm diameter) will be filed to produce flat, cylindrical ends and the luers will be fitted to calibrated brass weights with the desired force (100, 200, and 400 mN) level for each stimulus. Each loaded needle will be placed inside a separate 10 cc syringe where it will be able to move freely. Each stimulus will be applied for one second perpendicular to the skin 10 times within each area of interest in a pseudorandom order. The subjects will indicate whether the stimulus is perceived as touch, pressure, sharp, or other. The percentages of each reply will be calculated and then combined into group grand means for comparison. The 50% sharpness detection threshold will be calculated as the weighted needle that caused five or more sharp responses after 10 consecutive stimuli.

Grooved Pegboard Test—

Manual dexterity will be assessed with the grooved pegboard test. Subjects will be instructed to fill a five-by-five slotted pegboard in an ordered fashion and the times for both dominant and non-dominant hands will be recorded.

Thermal Detection Thresholds—

The threshold for heat pain will be determined using the Marstock technique. A radiometer will be used at the outset of testing to ascertain the baseline skin temperature at all testing sites. All tests and measurements will be conducted at room temperature 22° C. Thermal ramps will be applied using a 3.6×3.6 cm Peltier thermode from a baseline temperature of 32° C. Skin heating will be at a ramp of 0.30° C./s, and skin cooling will be at a ramp of −0.5° C./s. Subjects will be instructed to signal when the stimulus is perceived as first becoming warmer and then painfully hot, or as first becoming cooler and then painfully cold. If a subject fails to reach a given threshold before the cutoff temperature of 51.5° C. for the ascending ramp or 3° C. held for 10 seconds in the cooling test, the cutoff values will be assigned for any that are not reached. The final threshold value for each skin sensation in each patient will be determined by averaging the results of three heating and cooling trials.

Statistical Analysis—

The thresholds for touch detection will be compared using nonparametric methods (Wilcoxon's test). The sharpness detection, thermal thresholds, and times in the grooved pegboard tests will be compared using analysis of variance and post hoc comparison of the means with Duncan's multiple range tests. Comparisons of mechanical and thermal thresholds will be performed between healthy subjects and patients for the different areas of the tested skin. Further analyses will be performed between glabrous and volar skin within the patient group. For every comparison performed in the present study, $p<0.05$ will be considered significant.

Following initial assessment of the above criteria, subjects will be divided into the following groups:

a) Healthy controls
b) No treatment
c) Vehicle-only placebo, administered s.c., once daily for 14 days
d) peptide conjugate, 10 mg/kg, administered s.c., once daily for 14 days
e) aromatic-cationic peptide (equivalent molar doses of aromatic-cationic peptide based on concentration of the aromatic-cationic peptide administered in the 10 mg/kg peptide conjugate group), administered s.c., once daily for 14 days
f) TBM (equivalent molar doses of TBM based on concentration of the TBM administered in the 10 mg/kg peptide conjugate group), administered s.c., once daily for 14 days
g) TBMs in combination with aromatic-cationic peptides (e.g., an equivalent molar dose of TBM based on the concentration of TBM administered in the 10 mg/kg peptide conjugate treatment group and an equivalent molar dose of aromatic-cationic peptide based on the concentration of aromatic-cationic peptide administered in the 10 mg/kg peptide conjugate treatment group), administered s.c., once daily for 14 days.

Following the 14 day treatment period, subjects will be re-assessed according to the above criteria, with statistical analysis as described above.

Results—

It is expected that neuropathy subjects administered the peptide conjugate, aromatic-cationic peptide or TBM (with or without aromatic-cationic peptides) for a period of 14 days will report a reduction in hyperalgesia symptoms compared to subjects administered no treatment or a vehicle-only placebo. The reduction in hyperalgesia will be manifested in improved scoring for touch and sharpness detection thresholds, grooved pegboard tests, and thermal detection tests compared to control subjects. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that TBMs (with or without aromatic-cationic peptides) or peptide conjugates of the present technology are useful in the treatment of vincristine-induced hyperalgesia, and drug-induced hyperalgesia generally. The results will show that the TBMs (with or without aromatic-cationic peptides) or peptide conjugates of the present technology are useful in the treatment of drug-induced peripheral neuropathy or hyperalgesia.

Example 69—Use of Compositions of the Present Technology in the Prevention of Hyperalgesia in Humans This Example will demonstrate use of the methods and compositions of the present technology in the prevention of hyperalgesia.

Subjects at risk for developing hyperalgesia will be recruited as they present in clinic for the treatment of conditions associated with the development of peripheral neuropathy or hyperalgesia. Independent studies will address neuropathy and hyperalgesia resulting from, caused by, or otherwise associated with genetic disorders, metabolic/endocrine complications, inflammatory diseases, vitamin deficiencies, malignant diseases, and toxicity, such as alcohol, organic metal, heavy metal, radiation, and drug toxicity. Subjects will be selected such that they are at risk for developing a single type of neuropathy or hyperalgesia, having no risk factors outside the scope of the study in which the subject is enrolled, and as yet not having symptoms associated with neuropathy or hyperalgesia. Subjects will be screened for their willingness to enroll in the study, and informed consent will be obtained. Healthy subjects will also be recruited for collection of comparison data.

After a focused interview about the medical history, baseline measurements of touch and sharpness detection thresholds, grooved pegboard tests, and thermal detection thresholds will be determined according to the methods described above, with statistical analysis as described above.

Following initial assessment of the above criteria, subjects will be divided into the following groups:
a) Healthy controls
b) No treatment
c) Vehicle-only placebo, administered s.c., once daily
d) peptide conjugate, 10 mg/kg, administered s.c., once daily for 14 days
e) aromatic-cationic peptide (equivalent molar doses of aromatic-cationic peptide based on concentration of the aromatic-cationic peptide administered in the 10 mg/kg peptide conjugate group), administered s.c., once daily for 14 days
f) TBM (equivalent molar doses of TBM based on concentration of the TBM administered in the 10 mg/kg peptide conjugate group), administered s.c., once daily for 14 days
g) TBMs in combination with aromatic-cationic peptides (e.g., an equivalent molar dose of TBM based on the concentration of TBM administered in the 10 mg/kg peptide conjugate treatment group and an equivalent molar dose of aromatic-cationic peptide based on the concentration of aromatic-cationic peptide administered in the 10 mg/kg peptide conjugate treatment group), administered s.c., once daily for 14 days Subjects will be evaluated weekly during the trial for sharpness detection thresholds, grooved pegboard tests, and thermal detection thresholds. The trial will continue for a period of 28 days, or until the no-treatment and placebo control groups display hyperalgesia according to the above criteria, at which point subjects will undergo a final assessment.

Results—

It is expected that at-risk subjects that are treated with the peptide conjugate, aromatic-cationic peptide or TBM (with or without aromatic-cationic peptides) will show attenuated development of neuropathy or hyperalgesia compared to untreated and placebo controls. It is anticipated that administration of peptide conjugates of the present technology will have synergistic effects in this regard compared to that observed with either aromatic-cationic peptides or TBMs (alone or in combination with aromatic-cationic peptides). It is anticipated that administration of TBM in combination with aromatic-cationic peptides will have synergistic effects in this regard compared to that observed with either aromatic-cationic peptides or TBMs alone.

These results will show that the TBMs (with or without aromatic-cationic peptides) or peptide conjugates of the present technology are useful in the prevention of neuropathy and hyperalgesia generally.

Example 70: Effects of Compositions of the Present Technology on Heart Mitochondrial Cardiolipin in a Dog Model of Heart Failure This Example demonstrates the effect of peptide conjugates on levels of heart mitochondrial cardiolipin in dogs with coronary microembolization-induced heart failure. In particular, the effects of D-Arg-2'6'-Dmt-Lys-Phe-NH$_2$-TBM conjugate on levels of the 18:2-18:2-18:2-18:2 cardiolipin species are evaluated.

Heart failure is induced in dogs via multiple sequential intracoronary microembolizations as described in Sabbah, et al., *Am J Physiol*. (1991) 260:H1379-84, herein incorporated by reference in its entirety. Group I dogs are subsequently treated with a daily dose of 0.25 mg/kg/day of the peptide conjugate; Group II dogs are treated with only TBM at an equivalent molar dose of a daily dose of the TBM in the 0.25 mg/kg/day dose of the peptide conjugate; Group III dogs are treated with D-Arg-2'6'-Dmt-Lys-Phe-NH$_2$ at an equivalent molar dose of the D-Arg-2'6'-Dmt-Lys-Phe-NH$_2$ in the daily dose of 0.25 mg/kg/day of the peptide conjugate; Group IV dogs are treated with TBMs in combination with D-Arg-2'6'-Dmt-Lys-Phe-NH$_2$ (e.g., an equivalent molar dose of TBM based on the concentration of TBM administered in the 0.25 mg/kg/day dose of the peptide conjugate treatment group and an equivalent molar dose of D-Arg-2'6'-Dmt-Lys-Phe-NH$_2$ based on the concentration of D-Arg-2'6'-Dmt-Lys-Phe-NH$_2$ administered in the 0.25 mg/kg/day dose of the peptide conjugate treatment group). Group V dogs are treated with drug vehicle and serve as controls. Treatment with the various agents of Groups I, II, III, and IV are started upon induction of heart failure (HF), defined as left ventricular ejection fraction of approximately 30%. Doses are administered intravenously. At the end of the treatment phase (12 weeks), dogs in the control and treatment groups are sacrificed and a sample of heart muscle from the left ventricle is removed, washed with saline, and immediately frozen and stored at −80° C. For cardiolipin analysis, lipids are extracted from the heart tissue sample with a chloroform/methanol solution (Bligh Dyer extraction). Individual lipid extracts are reconstituted with chloroform:methanol (1:1), flushed with N2, and then stored at −20° C. before analysis via electrospray ionization mass spectroscopy using a triple-quadrupole mass spectrometer equipped with an automated nanospray apparatus. Enhanced multidimensional mass spectrometry-based shotgun lipidomics for cardiolipin is performed as described by Han, et al., "*Shotgun lipidomics of cardiolipin molecular species in lipid extracts of biological samples,*" *J Lipid Res* 47(4)864-879 (2006).

It is anticipated that the levels of 18:2 cardiolipin species will be significantly reduced in untreated heart failure dogs (Heart Failure, Control) as compared to cardiac tissue from normal subjects (Normal). It is further anticipated that subjects treated with D-Arg-2'6'-Dmt-Lys-Phe-NH$_2$-TBM conjugates, TBM (alone or in combination with D-Arg-2'6'-Dmt-Lys-Phe-NH$_2$), or D-Arg-2'6'-Dmt-Lys-Phe-NH$_2$ will have 18:2 cardiolipin levels that are similar to normal subjects, and greater than the heart failure control subjects. It is anticipated that administration of peptide conjugates of the present technology will have synergistic effects in this regard (e.g., D-Arg-2'6'-Dmt-Lys-Phe-NH$_2$-TBM conjugates are more therapeutically effective at normalizing cardiolipin levels compared to treatment with either D-Arg-2'6'-Dmt-Lys-Phe-NH$_2$ or TBM (alone or in combination with D-Arg-2'6'-Dmt-Lys-Phe-NH$_2$)). It is anticipated that administration of TBM in combination with D-Arg-2'6'-Dmt-Lys-Phe-NH$_2$ will have synergistic effects in this regard compared to that observed with either D-Arg-2'6'-Dmt-Lys-Phe-NH$_2$ or TBMs alone.

The results will show that TBMs (with or without aromatic-cationic peptides) or peptide conjugates of the present technology are useful in the prevention and treatment of diseases and conditions associated with aberrant cardiolipin levels. These results show that TBMs (with or without aromatic-cationic peptides) or peptide conjugates of the present technology are useful in methods comprising administration of the peptide conjugates to subjects in need of normalization of cardiolipin levels and remodeling.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A method for delivering an aromatic-cationic peptide and/or a therapeutic biological molecule to a cell, the method comprising contacting the cell with a peptide conjugate, wherein the peptide conjugate comprises the therapeutic biological molecule conjugated to an aromatic-cationic peptide, wherein the aromatic-cationic peptide is selected from the group consisting of: 2',6'-dimethyl-Tyr-D-Arg-Phe-Lys-$NH_2$, Phe-D-Arg-Phe-Lys-$NH_2$, and D-Arg-2',6'-Dmt-Lys-Phe-$NH_2$, and wherein the therapeutic biological molecule is frataxin.

2. A method according claim 1, wherein the therapeutic biological molecule is conjugated to the aromatic-cationic peptide by a linker.

3. A method according to claim 1, wherein the therapeutic biological molecule and aromatic-cationic peptide are chemically bonded.

4. A method according to claim 1, wherein the therapeutic biological molecule and aromatic-cationic peptide are physically bonded.

5. A method according to claim 2, wherein the aromatic-cationic peptide and the therapeutic biological molecule are linked using a labile linkage that is hydrolyzed in vivo to uncouple the aromatic-cationic peptide and the therapeutic biological molecule.

6. A method according claim 5, wherein the labile linkage comprises an ester linkage.

7. A peptide conjugate comprising a therapeutic biological molecule conjugated to an aromatic-cationic peptide, wherein the aromatic-cationic peptide is Phe-D-Arg-Phe-Lys-$NH_2$ or D-Arg-2',6'-Dmt-Lys-Phe-$NH_2$, and wherein the therapeutic biological molecule is frataxin.

8. A peptide conjugate according to claim 7, wherein the therapeutic biological molecule is conjugated to the aromatic-cationic peptide by a linker.

9. A peptide conjugate according to claim 7, wherein the therapeutic biological molecule and aromatic-cationic peptide are chemically bonded.

10. A peptide conjugate according to claim 7, wherein the therapeutic biological molecule and aromatic-cationic peptide are physically bonded.

11. A peptide conjugate according to claim 7, wherein the aromatic-cationic peptide and the therapeutic biological molecule are linked using a labile linkage that is hydrolyzed in vivo to uncouple the aromatic-cationic peptide and the therapeutic biological molecule.

12. A peptide conjugate according to claim 11, wherein the labile linkage comprises an ester linkage.

* * * * *

```
                         SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Dmt

<400> SEQUENCE: 1

Arg Xaa Lys Phe Cys
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Tyr Lys Phe
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Arg Phe Lys
1

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Arg Phe Lys Glu Cys Gly
1               5
```

```
<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Arg Phe Lys Glu His Trp Arg
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Leu Gly
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Leu Ala Leu
1
```